(12) United States Patent
Cindrich et al.

(10) Patent No.: US 9,364,606 B2
(45) Date of Patent: Jun. 14, 2016

(54) PATCH-LIKE INFUSION DEVICE

(71) Applicant: Becton, Dickinson and Company, Franklin Lakes, NJ (US)

(72) Inventors: Chris Cindrich, Draper, UT (US); Ralph Sonderegger, Farmington, UT (US); Glade Howell, Sandy, UT (US); Weston Harding, Lehi, UT (US); Alex Lastovich, Raleigh, NC (US); Lionel Vedrine, Ridgewood, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 193 days.

(21) Appl. No.: 13/797,544

(22) Filed: Mar. 12, 2013

(65) Prior Publication Data

US 2013/0204191 A1    Aug. 8, 2013

Related U.S. Application Data

(63) Continuation of application No. 10/567,051, filed as application No. PCT/US2004/026109 on Aug. 12, 2004, now Pat. No. 8,444,604.

(60) Provisional application No. 60/494,286, filed on Aug. 12, 2003, provisional application No. 60/558,611, filed on Apr. 2, 2004.

(51) Int. Cl.
| | |
|---|---|
| *A61M 5/32* | (2006.01) |
| *A61M 5/158* | (2006.01) |
| *A61M 5/142* | (2006.01) |
| *A61M 5/145* | (2006.01) |

(52) U.S. Cl.
CPC ........... *A61M 5/158* (2013.01); *A61M 5/14248* (2013.01); *A61M 2005/1426* (2013.01); *A61M 2005/14506* (2013.01); *A61M 2209/06* (2013.01)

(58) Field of Classification Search
CPC ............ A61M 5/14248; A61M 5/158; A61M 2005/14252; A61M 2005/1426; A61M 2005/1583
USPC .............................. 604/164.08, 192, 198, 263
See application file for complete search history.

(56) References Cited

U.S. PATENT DOCUMENTS

| | | | |
|---|---|---|---|
| 549,656 A | 11/1895 | Pickering | 47/17 |
| 3,048,171 A | 8/1962 | Grau | 604/134 |

(Continued)

FOREIGN PATENT DOCUMENTS

| | | | | |
|---|---|---|---|---|
| DE | 40 39 191 C1 | 11/1991 | | A61M 5/145 |
| WO | WO 87/04631 | 8/1987 | | A61M 37/00 |

(Continued)

*Primary Examiner* — Emily Schmidt
(74) *Attorney, Agent, or Firm* — Dickinson Wright PLLC

(57) ABSTRACT

A system and method for a patch-like, self-contained substance infusion device (700) which can be attached to a skin surface via an adhesive contact surface. A push button (780) activation assembly can then be used to remove an interlock (730), allowing a disk or Belleville spring (735) assembly to apply an essentially even and constant pressure to the contents of a fluid reservoir assembly (710). This allows the release of one or more spring-loaded patient needles (760) into the skin surface, and establishes a fluid communication path between the patient needles (760) and the pressurized fluid reservoir contents thereby delivering an infusion into the skin. The push button (780) activation assembly further allows the release of one or more improved safety mechanisms (794) after use.

19 Claims, 149 Drawing Sheets

(56) References Cited

U.S. PATENT DOCUMENTS

| | | | |
|---|---|---|---|
| 3,682,365 A | 8/1972 | Reifers et al. | 229/407 |
| 3,814,097 A | 6/1974 | Ganderton et al. | 128/268 |
| 3,951,393 A | 4/1976 | Smirl | 604/304 |
| 3,964,482 A | 6/1976 | Gerstel et al. | 604/890.1 |
| 4,196,732 A | 4/1980 | Wardlaw | 141/2 |
| 4,258,711 A | 3/1981 | Tucker et al. | 604/502 |
| 4,316,463 A | 2/1982 | Schmitz et al. | 604/135 |
| 4,340,048 A | 7/1982 | Eckenhoff | 604/890.1 |
| 4,525,164 A | 6/1985 | Loeb et al. | 604/131 |
| 4,552,561 A | 11/1985 | Eckenhoff et al. | 604/891.1 |
| 4,664,654 A | 5/1987 | Strauss | 604/198 |
| 4,772,263 A | 9/1988 | Dorman et al. | 604/132 |
| 4,781,688 A | 11/1988 | Thoma et al. | 604/132 |
| 4,790,434 A | 12/1988 | Schoberg et al. | 206/387.14 |
| 4,886,499 A | 12/1989 | Cirelli et al. | 604/131 |
| 4,921,475 A | 5/1990 | Sibalis | 604/20 |
| 5,011,477 A | 4/1991 | Winchell et al. | 604/132 |
| 5,045,064 A | 9/1991 | Idriss | 604/132 |
| 5,085,656 A | 2/1992 | Polaschegg | 604/891.1 |
| 5,090,963 A | 2/1992 | Gross et al. | 604/132 |
| 5,250,023 A | 10/1993 | Lee et al. | 604/20 |
| 5,279,544 A | 1/1994 | Gross et al. | 604/20 |
| 5,554,131 A | 9/1996 | Lacivita | 604/198 |
| 5,649,910 A | 7/1997 | Kriesel et al. | 604/133 |
| 5,656,032 A | 8/1997 | Kriesel et al. | 604/132 |
| 5,693,018 A | 12/1997 | Kriesel et al. | 604/132 |
| 5,716,343 A | 2/1998 | Kriesel et al. | 604/132 |
| 5,735,818 A | 4/1998 | Kriesel et al. | 604/132 |
| 5,814,020 A | 9/1998 | Gross | 604/141 |
| 5,848,990 A | 12/1998 | Cirelli et al. | 604/136 |
| 5,858,001 A | 1/1999 | Tsals et al. | 604/135 |
| 5,858,005 A | 1/1999 | Kriesel | 604/180 |
| 5,885,250 A | 3/1999 | Kriesel et al. | 604/132 |
| 5,891,086 A | 4/1999 | Weston | 604/70 |
| 5,921,962 A | 7/1999 | Kriesel et al. | 604/132 |
| 5,931,814 A | 8/1999 | Alex et al. | 604/131 |
| 5,957,895 A | 9/1999 | Sage et al. | 604/181 |
| 5,961,492 A | 10/1999 | Kriesel et al. | 604/132 |
| 5,976,111 A | 11/1999 | Hart | 604/198 |
| 5,997,501 A | 12/1999 | Gross et al. | 604/65 |
| 6,074,369 A | 6/2000 | Sage et al. | 604/181 |
| 6,099,504 A | 8/2000 | Gross et al. | 604/140 |
| 6,132,755 A | 10/2000 | Eicher et al. | 424/427 |
| 6,186,982 B1 | 2/2001 | Gross et al. | 604/132 |
| 6,302,866 B1 | 10/2001 | Marggi | 604/174 |
| 6,500,150 B1 | 12/2002 | Gross et al. | 604/131 |
| 6,589,229 B1 | 7/2003 | Connelly et al. | 604/890.1 |
| 6,595,956 B1 | 7/2003 | Gross et al. | 604/141 |
| 6,611,707 B1 | 8/2003 | Prausnitz et al. | 604/21 |
| 6,656,147 B1 | 12/2003 | Gertsek et al. | 604/28 |
| 6,824,529 B2 | 11/2004 | Gross et al. | 604/143 |
| 6,843,782 B2 | 1/2005 | Gross et al. | 604/141 |
| 6,923,791 B2 | 8/2005 | Douglas | 604/167.05 |
| 7,014,625 B2 | 3/2006 | Bengtsson | 604/131 |
| 7,250,037 B2 | 7/2007 | Shermer et al. | 604/134 |
| 7,530,964 B2 | 5/2009 | Lavi et al. | 604/110 |
| 7,678,079 B2 | 3/2010 | Shermer et al. | 604/134 |
| 2002/0022798 A1 | 2/2002 | Connelly et al. | 604/93.01 |
| 2002/0055711 A1 | 5/2002 | Lavi et al. | 604/110 |
| 2002/0095134 A1 | 7/2002 | Pettis et al. | 604/506 |
| 2002/0170928 A1 | 11/2002 | Grychowski et al. | 222/251 |
| 2003/0045837 A1 | 3/2003 | Delmore et al. | 604/173 |
| 2003/0073609 A1 | 4/2003 | Pinkerton | 514/1 |
| 2003/0109827 A1 | 6/2003 | Lavi et al. | 604/134 |
| 2003/0135159 A1 | 7/2003 | Daily et al. | 604/141 |
| 2003/0208167 A1 | 11/2003 | Prausnitz et al. | 604/272 |
| 2004/0129039 A1* | 7/2004 | Reetz et al. | 70/63 |
| 2004/0138612 A1* | 7/2004 | Shermer et al. | 604/93.01 |
| 2005/0065466 A1 | 3/2005 | Vedrine | 604/93.01 |
| 2005/0065472 A1 | 3/2005 | Cindrich et al. | 604/134 |
| 2005/0277882 A1 | 12/2005 | Kriesel | 604/131 |
| 2007/0203454 A1 | 8/2007 | Shermer et al. | 604/135 |
| 2008/0215015 A1 | 9/2008 | Cindrich et al. | 604/257 |

FOREIGN PATENT DOCUMENTS

| | | | |
|---|---|---|---|
| WO | WO 95/13838 | 5/1995 | A61M 5/142 |
| WO | WO 97/10012 | 3/1997 | A61M 5/142 |
| WO | WO 97/21457 | 6/1997 | A61M 5/20 |
| WO | WO 97/41917 | 11/1997 | A61M 37/00 |
| WO | WO 00/74763 A2 | 12/2000 | A61M 37/00 |
| WO | 01/89607 A2 | 11/2001 | |
| WO | WO 02/083214 A1 | 10/2002 | A61M 5/46 |
| WO | WO 2004/032990 A2 | 4/2004 | |
| WO | WO 2005/002649 A1 | 1/2005 | A61M 5/142 |

* cited by examiner

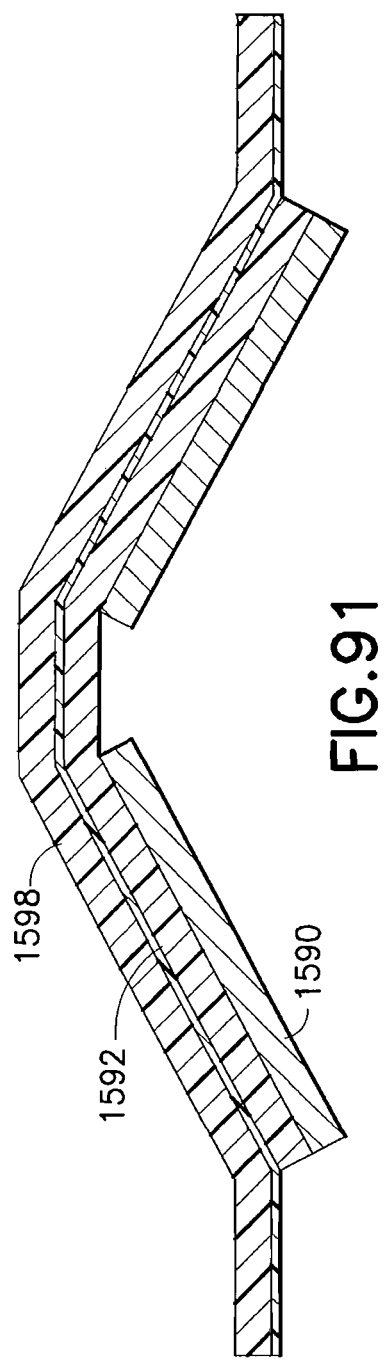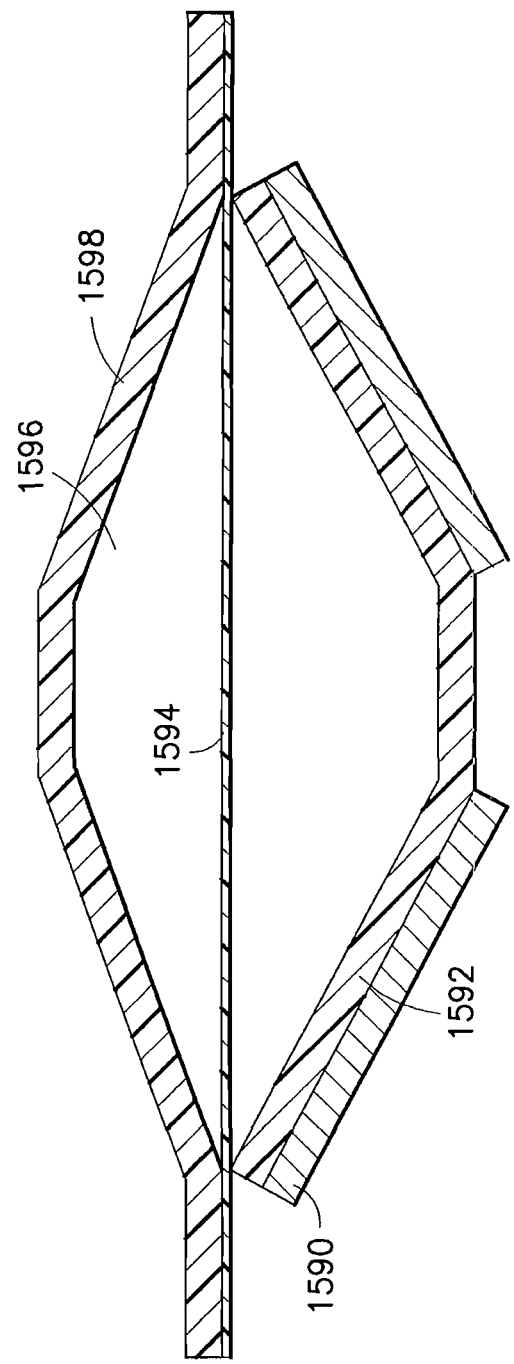

PATCH-LIKE INFUSION DEVICE

CROSS-REFERENCE TO RELATED APPLICATIONS

This application is a continuation of U.S. patent application Ser. No. 10/567,051, filed Jan. 29, 2007, now U.S. Pat. No. 8,444,604, which is the National Stage of International Application No. PCT/US04/26109, filed Aug. 12, 2004, which claims priority under 35 U.S.C. §119(e) from a U.S. Provisional Patent Application of Chris Cindrich et al. entitled "Patch-Like Infusion Device", Ser. No. 60/494,286, filed on Aug. 12, 2003, and from a U.S. Provisional Patent Application of Chris Cindrich et al. entitled "Patch-Like Infusion Device with Improved Valve, Spring and Safety Mechanisms", Ser. No. 60/558,611, filed Apr. 2, 2004, the entire content of each of said prior applications being incorporated herein by reference. This application contains subject matter which is related to that of a U.S. patent application of Charles D. Shermer et al. entitled "Patch-Like Infusion Device", Ser. No. 10/623,702, filed on Jul. 22, 2003, now U.S. Pat. No. 7,250,037, the entire content of which is also incorporated herein by reference.

FIELD OF THE INVENTION

The present invention relates generally to a substance delivery device having improved valve, spring and safety mechanisms and to a patch-like, self-contained substance infusion device that can be used to deliver a variety of substances or medications to a patient.

BACKGROUND OF THE INVENTION

A very large number of people, such as those suffering from conditions such as diabetes use some form of infusion therapy, such as daily insulin infusions to maintain close control of their glucose levels. Currently, in the insulin infusion treatment example, there are two principal modes of daily insulin therapy. The first mode includes syringes and insulin pens. These devices are simple to use and are relatively low in cost, but they require a needle stick at each injection typically three to four times per day. The second mode includes infusion pump therapy, which entails the purchase of an expensive pump that lasts for about three years. The initial cost of the pump is a high barrier to this type of therapy. From a user perspective, however, the overwhelming majority of patients who have used pumps prefer to remain with pumps for the rest of their lives. This is because infusion pumps, although more complex than syringes and pens, offer the advantages of continuous infusion of insulin, precision dosing and programmable delivery schedules. This results in closer glucose control and an improved feeling of wellness.

As patients on oral agents eventually move to insulin and their interest in intensive therapy increases, users typically look to insulin pumps. However, in addition to their high cost (roughly 8 to 10 times the daily cost of syringe therapy) and limited lifetime, insulin pumps represent relatively old technology and are cumbersome to use. Also, from a lifestyle standpoint, the tubing (known as the "infusion set") that links the pump with the delivery site on the user's abdomen is very inconvenient and the pumps are relatively heavy, making carrying the pump a burden.

Therefore interest in better therapy is on the rise, accounting for the observed growth in pump therapy and increased number of daily injections. In this and similar infusion examples, what is needed to fully meet this increased interest is a form of insulin delivery or infusion that combines the best features of daily injection therapy (low cost and ease of use) with those of the insulin pump (continuous infusion and precision dosing) and that also avoids the disadvantages of each.

Several attempts have been made to provide ambulatory or "wearable" drug infusion devices that are low in cost and convenient to use. Some of these devices are intended to be partially or entirely disposable. In theory, devices of this type can provide many of the advantages of an infusion pump without the attendant cost and inconvenience. Unfortunately, however, many of these devices suffer from disadvantages including user discomfort (due to the gauge and/or length of injection needle used), compatibility and interaction between the substance being delivered and the materials used in the construction of the infusion device, and possible malfunctioning if not properly activated by the user (e.g., "wet" injections resulting from premature activation of the device). Difficulties in manufacturing and in controlling needle penetration depth have also been encountered, particularly when short and/or fine-gauge injection needles are used. The possibility of needle-stick injuries to those who come into contact with the used device has also been problematic.

Accordingly, a need exists for an alternative to current infusion devices, such as infusion pumps for insulin, that further provides simplicity in manufacture and use improvements for insulin and non-insulin applications.

SUMMARY OF THE INVENTION

An object of the present invention is to provide a patch-like infusion device which can be conveniently worn against the skin while providing infusion of a desired substance, and providing minimal discomfort by using one or more microneedles.

Another object of the present invention is to provide a patch-like infusion device which provides a hidden patient needle or needles prior to and during use, unlike a conventional syringe.

Another object of the present invention is to provide a patch-like infusion device which can be secured to a patient via an adhesive surface, and thereafter allows the pressurizing of a content reservoir, patient needle implantation and reservoir content delivery through an activation step.

Another object of the present invention is to provide a patch-like infusion device which provides pressurizing a content reservoir using a bladder and Belleville or other disk-type spring assembly.

Another object of the present invention is to provide a patch-like infusion device which allows pressurizing the contents of a content reservoir by removing a Belleville spring retaining disk.

Another object of the present invention is to provide a patch-like infusion device which can be activated via a reasonable force applied to a vertical or horizontal push surface in an activation step.

Another object of the present invention is to provide a patch-like infusion device which allows for visual inspection of the device contents before, during and after use.

Another object of the present invention is to provide a patch-like infusion device which allows for removal of a patient needle cap and/or adhesive cover in one or more motions.

Another object of the present invention is to provide a patch-like infusion device which facilitates self-injection and reduces or eliminates variations in injection techniques between users Another object of the present invention is to provide a patch-like infusion device which includes improved shielding mechanisms for protecting the patient needle or needles upon intentional or accidental removal from the skin surface.

Another object of the present invention is to provide a patch-like infusion device which includes improved valve mechanisms for providing a sterile barrier and pressure seal prior to and during device use.

Another object of the present invention is to provide a patch-like infusion device which includes improved Belleville spring and spring pin mechanisms for use with the infusion device.

Another object of the present invention is to provide a patch-like infusion device which includes improved molding techniques to better utilize construction materials.

Another object of the present invention is to provide a patch-like infusion device which includes improved microneedle construction techniques and materials.

Another object of the present invention is to provide a patch-like infusion device which includes improved activation mechanisms including pivot arms and magnetic apparatus.

Another object of the present invention is to provide a patch-like infusion device which includes improved manifold spring mechanisms.

Another object of the present invention is to provide a patch-like infusion device which includes improved fill mechanisms, fill indicators and sterile packaging.

These and other objects are substantially achieved by providing a system and method for a patch-like, wearable, self-contained substance infusion device which provides one or more substantially hidden patient needles which can be placed in fluid communication with a content reservoir assembly that includes a rigid bladder portion used in conjunction with a non-distensible bladder film, such as a metallized film. A push type activation assembly is provided which can then be used to remove a retaining pin and allow a Belleville spring assembly to apply an essentially even and constant pressure to the contents of a reservoir assembly. The push type activation assembly then releases and seats one or more spring-loaded patient needles into the patient's skin and establishes a fluid communication path between the patient needles and the pressurized reservoir contents, thereby delivering an infusion of contents into the skin of the user. Upon completion and removal of the infusion device, a number of safety mechanisms can be engaged to cover the needles for disposal.

BRIEF DESCRIPTION OF THE DRAWINGS

The various objects, advantages and novel features of the preferred embodiments of the present invention will be more readily appreciated from the following detailed description when read in conjunction with the appended drawings, in which:

FIGS. 91 and 92 are cross-sectional views of the overmolded Belleville spring of FIG. 90 in a released and flexed position, respectively;

FIG. 152 is a perspective view of the manifold spring of FIG. 150 in an activated position;

FIG. 153 is a perspective view of another improved manifold spring in an unactivated position installed within an exemplary device;

FIG. 154 is a perspective view of the manifold spring of FIG. 153 in an activated position;

FIG. 155 is a perspective view of another improved manifold spring in an unactivated position;

FIG. 156 is a perspective view of the manifold spring of FIG. 155 in an activated position;

FIG. 157 is a cross-sectional view showing a fill hole provided by the button;

FIG. 158 is a cross-sectional view showing a valve assembly in place after filling;

FIG. 159 is a cross-sectional view showing the closing of the button window after filling of the valve assembly of FIG. 158;

FIG. 160 is a cross-sectional view showing the closed window of the valve assembly of FIG. 158;

FIG. 161 is a view showing valve, button valve hole and button alignment before rotation;

FIG. 162 is a view showing valve, button valve hole and button alignment after rotation;

FIG. 163 is a cross-sectional view showing valve, button valve hole and button alignment after rotation;

Figure 164:
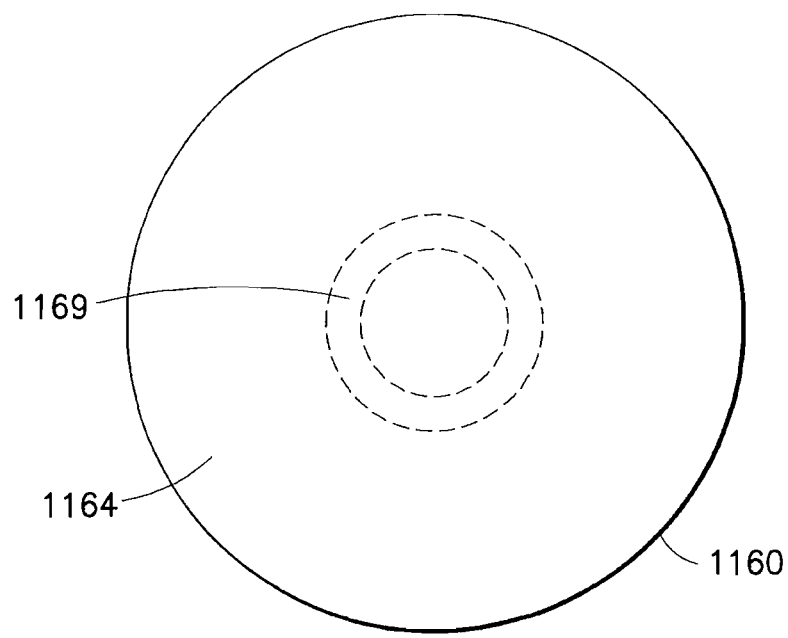
Figure 165:
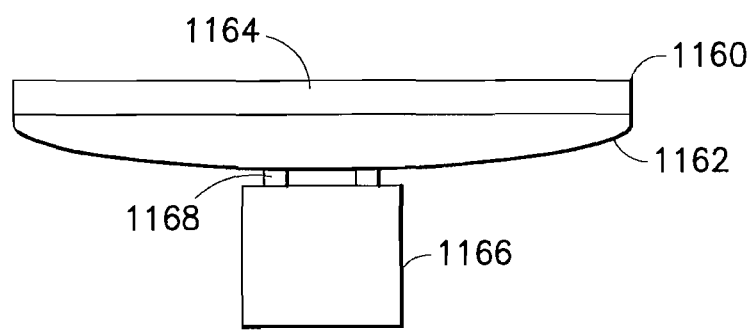
Figure 166:
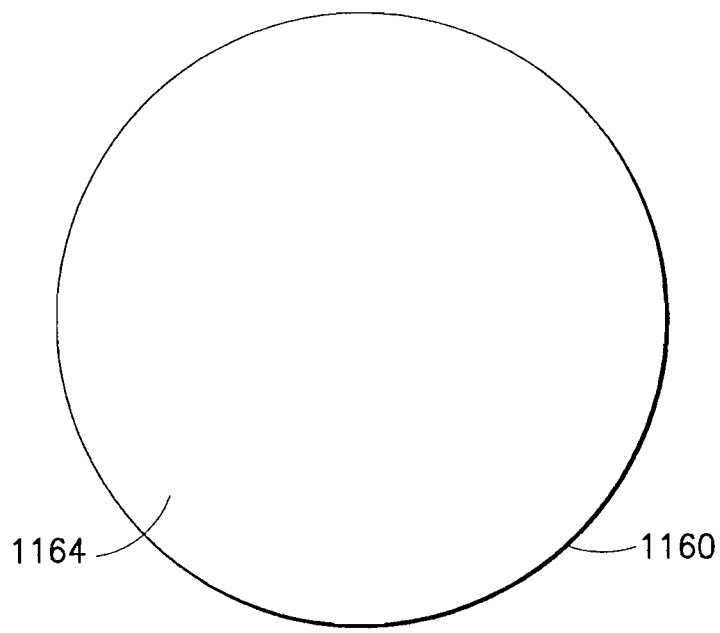
Figure 167:
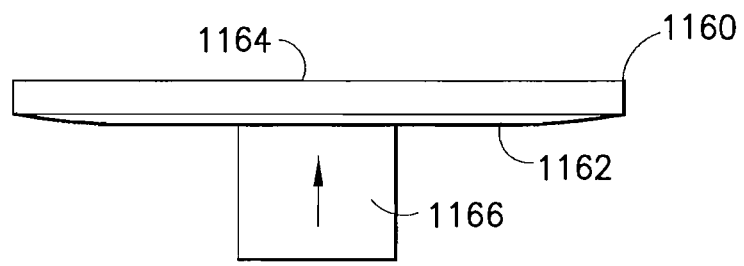
Figure 168:
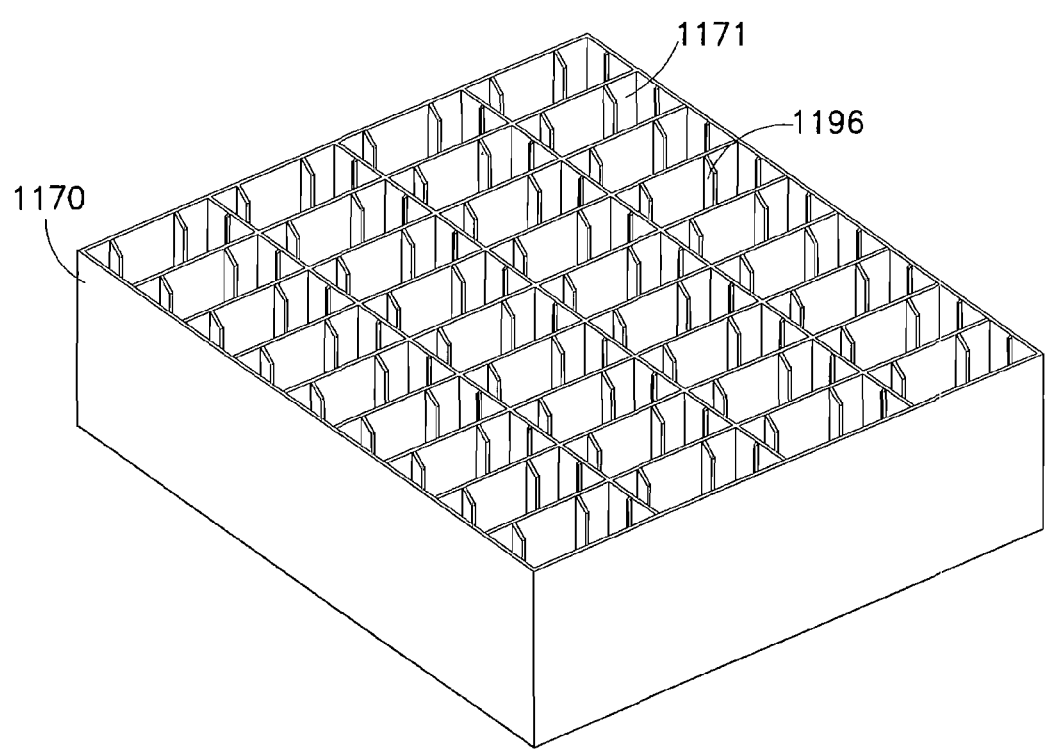
Figure 169:
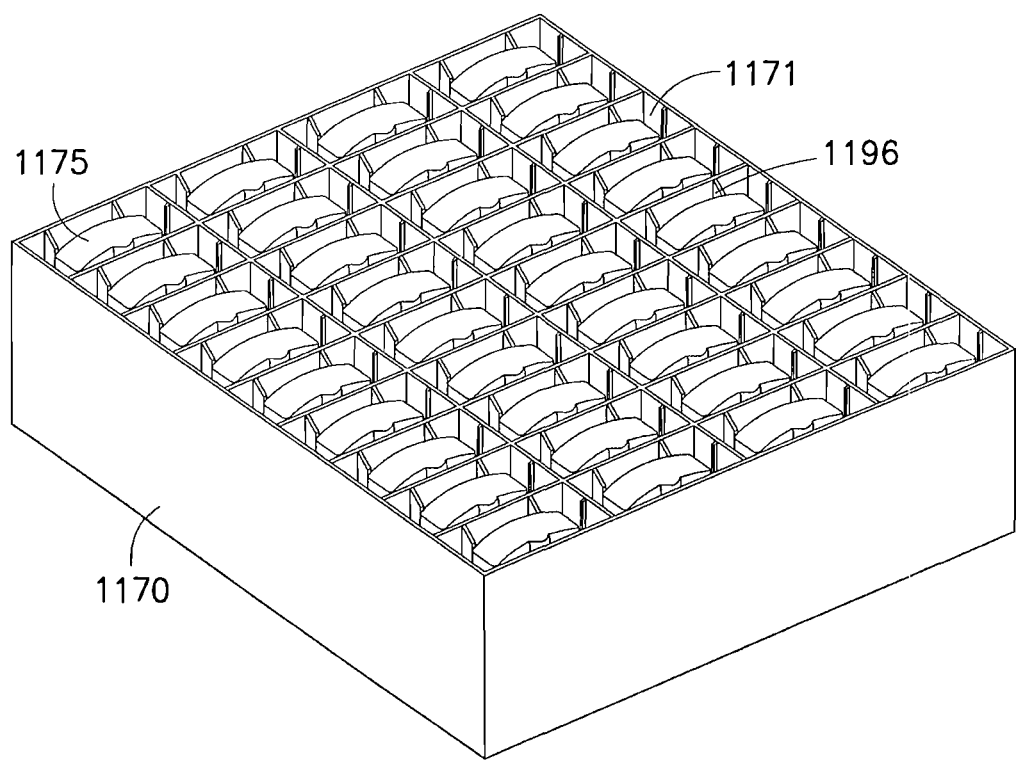
Figure 170:
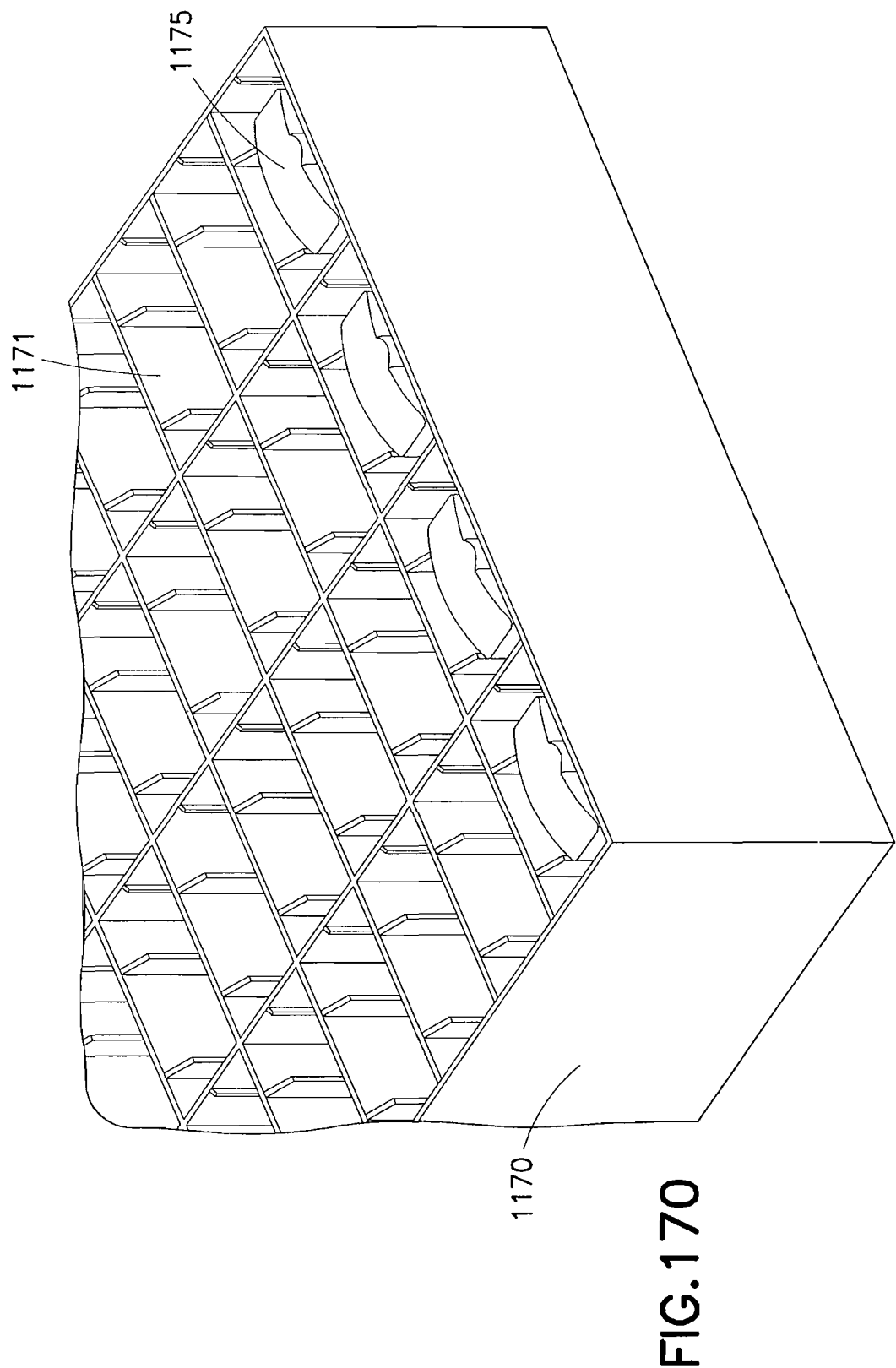
Figure 171:
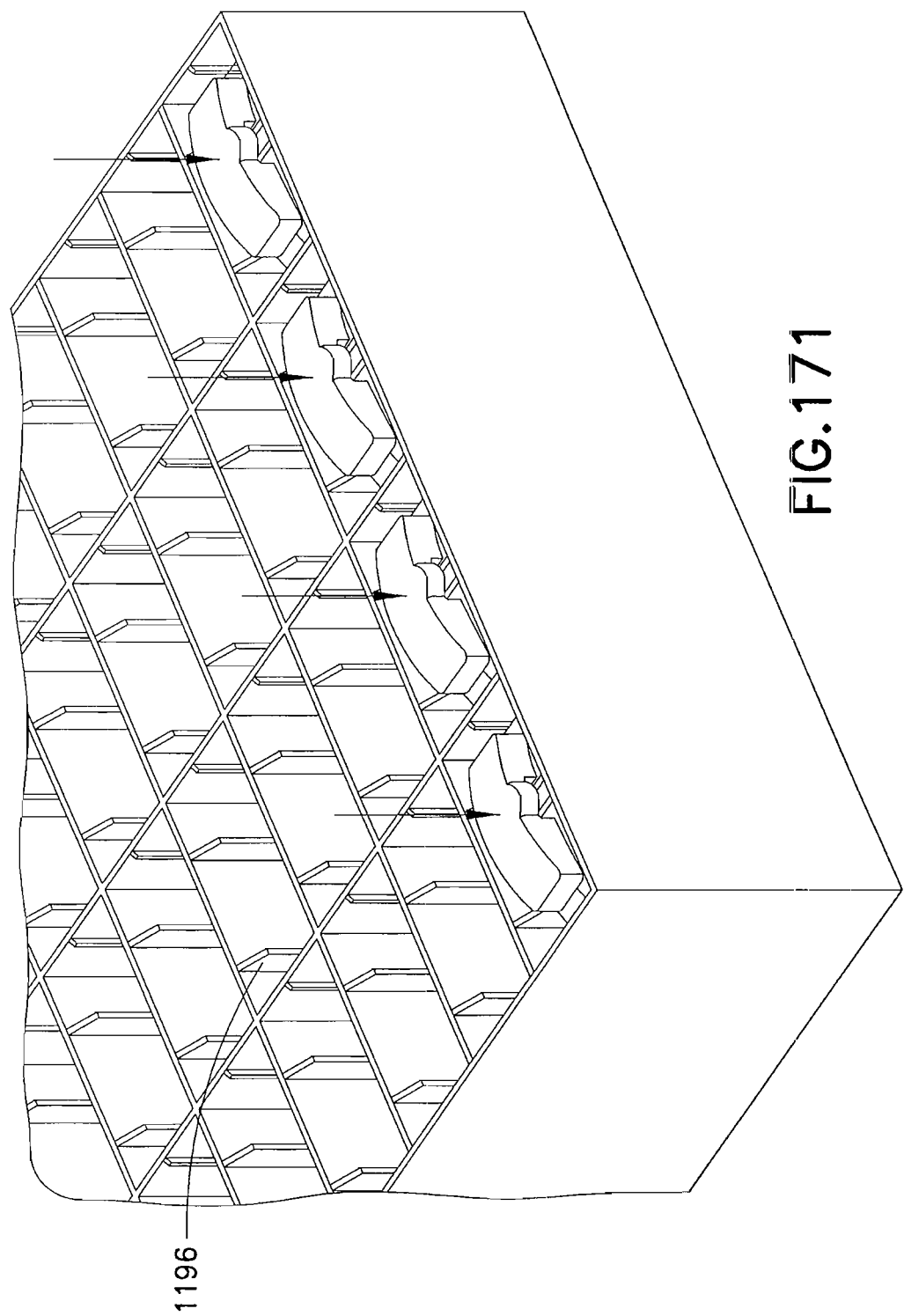
Figure 172:
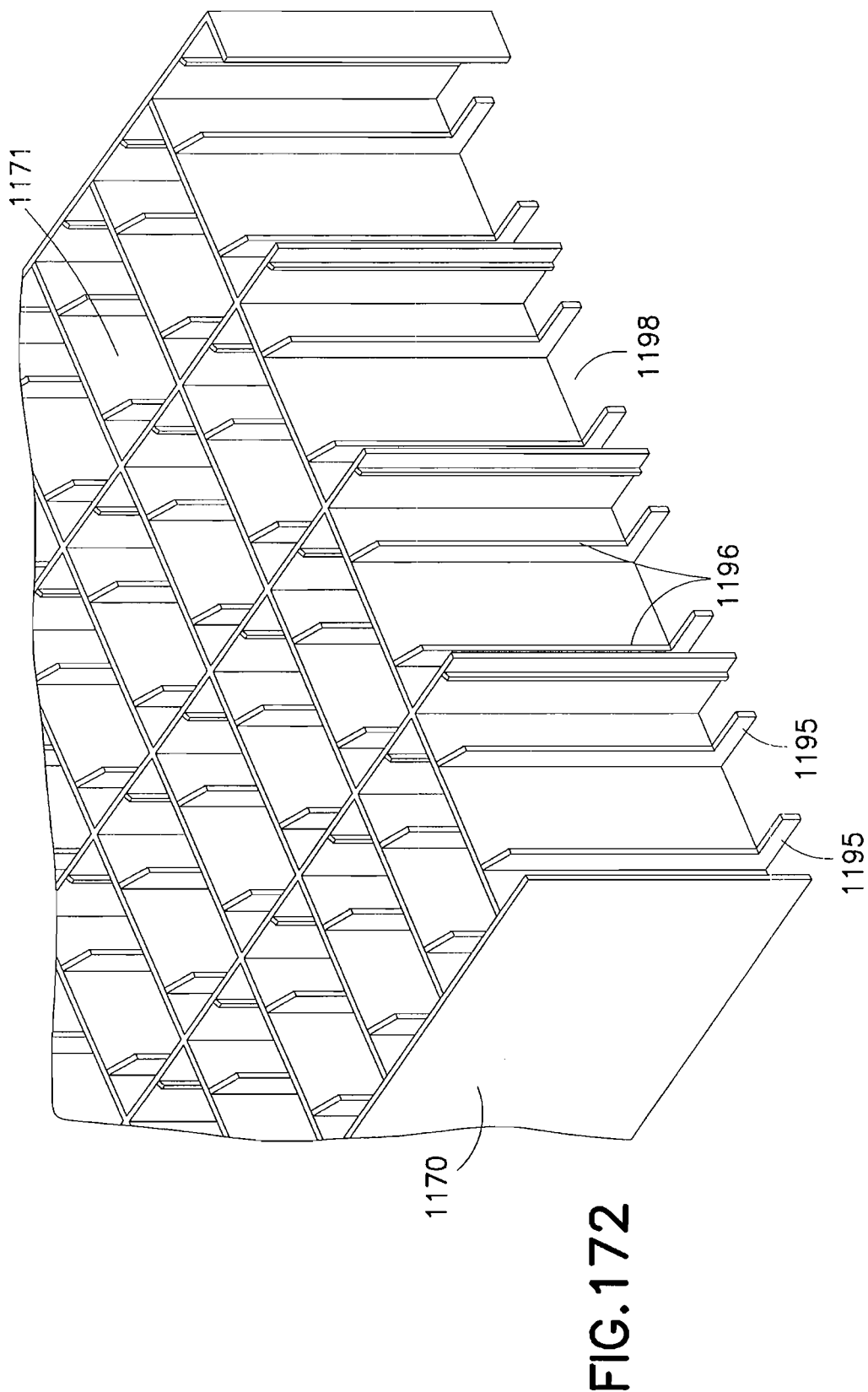
Figure 173:
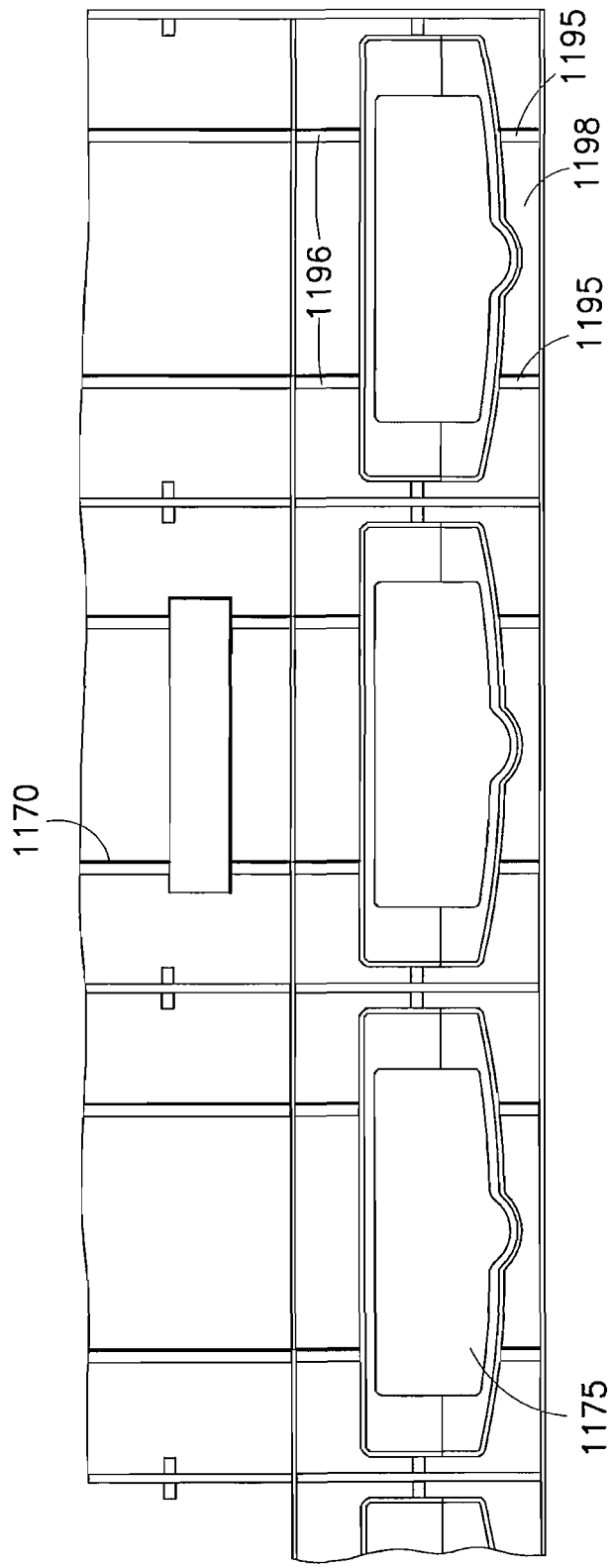
Figure 174:
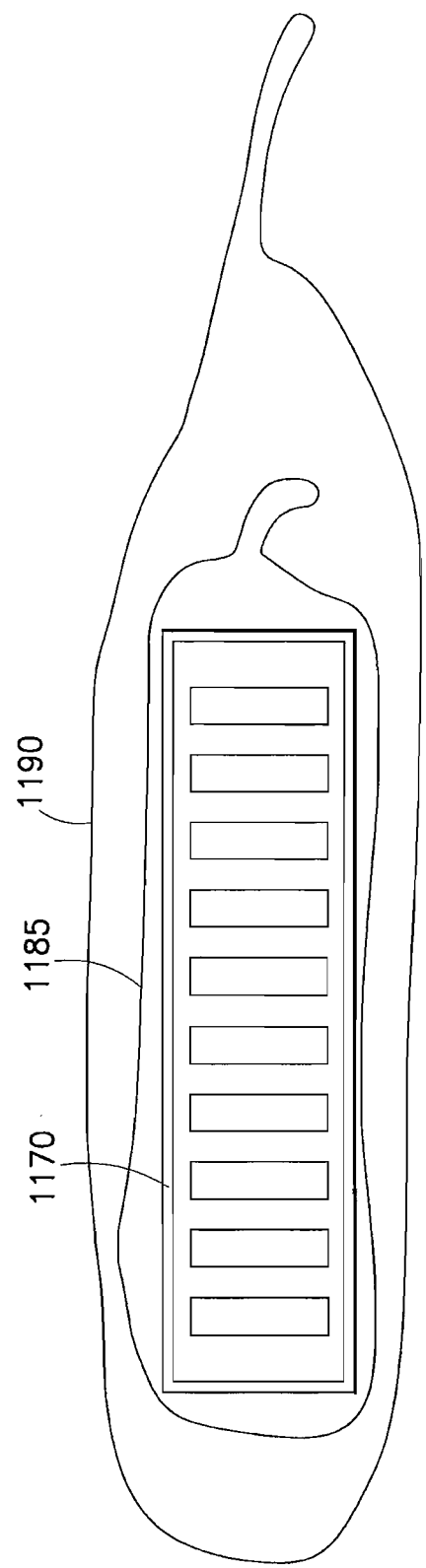
Figure 175:
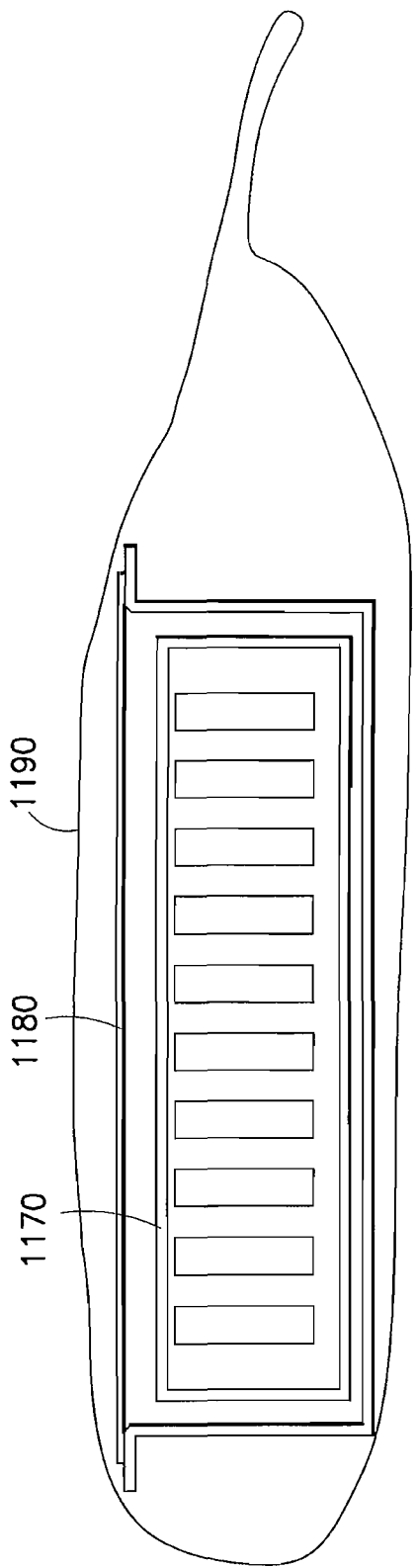

FIG. 164 is a top view of a reservoir illustrating a sign visible before injection;

FIG. 165 is a side view of the reservoir of FIG. 164 illustrating a sign visible before injection;

FIG. 166 is a top view of a reservoir illustrating an absent sign after injection;

FIG. 167 is a side view of the reservoir of FIG. 166 illustrating an absent sign after injection;

FIG. 168 is an isometric view of a nest-type packaging system when empty;

FIG. 169 is an isometric view of the nest-type packaging system of FIG. 168 when filled;

FIG. 170 is an isometric view of the nest-type packaging system of FIG. 168 having four devices for filling;

FIG. 171 is an isometric view of the nest-type packaging system of FIG. 168 having four devices in an up position for filling;

FIG. 172 is a cross-sectional view of the nest-type packaging system of FIG. 168;

FIG. 173 is a top view of the nest-type packaging system of FIG. 168 when filled;

FIG. 174 is a cross-sectional view of the nest-type packaging system of FIG. 168 in double bags; and FIG. 175 is a cross-sectional view of the nest-type packaging system of FIG. 168 when boxed and bagged.

Throughout the drawings, like reference numerals will be understood to refer to like parts, components or structures.

DETAILED DESCRIPTION OF THE EXEMPLARY EMBODIMENTS

The embodiments of the present device described below can be used as a convenient, patch-like device to deliver a pre-measured dose of a substance, such as a drug or medication, to a user through an adhesive attached infusion device. The device is self-contained and is attached to the skin surface of the user by adhesive disposed on a bottom surface. Once properly positioned and activated by the user, the pressure of a released Belleville spring or other disk-type spring on a reservoir surface within the device can be used to empty the contents of the flexible reservoir through one or more patient microneedles via a needle manifold. The substance within the reservoir is then delivered through the skin of the user by the microneedles which are driven into the skin. It will be understood that other embodiments are possible in which the Belleville or disk spring is replaced with a different type of stored energy device which may be mechanical, electrical and/or chemical in nature.

As will be appreciated by one skilled in the art, there are numerous ways of carrying out the patch-like injection or infusor system disclosed herein. Although reference will be made to the embodiments depicted in the drawings and the following descriptions, the embodiments disclosed herein are not meant to be exhaustive of the various alternative designs and embodiments that are encompassed by the disclosed invention. In each disclosed embodiment, the device is referred to as an infusor; however, the device may also inject substances at a much faster bolus rate than is commonly accomplished by infusor devices. For example, the contents can be delivered in a period as short as several seconds, or as long as several days.

Figure 1:
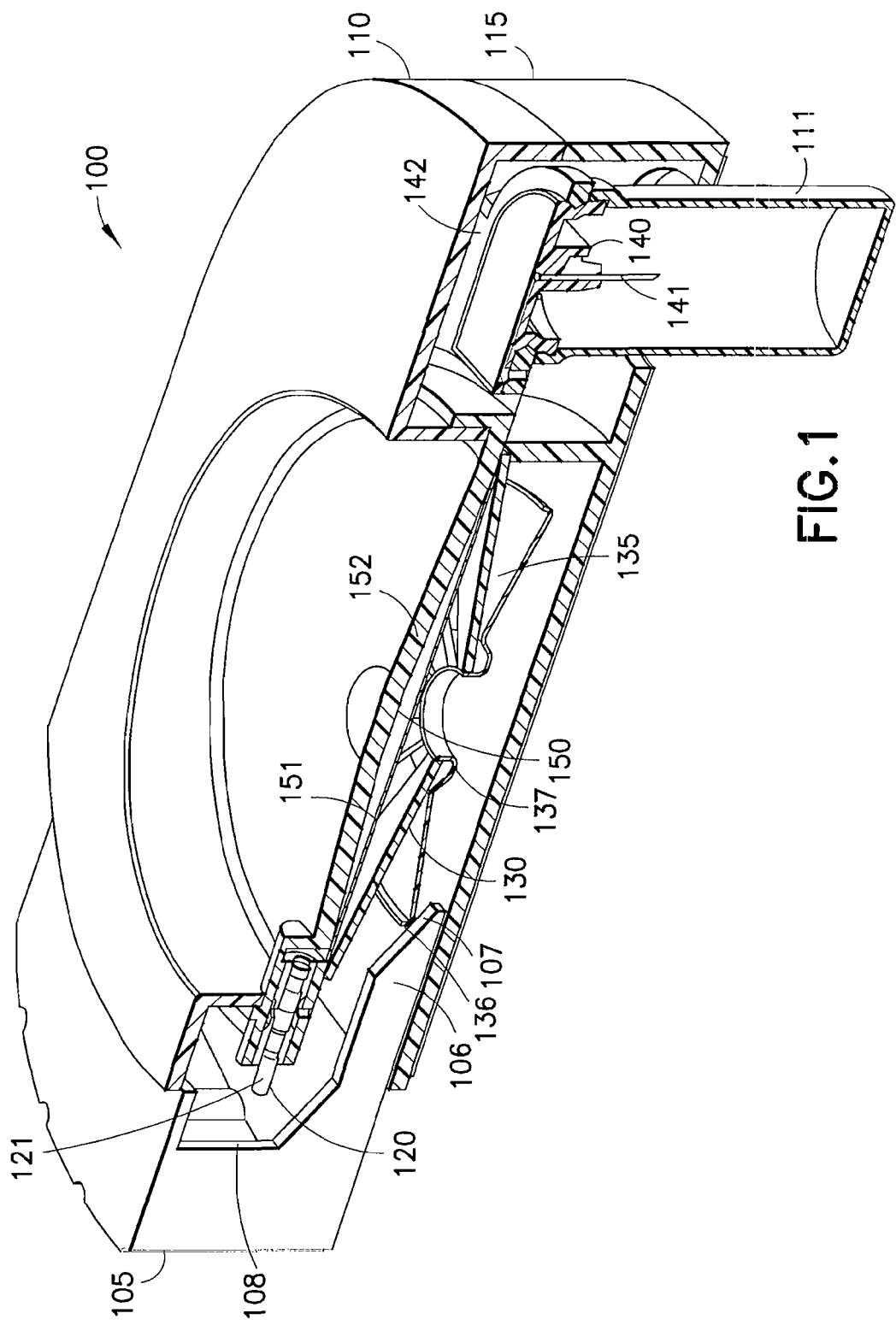
FIG. 1 is a cross-sectional view of a first embodiment of a patch-like injector or infusor system using a side push button surface prior to activation.
Figure 2:
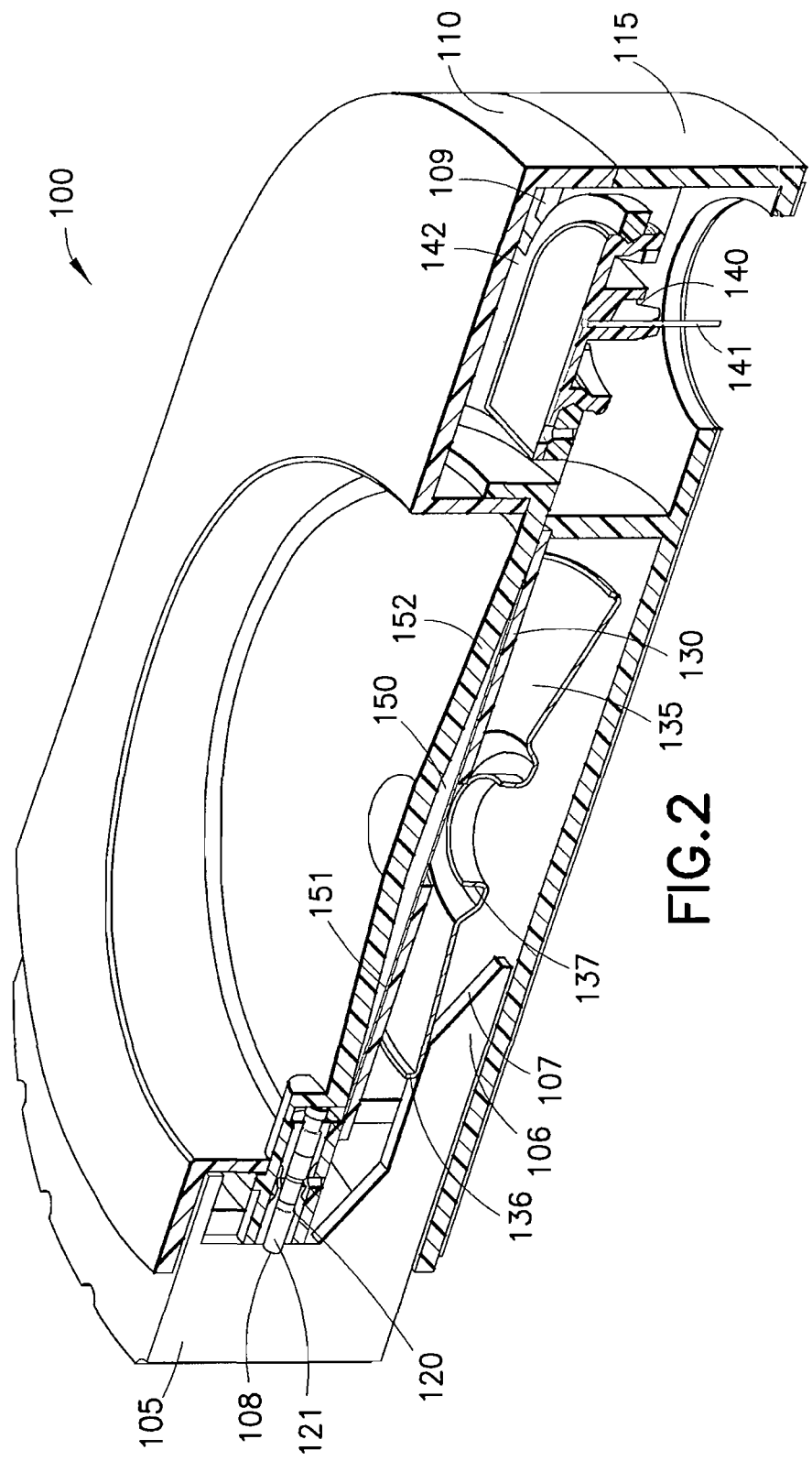
FIG. 2 is another cross-sectional view of the first embodiment of a patch-like injector or infusor system using a side push button surface subsequent to activation.
Figure 3:
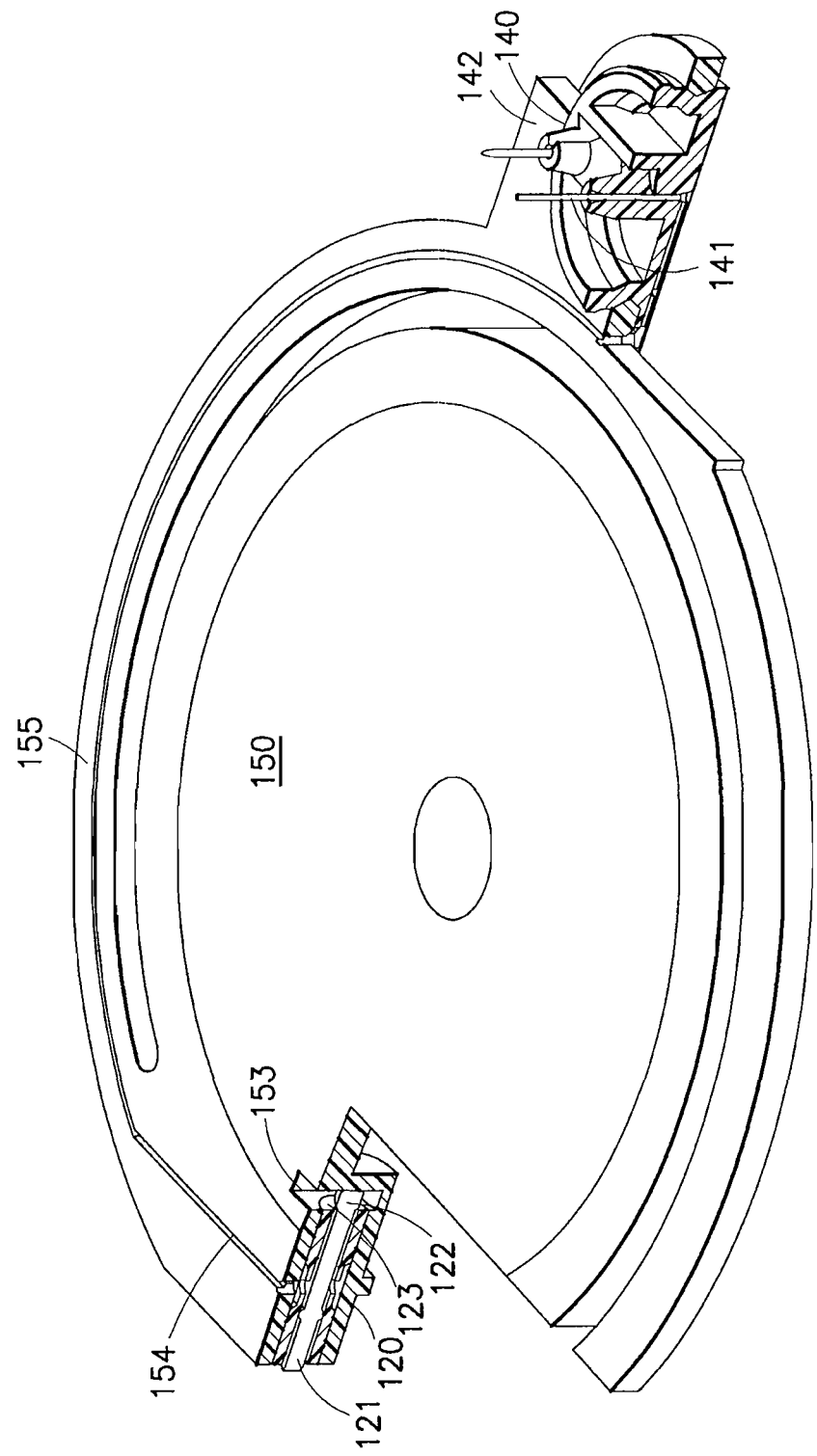
FIG. 3 is a cross-sectional view of a reservoir subassembly of the patch-like injector or infusor system of FIG. 1.
Figure 4:
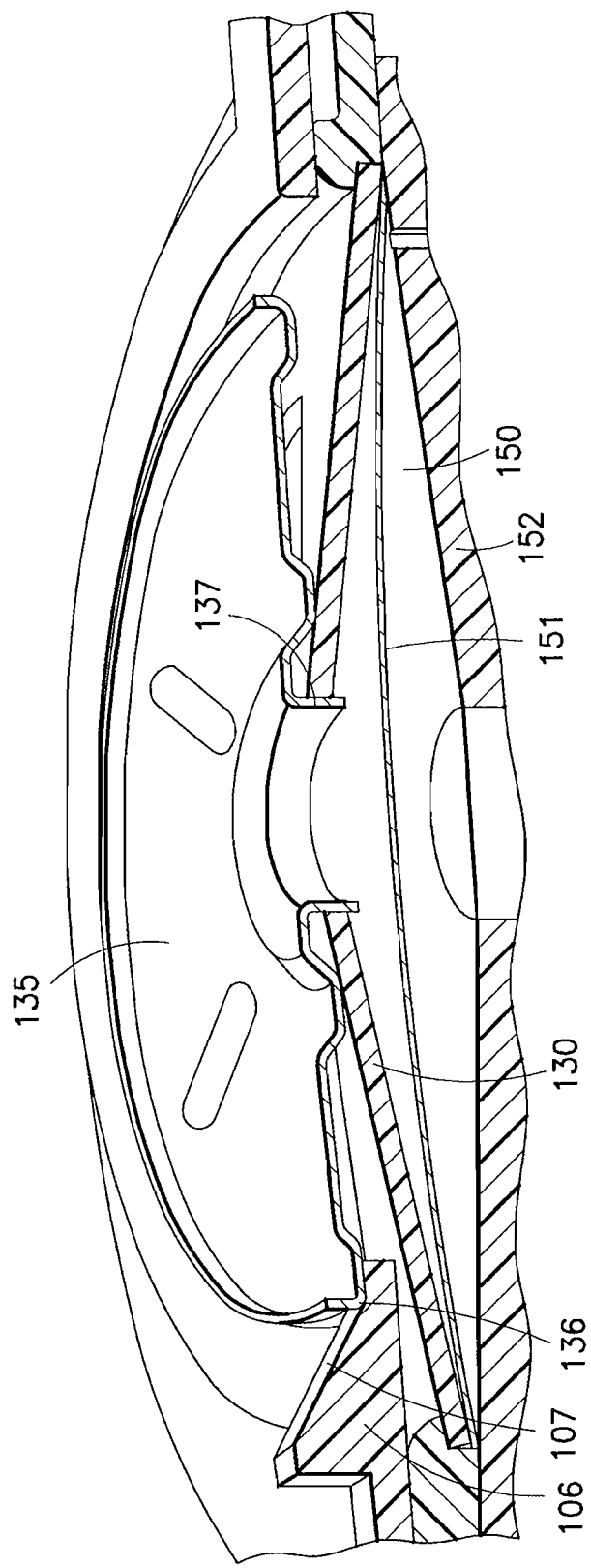
FIG. 4 is a cross-sectional view of a Belleville spring subassembly of the patch-like injector or infusor system of FIG. 1.

In a first embodiment of the device, shown in FIGS. 1 through 4, a push-button design 100 is shown wherein the activation and energizing of the device is accomplished in a single multi-function/step process. FIG. 1 is cross-sectional view of a first embodiment of a patch-like injector or infusor system using a side push button in an unactivated state, FIG. 2 is cross-sectional view of the embodiment shown in an activated state, FIG. 3 is cross-sectional view of the reservoir subassembly of the embodiment shown in FIG. 1, and FIG. 4 is cross-sectional view of the Belleville spring assembly of the embodiment shown in FIG. 1.

The device of FIGS. 1 through 4 includes a push button 105, an upper housing 110, a lower housing 115, a reservoir valve assembly 120, a Belleville spring 130, a spring retention disk 135, a manifold assembly 140, at least one patient needle 141 and a reservoir 150. The device can further include a needle shield 111, which protects the needles 141 and is removed before use. The push button includes at least one incline member 106 which has an inclined surface 107 to engage the outer diameter 136 of the disk 135 as the button 105 moves during activation. As the button 105 is pushed inward as shown in FIG. 2, the incline 107 displaces at least one side of the disk 135 upward, which results in an inner diameter 137 of the disk being displaced downward. In doing so, the inner diameter 137 of the disk 135 is pulled from the center of the Belleville spring 130, releasing the spring 130 to then apply a force to a flexible member 151 of the reservoir 150, compressing the contents against a rigid member 152 of the reservoir 150. As shown in FIG. 4, the reservoir 150 includes a flexible member 151 and a rigid member 150 adjacent to a Belleville spring 130. The Belleville spring 130 is held away from the flexible member 151 through an interference fit with the protruding inner diameter 137 of disk 135.

The button 105 further includes a surface 108 to contact a valve member 121 of the valve assembly 120 to establish a flow path between the reservoir 150 and the patient needle 141. As shown in FIG. 3, the push-pull type valve assembly 120 establishes a flow path between a reservoir outlet 153 and a outer circumference fluid path 154, when the valve member 121 is pushed inward. When pushed inward, an enlarged valve member end 122 is displaced from a pocket 123, allowing flow from the reservoir 150, around a reduced diameter of the valve member 121, and into the fluid path 154 towards the manifold assembly 140, and needle 141 therein. The fluid path 154 is provided within a fluid path arm 155 which can also be used to urge the needle manifold 140.

As the push button 105 is pushed inward, a support member 109 is moved free of a shoulder 142 of the manifold assembly 140, allowing the manifold assembly 140 to be driven downward toward a patient's skin surface (not shown). The manifold assembly can be driven by a number of means, such as coil springs, or through the flex characteristics of the outer diameter fluid path arm 155. The fluid path arm 155 can be configured to force the manifold assembly 140 when released by the support member 109.

In the embodiment shown in FIGS. 1 through 4, as the push button 105 is pushed, three functions are achieved in an ordered and/or simultaneous fashion. First, the movement of the push button 105 opens at least one valve assembly 120 allowing fluid communication between the reservoir 150 and the patient needles 141. Second, the movement of the push button 105 dislodges the spring retention disk 135, releasing the Belleville spring 130, and third, the movement of the push button 105 removes the support member 109 from the patient needle manifold 140 allowing the manifold 140 to travel as urged by a means, such as the fluid path arm 155 or a manifold spring (not shown).

Specifically, the push button 105 includes the series of inclines 107 which engage the spring retention disk 135 as the push button 105 is slidably moved, and release the Belleville spring 130 thereby pressurizing the contents of the reservoir 150. The push button 105 also engages the push valve 120, initiating flow between the now pressurized reservoir 150 and the manifold assembly 140. The push button 105 further removes or displaces one or more support members 109 from the patient needle manifold assembly 140, allowing the manifold 140 to be driven by a drive means, such as the fluid path arm 155 or one or more drive springs (not shown), and seat the patient needles 141.

The push/pull valve assembly 120 of the embodiment shown in FIG. 1 is constructed to restrict flow between the reservoir chamber (i.e., as provided between elements 151 and 152 of the reservoir 150), and the patient needle manifold 140 until pushed into an open position by the push button 105, and can be comprised of any number of valve assemblies 120, 222, 242 and 262 as described in greater detail below.

Figure 5:
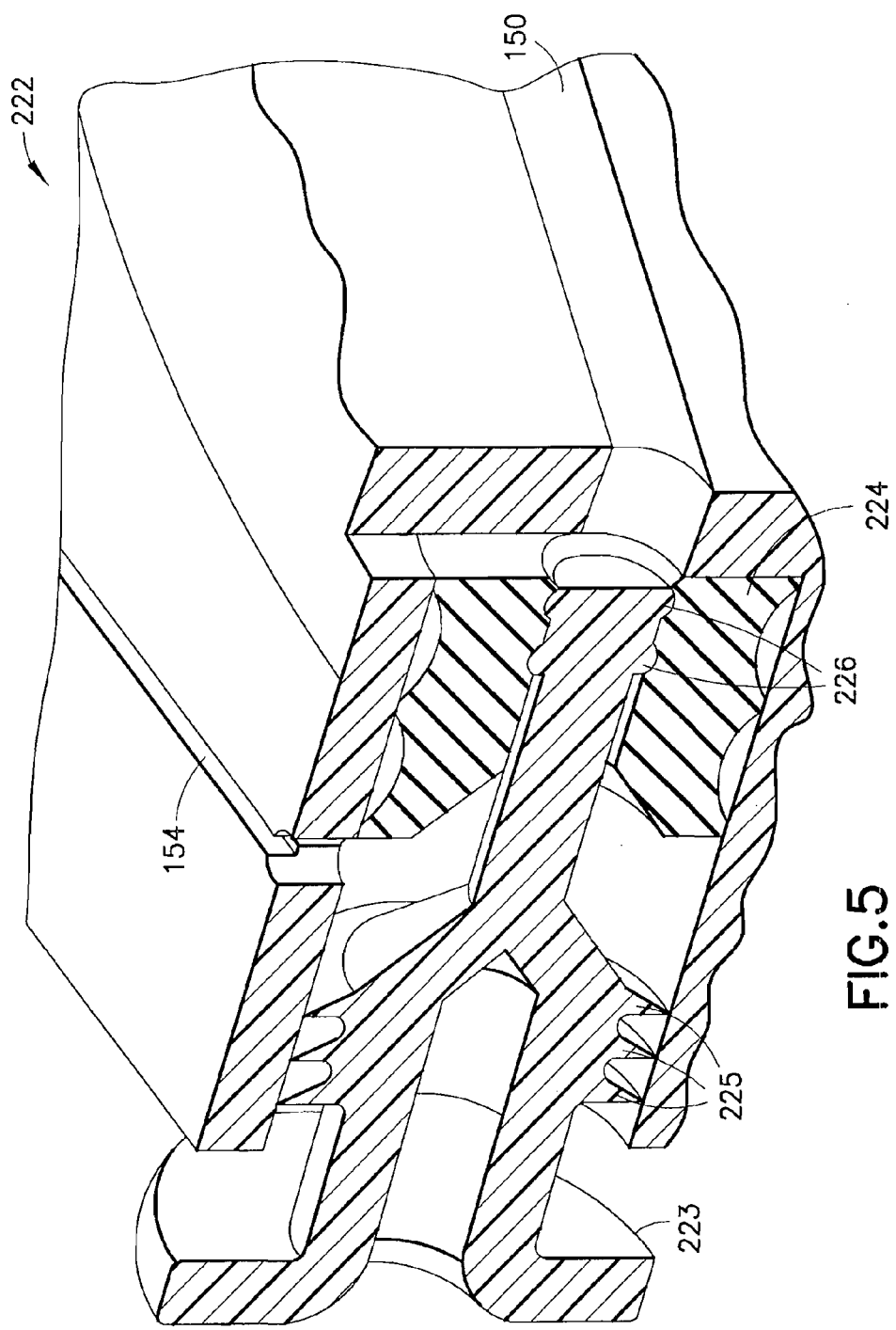
FIG. 5 is a cross-sectional view of a first embodiment of a push valve subassembly of the patch-like injector or infusor system of FIG. 1 in a closed position.
Figure 6:
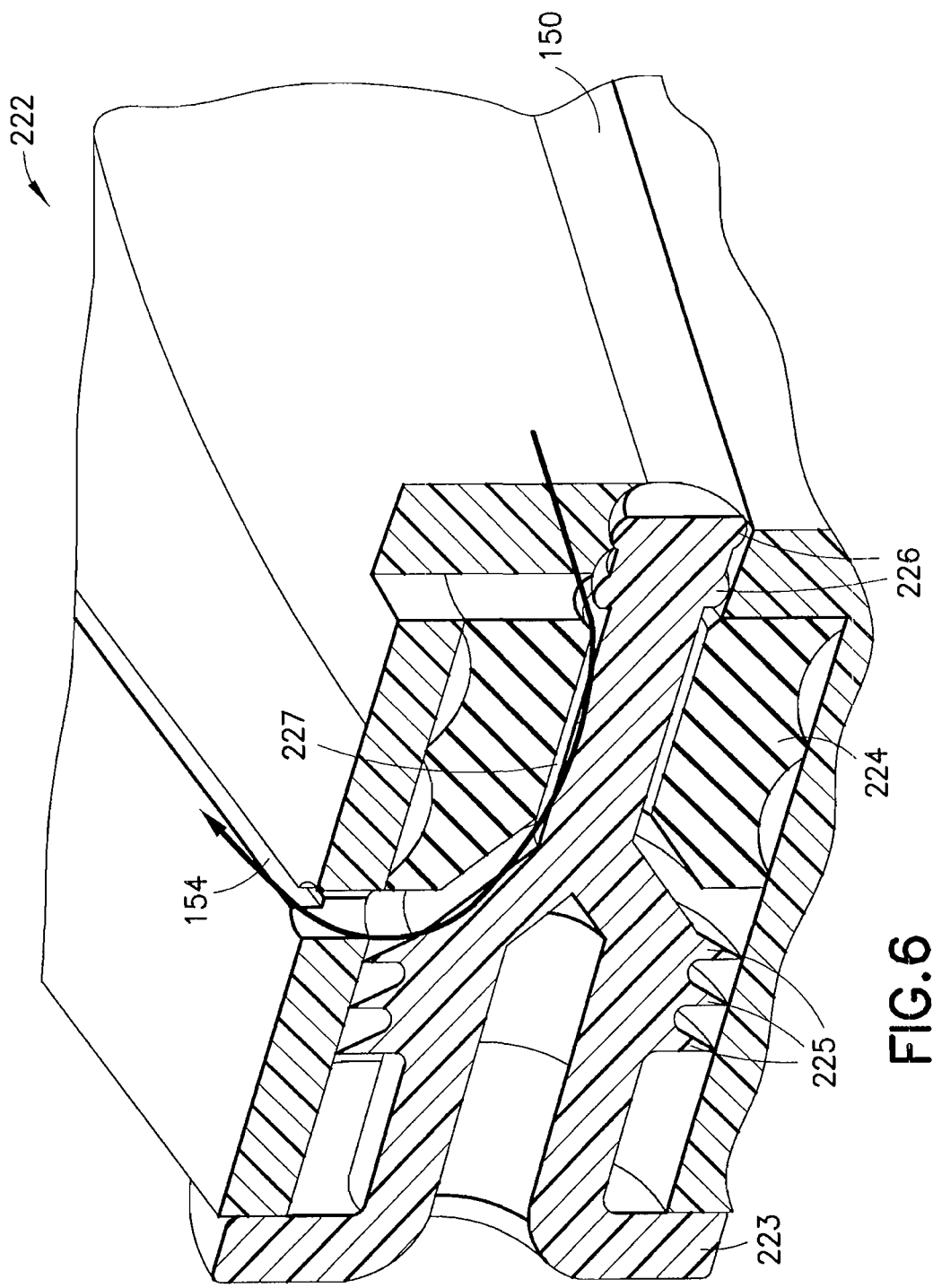
FIG. 6 is a cross-sectional view of the first embodiment of the push valve subassembly of the patch-like injector or infusor system of FIG. 1 in an open position.

A first embodiment of a push valve assembly 222 is shown in FIGS. 5 and 6. FIG. 5 is cross-sectional view of the valve assembly in a closed position and FIG. 6 is cross-sectional view of the valve assembly of FIG. 5 in an open position. The valve assembly 222 includes a plastic button 223 slidably engaged within a rubber stopper 224 in fluid communication with the reservoir 150. The valve assembly 222 has as an initial state and an activated state, and includes a large diameter distal end having a distal set of radially projecting fins, or ribs 225, and a reduced diameter proximal end having a proximal set of detents 226. In the initial state, the valve 222 distal ribs 225 serve to prevent microbial ingress into the fluid path 227, and the proximal detents create a seal to trap the drug safely within the reservoir 150. Both sets of ribs 225 and detents 226 are performing critical tasks in preventing fluid loss from inside the reservoir over long periods of time as well as preventing contamination of the drug from outside the reservoir over the same period of time.

In use, the button 223 will eventually be pushed into an activated state by the movement of the push button 105 and the set of detents will be advanced from engagement with the rubber stopper 124, which permits the drug to flow from the reservoir 150, past the detents 226 and into the valve fluid path 154. At the same time, the distal set of ribs 225 are by nature also pushed in and the location of the ribs 225 themselves translate into a position such that they direct the fluid from the reservoir 150, through the valve fluid path 227, and down the fluid path 154 to the patient needle manifold (not shown).

In the position shown in FIG. 5, the plastic button 223 includes the reduced diameter proximal end having detents 226 seated securely within the rubber stopper 124 and prevents any fluid escaping the reservoir 150. As the plastic button 223 is engaged and displaced within the rubber stopper 224 by the push button 105, an opening is created at the proximal end which allows fluid communication from the reservoir 150 as shown by the arrow in FIG. 6. The valve assembly 222 can be included in the reservoir subassembly 150, such that a continuous fluid path 154 can be provided by the reservoir subassembly 150 between the reservoir contents and the patient microneedles 141.

Figure 7:
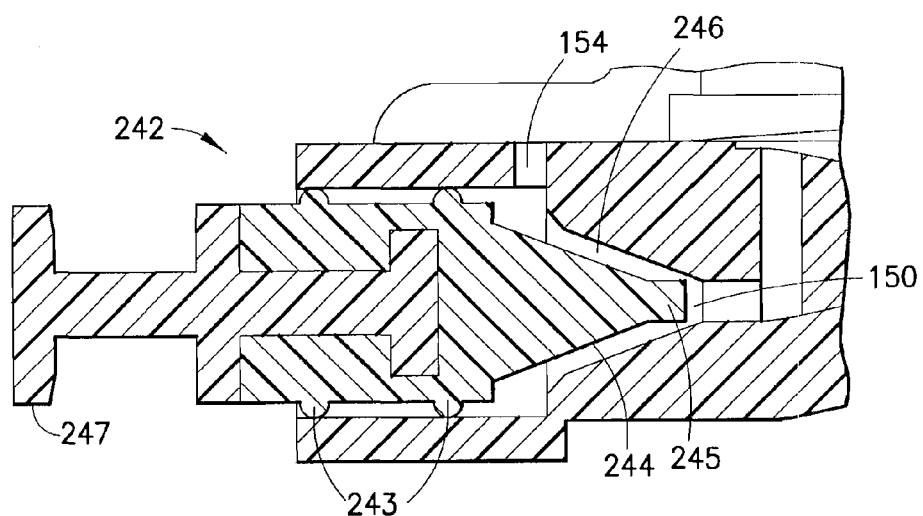
FIG. 7 is a cross-sectional view of a second embodiment of a pull valve subassembly of the patch-like injector or infusor system of FIG. 1.

A second embodiment of a valve assembly 242 is shown in FIG. 7. FIG. 7 is cross-sectional view of the second valve assembly embodiment in an open position. The valve assembly 242 includes a plastic button 247, and is configured to operate as a pull valve. As shown in FIG. 7, when pushed forward, the plastic button 247 mateably engages the reservoir 150 opening and prevents fluid communication from the reservoir 150. When pulled from the reservoir 150 opening, the gap produced allows fluid communication along the conical face of the button 247 and to the fluid path 154 toward the patient needle manifold (not shown).

The valve assembly 242 has as an initial state and an activated state, and includes a large diameter distal end having a distal set of detents 243, a conical section 244 and a reduced diameter proximal end 245. In the initial state, the valve 242 distal detents 243 serve to prevent microbial ingress into the fluid path 246, and the conical section 244 and proximal end 245 create a seal to trap the drug safely within the reservoir 150. Each of the detents 243, conical section 244 and reduced diameter proximal end 245 prevent fluid loss from inside the reservoir 150 over long periods of time as well as prevent contamination of the drug from outside the reservoir over the same period of time.

In use, the button 247 will eventually be pulled into an activated state by the movement of an alternate push button version (not shown) and the conical section 244 and reduced diameter proximal end 245 will be advanced from engagement with the reservoir 150 opening, which permits the drug to flow from the reservoir 150, past the reduced diameter proximal end 245 and into the valve fluid path 246. At the same time, the distal set of detents 243 translate into a position such that they direct the fluid from the reservoir 150, through the valve fluid path 246, and down the fluid path 154 to the patient needles (not shown).

Figure 8:
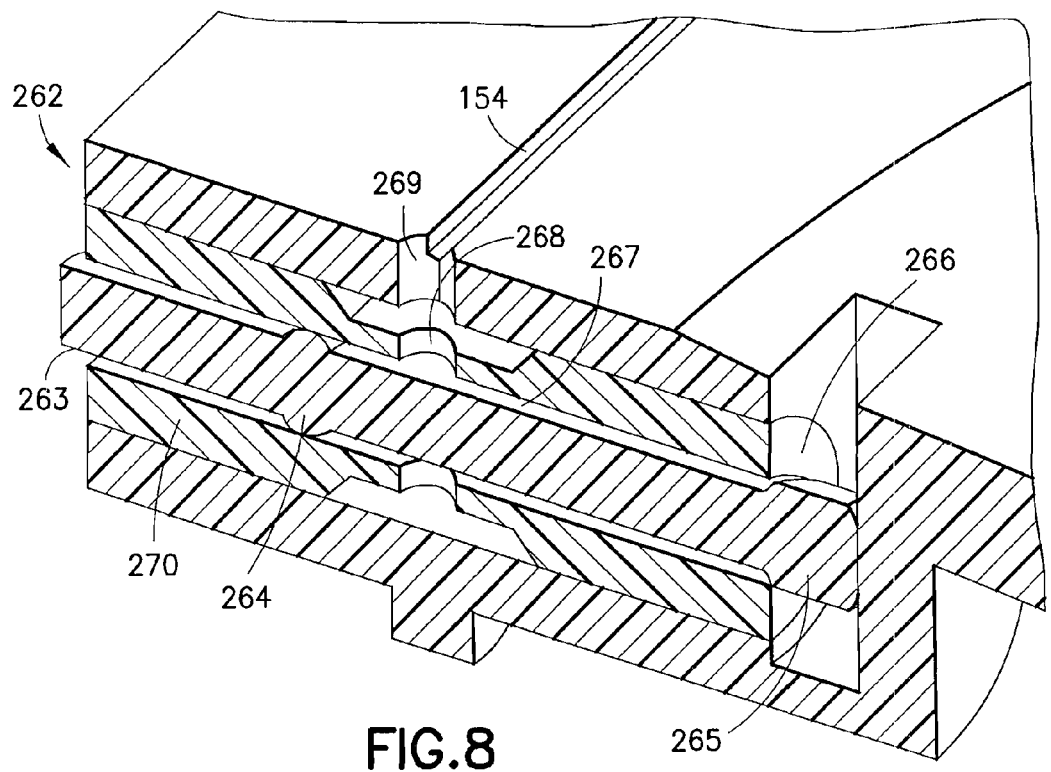
FIG. 8 is a cross-sectional view of a third embodiment of a push/pull valve subassembly of the patch-like injector or infusor system of FIG. 1.

A third embodiment of a valve assembly 262 is shown in FIG. 8. FIG. 8 is cross-sectional view of the third valve assembly embodiment in an open position, and includes a plastic member 263, configured to operate as either a push or pull valve. As shown in FIG. 8, when pulled outward, the plastic member 263 obstructs the reservoir opening and prevents fluid communication from the reservoir 150. When pushed forward the plastic member aligns an opening and allows fluid communication between the reservoir 150 and the patient needle manifold 140 (not shown).

The valve assembly 262 has as an initial state and an activated state, and includes a distal end having a distal set of detents 264, and an enlarged diameter proximal end 265. In the initial state, the valve 262 distal detents 264 serve to prevent microbial ingress into the fluid path 267, and the enlarged proximal end 265 creates a seal with the end 266 of a plug insert member 270 to trap the drug safely within the reservoir 150. Each of the detents 264 and the enlarged diameter proximal end 265 prevent fluid loss from inside the reservoir 150 over long periods of time as well as prevent contamination of the drug from outside the reservoir over the same period of time.

In use, the member 263 will eventually be pushed into an activated state by the movement of a the push button 105 and the enlarged proximal end 265 will be advanced from engagement with the end 266 of the plug insert member 270, which permits the drug to flow from the reservoir 150, past the enlarged proximal end 265 and into the valve fluid path 267. At the same time, the distal set of detents 264 translate into a position such that they direct the fluid from the reservoir 150, through the valve fluid path 267, and down the fluid path 154 through openings 268 and 269 to the patient needles (not shown).

Figure 9:
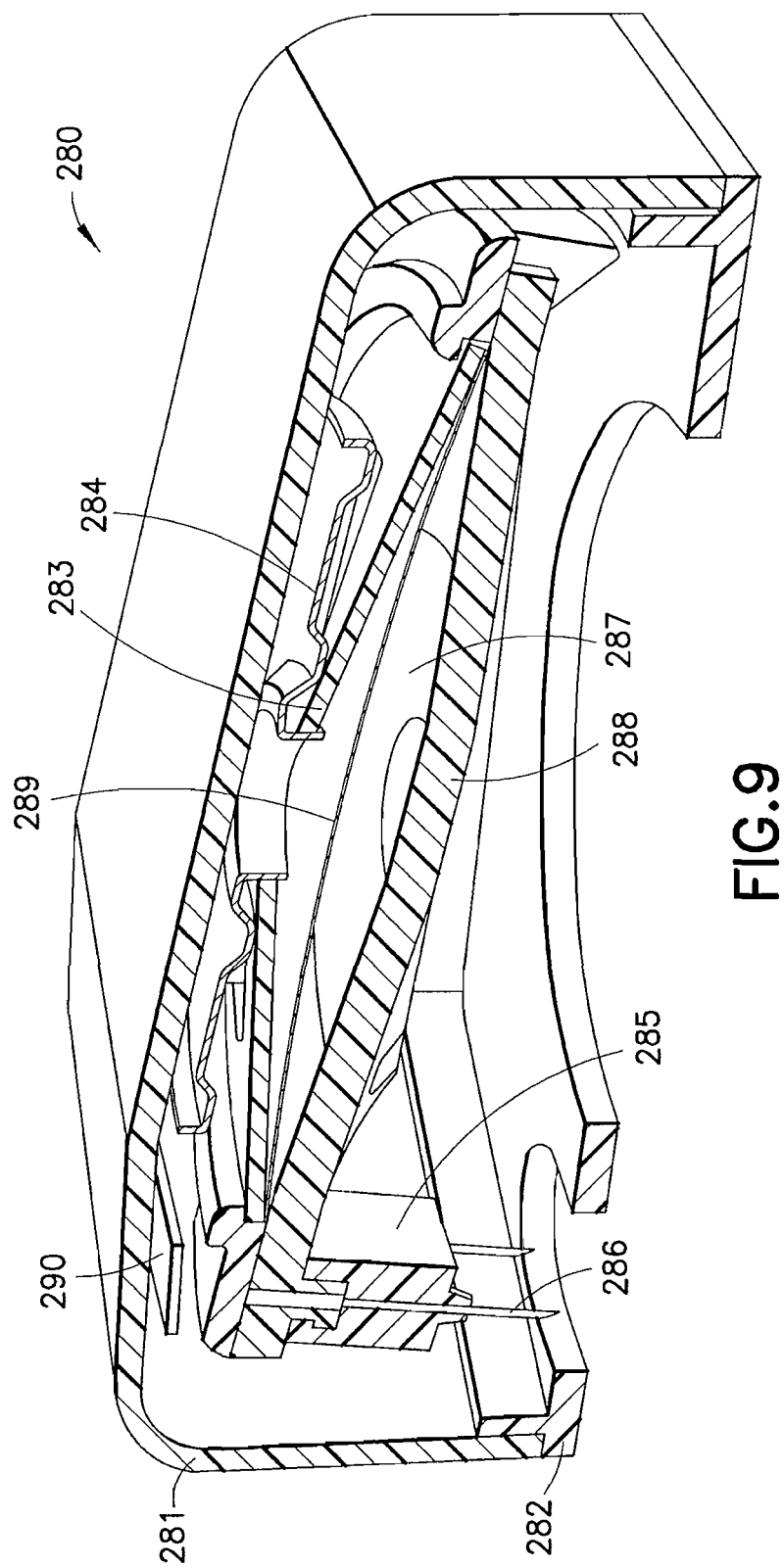
FIG. 9 is a cross-sectional view of a second embodiment of a patch-like injector or infusor system using a top push button surface prior to activation.
Figure 10:
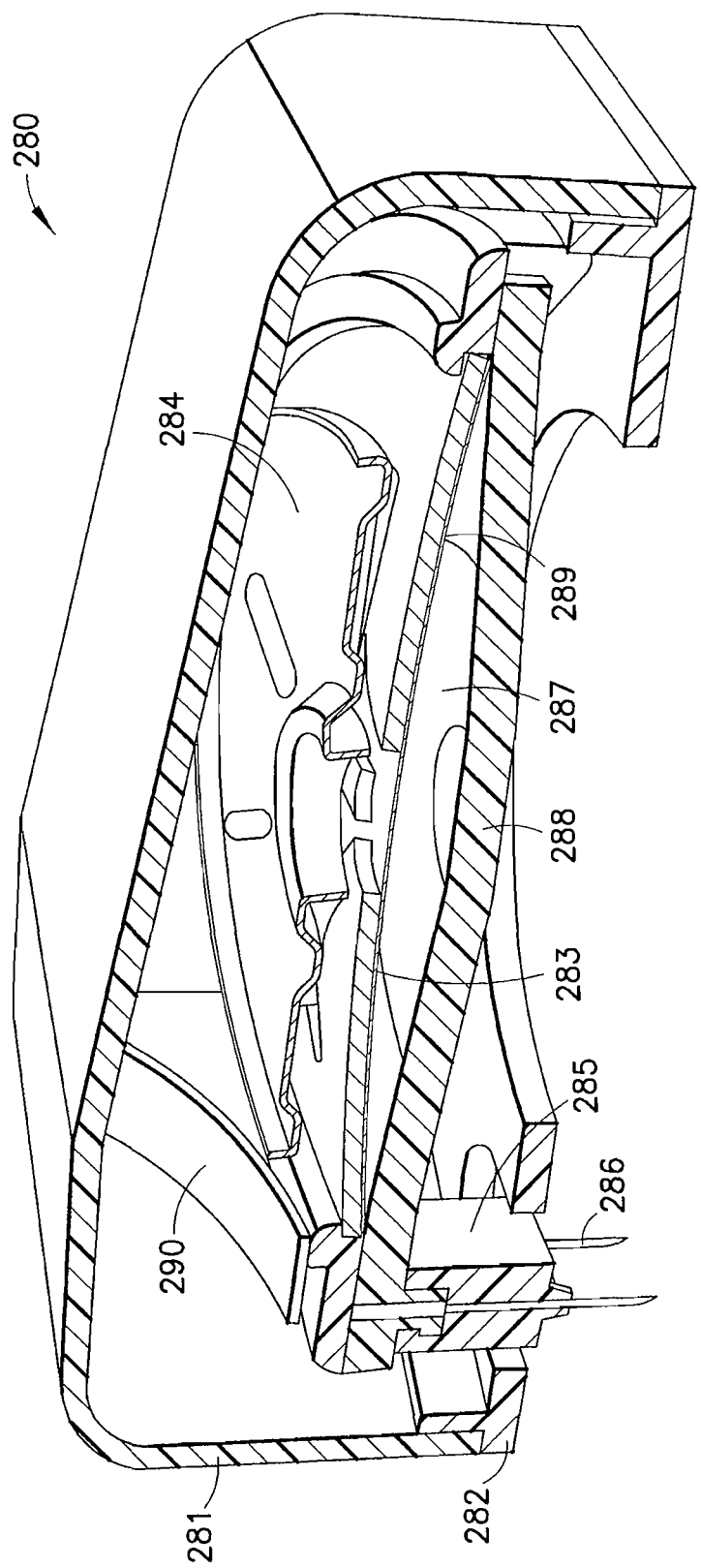
FIG. 10 is a cross-sectional view of the second embodiment of a patch-like injector or infusor system of FIG. 9 subsequent to activation.
Figure 11:
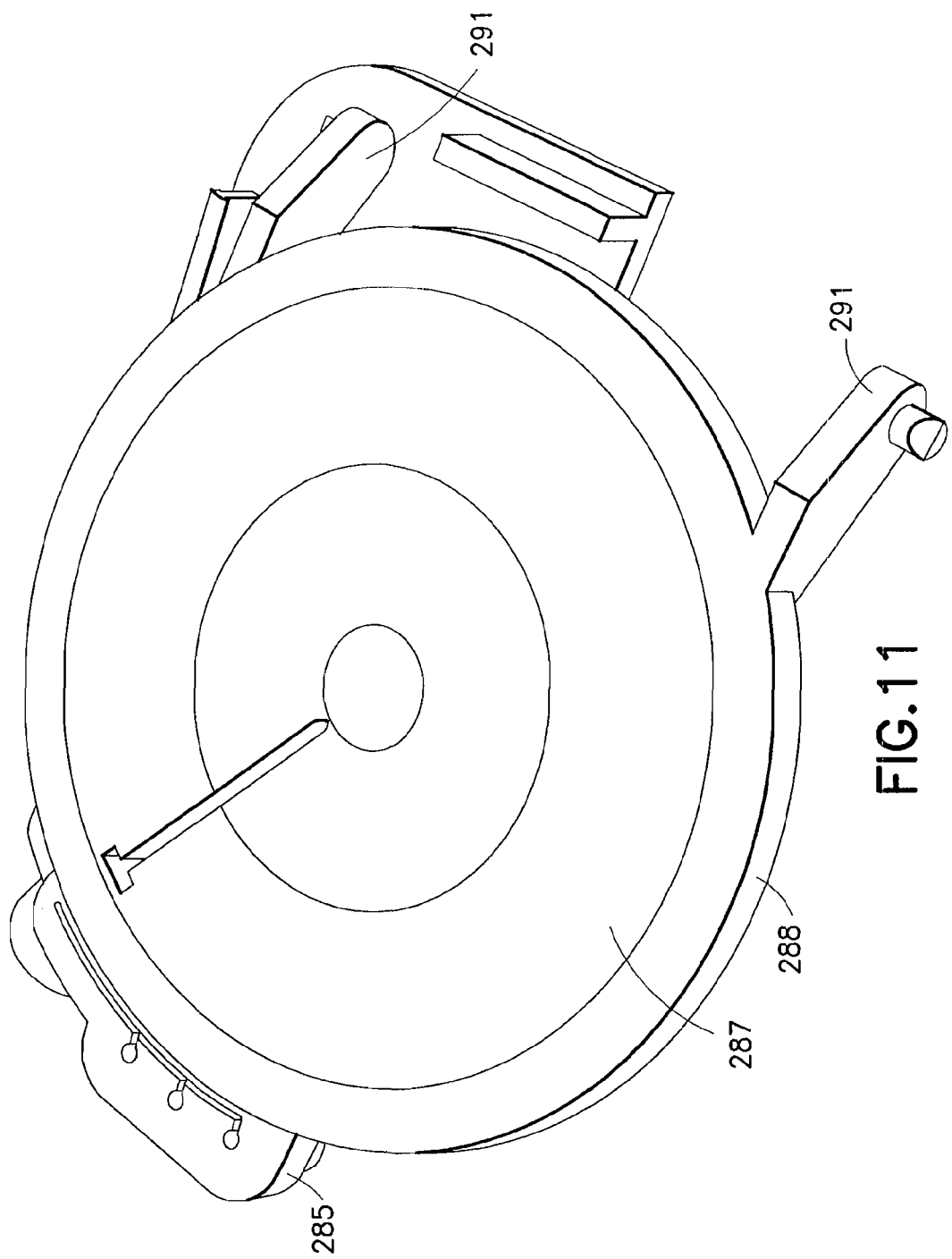
FIG. 11 is a top view from a first perspective angle of the reservoir subassembly of the second embodiment of a patch-like injector or infusor system of FIG. 9.

In a second embodiment of the device, shown in FIGS. 9 through 11, a push-button design 280 is shown wherein activation of the device is also accomplished in a single multi-function/step process but the needle manifold and reservoir assembly, are rotated about a hinge disposed at a point opposite the needle manifold. FIG. 9 is cross-sectional view of the second embodiment of a patch-like injector or infusor system using a top push button surface in an unactivated state, FIG. 10 is cross-sectional view of the second embodiment shown in an activated state, and FIG. 11 is top view of the reservoir subassembly of the embodiment shown in FIGS. 9 and 10. As with the first embodiment, a single step can be used to activate the device.

The device of FIGS. 9 through 11 includes an upper housing 281, a lower housing 282, a Belleville spring 283, a spring retention disk 284, a manifold assembly 285, at least one patient needle 286 and a reservoir 287 having a flexible member 289 and a rigid member 288. In the embodiment shown in FIGS. 9 through 11, the Belleville spring 283 is held and subsequently released by the disk 284 and compressing the reservoir 287 substantially similar to the spring 130, disk 135 and reservoir 150 of FIG. 1, but in an inverted position, such that the rigid member 288 of the reservoir 287 is constructed including the manifold assembly 285 at a first end, and a hinge mechanism 291 at a second end.

In the embodiment of FIGS. 9 through 11, through a release means, such as a button (not shown), the hinged reservoir 287 is released, thereby releasing the Belleville spring 283 to then apply a force to the flexible member 289 of the reservoir 287, compressing the contents against the rigid member 288 of the reservoir 287. As shown in FIG. 10, when released, a spring 290 drives the manifold assembly 285 and reservoir 287 downward toward a patient's skin surface (not shown) and away from the disk 284, releasing the Belleville spring 283 and pressurizing the reservoir contents. Any number of valve assemblies can be used to establish the fluid path between the reservoir 287 and the manifold 285.

In the embodiment shown in FIGS. 9 through 11, upon release, the Belleville spring 283, manifold assembly 285, patient needle 286 and reservoir 287 are rotated into an activated and in-use position, and the desired three functions are achieved in an ordered and/or simultaneous fashion. First and second, the activation allows the spring 290 to rotate the reservoir 287 and manifold 285, which dislodges the spring retention disk 284, releasing the Belleville spring 283 and initiating flow from the reservoir 287. Third, the activation further allows the manifold 285 to travel as urged by the manifold spring 290 and seat the needles 286.

Figure 12:
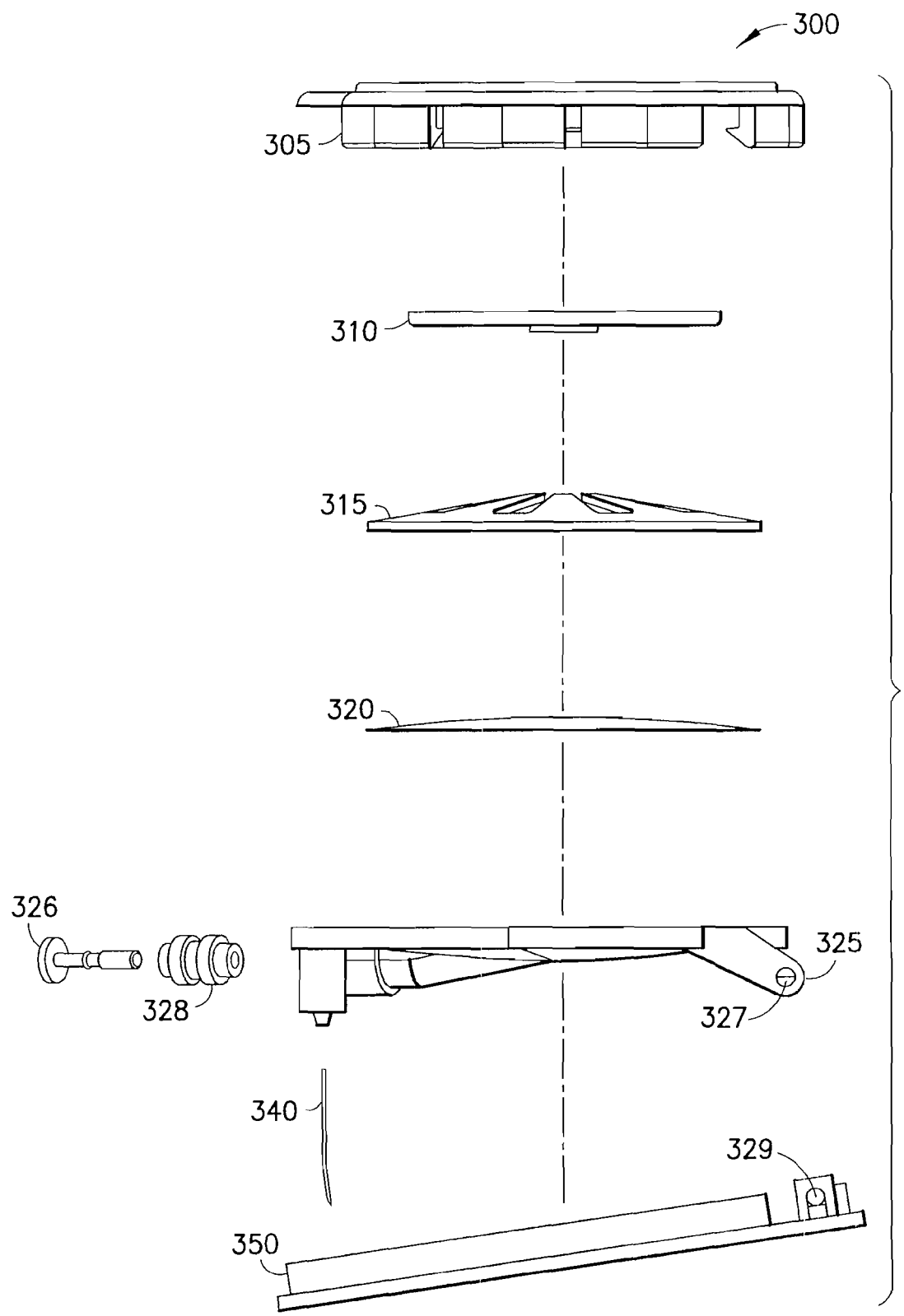
FIGS. 12 and 13 are exploded views of another version of the second embodiment of the patch-like injector or infusor system using a top push button surface.
Figure 13:
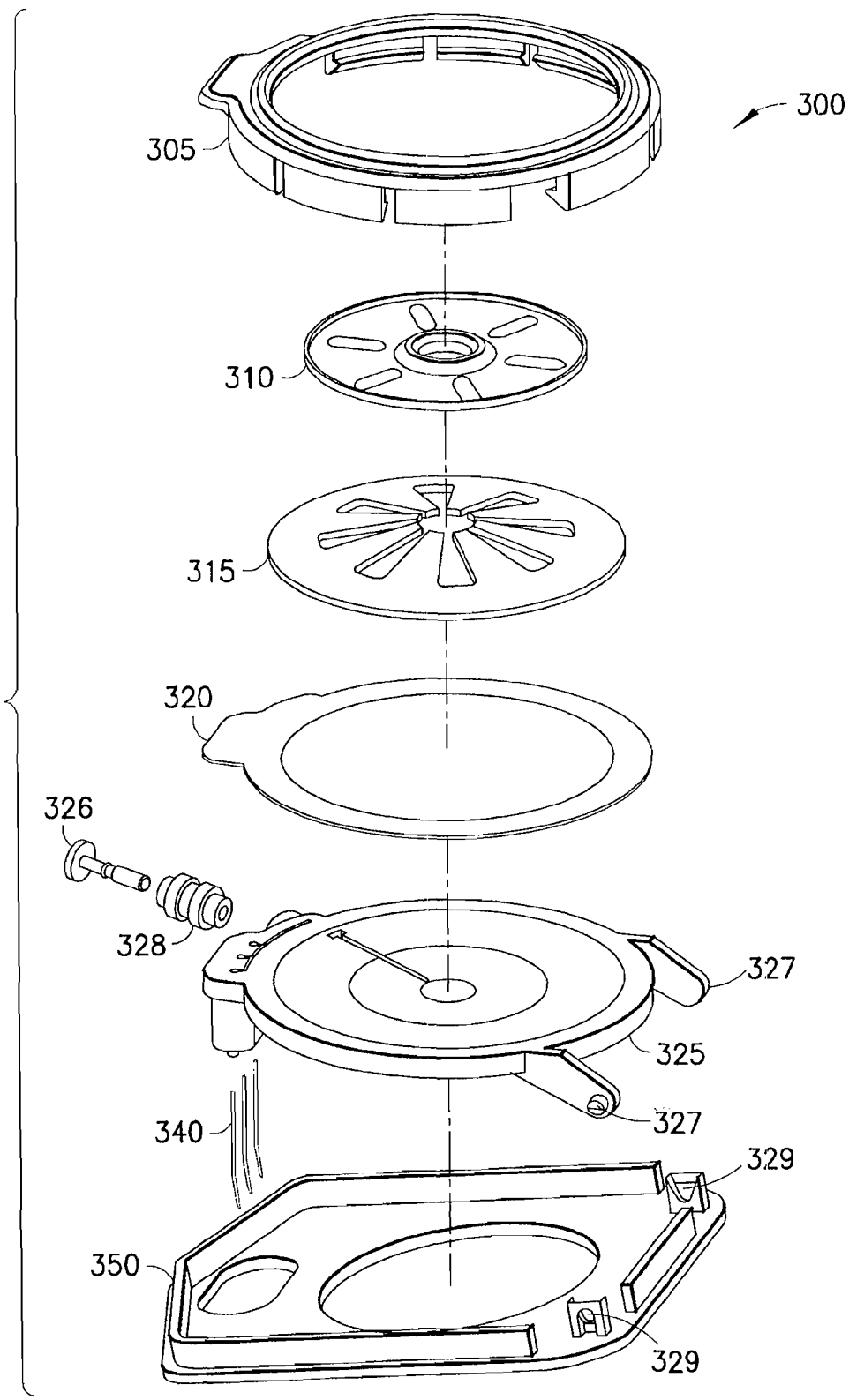
Figure 22:
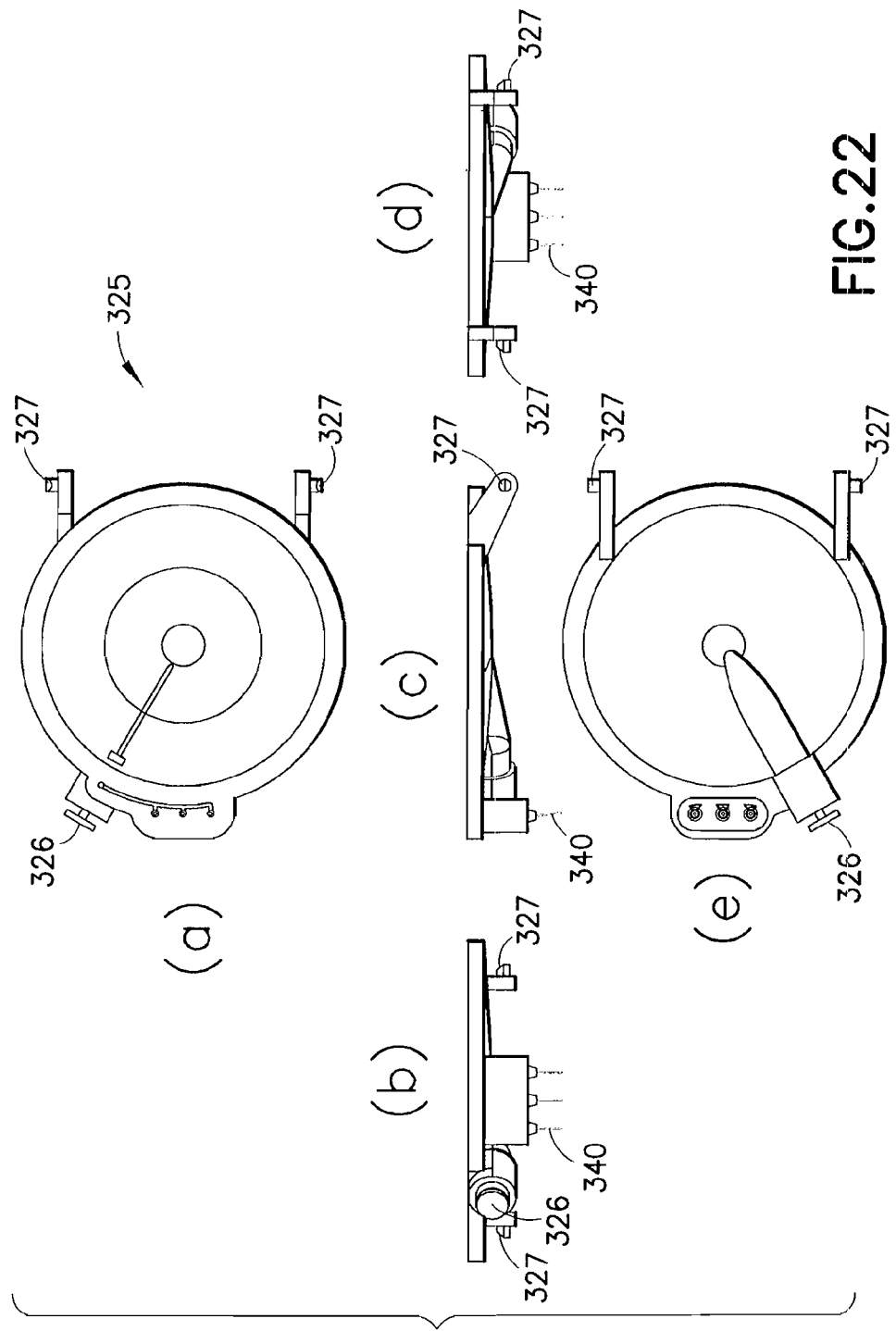
FIGS. 22(a) through 22(e) are multiple views of the reservoir subassembly of the patch-like injector or infusor system of FIG. 12.
Figure 23:
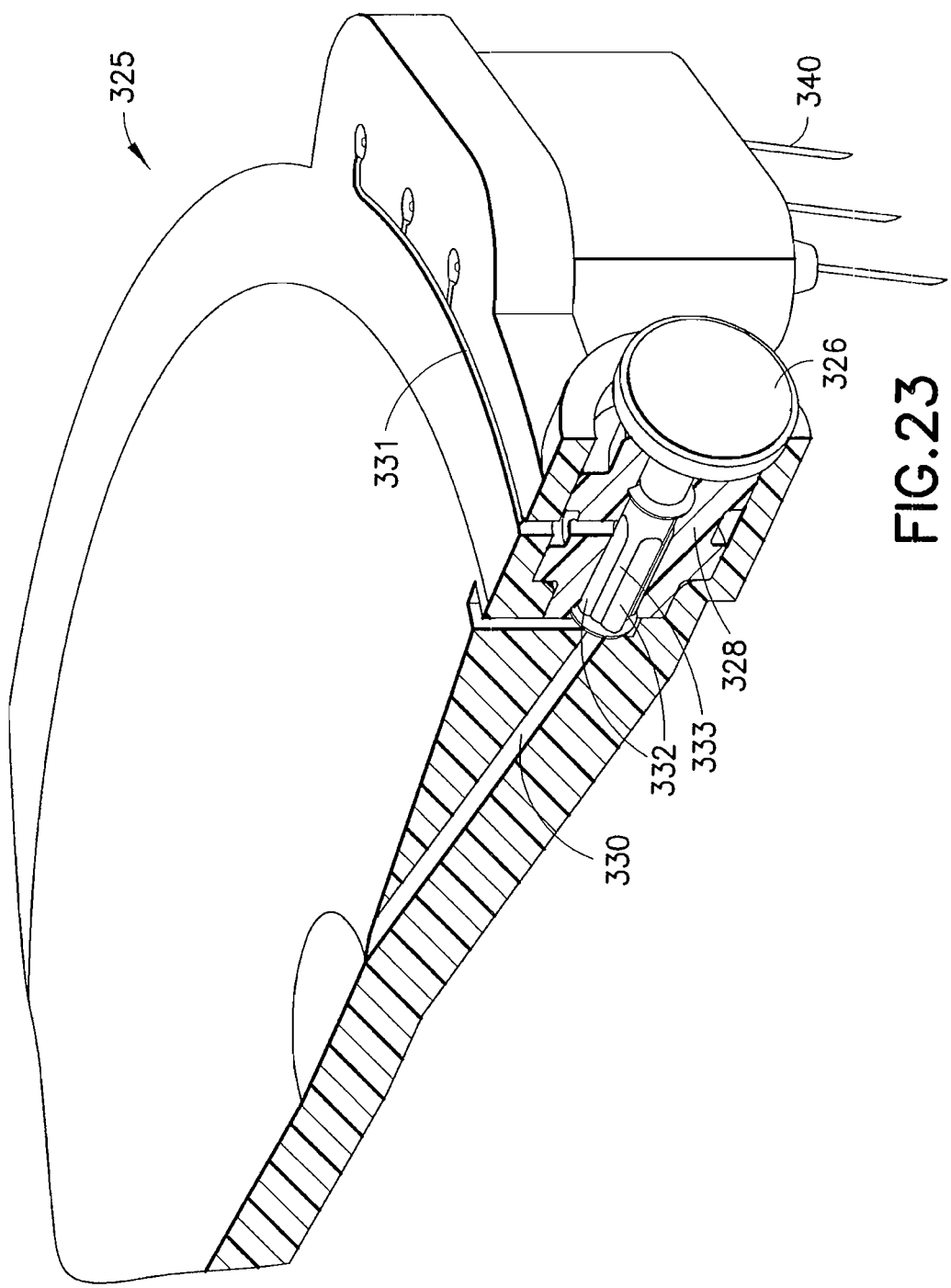
FIG. 23 is a cross-sectional view of a valve subassembly of the patch-like injector or infusor system of FIG. 12 in a closed position.
Figure 24:
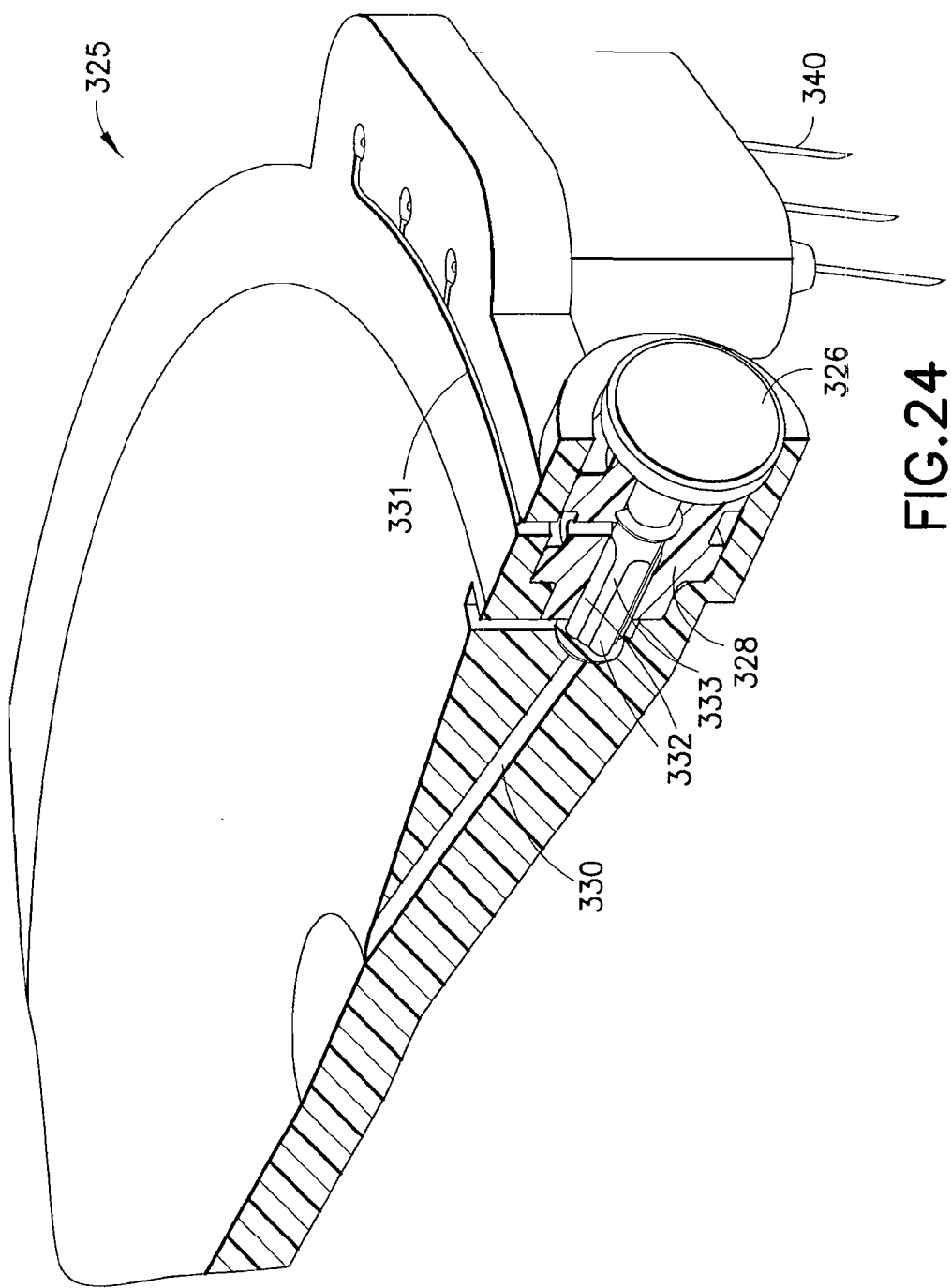
FIG. 24 is a cross-sectional view of a valve subassembly of the patch-like injector or infusor system of FIG. 12 in an open position.

Another version of the second embodiment is shown in FIGS. 12 through 24. In the version of the second embodiment shown in FIGS. 12 through 24, a push-button design 300 is shown wherein the activation of the device is accomplished in a single multi-function/step process. FIGS. 12 and 13 are exploded views of the second embodiment of a patch-like injector or infusor system using a top push button surface to allow a user to press down upon an upper housing 305 and rotate the device into an activated and in-use position. FIGS. 14 through 17 are views of the second embodiment of the patch-like injector or infusor system of FIG. 12 prior to activation. FIGS. 18 through 21 are views of the second embodiment of the patch-like injector or infusor system of FIG. 12 subsequent to activation. FIGS. 22(a) through 22 (e) are multiple views of the reservoir subassembly of the patch-like injector or infusor system of FIG. 12. FIGS. 23 and 24 are views of the reservoir subassembly and valve subassembly of the patch-like injector or infusor system of FIG. 12 in a closed and open position, respectively.

As shown in FIGS. 12 and 13, the second embodiment of the present invention comprises an infusion device 300 having an upper housing 305, a Belleville spring retention disk 310, at least one Belleville spring 315, a reservoir film 320, a reservoir subassembly 325, at least one patient microneedle 340, and a lower housing 350. The reservoir subassembly 325 further includes a valve spool 326 and valve seat 328, and a pivot mechanism 327, such as a pin. The pivot mechanism 327 is received by at least one pin opening 329 disposed on the lower housing allowing the upper housing 305, Belleville spring retention disk 310, Belleville spring 315, reservoir film 320, reservoir subassembly 325, and patient microneedle 340 to rotate into an activated and in-use position. A user can press upon the upper housing 305 to release the Belleville spring 315 from the disk 310, which then applies a force to the flexible member 320, compressing the contents against the reservoir subassembly 325. The motion of the user further drives the patient microneedles 340 downward toward a patient's skin surface (not shown) and away from the disk 310. Simultaneously, the user can activate a push or pull type valve subassembly (i.e., valve spool 326 and valve seat 328) described in greater detail below with reference to FIGS. 23 and 24, to establish the fluid path between the reservoir and the patient microneedles 340.

Figure 14:
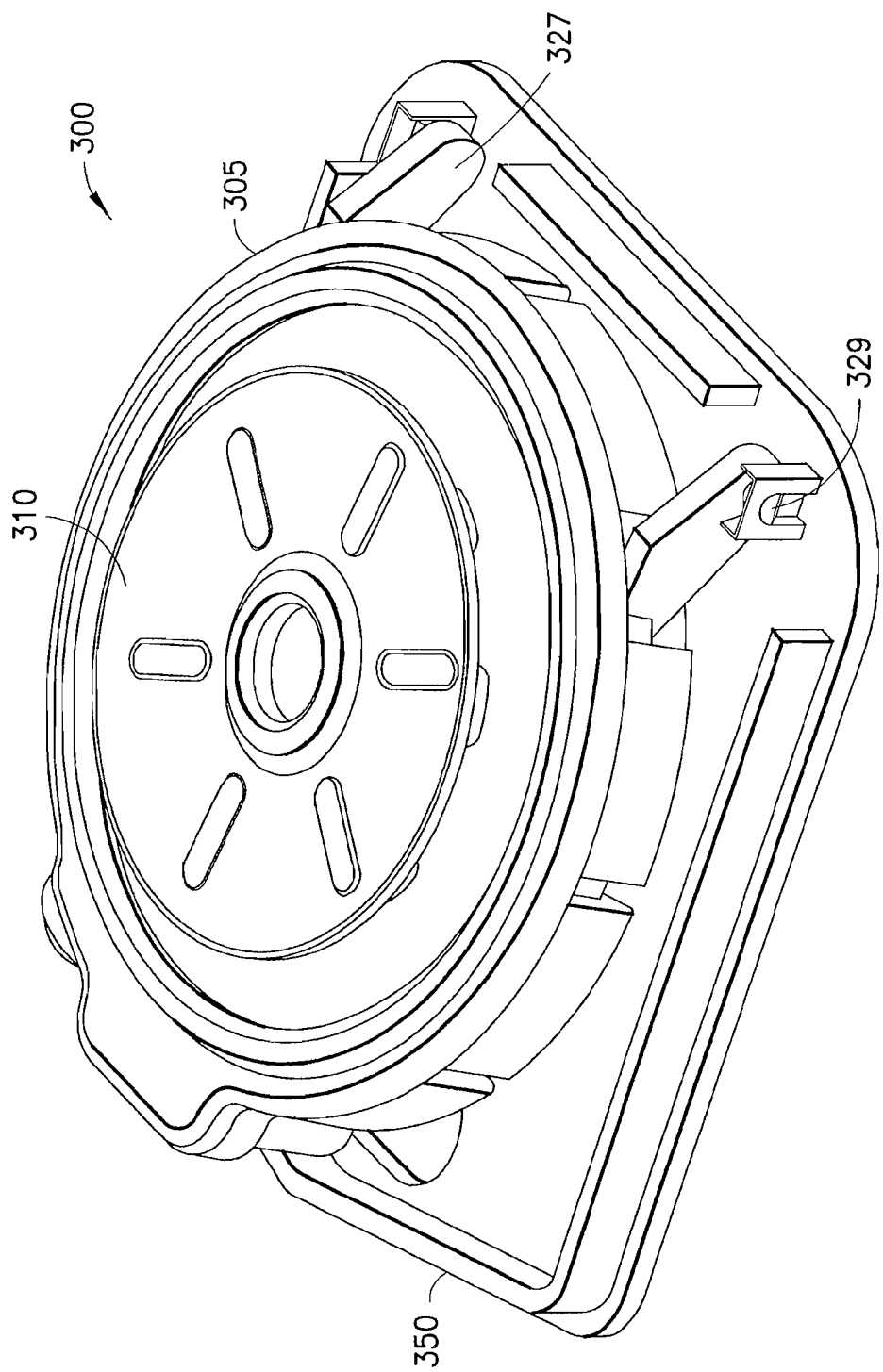
FIG. 14 is a top view from a first perspective angle of the patch-like injector or infusor system of FIG. 12 prior to activation.
Figure 15:
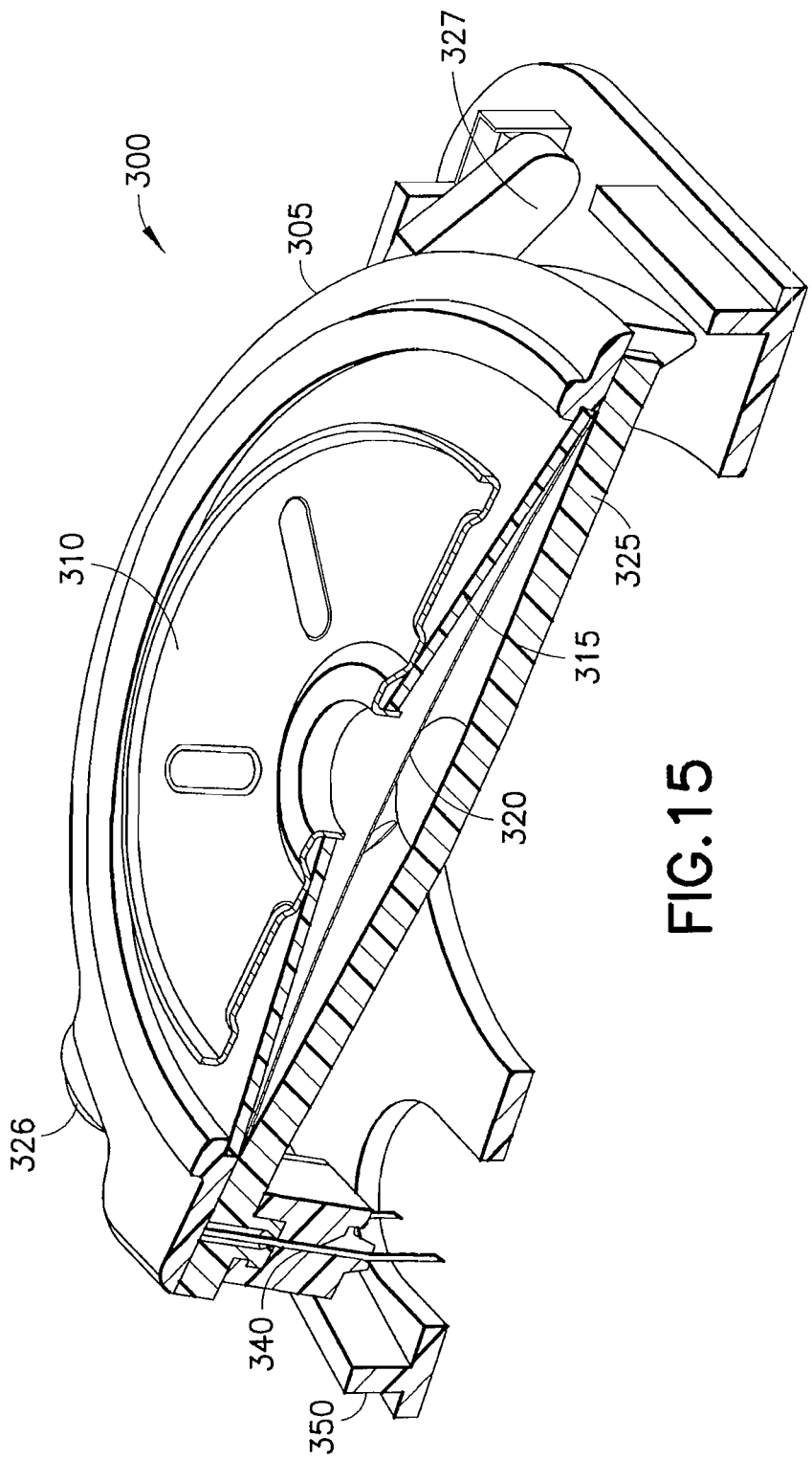
FIG. 15 is a cross-sectional view of the patch-like injector or infusor system of FIG. 12 prior to activation.
Figure 16:
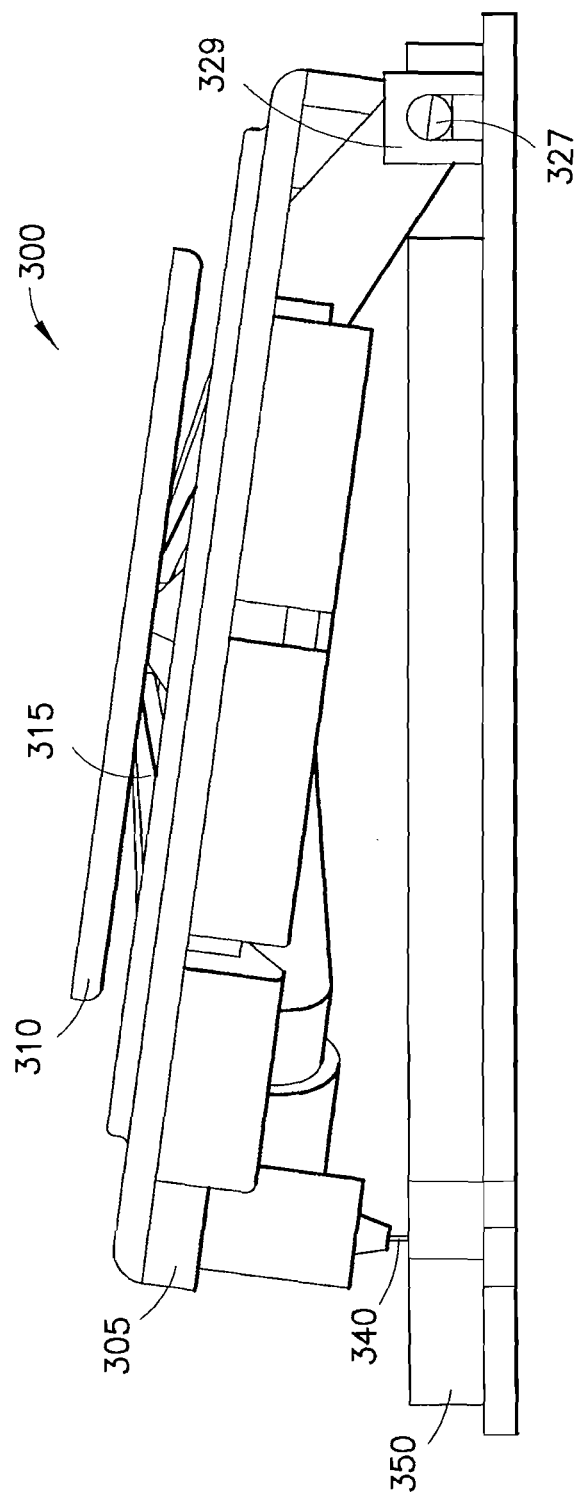
FIG. 16 is a side elevational view of the patch-like injector or infusor system of FIG. 12 prior to activation.
Figure 17:
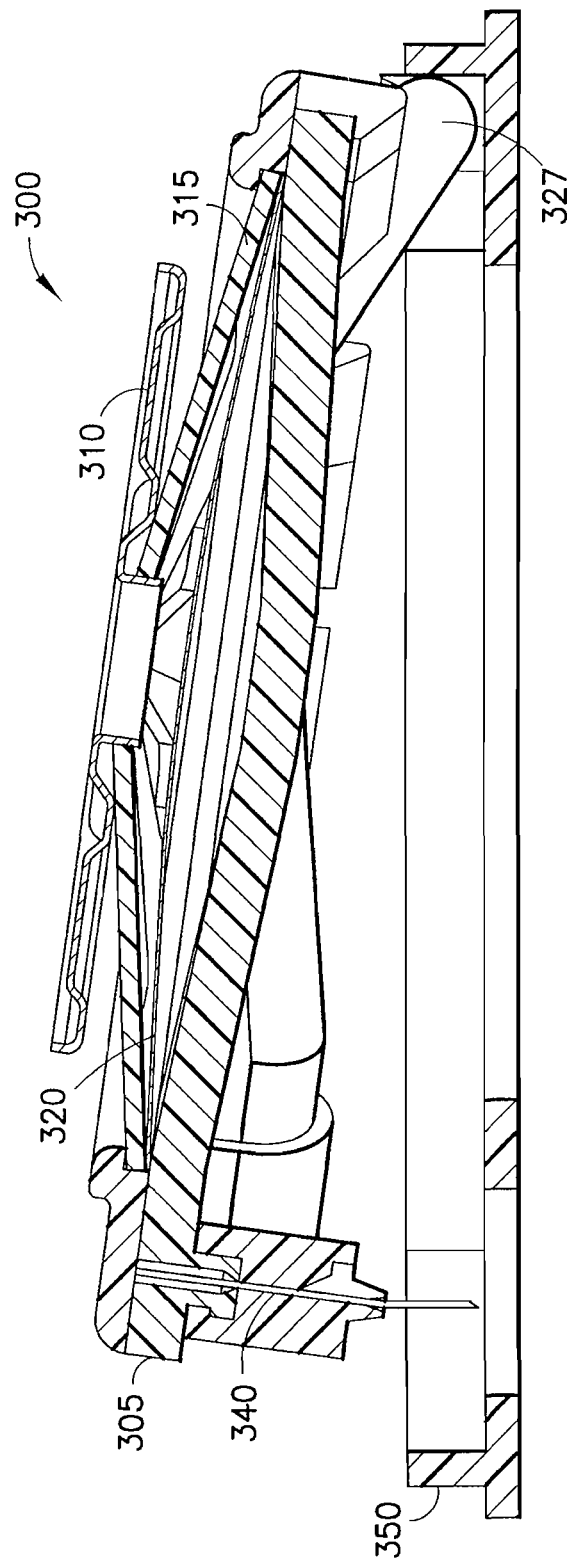
FIG. 17 is another cross-sectional view of the patch-like injector or infusor system of FIG. 12 prior to activation.

FIGS. 14 through 17 are views of the device 300 of FIG. 12 prior to activation. FIG. 14 is an isometric view illustrating the rotating components (i.e., the upper housing 305, Belleville spring retention disk 310, Belleville spring 315, reservoir film 320, reservoir subassembly 325, and patient microneedles 340) prior to being rotated into an activated and in-use position about the lower housing 350. FIG. 15 is a cross-sectional view illustrating the positioning of the rotating components before activation and placement into the in-use position. FIG. 16 is a side elevational view illustrating the separation of the rotating components from the lower housing 350 before activation and placement into the in-use position.

Figure 18:
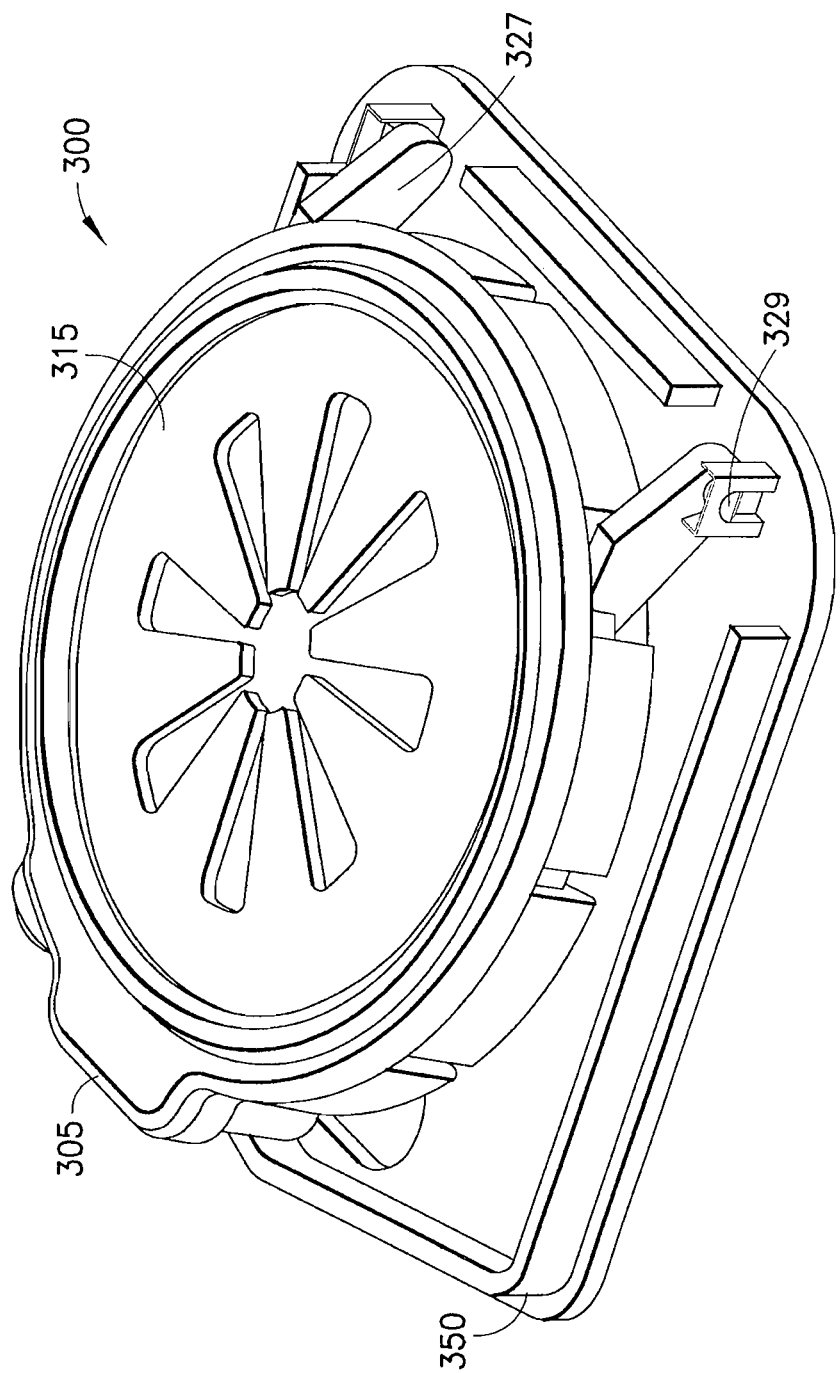
FIG. 18 is a top view from a first perspective angle of the patch-like injector or infusor system of FIG. 12 subsequent to activation.
Figure 19:
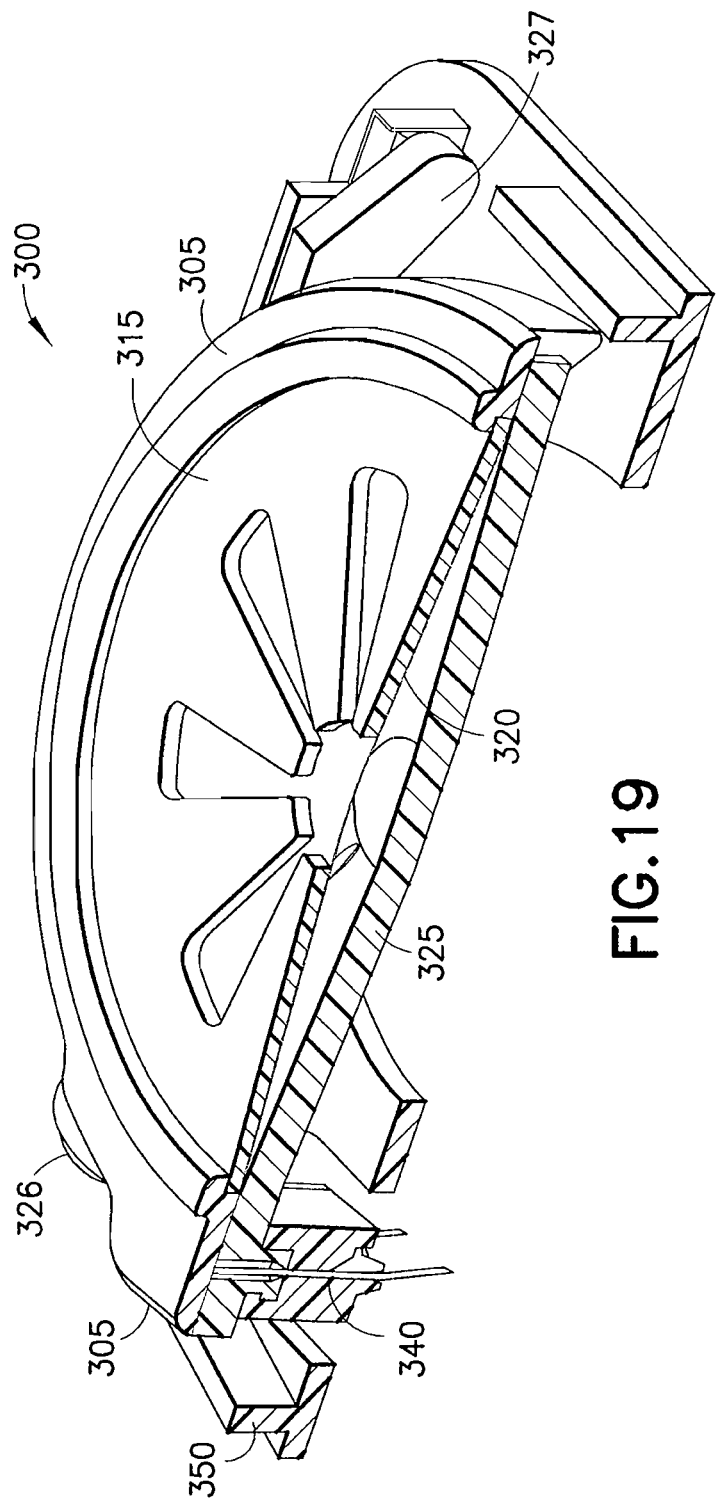
FIG. 19 is a cross-sectional view of the patch-like injector or infusor system of FIG. 12 subsequent to activation.
Figure 20:
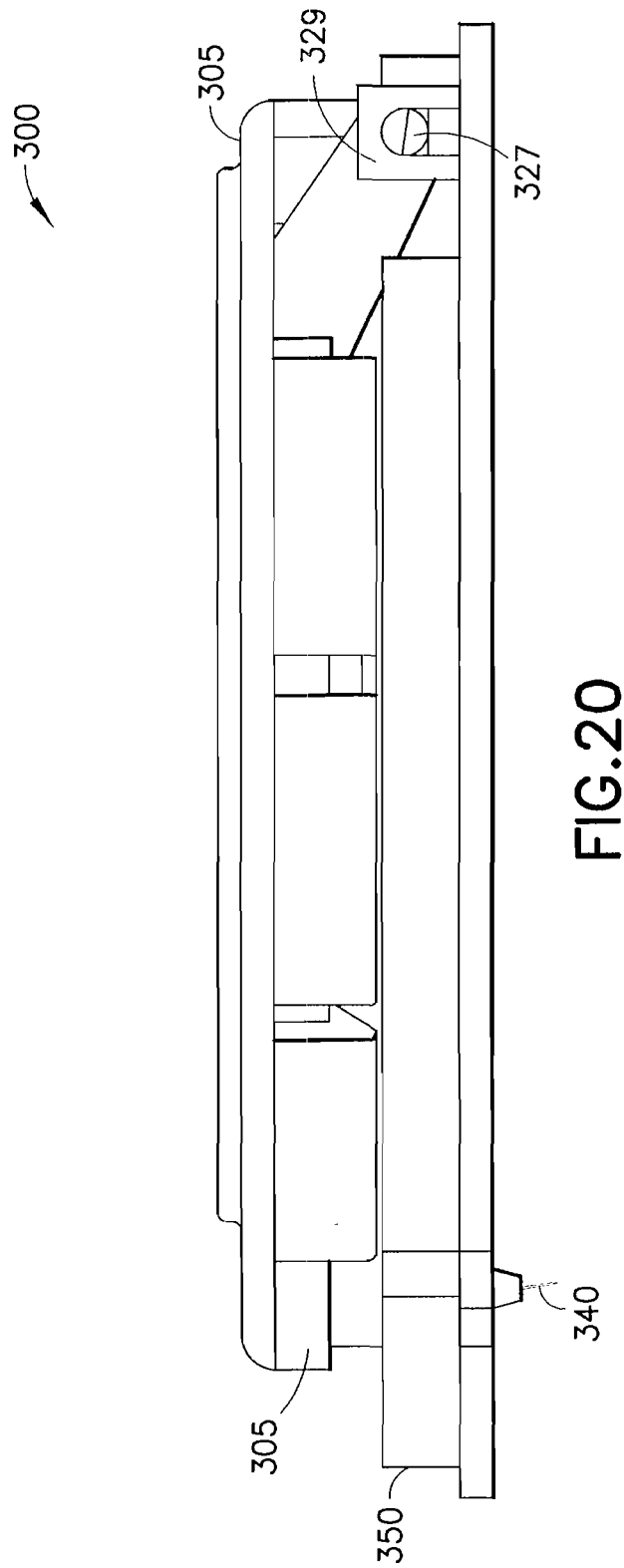
FIG. 20 is a side elevational view of the patch-like injector or infusor system of FIG. 12 subsequent to activation.
Figure 21:
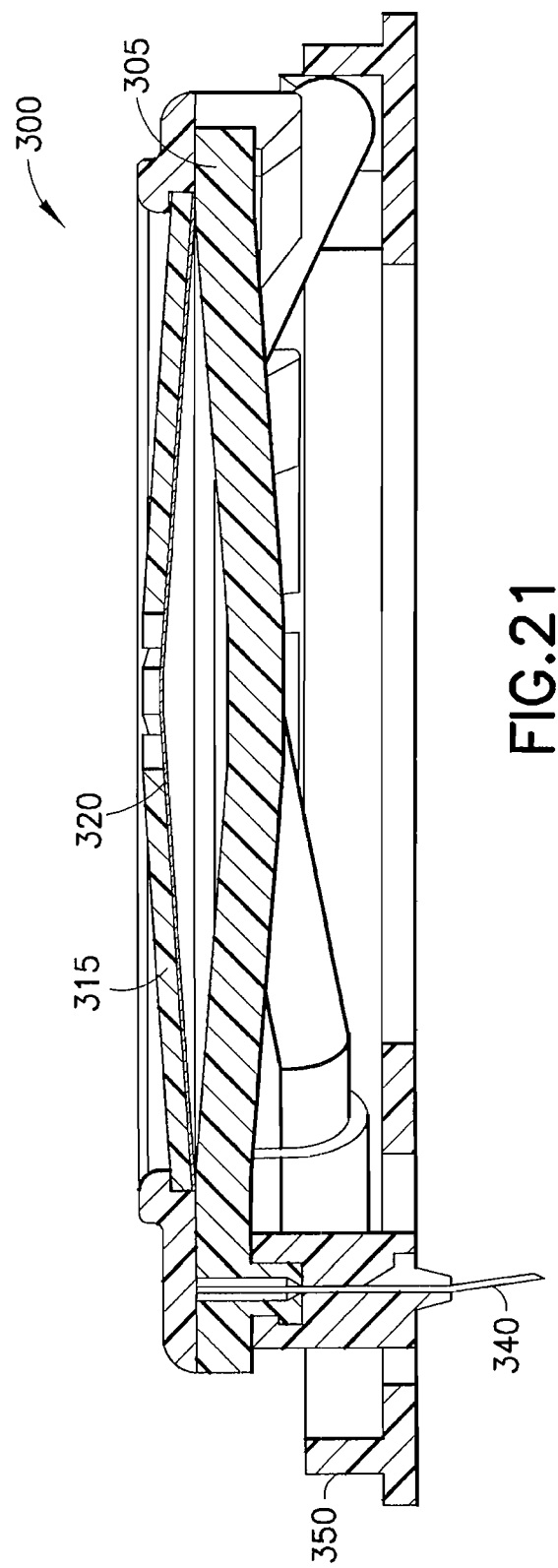
FIG. 21 is another cross-sectional view of the patch-like injector or infusor system of FIG. 12 subsequent to activation.

FIGS. 18 through 21 are views of the device 300 of FIG. 12 subsequent to activation. FIG. 18 is an isometric view illustrating the rotating components (i.e., the upper housing 305, Belleville spring retention disk 310, Belleville spring 315, reservoir film 320, reservoir subassembly 325, and patient microneedles 340) rotated into an activated and in-use position about the lower housing 350. FIG. 19 is a cross-sectional view illustrating the positioning of the rotating components after activation and placement into the in-use position. FIG. 20 is a side elevational view illustrating the engagement of the rotating components with the lower housing 350 after activation and placement into the in-use position.

FIGS. 22(a) through 22 (e) are multiple views of the reservoir subassembly of the device 300 of FIG. 12. FIG. 22(a) is a top view of the reservoir subassembly of the device 300 of FIG. 12. FIG. 22(b) is a first side view, FIG. 22(c) is a second side view, and FIG. 22(d) is a third side view of the reservoir subassembly of the device 300 of FIG. 12. FIG. 22(e) is a bottom view of the reservoir subassembly of the device 300 of FIG. 12.

FIGS. 23 and 24 are detailed views of the reservoir subassembly 325 and valve subassembly (i.e., valve spool 326 and valve seat 328) of the device 300 of FIG. 12 in a closed and open position, respectively. Specifically, the spool 326 includes a number of raised detents 332 which, when in the closed position as in FIG. 23, block a fluid path 333 between a reservoir path 330 and a patient needle path 331. When the spool 326 is pushed inward into the valve seat 328, the raised detents are moved clear of the fluid path allowing the contents of the reservoir to travel from the reservoir path 330 to the needle path 331 via path 333.

As with the first embodiment of the present invention 100 in FIG. 1, the second embodiment of the present invention 300 can be constructed to provide a patch-like, wearable, self-contained substance infusion device that can be used to deliver a variety of medications to a patient. The device 300, provides a hidden patient needle or needles 340 prior to and during use, and can be secured to a patient via an adhesive surface (not shown) disposed on the lower housing 350. The pressurization of the contents of the reservoir (i.e. contents contained between the reservoir film 320 and the reservoir subassembly 325) can be achieved by removing or displacing the spring retention disk 310, as described above, to pressurize the contents, and the device can then be further activated via a reasonable force applied to the top push surface of the upper housing 305 to seat the patient needles 340. In doing so, the device 300 facilitates self-injection and reduces or eliminates variations in injection techniques between users.

Figure 25:
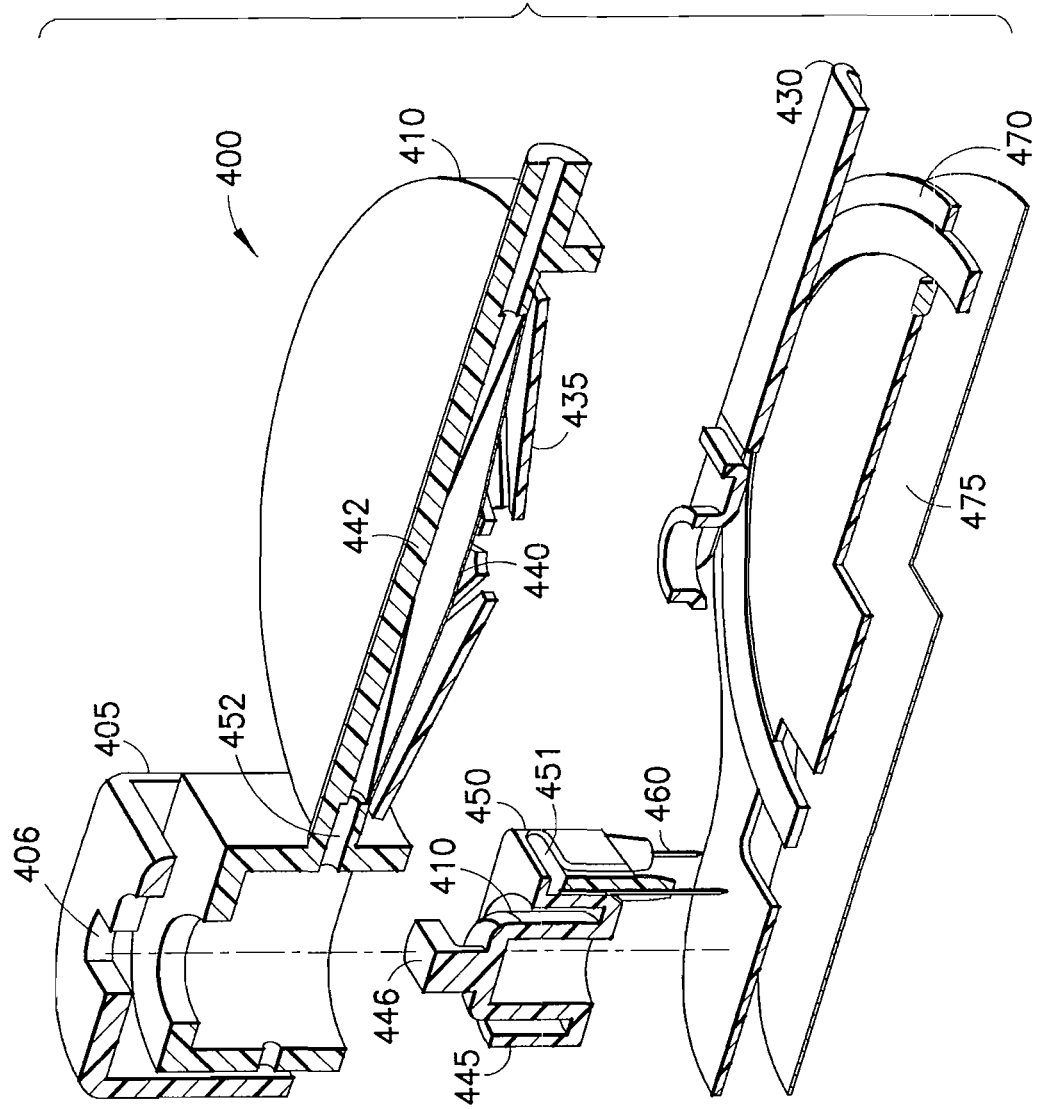
FIG. 25 is an exploded view of a third embodiment of a patch-like injector or infusor system.
Figure 26:
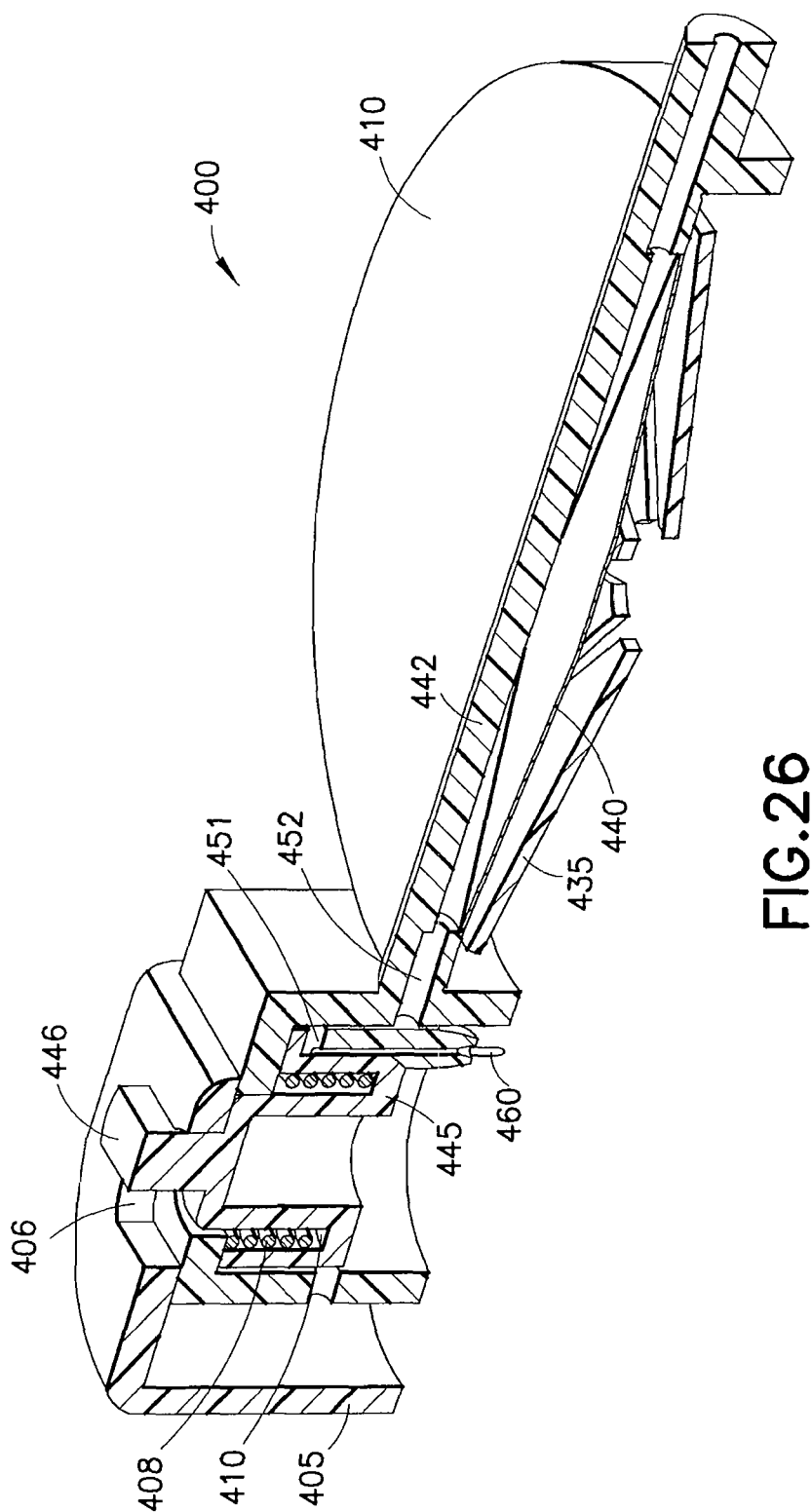
FIG. 26 is a cross-sectional view of the patch-like injector or infusor system of FIG. 25 prior to activation.
Figure 27:
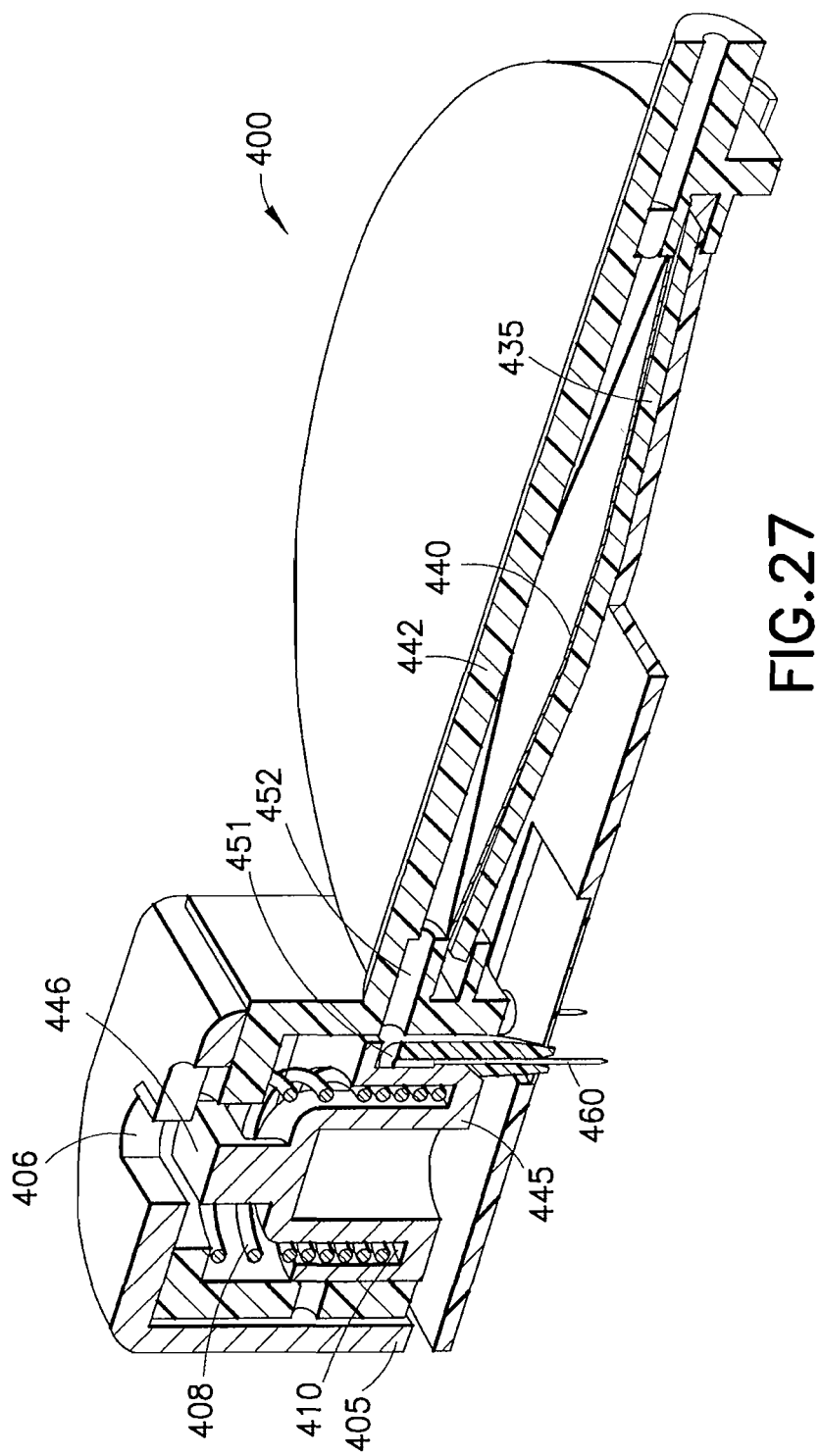
FIG. 27 is a cross-sectional view of the patch-like injector or infusor system of FIG. 25 subsequent to activation.

In a third embodiment of the device, shown in FIGS. 25 through 27, a push-button design 400 is shown wherein the activation and energizing of the device is also accomplished in a single multi-function/step process. FIG. 25 is an exploded view of the third embodiment of a patch-like injector or infusor system. FIGS. 26 and 27 are cross-sectional views of the third embodiment of the patch-like injector or infusor system of FIG. 25 prior to, and subsequent to activation.

In the third embodiment of the present invention shown in FIGS. 25 through 27, an infusion device 400 includes a push button 405, a reservoir subassembly 410, a Belleville spring retention handle 430, at least one Belleville spring 435, a reservoir film 440, a reservoir firm surface 442, a "T" pin 445, at least one patient microneedle 460, and a lower housing 470. The T pin 445 further includes a valve assembly 450, and the lower housing 470 can include an adhesive surface 475.

As shown in FIGS. 25 through 27, the embodiment of the present invention 400 can be constructed to provide a patch-like, wearable, self-contained substance infusion device that can be used to deliver a variety of medications to a patient. The device 400, provides the hidden patient needle or needles 460 prior to and during use, and can be secured to a patient via the adhesive surface 475. The pressurization of the contents of the reservoir (i.e., contents provided between the reservoir film 440 and the reservoir firm surface 442), can be achieved by removing or displacing the spring retention handle 430, thereby releasing the Belleville spring 435 to pressurize the reservoir contents. The device can then be further activated by slidably engaging the push button 405 inward towards the device. As the push button 405 travels, a stepped opening 406 in the button 405 releases a right angle member 446 of the T pin 445, thereby releasing the T pin 445 and allowing the patient needles 460 to drop as driven forward by a coil spring 408 disposed in a circular opening 410 within the T pin 445. In doing so, the patient microneedles 460 seat. As the T pin 445 drops, the opening 451 of valve 450 aligns with a fluid channel 452 in fluid communication with the reservoir, thereby creating a fluid path between the reservoir contents and the patient needles 460.

FIGS. 26 and 27 are cross-sectional views of the device 400 prior to, and subsequent to activation. In FIG. 26 (shown without the spring retention handle 430, lower housing 470, and the adhesive surface 475 for simplicity), the T pin 445 is held up by the stepped opening 406, compressing the spring 408. Once the spring retention handle 430 is removed releasing the Belleville spring 435, the device 400 can be placed in position on the skin surface (not shown). As the button 405 is pushed, the stepped surface 406 releases the right angle member 446 of the T pin 445, thereby releasing the T pin 445 and allowing the patient needles 460 to drop as shown in FIG. 27. In FIG. 27, the patient microneedles 460 seat and the opening 451 of valve 450 aligns with the fluid channel 452 in fluid communication with the reservoir, thereby creating a fluid path between the reservoir contents and the patient needles 460.

Figure 31:
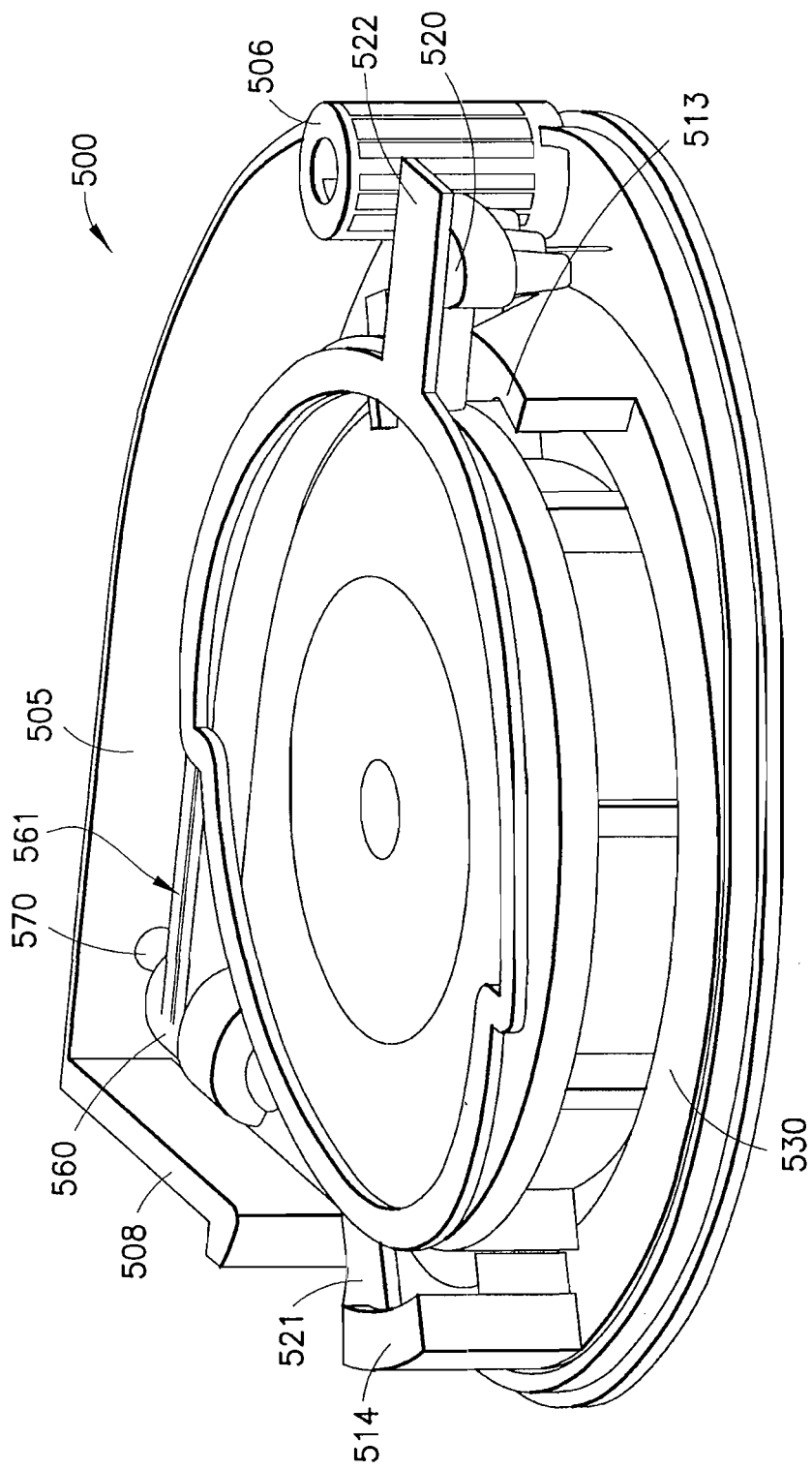
FIG. 31 is another top view from a fourth perspective angle of the patch-like injector or infusor system of FIG. 28 subsequent to retraction.
Figure 32:
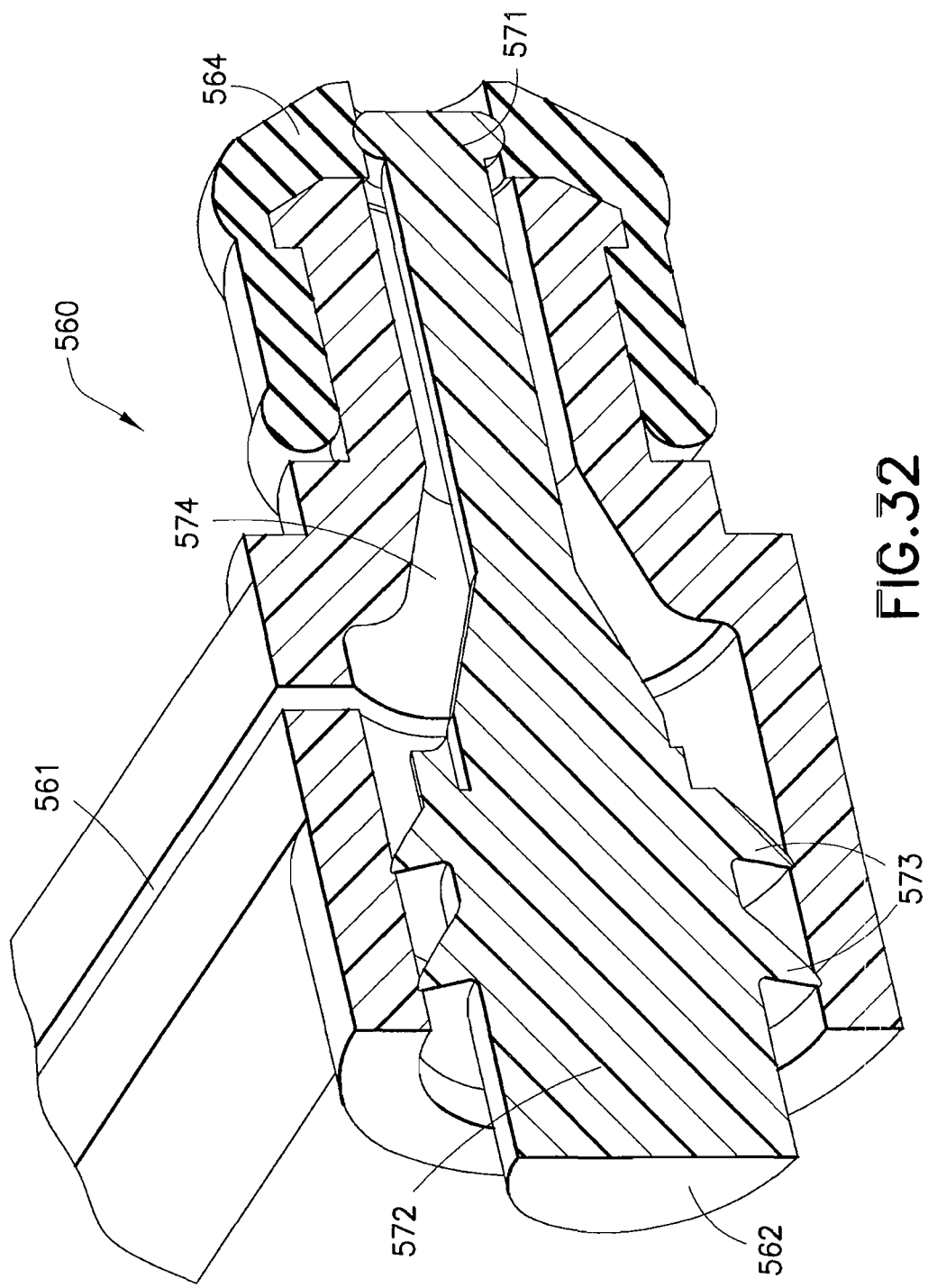
FIG. 32 is a cross-sectional view of a valve subassembly of the patch-like injector or infusor system of FIG. 28 in a closed position.
Figure 33:
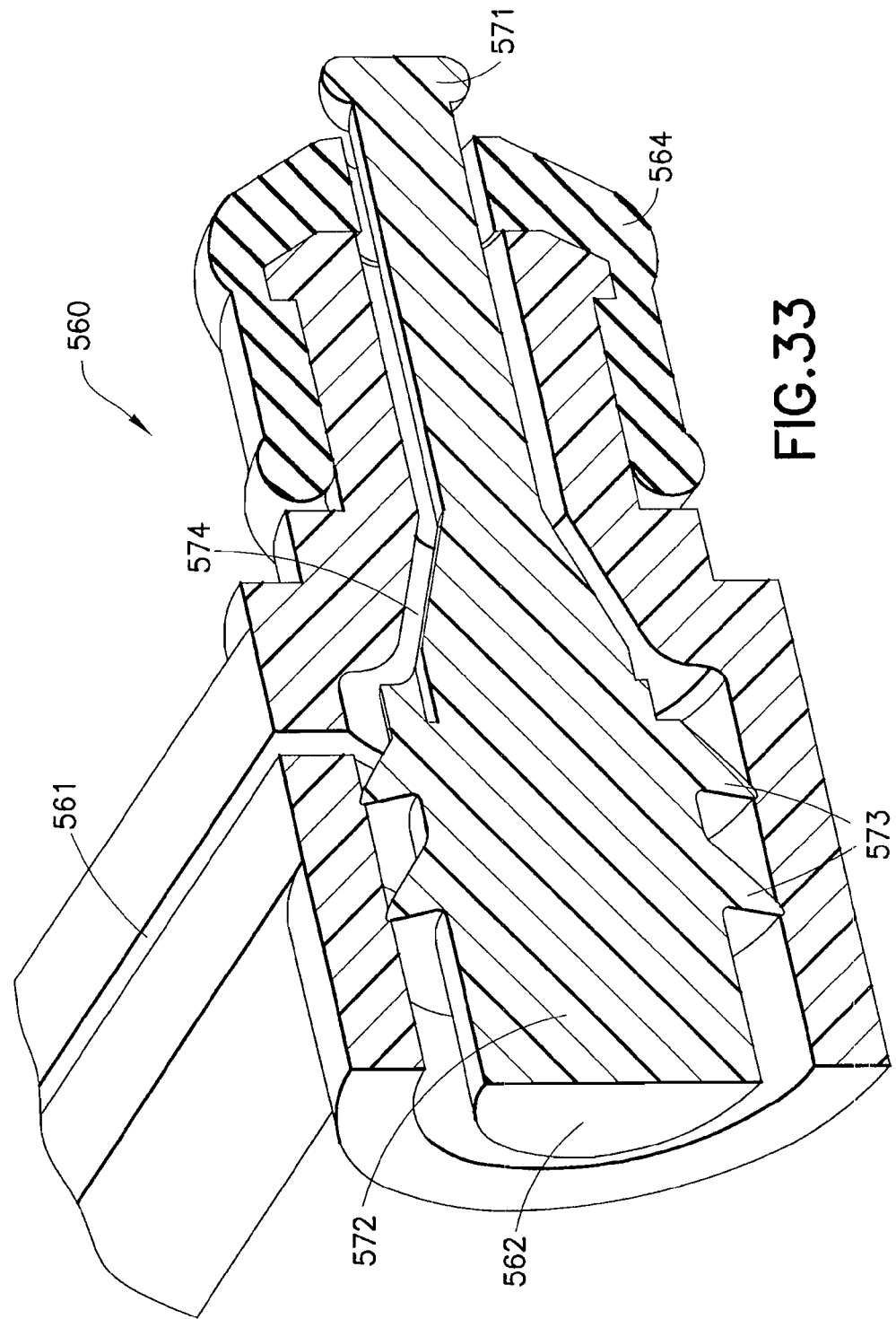
FIG. 33 is a cross-sectional view of a valve subassembly of the patch-like injector or infusor system of FIG. 28 in an open position.

In a fourth embodiment of the device shown in FIGS. 28 through 31, a push-button design 500 is shown wherein the activation and energizing of the device is also accomplished in a single multi-function/step process. FIGS. 28 through 31 are top views of the fourth embodiment of a patch-like injector or infusor system. FIGS. 32 and 33 are partial cross-sectional views of a valve subassembly of the patch-like injector or infusor system of FIG. 28 in a closed and open position, respectively.

Figure 28:
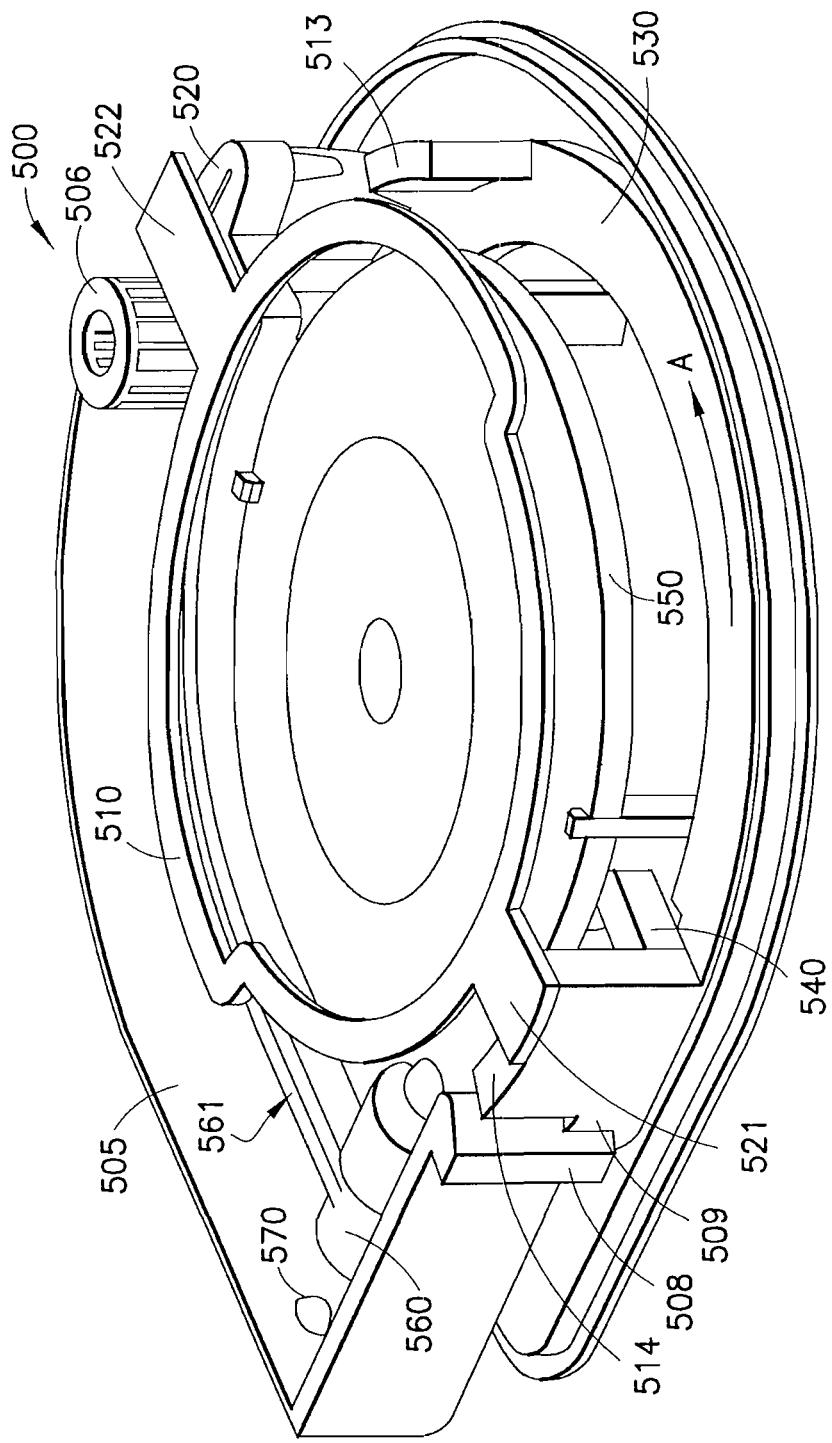
FIG. 28 is a top view from a first perspective angle of a fourth embodiment of a patch-like injector or infusor system prior to activation.
Figure 29:
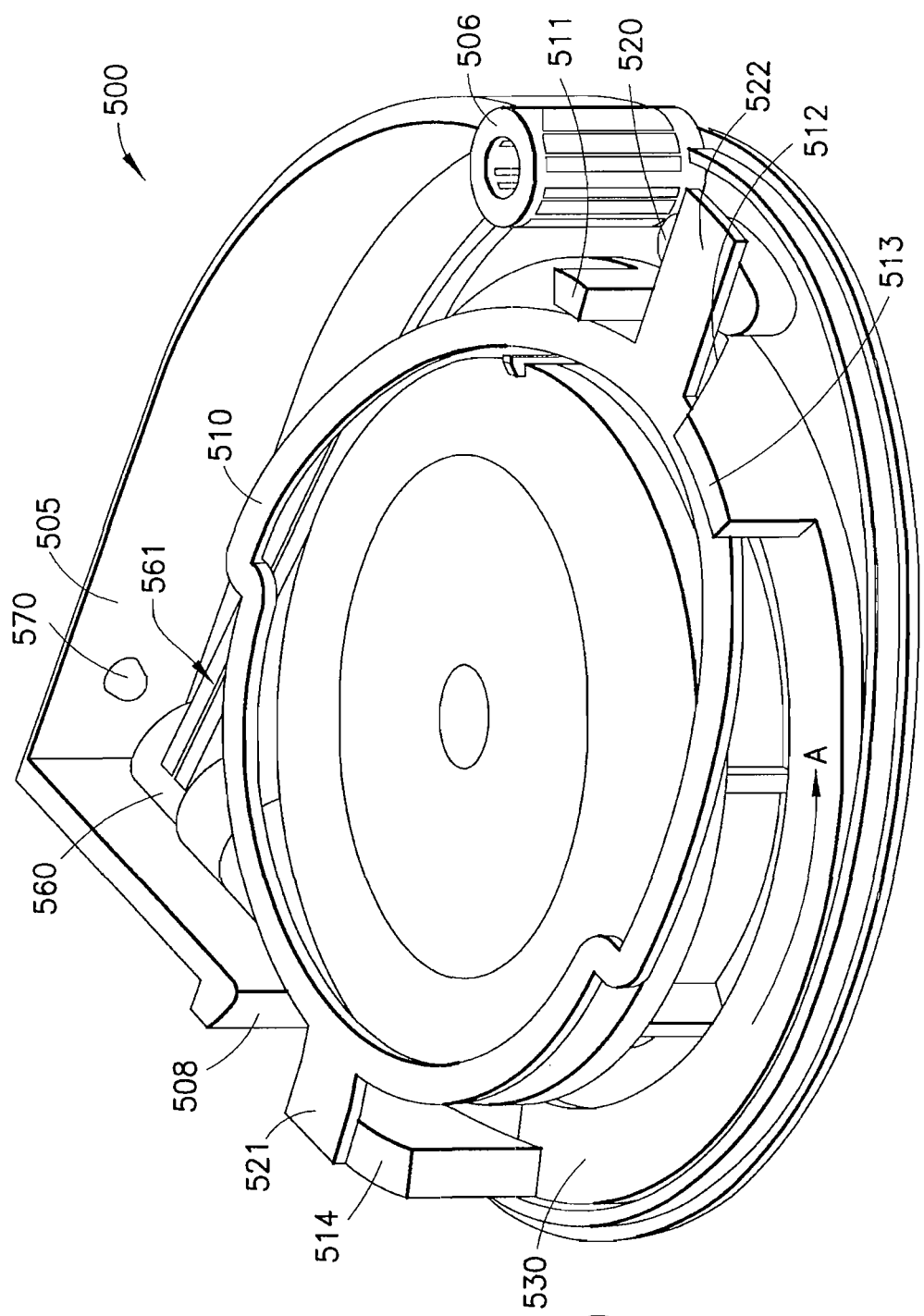
FIG. 29 is another top view from a second perspective angle of the patch-like injector or infusor system of FIG. 28 subsequent to activation and prior to retraction.
Figure 30:
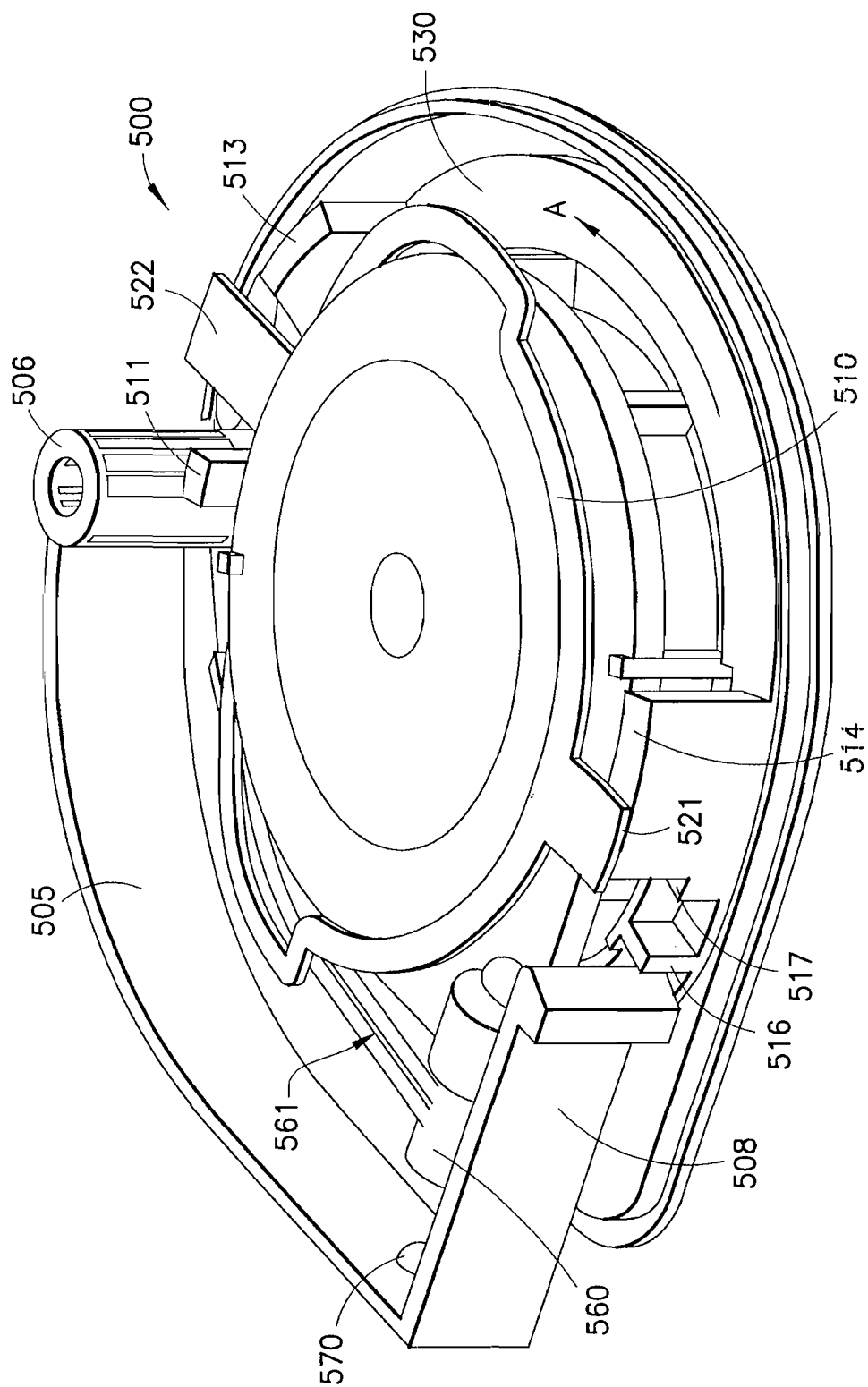
FIG. 30 is another top view from a third perspective angle of the patch-like injector or infusor system of FIG. 28 subsequent to activation and prior to retraction.

As shown in FIGS. 28 through 31, the device includes a button 505, a spring 510, a manifold arm 520, an activation ring 530, a pop opener 540, a reservoir 550, a valve assembly 560 and a valve engagement detent 570. The spring 510 has a first and second tab 521 and 522, at opposite sides respectively, and is secured within the device 500 to exert a downward force via the first tab when the second tab is raised, and to exert a downward force via the second tab when the first tab is raised, the force being exerted upon the ring 530 component (i.e., 511, 513, 514) or the manifold component (i.e., 520) beneath the respective tab. A Belleville spring (not shown) is also provided beneath the reservoir 550. A cover (not shown) is also provided to cover the above components but omitted here for illustration purposes. The device of FIG. 28 is configured to operate between a loaded position, as shown in FIG. 28, an activated, or fired position, shown in FIGS. 29 and 30, and a retracted position shown in FIG. 31.

Specifically, as shown in FIG. 28, after application of the patch-like device 500 upon a skin surface (not shown) substantially as described above, a force applied to the push button 505 will cause the push button 505 to pivot, or flex about point 506. As the button 505 pivots, the linear member 508 of the push button 505 contacts the activation ring 530 at a first detent 509, rotating the ring 530 as shown by the arrow A. As the ring 530 rotates, the spring 510 drops from a perch 511 into a groove 512 and drives the manifold and manifold arm 520 downwards. Also, as the ring 530 rotates, the pop opener 540 is engaged by an incline 582 (see FIGS. 35 and 36) on the ring 530 which serves to disengage the pop opener 540 from the Belleville spring, releasing the Belleville spring and thereby pressurizing the reservoir 550 contents. Once the push button 505 is released a first time, the linear member 508 of the push button 505 is retracted by the spring force of the pivot point 506, releasing the first activation ring 530 first detent 509, and seating behind a second activation ring detent 516, shown in FIG. 30. In doing so, pushing the push button 505 a second time rotates the activation ring 530 further, releasing the opposite tab 521 of the spring 510 into opening 517, and diving the previously lower spring tab 522 up an incline and upon perch 513, allowing the manifold arm 520 to rise and retract the patient needles 541 as shown in FIG. 31.

In addition to the above, the push button 505 also engages the valve assembly 560 via a detent 570. The valve, shown and described in greater detail with reference to FIGS. 32 and 33, is pushed into an open position allowing fluid communication as provided by a continuous path 561, between the valve 560 and through the manifold arm 520. As shown in FIGS. 32 and 33, the valve assembly 560 includes a soft plastic member 572 extending between a contact surface 562 and an enlarged proximal end 571 disposed within a rubber seal 564 when in a closed position. The valve assembly 560 can be constructed within the manifold arm 520 (i.e., within a molded coupling between the manifold arm 520 and the reservoir 550) to provide a continuous fluid communication path within the single reservoir assembly.

Specifically, as shown in FIG. 32, the push valve assembly 560 includes a soft member 572 slidably engaged within a rubber seal 564 in fluid communication with the reservoir 550. The valve assembly 560 has as an initial state and an activated state, and includes a large diameter distal end having a distal set of radially projecting fins, or ribs 573, and a reduced diameter body extending to an enlarged proximal end 571. In the initial state, the valve 560 distal ribs 573 serve to prevent microbial ingress into the fluid path 574, and the enlarged proximal end 571 creates a seal to trap the drug safely within the reservoir 550. Both sets of ribs 573 and end 571 are performing critical tasks in preventing fluid loss from inside the reservoir over long periods of time as well as preventing contamination of the drug from outside the reservoir over the same period of time.

In use, the member 572 will eventually be pushed into an activated state by the movement of the push button 505, and contact between the detent 570 and the contact surface 562. As shown in FIG. 33, the movement of the member 572 advances the enlarged proximal end 571 from an engagement position with the rubber seal 564, which permits the drug to flow from the reservoir 550, past the enlarged proximal end 571 and into the valve fluid path 574. At the same time, the distal set of ribs 573 are by nature also pushed in and the location of the ribs 573 themselves translate into a position such that they direct the fluid from the reservoir 550, through the valve fluid path 574, and down the fluid path 561 to the patient needle manifold (not shown).

Figure 34:
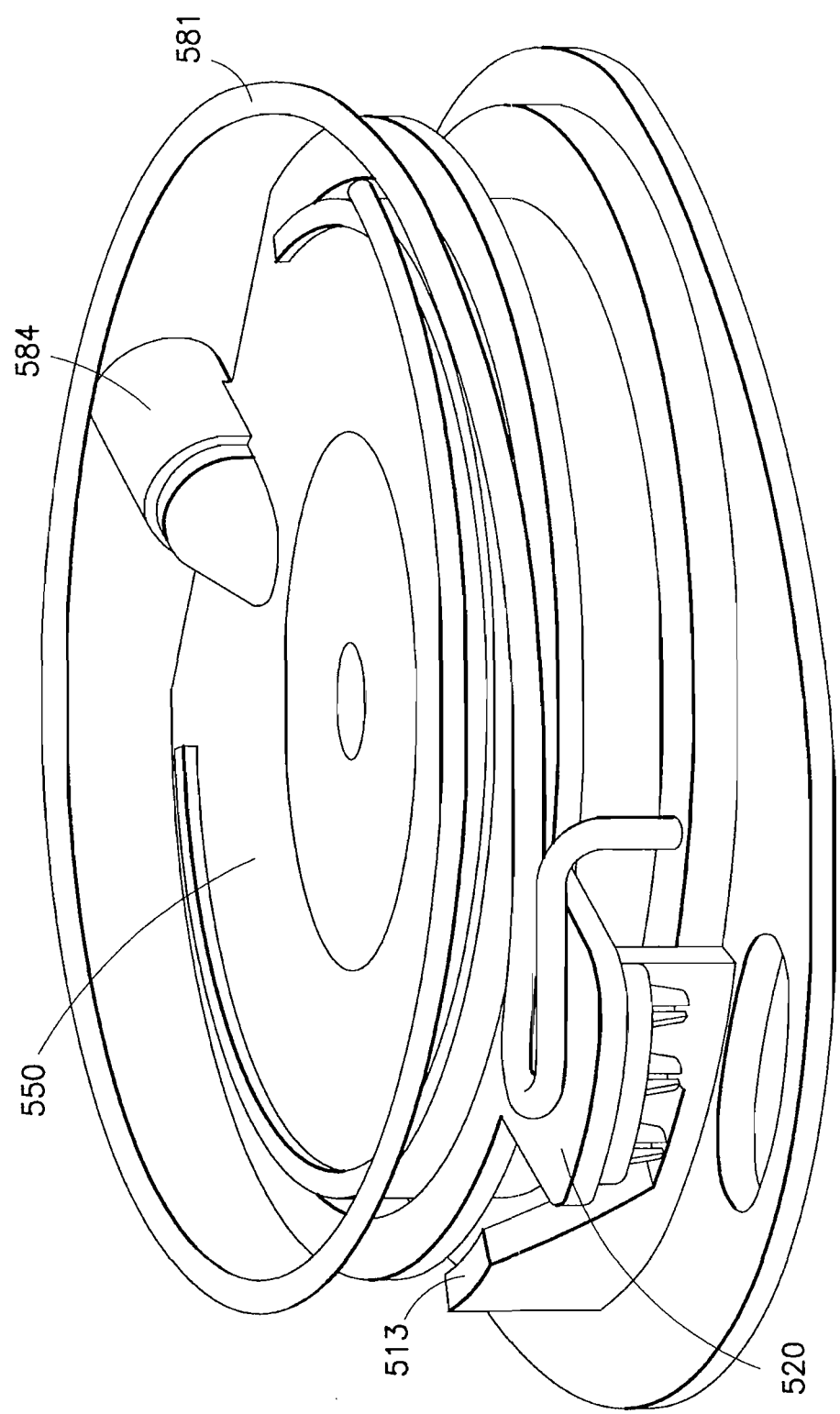
FIG. 34 is a top view from a first perspective angle of another version of the fourth embodiment of a patch-like injector or infusor system.
Figure 35:
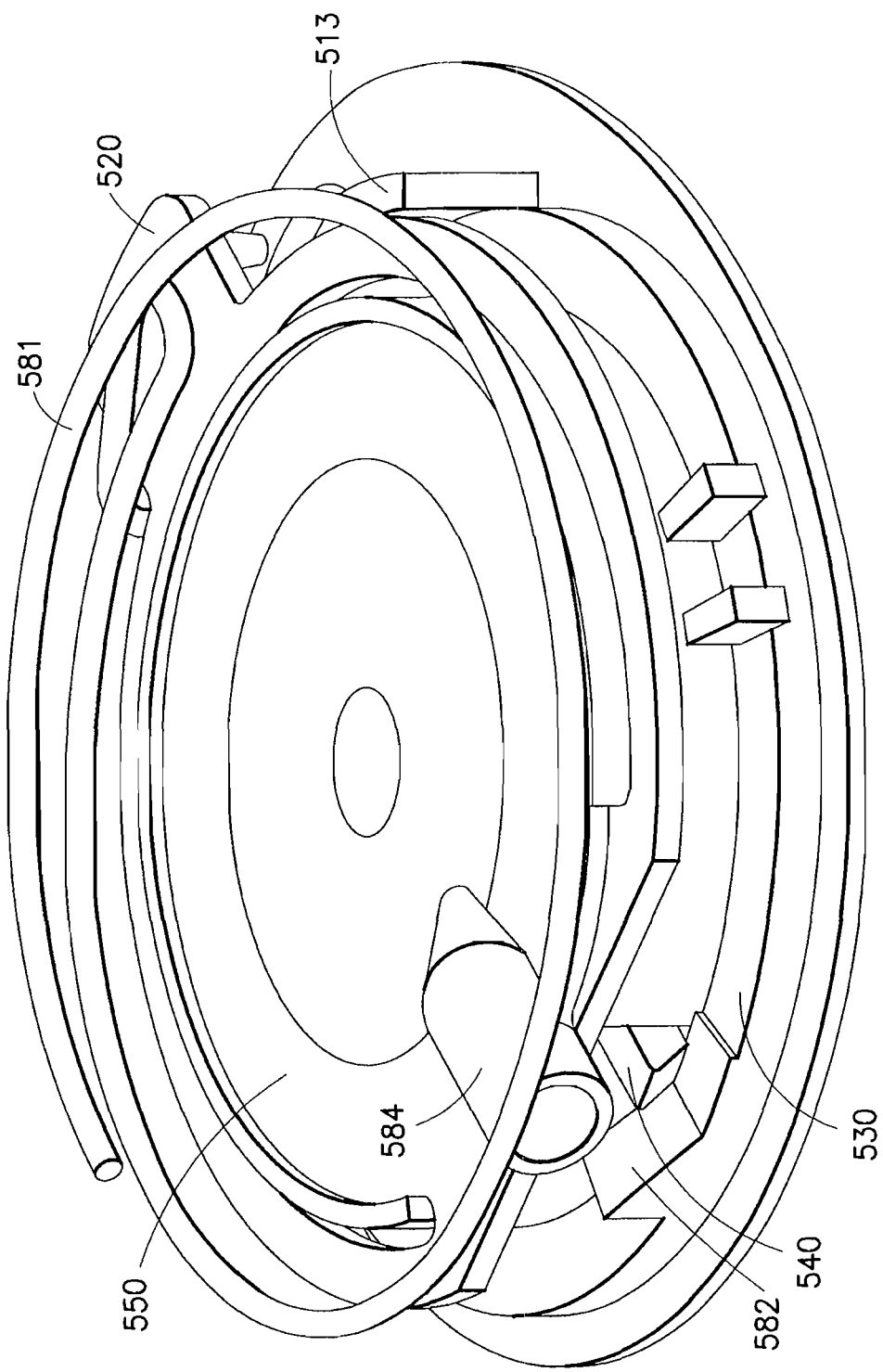
FIG. 35 is another top view from a second perspective angle of the patch-like injector or infusor system of FIG. 34.
Figure 36:
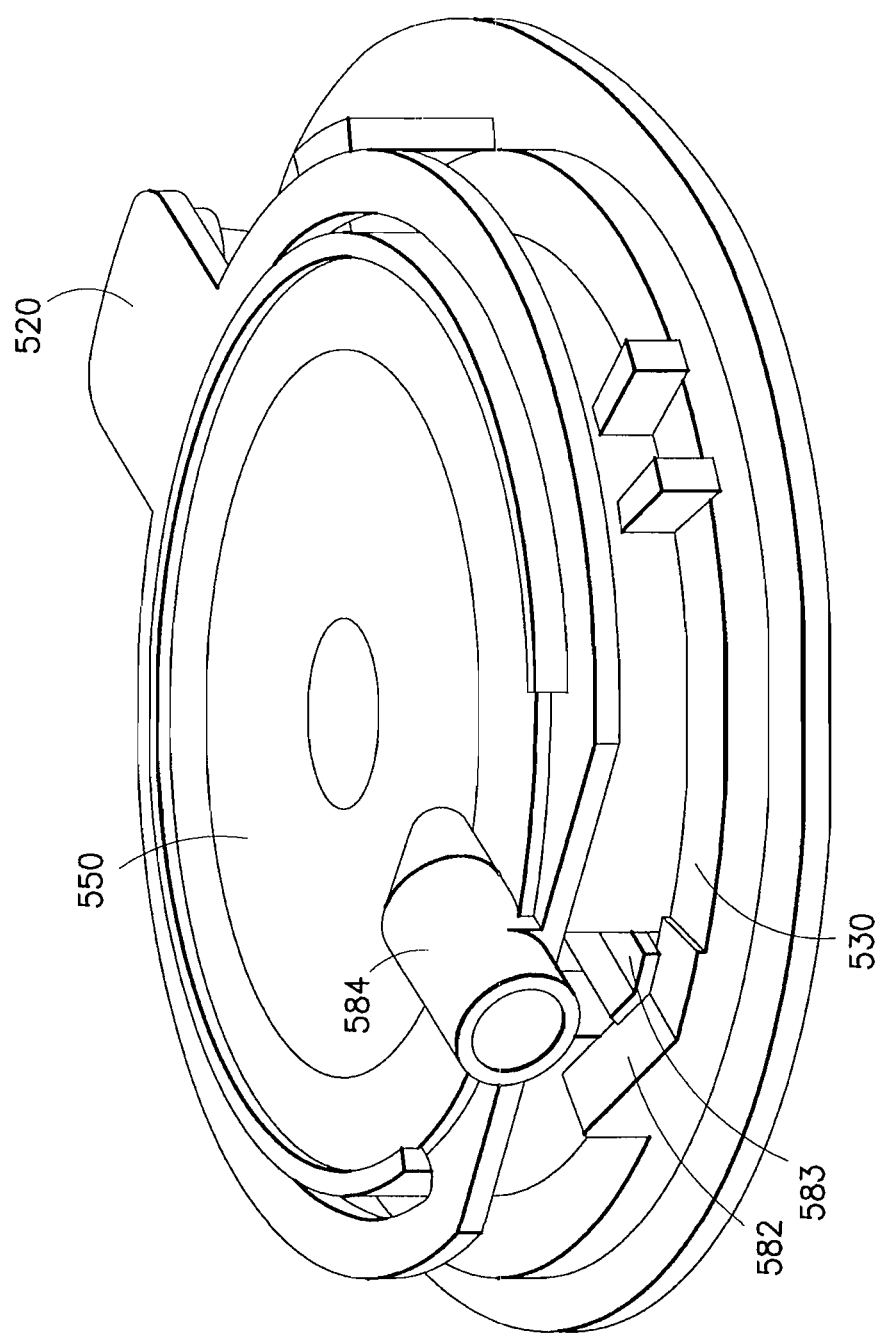
FIG. 36 is top view from a first perspective angle of still another version of the fourth embodiment of a patch-like injector or infusor system.

In a second version of the fourth embodiment shown in FIGS. 34, 35 and 36, alternate spring and valve versions can be used in place of the stamped metal flat spring 510 and valve assembly 560 of FIGS. 28 through 31. In FIGS. 34 and 35, a spring 581 is shown having a substantially circular cross-section and coiled above the reservoir 550 and manifold arm 520. Additionally, any number of valve assemblies 584, such as those described in greater detail below, can be provided in place of the push type valve assembly 560 of FIG. 28. In addition, a combination of activation ring and spring can be used in the other embodiments described above. In doing so, the benefits of an activation ring for multiple push button functions can be provided.

FIGS. 35 and 36 are further provided to show the pop opener 540 which engages an incline 582 as the ring 530 is turned, which serves to disengage the pop opener 540 from the Belleville spring (not shown), releasing the Belleville spring and thereby pressurizing the reservoir 550 contents. In FIG. 36, a second version of the Pop opener 583 is shown, which engages the incline 582 substantially as described above.

Figure 42:
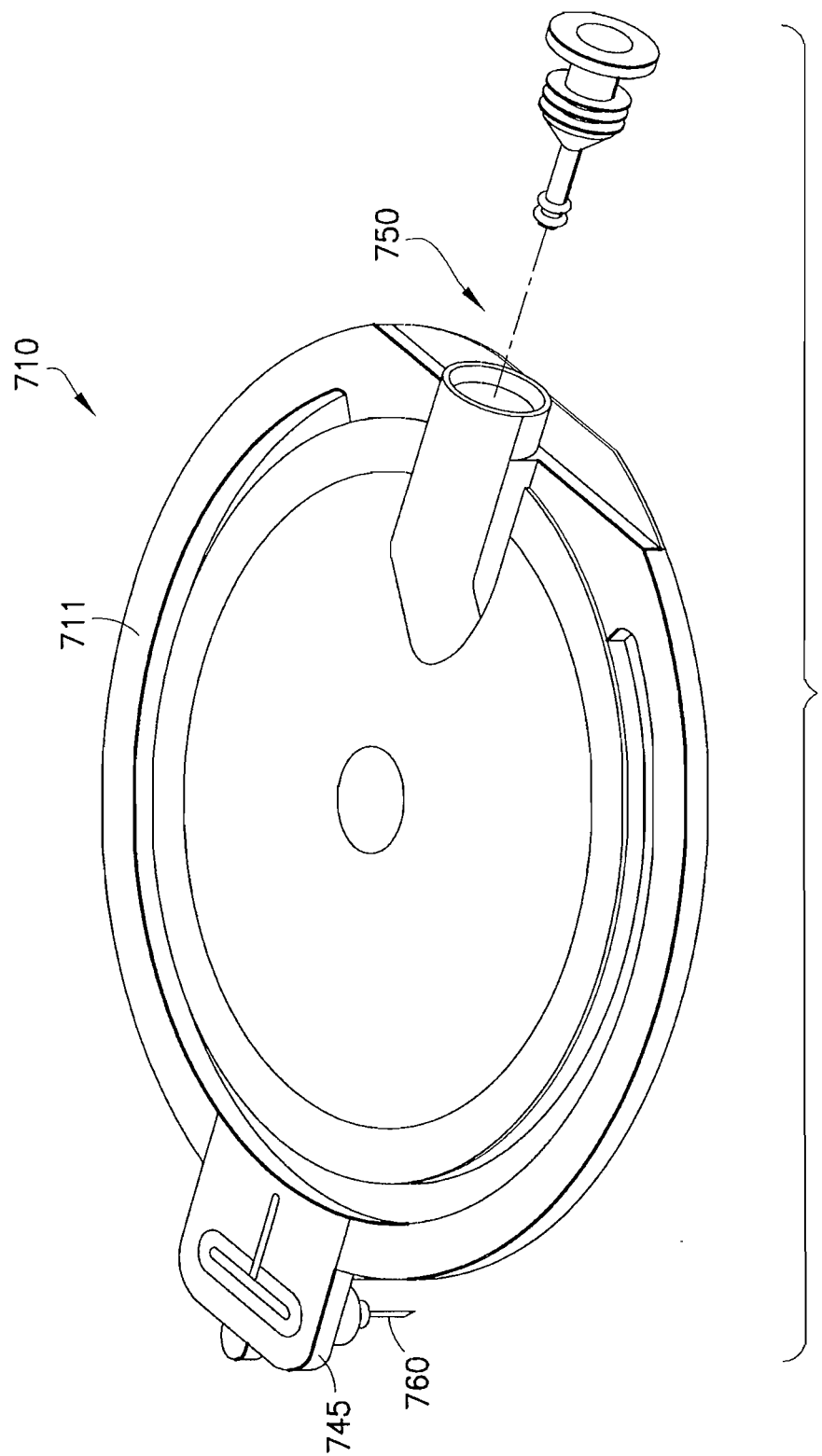
FIGS. 42 and 43 are top views of the reservoir subassembly of the patch-like injector or infusor system of FIG. 37.
Figure 43:
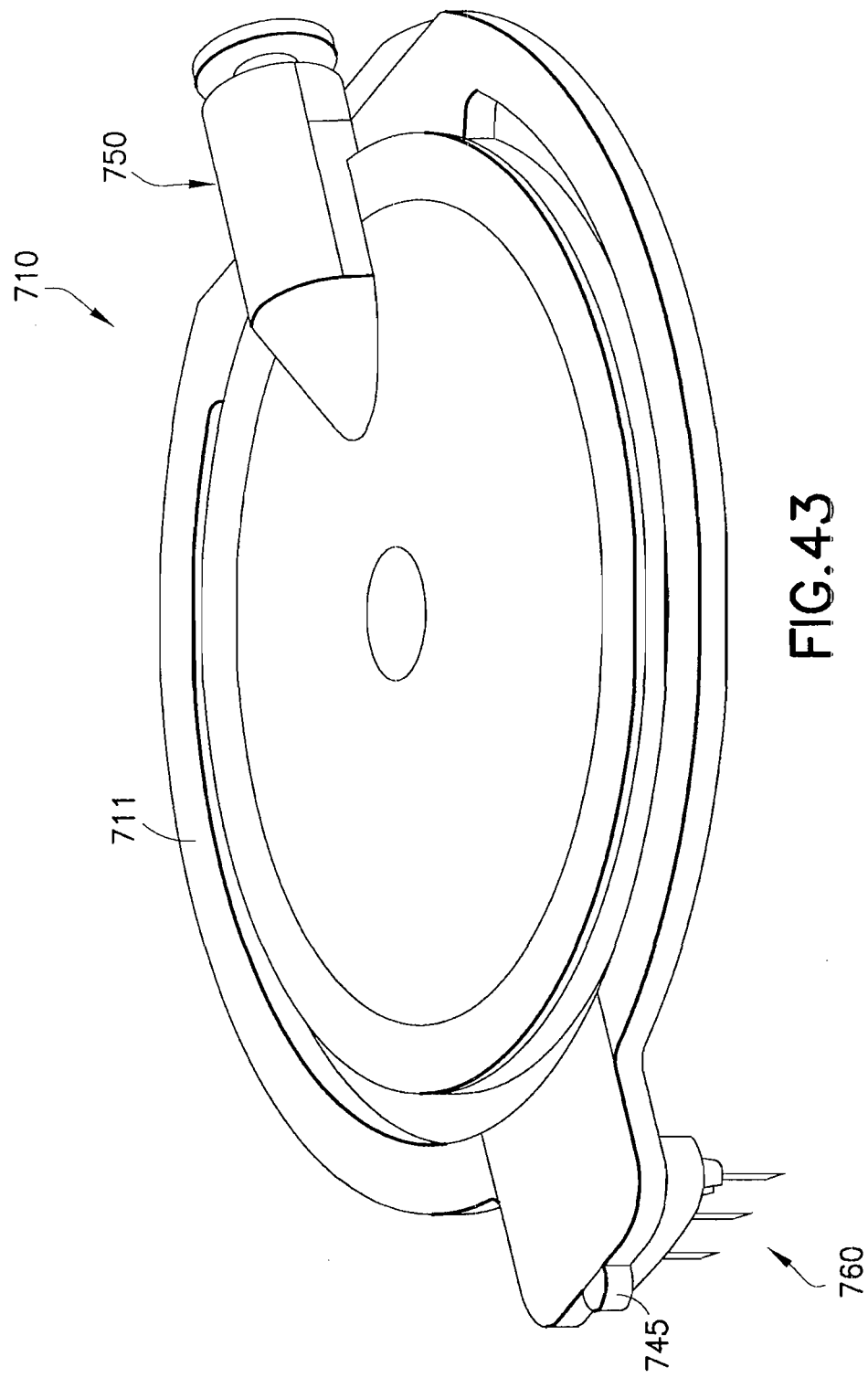
Figure 44:
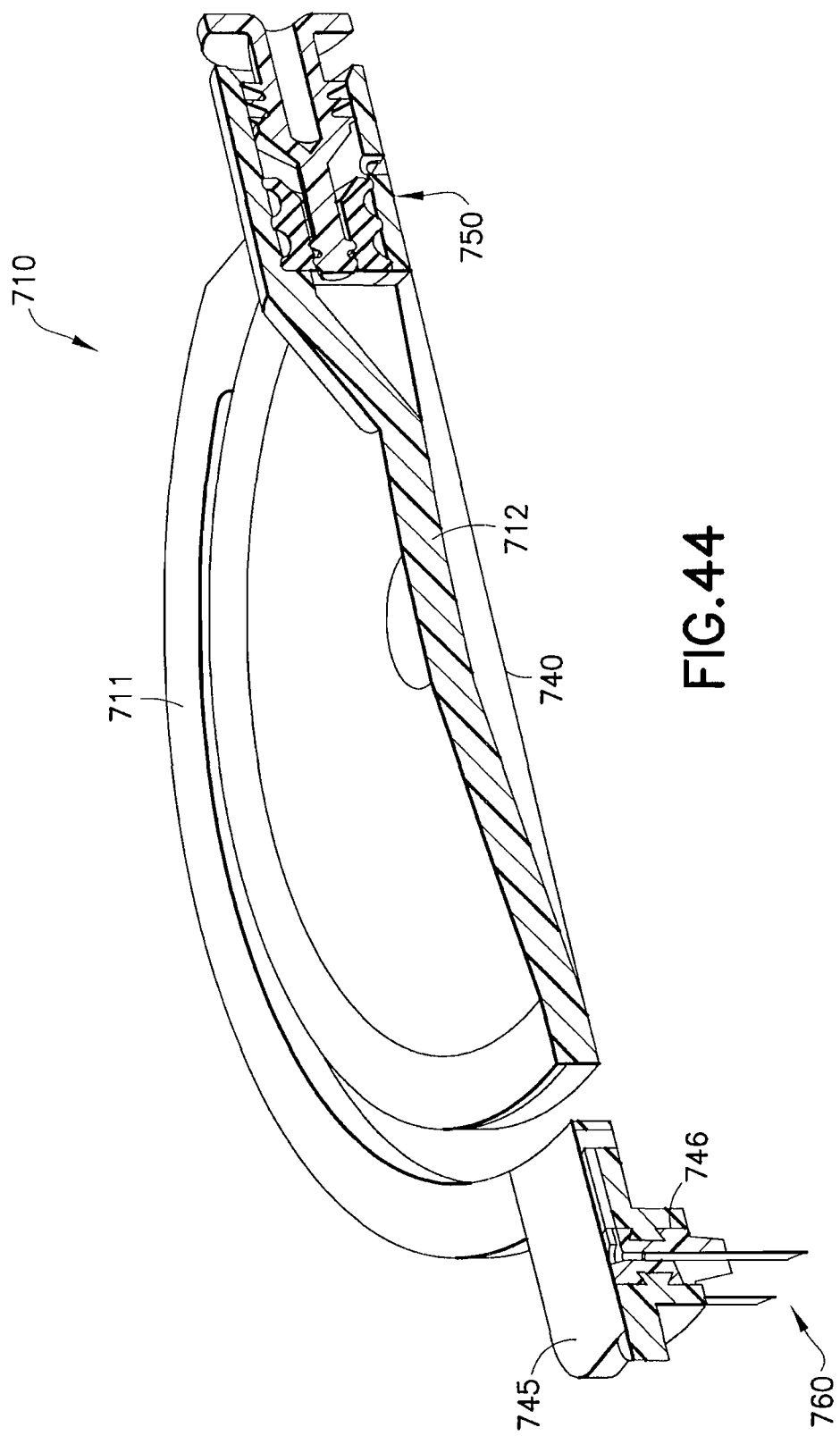
FIGS. 44 through 48 are cross-sectional views of the reservoir and valve subassembly of the patch-like injector or infusor system of FIG. 37.
Figure 46:
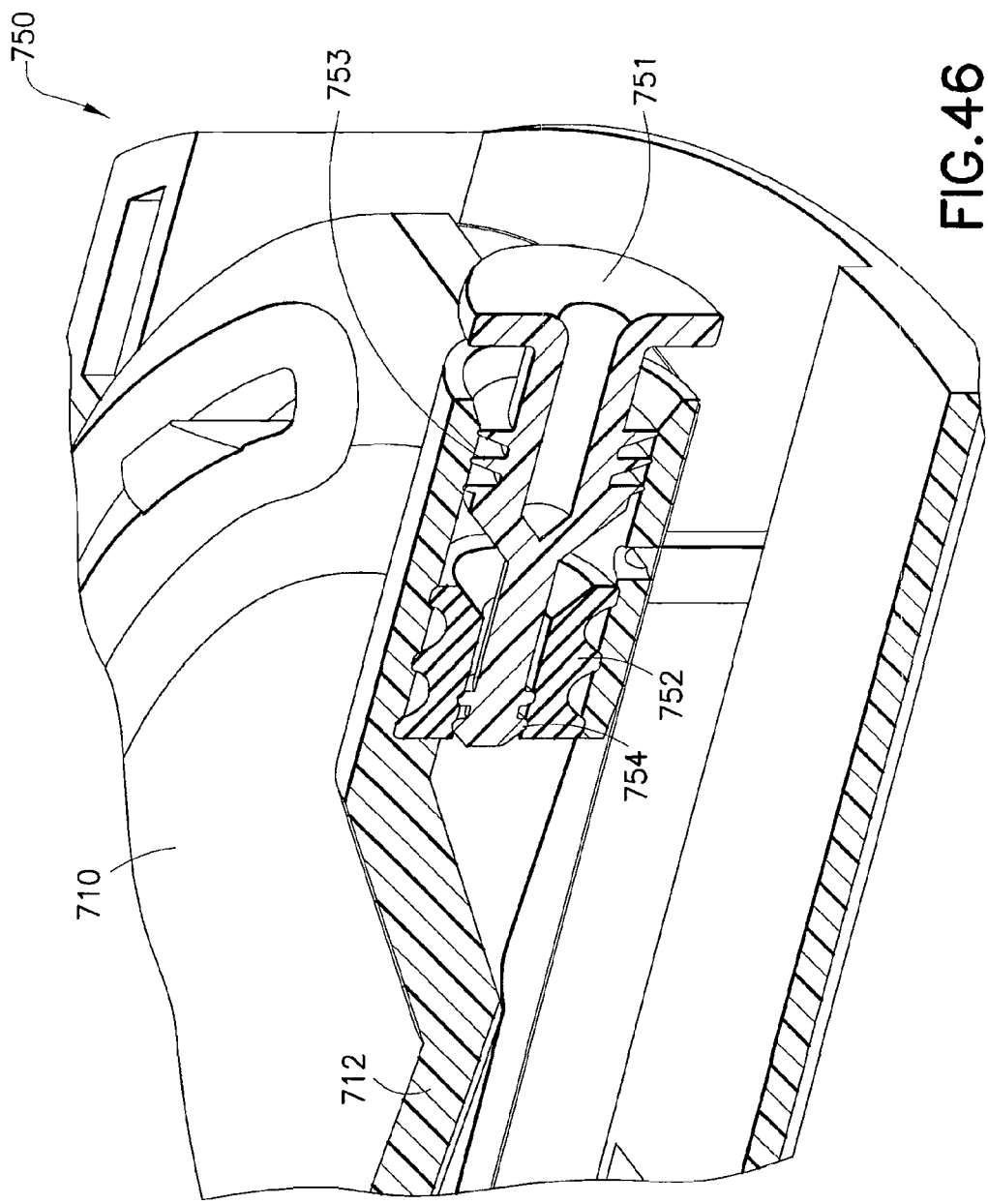
Figure 47:
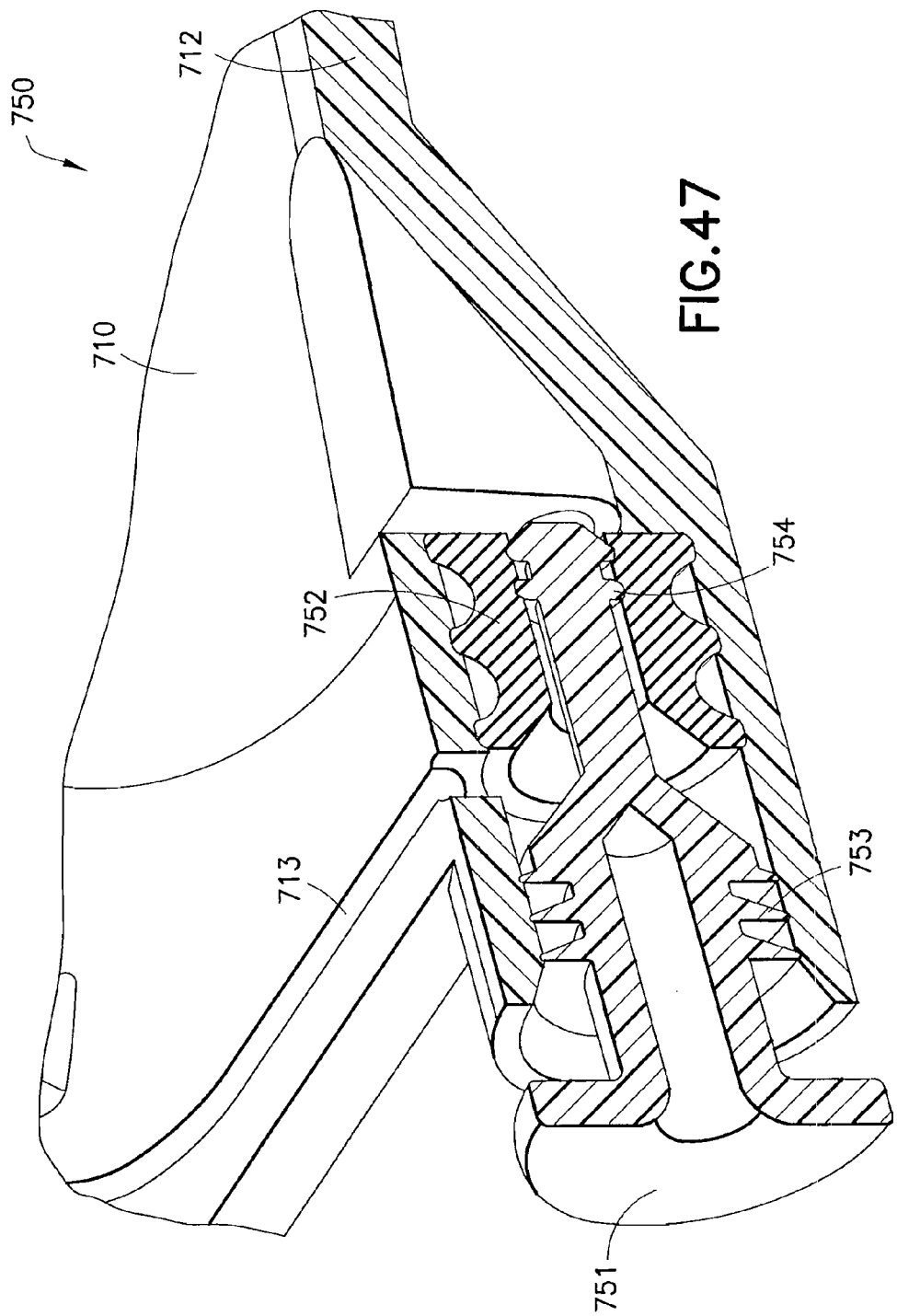
Figure 48:
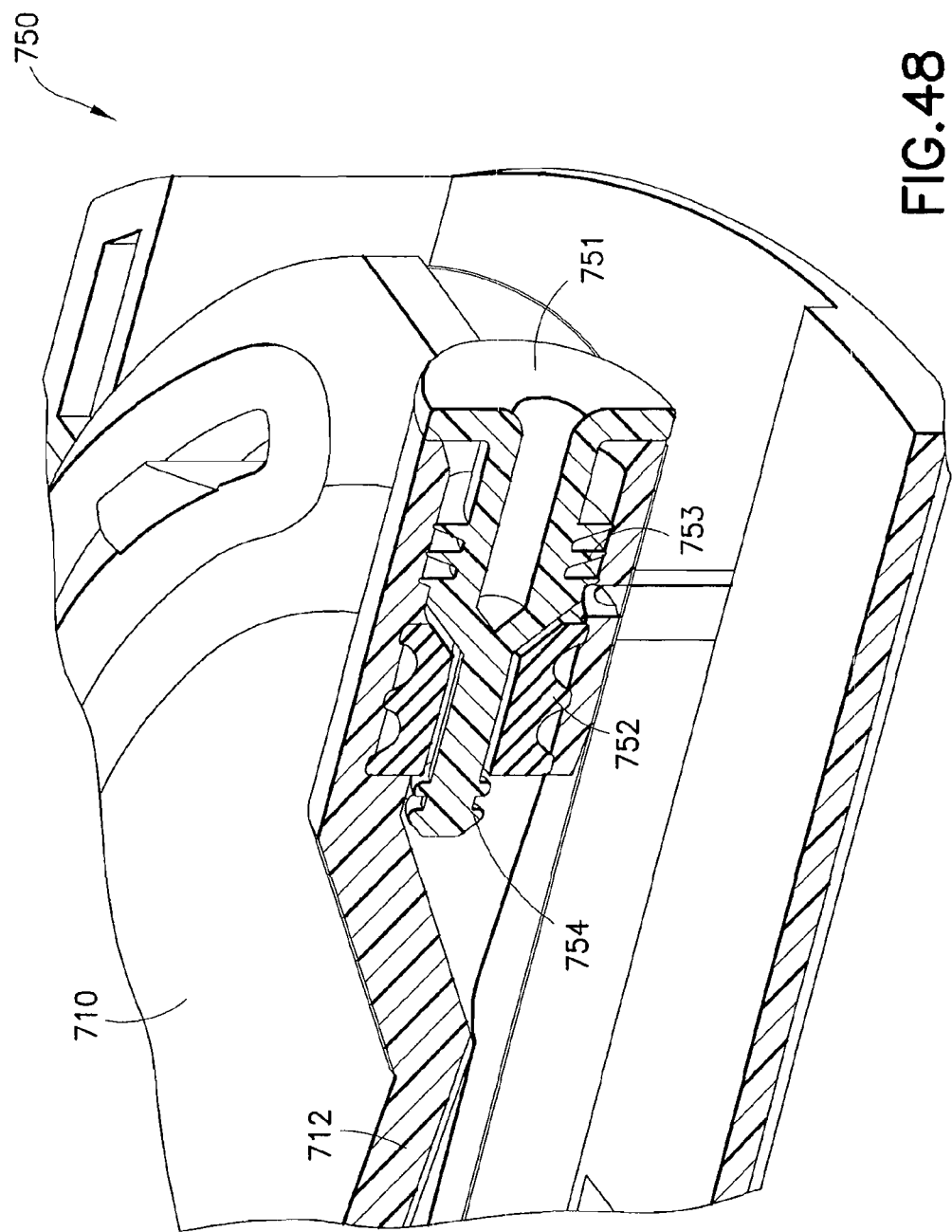
Figure 49:
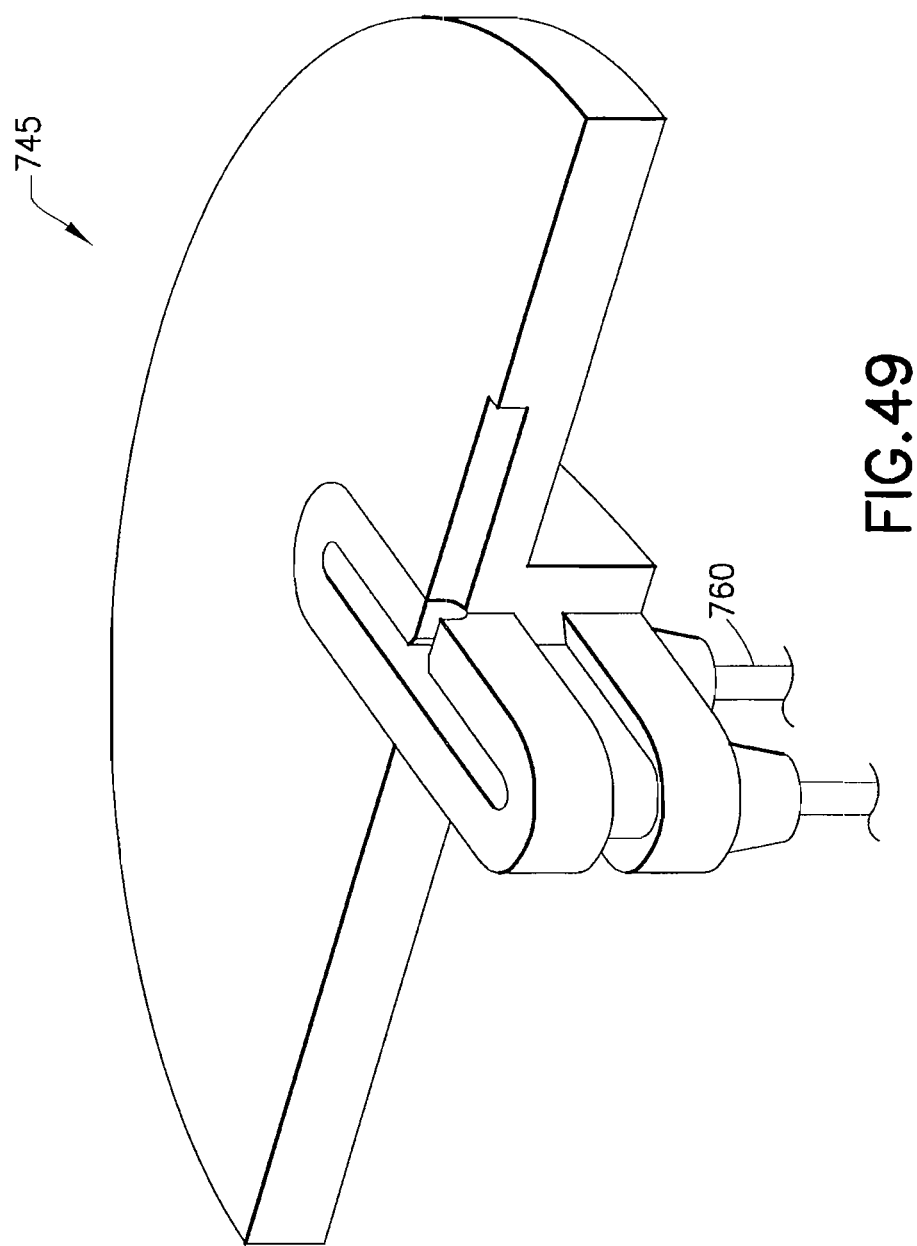
FIG. 49 is a cross-sectional view of a two-shot patient needle manifold subassembly of the patch-like injector or infusor system of FIG. 37.

In a fifth embodiment of the device, shown in FIGS. 37 through 41, a push-button design 700 is shown wherein the activation and energizing of the device is also accomplished in a single multi-function/step process. FIGS. 37 through 41 are cross-sectional views of the fifth embodiment of a patch-like injector or infusor system. FIGS. 42 through 44 are cross-sectional views of the reservoir subassembly of the patch-like injector or infusor system of FIG. 37. FIGS. 46 through 48 are cross-sectional views of a valve subassembly of the patch-like injector or infusor system of FIG. 37 in closed and open positions, and FIG. 49 is a view of a two-shot patient needle manifold subassembly of the patch-like injector or infusor system of FIG. 37. FIGS. 50 through 54 are views of example assembly steps of the patch-like injector or infusor system of FIG. 37.

In the fifth embodiment of the present invention, an infusion device 700 includes an upper housing 705, reservoir 710, a Belleville spring retention handle 730, at least one Belleville spring 735, a reservoir film 740, a patient needle manifold 745, at least one patient microneedle 760, and a lower housing 770. The reservoir 710 is shown in greater detail in FIGS. 42 through 44, and further includes an outer circumference arm 711 having a fluid communication path 713 extending from the valve assembly 750 to the manifold 745. The reservoir 710 further includes a rigid portion 712 disposed opposite the film 740, capturing a substance therebetween and placing it in fluid communication with the valve assembly 750. The manifold 745 can incorporate a dissimilar material dovetail bonding 746 described in greater detail below with reference to FIG. 101. The device further includes a valve assembly 750 adjacent to a push button 780. The valve assembly 750 is shown in greater detail in FIGS. 45 through 46. Finally, an improved safety assembly is provided to activate and shield the microneedles after use, and is described and shown in greater detail below.

As shown in FIGS. 37 through 41, the embodiment of the present invention 700 can be constructed to provide a patch-like, wearable, self-contained substance infusion device that can be used to deliver a variety of medications to a patient. The device 700, provides a hidden patient needle or needles 760 prior to and during use, and can be secured to a patient via an adhesive surface (not shown) disposed on the lower housing 770. The activation of the device 700 following proper placement can be achieved through a simple motion of the push button 780. Specifically, the slidable engagement of the push button 780 serves to release the Belleville spring 735, thereby pressurizing the contents of the reservoir 710. The push button 780 engagement further serves to open a valve assembly 750, establishing a continuous fluid communication path between the reservoir 710 contents and the patient microneedles 760. Finally, the push button 780 engagement serves to release a support member (not shown) from the patient needle manifold 745, allowing the patient needles 760 to seat and completing device activation. In achieving the above functions, the push button 780 engagement further serves to release a safety assembly described in greater detail below, thereby reducing the risk of sticks by the patient needles 760. A significant benefit of the embodiment described above includes the ability to achieve each of these functions in a single push button action. Additionally, another significant benefit includes the use of a continuous fluid communication path comprised of the reservoir subassembly.

Returning to FIG. 37, once the device 700 is properly positioned substantially as described above, the device 700 is activated by sliding the push button 780 inward towards the device. This slidable engagement drives an incline 782 towards the retention handle 730. As the incline 782 and retention handle 730 engage, the retention handle 730 is displaced from a position securing the Belleville spring 735, allowing the spring 735 to pressurize the reservoir 710. Specifically, this step releases the Belleville spring 735 allowing it to press against the flexible film 740 of the reservoir 710, pressurizing the reservoir contents between the film 740 and the rigid portion 712. This activation step also serves to displace a support from beneath manifold 745, releasing the patient needle manifold 745 which is urged downward by the compression of the outer circumference arm 711 (or any number of springs as described above) and seating the patient needles 760. As further shown in FIGS. 42 through 45, the outer circumference arm 711 can also extend about the opposite side of the reservoir 710 to provide a substantially continuous outer circumference arm that can act as a needle stabilizer, extending from the valve assembly 750 to the manifold 745. As shown in FIG. 42, the needle stabilizer can be provided about an arcuate path around the periphery of the reservoir, opposite to the needle conduit comprised of the outer circumference arm 711 and fluid path 713 therein, to stabilize the needles when the outer circumference arm 711 is used as the downward urging spring. Finally, the activation step also serves to open the valve assembly 750, establishing a fluid communication path between the reservoir 710 and the patient needles 760.

Figure 45:
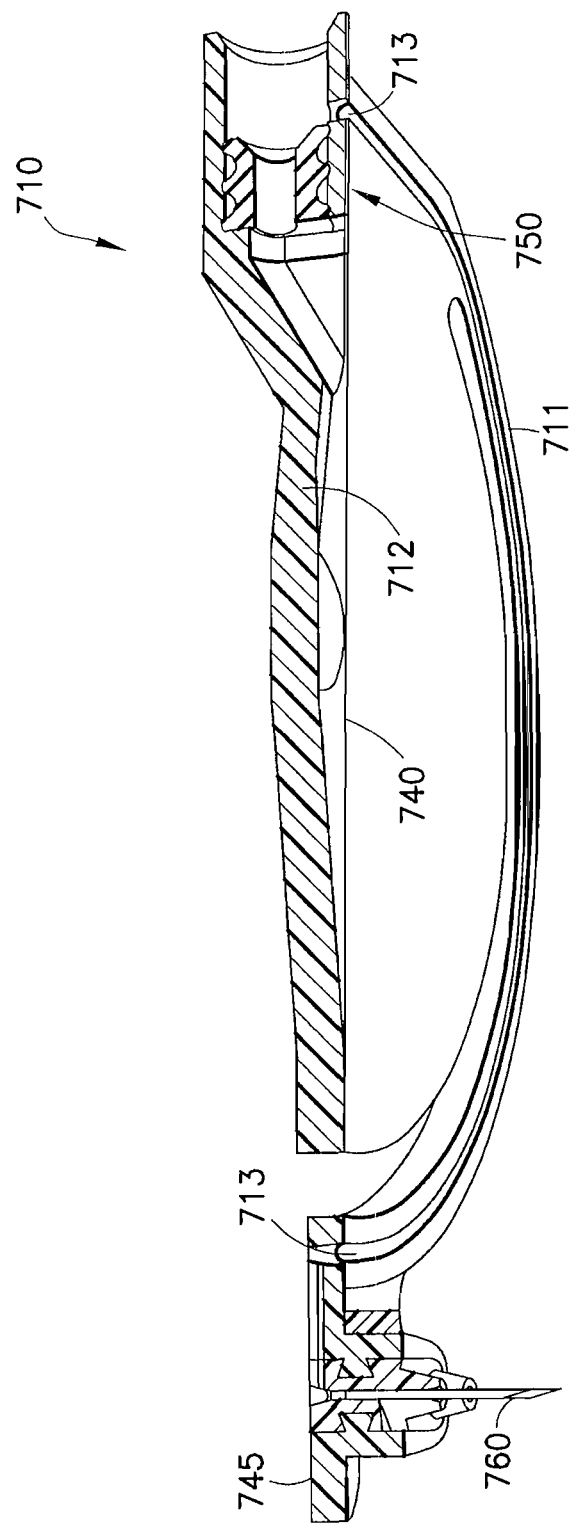

Specifically, as shown in cross-sectional views FIGS. 45, 46 and 47, the valve assembly 750 includes a plastic button 751 slidably engaged within a rubber stopper 752 in fluid communication with the reservoir 710. That is, for fluid communication, the released contents of the reservoir first leave the containment of the reservoir, and are directed to then travel to the needle. The valve assembly 750 has as an initial state and an activated state, and includes a large diameter distal end having a distal set of radially projecting fins, or ribs 753 forming a body seal, and a reduced diameter proximal end having a proximal set of detents 754 forming a reservoir seal. As shown in FIG. 47, the reservoir seal of detents 754 is within the fluid flow path, whereas only one side, the inner side, of the body seal is ever in contact with the fluid flow path. The outer side of the body seal of ribs 753 facing the button 751 is never in contact with the fluid flow path. In use, the button 751 will eventually be pushed into an activated state by the movement of the push button 780 and the set of detents 754 will be advanced from engagement with the rubber stopper 752, which permits the drug to flow from the reservoir 710, past the detents 754 and into the fluid path 713. As stated above, a significant benefit to each embodiment described above includes the ability to achieve each step in a single push button action. Additionally, another significant benefit includes the use of a continuous fluid communication path comprised of the reservoir subassembly.

Figure 50:
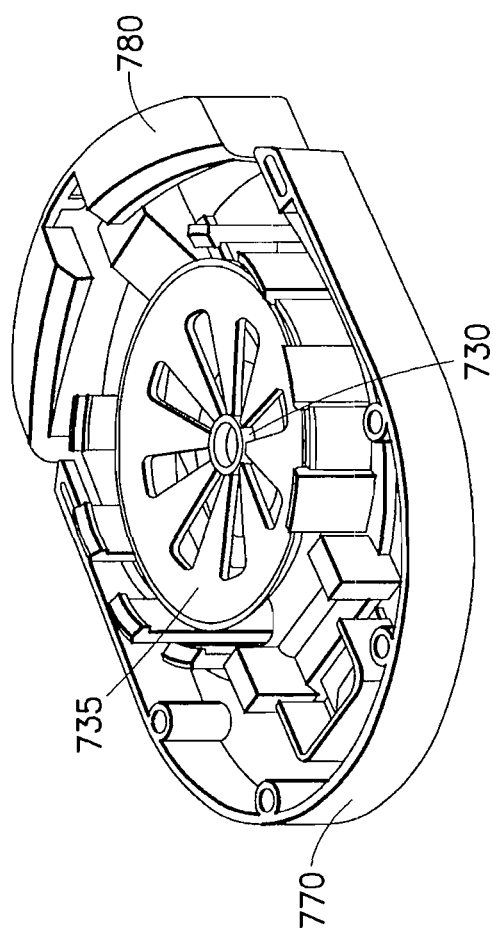
FIGS. 50 through 54 are views from a first perspective angle of assembly steps of the patch-like injector or infusor system of FIG. 37.
Figure 51:
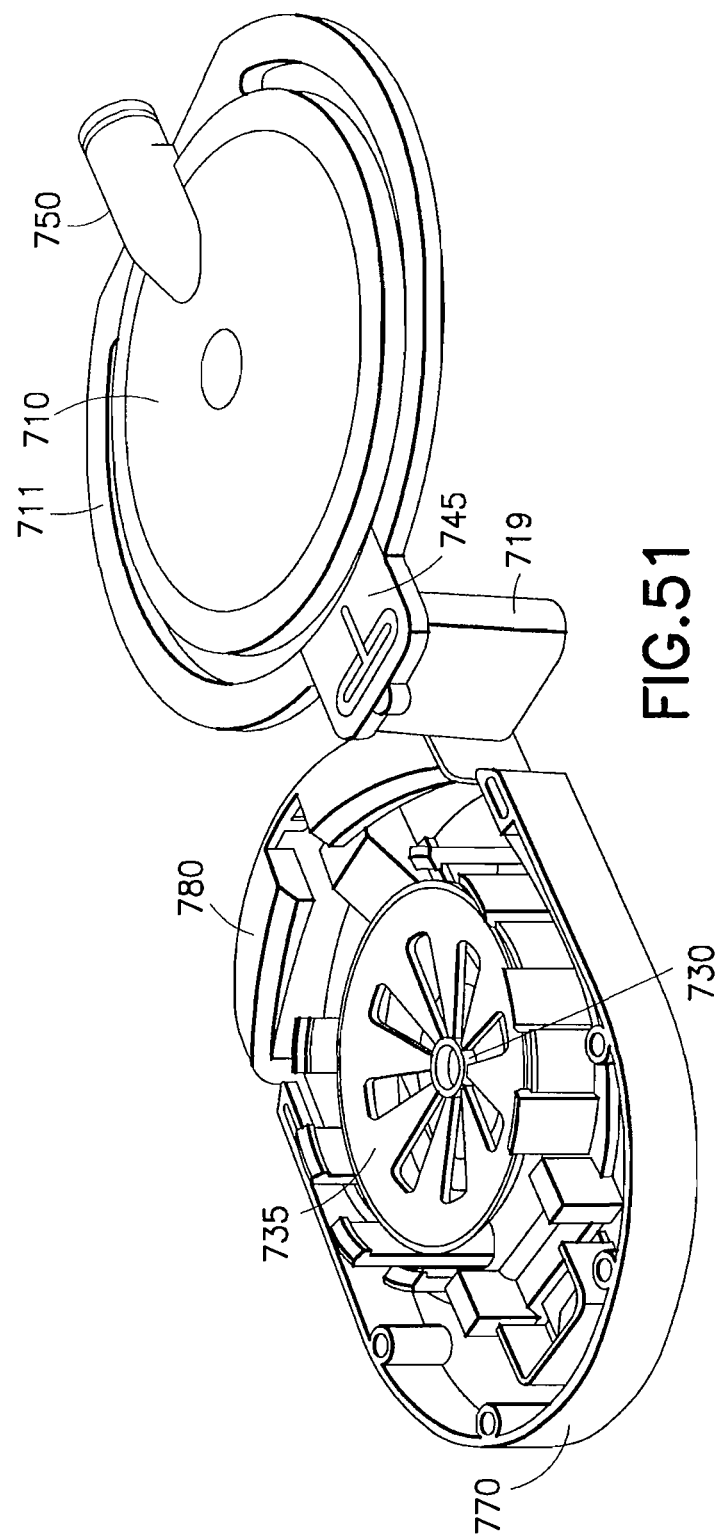
Figure 52:
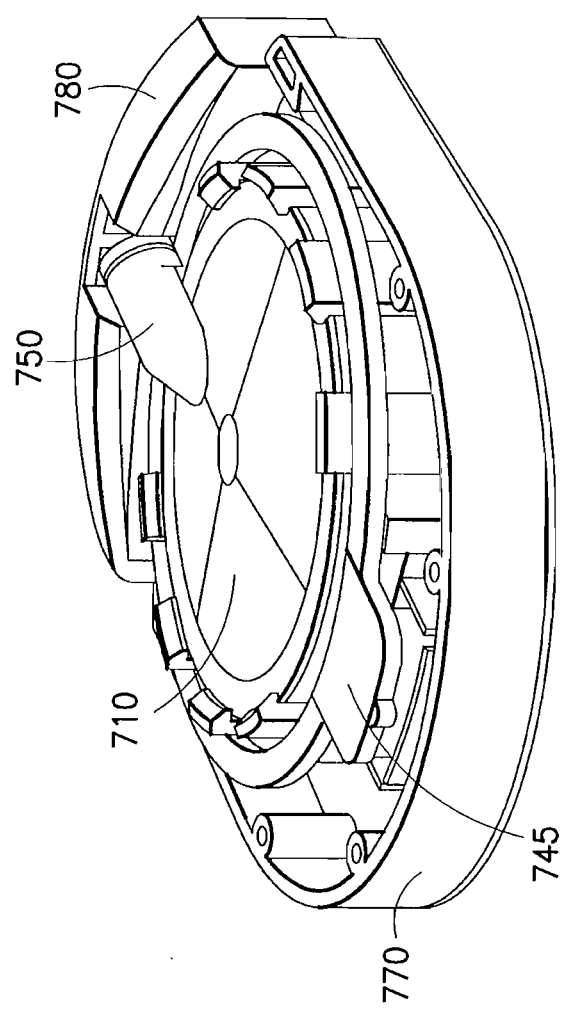
Figure 53:
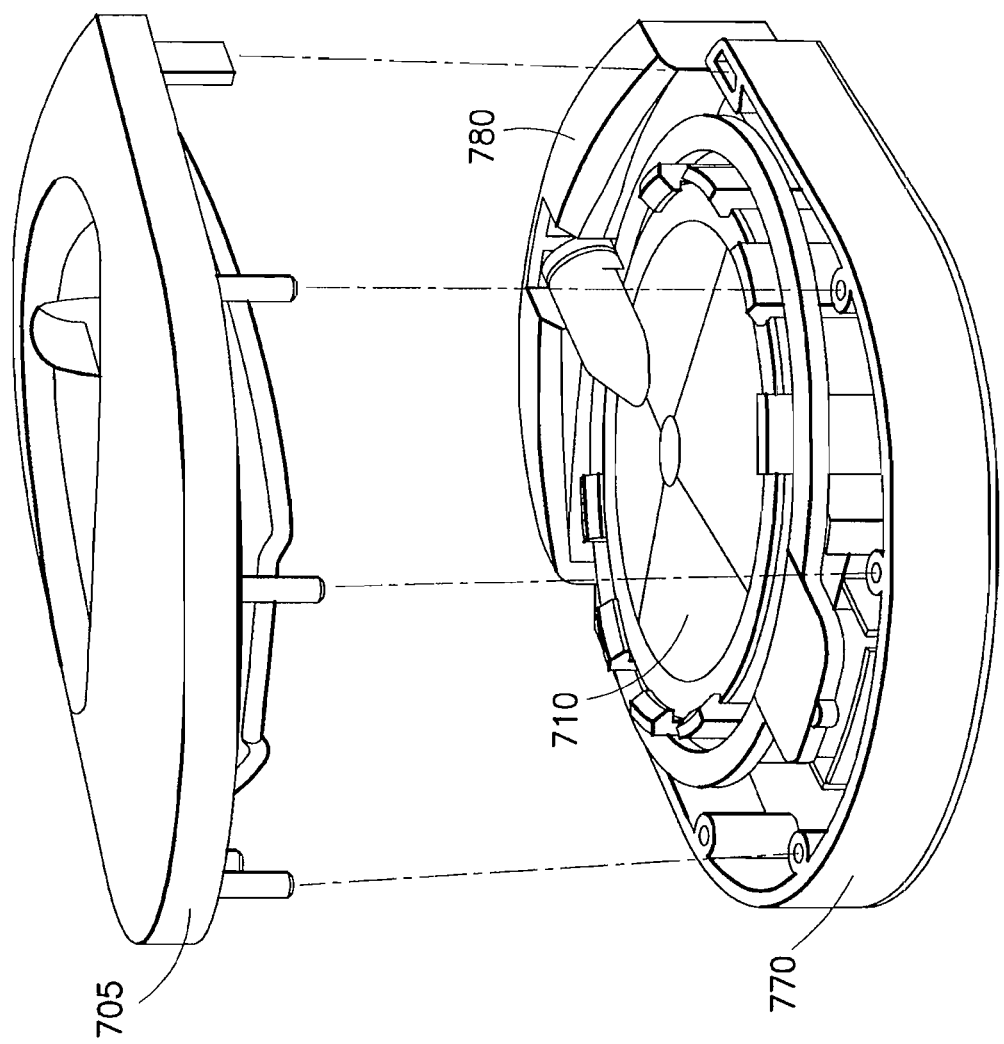
Figure 54:
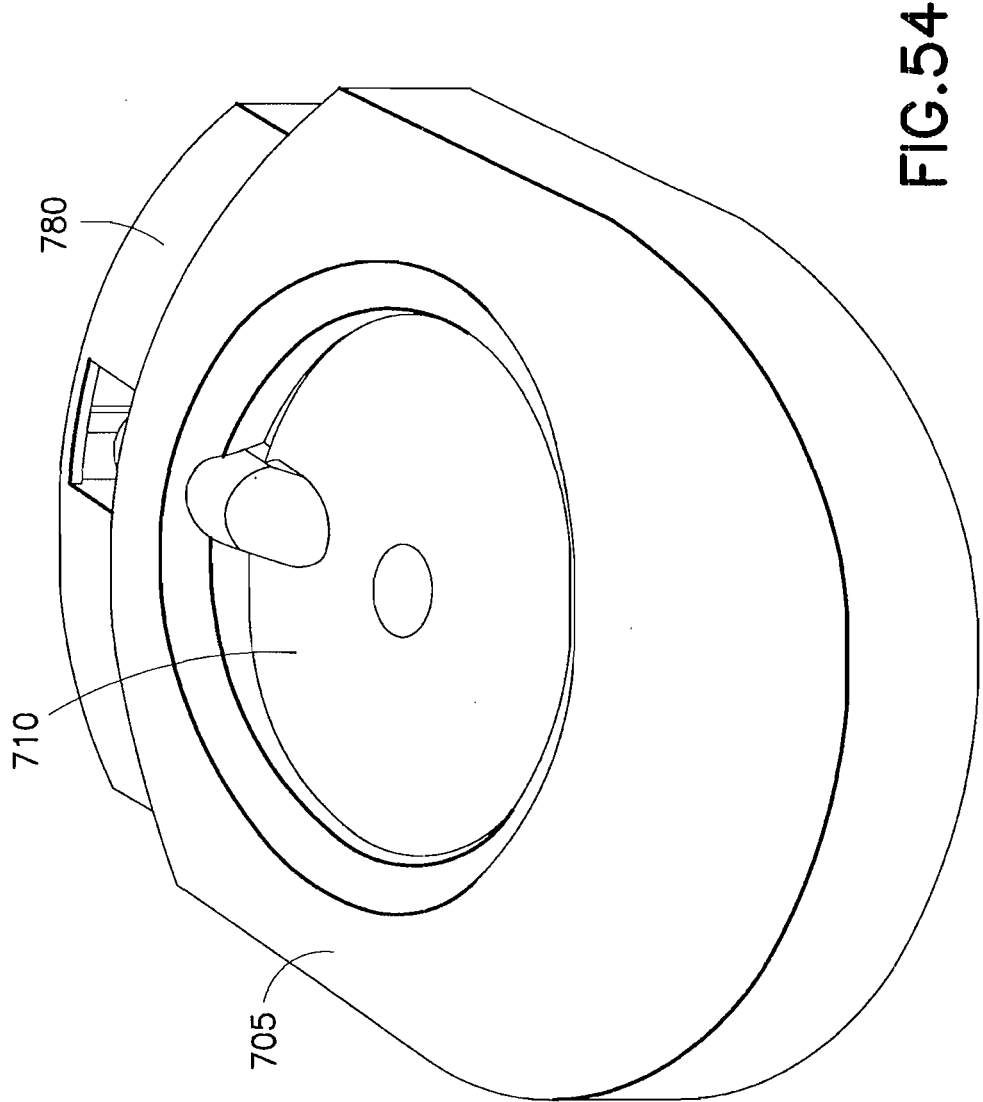
Figure 55:
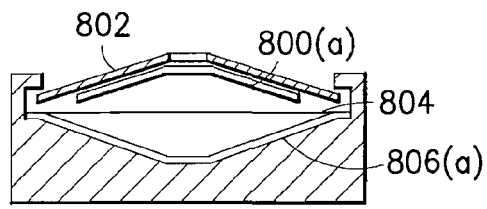
FIGS. 55 through 60 are cross-sectional views of a Belleville spring and follower.

A series of assembly FIGS. 50 through 54 show an example assembly process for the above device. In FIG. 50, the lower housing 770, secured Belleville spring 730, and a push button 780 are prepared to receive the reservoir and upper housing. In FIG. 51, the reservoir 710, and manifold 745 (including an optional needle cap 719) are prepared to drop into the lower housing 770. In FIG. 53, the upper housing 705 is then prepared to drop onto the lower housing 770.

In each embodiment described above, the reservoir (i.e., 150 of FIG. 4) of the infusion device can be comprised of a rigid portion (i.e., 152 of FIG. 4) used in conjunction with one or more non-distensible but flexible films (i.e., 151 of FIG. 4), such as metallized films, and can contain any number of substances between either a first and second film, where either the first or second film is also positioned against the rigid portion, or between a first film and the rigid portion. The rigid portion, or reservoir base, can be comprised of and serve as a hard portion of the reservoir against which the flexible film can be pressed. The rigid portion can contain a dished out central section and a flange, provided about the perimeter of the rigid portion to allow for heat sealing the flexible film, or film lid to the rigid portion and forming a content reservoir, or chamber, therebetween. As at least one wall of the chamber comprises a flexible film and at least one wall of the chamber comprises a rigid surface, one or more Belleville springs (i.e., 130 of FIG. 4) can be placed adjacent to the flexible film and used to apply a substantially constant pressure to the flexible film, and pressurize the reservoir chamber and contents.

The Belleville spring, which can be further provided having a spring follower as described in greater detail below, is provided to apply a substantially even and constant pressure to the flexible film of the reservoir, compressing the contents of the reservoir between the flexible film and the rigid portion, and forcing the contents from the reservoir through one or more flow paths via a valve assembly (i.e., 120 of FIG. 1) where desired. As noted above, the reservoir can also be made up of two or more flexible, non-distensible films, wherein the contents can be contained between the films and at least one film is attached to the rigid portion to provide a rigid base for compressing and pressurizing the contents of the reservoir. In yet another embodiment of the reservoir subassembly, the flow rate is automatically adjusted from an initial high rate to one or more stepped-down lower flow rates. Additional details of an adjusting flow rate are further discussed in a U.S. patent application of Jim Fentress et al., Ser. No. 10/396,719, filed Mar. 26, 2003, entitled "Multi-Stage Fluid Delivery Device And Method", the entire content of which is incorporated herein by reference.

The flexible film of the reservoir subassembly (i.e., element 151 of FIG. 4) can be made of non-distensible materials or laminates, such as metal-coated films or other similar substances. For example, one possible flexible laminate film which can be used in the reservoir of the first embodiment (i.e., element 151 of FIG. 4) can be comprised of a first polyethylene layer, a second chemical layer as known to those skilled in the art to provide an attachment mechanism for a third metal layer which is chosen based upon barrier characteristics, and followed by a fourth layer comprised of either polyester or nylon. By utilizing a metal-coated or metallized film in conjunction with a rigid portion, the barrier properties of the reservoir are improved, thereby increasing or improving the shelf life of the contents contained within. For example, where reservoir content includes insulin, the primary materials of contact in the reservoir of the embodiments described above include linear, low-density polyethylene (LLDPE), low-density polyethylene (LDPE), cyclic olefin copolymer (COC) and Teflon. As described in greater detail below, the primary materials of contact in the remaining flow path of the reservoir contents include polyethylene (PE), medical grade acrylic, and stainless steel. Such materials which are in extended contact with the contents of the reservoir preferably pass ISO 10-993 and other applicable biocompatibility testing.

The reservoir is further preferably able to be stored for the prescribed shelf life of the reservoir contents in applicable controlled environments without adverse effect to the contents and is capable of applications in a variety of environmental conditions. Additionally, the barrier provided by the components of the reservoir do not permit the transport of gas, liquid and solid materials into or out of the contents at a rate greater than that allowable to meet the desired shelf life. In the embodiments shown above, the reservoir materials are capable of being stored and operated in a temperature range of approximately 34 to 120 degrees F., and can have a shelf life of two or more years.

In addition to satisfying stability requirements, the reservoir can further ensure operation by successfully passing any number of leak tests, such as holding a 30 psi sample for 20 minutes without leaking. Additional filling, storage and delivery benefits resulting from the configuration of the reservoir include minimized headspace and adaptability as described in greater detail below.

The reservoir is preferably evacuated prior to filling, as described in greater detail below. By evacuating the reservoir prior to filling and having only a slight depression in the hard floor of the rigid portion, headspace and excess waste within the reservoir can be minimized. In addition, the shape of the reservoir can be configured to adapt to the type of energizing mechanism used, e.g., a disk or Belleville spring having any number of diameter and height dimensions. Additionally, using an evacuated flexible reservoir during filling minimizes any air or bubbles within the filled reservoir. The use of a flexible reservoir is also very beneficial when the device is subjected to external pressure or temperature variations, which can lead to increased internal reservoir pressures. In such case, the flexible reservoir expands and contracts with the contents, thereby preventing possible leaks due to expansion and contraction forces.

Yet another feature of the reservoir includes the ability to permit automated particulate inspection at the time of fill or by a user at the time of use. One or more reservoir barriers, such as the rigid portion, can be molded of a transparent, clear plastic material, which allows inspection of the substance contained within the reservoir. The transparent, clear plastic material is preferably a cyclic olefin copolymer that is characterized by high transparency and clarity, low extractables and biocompatibility with the substance contained in the reservoir. In such applications, the reservoir includes minimal features which could possibly obstruct inspection (i.e. rotation during inspection is permitted).

A fluid path between the reservoir (i.e., 150 of FIG. 4) and the patient microneedles (i.e., 141 in FIG. 1) in the embodiments described above is constructed of materials similar or identical to those described above for the reservoir, and that satisfy numerous biocompatibility and storage tests. For example, as shown in Table 1 below, where device content includes insulin, the primary materials of contact in the reservoir of the embodiments include linear, low-density polyethylene, cyclic olefin copolymer and Teflon, and can also include a transparent, clear plastic. The primary materials of contact in the remaining flow path between the reservoir and the microneedles of the patient needle manifold include polyethylene, medical grade acrylic, and/or stainless steel.

TABLE 1

| Path Component | Material |
| --- | --- |
| Reservoir | Polyethylene, cyclic olefin copolymer and/or Teflon |
| Reservoir Film | Metal-coated film, such as polyethylene, aluminum, polyester and/or nylon with a chemical tie layer, such as the product A83, manufactured by Beacon Converters of Saddle Brook N.J. |
| Patient Needle Manifold | Polyethylene and/or medical grade acrylic |
| Patient Needle | Stainless steel |

Specifically, the patient needles (i.e., 141 of FIG. 1) can be constructed of stainless steel, and the patient needle manifold (i.e. 140 of FIG. 1) can be constructed of polyethylene and/or medical grade acrylic. Such materials when in extended contact with the contents of the reservoir preferably pass ISO 10-993 biocompatibility testing.

As shown in each embodiment above, a disk or Belleville spring (i.e., 130 of FIG. 1) is included in the devices for applying an essentially even, constant force to the reservoir to force the contents from the reservoir, and is hereinafter sometimes referred to as a constant force spring. The constant force spring is used to store energy that, when released by device energizing, pressurizes the reservoir at the time of use. The Belleville spring is held in a flexed state by a retention disk, or handle (i.e., 135 in FIG. 1), that is positioned at the center of a plurality of spring fingers. In doing so, the Belleville spring is prevented from putting stress on the film (i.e., 151 of FIG. 4) of the reservoir or any remaining device components during storage. The retaining disk is sufficiently rigid to resist spring tension and deformation, and should not fail under normal tensile load.

When the retention disk is pulled free of the Belleville spring, the fingers of the spring drop, and in doing so, exert a force on the film lid of the reservoir. The edge of the Belleville spring is trapped about an outer circumference of the reservoir. The Belleville spring can be configured to preferably create a pressure within the reservoir of from about 1 to 50 psi, and more preferably from about 2 to about 25 psi, and most preferably from about 15 to about 20 psi for intradermal delivery of the reservoir contents. For sub-cutaneous injection or infusion, a range of about 2 to 5 psi may be sufficient. The Belleville spring can be sized between about 1.15 to 1.50 inches in diameter, preferably 1.26 inches, and further include a spring follower to allow for a full 600 µl delivery.

FIGS. 55 through 60 illustrate examples of various versions of a Belleville spring follower 800(*a*) through 800(*c*) which can each be used in association with a Belleville spring 802 in the embodiments described above. In each version, a displacement member 800 is provided adjacent to the Belleville spring 802, such that as the Belleville spring 802 travels between a flexed and relaxed position (i.e. is released by a retention member), the spring 802 exerts a substantially constant force upon the displacement member, or follower 800, rather than directly upon the flexible film (i.e., 151 of FIG. 4) of the reservoir. The follower 800 in turn applies a more evenly distributed force to the reservoir film 804.

Figure 56:
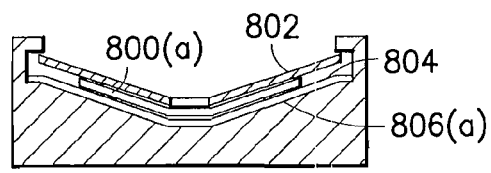
Figure 57:
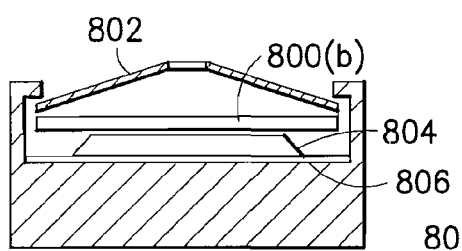
Figure 58:
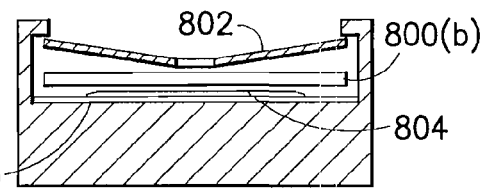
Figure 59:
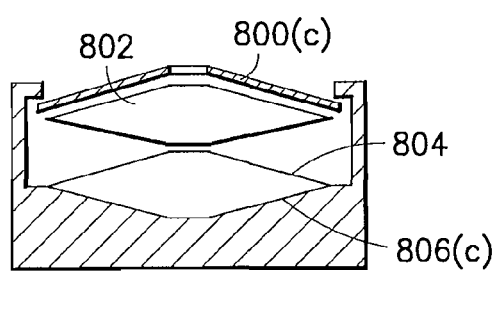
Figure 60:
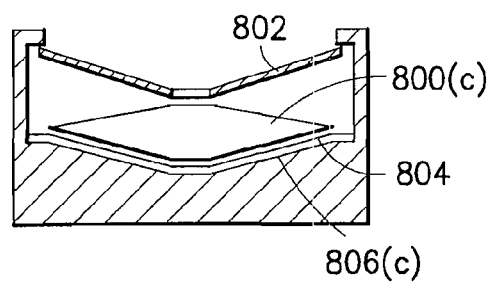

For example, as shown in Figure pairs 55 and 56, 57 and 58, and 59 and 60, which illustrate a flexed and released Belleville spring 802 position, respectively, the example followers 800(*a*), 800(*b*) and 800(*c*) conform to a shape of the rigid reservoir wall 806(*a*), 806(*b*), and 806(*c*). Therefore, when the Belleville spring 802 is released as shown in FIGS. 56, 58 and 60, the Belleville spring 802 forces the followers 800(*a*), 800(*b*) and 800(*c*) tightly against the rigid reservoir wall 806(*a*), 806(*b*), and 806(*c*) respectively, minimizing dead space losses. An overmolded Belleville spring, as described in greater detail below with reference to FIGS. 90 through 92, can also be provided to further minimize such losses.

Each embodiment described above also contains at least one patient needle, or microneedle (i.e., 141 of FIG. 1), but may contain several, such as the three microneedles. Each microneedle is preferably at least 31 gauge or smaller, such as 34 gauge, and is anchored within a patient needle manifold (i.e., 140 of FIG. 1) which can be placed in fluid communication with the reservoir. The microneedles, when more than one is included in the device, can also be of differing lengths, or gauges, or a combination of both differing lengths and gauges, and can contain one or more ports along a body length, preferably located near the tip of the needle or near the tip bevel if the needle has one.

In the embodiments described above, the use of multiple 34 gauge needles to deliver the reservoir contents is practical as the infusion occurs over a longer period than typically associated with an immediate syringe injection requiring a much larger cannula, or needle. In the disclosed embodiments, any microneedles can be used which target either an intradermal or subcutaneous space, however, the embodiments shown above include intradermal microneedles of between 1 and 4 mm in length (i.e., 2 mm), and the arrangement of these patient needles can be in a linear or nonlinear array, and can include any number of needles as required by the specific application.

The patient needles are positioned in a patient needle manifold. In the patient needle manifold of each embodiment described above (i.e., 140 of FIG. 1), at least one fluid communication path, or feed channel, is provided to each patient needle. The manifold may simply have a single path to one or more patient needles, or may provide multiple fluid paths or channels routing contents to each needle separately. These paths or channels may further comprise a tortuous path for the contents to travel, thereby affecting fluid pressures and rates of delivery, and acting as a flow restrictor. The channels or paths within the patient needle manifold can range in width, depth and configuration depending upon application, where channel widths are typically between about 0.015 and 0.04 inch, preferably 0.02 inch, and are constructed to minimize dead space within the manifold.

The devices described above are suitable for use in administering various substances, including medications and pharmaceutical agents, to a patient, and particularly to a human patient. As used herein, a pharmaceutical agent includes a substance having biological activity that can be delivered through the body membranes and surfaces, and particularly the skin. Examples, listed in greater detail below, include antibiotics, antiviral agents, analgesics, anesthetics, anorexics, antiarthritics, antidepressants, antihistamines, anti-inflammatory agents, antineoplastic agents, vaccines, including DNA vaccines, and the like. Other substances that can be delivered intradermally or subcutaneously to a patient include human growth hormone, insulin, proteins, peptides and fragments thereof. The proteins and peptides can be naturally occurring, synthesized or recombinantly produced. Additionally, the device can be used in cell therapy, as during intradermal infusion of dendritic cells. Still other substances which can be delivered in accordance with the method of the present invention can be selected from the group consisting of drugs, vaccines and the like used in the prevention, diagnosis, alleviation, treatment, or cure of disease, with the drugs including Alpha-1 anti-trypsin, Anti-Angiogenesis agents, Antisense, butorphanol, Calcitonin and analogs, Ceredase, COX-II inhibitors, dermatological agents, dihydroergotamine, Dopamine agonists and antagonists, Enkephalins and other opioid peptides, Epidermal growth factors, Erythropoietin and analogs, Follicle stimulating hormone, G-CSF, Glucagon, GM-CSF, granisetron, Growth hormone and analogs (including growth hormone releasing hormone), Growth hormone antagonists, Hirudin and Hirudin analogs such as hirulog, IgE suppressors, Insulin, insulinotropin and analogs, Insulin-like growth factors, Interferons, Interleukins, Leutenizing hormone, Leutenizing hormone releasing hormone and analogs, Low molecular weight heparin, M-CSF, metoclopramide, Midazolam, Monoclonal antibodies, Narcotic analgesics, nicotine, Non-steroid anti-inflammatory agents, Oligosaccharides, ondansetron, Parathyroid hormone and analogs. Parathyroid hormone antagonists, Prostaglandin antagonists, Prostaglandins. Recombinant soluble receptors, scopolamine, Serotonin agonists and antagonists, Sildenafil, Terbutaline, Thrombolytics, Tissue plasminogen activators, TNF-, and TNF-antagonist, the vaccines, with or without carriers/adjuvants, including prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, addiction, arthritis, cholera, cocaine addiction, diphtheria, tetanus, HIB, Lyme disease, meningococcus, measles, mumps, rubella, varicella, yellow fever, Respiratory syncytial virus, tick borne japanese encephalitis, pneumococcus, *streptococcus*, typhoid, influenza, hepatitis, including hepatitis A, B, C and E, otitis media, rabies, polio, HIV, parainfluenza, rotavirus, Epstein Barr Virus, CMV, chlamydia, non-typeable *haemophilus, moraxella catarrhalis*, human papilloma virus, tuberculosis including BCG, gonorrhoea, asthma, atheroschlerosis malaria, *E-coli*, Alzheimers, *H. Pylori, salmonella*, diabetes, cancer, herpes simplex, human papilloma and the like other substances including all of the major therapeutics such as agents for the common cold, Anti-addiction, anti-allergy, anti-emetics, anti-obesity, antiosteoporeteic, anti-infectives, analgesics, anesthetics, anorexics, antiarthrities, antiasthmatic agents, anticonvulsants, anti-depressants, antidiabetic agents, antihistamines, anti-inflammatory agents, antimigraine preparations, antimotion sickness preparations, antinauseants, antineoplastics, antiparkinsonism drugs, antipruritics, antipsychotics, antipyretics, anticholinergics, benzodiazepine antagonists, vasodilators, including general, coronary, peripheral and cerebral, bone stimulating agents, central nervous system stimulants, hormones, hypnotics, immunosuppressives, muscle relaxants, parasympatholytics, parasympathomimetrics, prostaglandins, proteins, peptides, polypeptides and other macromolecules, psychostimulants, sedatives, sexual hypofunction and tranquilizers and major diagnostics such as tuberculin and other hypersensitivity agents as described in U.S. Pat. No. 6,569,143, entitled "Method of Intradermally Injecting Substances", the entire content of which is expressly incorporated herein by reference.

Vaccine formulations which can be delivered in accordance with the system and method of the present invention can be selected from the group consisting of an antigen or antigenic composition capable of eliciting an immune response against a human pathogen, which antigen or antigenic composition is derived from HIV-1, (such as tat, nef, gp120 or gp160), human herpes viruses (HSV), such as gD or derivatives thereof or Immediate Early protein such as ICP27 from HSV1 or HSV2, cytomegalovirus (CMV (esp Human) (such as gB or derivatives thereof), Rotavirus (including live-attenuated viruses), Epstein Barr virus (such as gp350 or derivatives thereof), Varicella Zoster Virus (VZV, such as gpI, II and 1E63) or from a hepatitis virus such as hepatitis B virus (for example Hepatitis B Surface antigen or a derivative thereof), hepatitis A virus (HAV), hepatitis C virus and hepatitis E virus, or from other viral pathogens, such as paramyxoviruses: Respiratory Syncytial virus (RSV, such as F and G proteins or derivatives thereof), parainfluenza virus, measles virus, mumps virus, human papilloma viruses (HPV for example HPV6, 11, 16, 18), flaviviruses (e.g. Yellow Fever Virus, Dengue Virus, Tick-borne encephalitis virus, Japanese Encephalitis Virus) or Influenza virus (whole live or inactivated virus, split influenza virus, grown in eggs or MDCK cells, or whole flu virosomes or purified or recombinant proteins thereof, such as HA, NP, NA, or M proteins, or combinations thereof), or derived from bacterial pathogens such as *Neisseria* spp, including *N. gonorrhea* and *N. meningitidis* (for example capsular polysaccharides and conjugates thereof, transferrin-binding proteins, lactoferrin binding proteins, PilC, adhesins); *S. pyogenes* (for example M proteins or fragments thereof, C5A protease, lipoteichoic acids), *S. agalactiae, S. mutans; H. ducreyi; Moraxella* spp, including *M catarrhalis*, also known as *Branhamella catarrhalis* (for example high and low molecular weight adhesins and invasins); *Bordetella* spp, including *B. pertussis* (for example pertactin, pertussis toxin or derivatives thereof, filamenteous hemagglutinin, adenylate cyclase, fimbriae), *B. parapertussis* and *B. bronchiseptica; Mycobacterium* spp., including *M. tuberculosis* (for example ESAT6, Antigen 85A, -B or -C), *M. bovis, M. leprae, M. avium, M. paratuberculosis M. smegmatis; Legionella* spp, including *L. pneumophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* spp, including *V. cholera* (for example cholera toxin or derivatives thereof); *Shigella* spp, including *S. sonnei, S. dysenteriae, S. flexnerii; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S. paratyphi, S. choleraesuis, S. enteritidis; Listeria* spp., including *L. monocytogenes; Helicobacter* spp, including *H. pylori* (for example urease, catalase, vacuolating toxin); *Pseudomonas* spp, including *P. aeruginosa; Staphylococcus* spp., including *S. aureus, S. Epidermidis ; Enterococcus* spp., including *E. faecalis, E. faecium; Clostridium* spp., including *C. tetani* (for example tetanus toxin and derivative thereof), *C. botulinum* (for example *Botulinum* toxin and derivative thereof), *C. difficile* (for example *clostridium* toxins A or B and derivatives thereof); *Bacillus* spp., including *B. anthracis* (for example *botulinum* toxin and derivatives thereof); *Corynebacterium* spp., including *C. diphtheriae* (for example diphtheria toxin and derivatives thereof); *Borrelia* spp., including *B. Burgdorferi* (for example OspA, OspC, DbpA, DbpB), *B. garinii* (for example OspA, OspC, DbpA, DbpB), B. afzelii (for example OspA, OspC, DbpA, DbpB), *B. andersonii* (for example OspA, OspC, DbpA, DbpB), *B. Hermsii; Ehrlichia* spp., including *E. equi* and the agent of the Human Granulocytic Ehrlichiosis; *Rickettsia* spp, including *R. rickettsii; Chlamydia* spp., including *C. Trachomatis* (for example MOMP, heparin-binding proteins), *C. pneumoniae* (for example MOMP, heparin-binding proteins), *C. psittaci; Leptospira* spp., including *L. interrogans; Treponema* spp., including *T. pallidum* (for example the rare outer membrane proteins), *T. denticola, T. hyodysenteriae*; or derived from parasites such as *Plasmodium* spp., including *P. Falciparum; Toxoplasma* spp., including *T. gondii* (for example SAG2, SAG3, Tg34); *Entamoeba* spp., including *E. histolytica; Babesia* spp., including *B. microti; Trypanosoma* spp., including *T. cruzi; Giardia* spp., including *G. lamblia; Leshmania* spp., including *L. major; Pneumocystis* spp., including *P. Carinii; Trichomonas* spp., including *T. vaginalis; Schisostoma* spp., including *S. mansoni*, or derived from yeast such as *Candida* spp., including *C. albicans; Cryptococcus* spp., including *C. neoformans*, as described in PCT Patent Publication No. WO 02/083214, entitled "Vaccine Delivery System", the entire content of which is expressly incorporated herein by reference.

These also include other specific antigens for *M. tuberculosis*, for example Tb Ra12, Tb H9, Tb Ra35, Tb38-1, Erd 14, DPV, MTI, MSL, mTTC2 and hTCC1. Proteins for *M. tuberculosis* also include fusion proteins and variants thereof where at least two, preferably three polypeptides of *M. tuberculosis* are fused into a larger protein. Preferred fusions include Ra12-TbH9-Ra35, Erd14-DPV-MTI, DPV-MTI-MSL, Erd14-DPV-MTI-MSL-mTCC2, Erd14-DPV-MTI-MSL, DPV-MTI-MSL-mTCC2, TbH9-DPV-MTI. Most preferred antigens for *Chlamydia* include for example the High Molecular Weight Protein (HWMP), ORF3, and putative membrane proteins (Pmps). Preferred bacterial vaccines comprise antigens derived from *Streptococcus* spp. including *S. pneumoniae* (for example capsular polysaccharides and conjugates thereof, PsaA. PspA, streptolysin, choline-binding proteins) and the protein antigen Pneumolysin (Biochem Biophys Acta, 1989, 67, 1007; Rubins et al., Microbial Pathogenesis, 25.337-342), and mutant detoxified derivatives thereof. Other preferred bacterial vaccines comprise antigens derived from *Haemophilus* spp., including *H. influenzae* type B ("Hib", for example PRP and conjugates thereof), non typeable *H. influenzae*, for example OMP26, high molecular weight adhesins, P5, P6, protein D and lipoprotein D, and fimbrin and fimbrin derived peptides or multiple copy variants or fusion proteins thereof. Derivatives of Hepatitis B Surface antigen are well known in the art and include, inter alia, PreS1, PreS2 S antigens. In one preferred aspect the vaccine formulation of the invention comprises the HIV-antigen, gp120, especially when expressed in CHO cells. In a further embodiment, the vaccine formulation of the invention comprises gD2t as hereinabove defined.

In addition to the delivery of substances listed above, the device and method can also be used for withdrawing a substance from a patient, or monitoring a level of a substance in the patient. Examples of substances that can be monitored or withdrawn include blood, interstitial fluid or plasma. The withdrawn substances can then be analyzed for analytes, glucose, drugs and the like.

The embodiments of the present invention described above preferably include a push-surface (i.e. push button) design wherein the device can be positioned and affixed to a skin surface, and energized and/or activated by gently pressing a push button or push surface. Specifically, the user in a first step removes the device from a sterile packaging and removes an adhesive cover (not shown) and/or a needle cap. Upon removal of the device from the package and prior to use, the features described above allows the user to inspect both the device and the contents therein, including inspection for missing or damaged components, expiration dates(s), hazy or color-shifted drugs, and so forth. After use, the user can once again inspect the device to ensure the entire dose was delivered. In this regard, the device can include an end-of-dose indicator, as described in greater detail below, or an administered dose indicator for example, consisting of a readable gauge area that is at least 20% of the surface area of the device housing and accurate to within +/−10% of the labeled dose.

The next step is the positioning and application of the device to the user's skin surface. Like a patch, the user firmly presses the device onto the skin. The device includes a bottom surface having an adhesive layer to secure the device to the skin of the user. This bottom surface can be flat, contoured, or shaped in any suitable fashion, and includes an adhesive layer thereon, which would most likely be covered prior to shipping. Prior to use, the user peels back the adhesive covering, such as a film covering the adhesive, thereby exposing the adhesive for placement against the skin.

Once removed, the user is then able to place the device against the skin and press to ensure proper adhesion. As noted above, once properly positioned, the device is activated by sliding a button (i.e. 105 in FIG. 1) or pressing a push surface of a top housing (i.e., 305 of FIG. 12). This activation step releases the Belleville spring allowing it to press against the flexible film of the reservoir, pressurizing the reservoir. This activation step also serves to release the patient needle manifold and seat the patient needles. Finally, the activation step also serves to open one or more valve assemblies or fluid paths as described above, establishing a fluid communication path between the reservoir and the patient needles. A significant benefit to each embodiment described above includes the ability to achieve each step in a single push action. Additionally, another significant benefit includes the use of a continuous fluid communication path comprised entirely within the reservoir assembly.

Once activated, the user typically leaves the device in position, or wears the device, for some period of time, such as ten minutes to seventy-two hours for complete delivery of the device contents, and then removes and discards the device with no damage to the underlying tissue. However, upon intentional or accidental removal, one or more safety features can deploy as described in greater detail below to shield the exposed needles resulting from activation. The safety features however can be configured to not deploy if the button and button slide has not been pushed and the patient needles extended, preventing pre-use safety deployment.

To prevent inadvertent or accidental needle sticks, intentional re-use of the device, and to shield exposed needles, a locking needle safety mechanism can be provided and activated automatically immediately upon removal of the device from the skin surface. In a first version of a safety feature embodiment described in greater detail below, a flexible safety member can be provided which provides in part, an adhesive covered, flat surface portion that is in contact with the patient's skin. The member, once released, is held in position by the skin surface. Once the device is removed from the skin surface, the member extends to a position shielding the patient microneedles. The extended safety member is then locked into place and prevents accidental injury or exposure to the patient needles. Still other versions of a safety feature embodiment include a flexible patient needle cap (i.e., 111 of FIG. 1), which serves to protect the patient needles and provide a sterile barrier. The needle cap can serve to protect the patient needles during device manufacture, protect the user prior to use, and provide a sterility barrier at any point prior to removal. The needle cap can be attached via a press fit with the patient needle manifold.

In addition to the performance advantages described above, another advantage of the embodiments described above is the ability to make two or more distinct, self-contained subassemblies (i.e., a reservoir subassembly and a body subassembly) that allow for assembly flexibility. Each subassembly is self contained and stable, and provides the ability to separate the reservoir subassembly from remaining components, allowing separate filling and inspection of the reservoir, while preventing the unnecessary handling of the remaining components. Additionally, should any of the additional components be discarded, the costly reservoir contents can be excluded. Also, the reservoir subassembly contains no unnecessary parts and as a result, brings a low particle load into filling operations. Also, all stored energy components are in the body subassembly so they cannot be inadvertently deployed during filling of the reservoir. Specifically, no springs are included in the reservoir subassembly which prevents the chance of unwanted spring release during filling. As noted, minimal extraneous components in the reservoir subassembly reduce particle load, and only contain necessary components, such as the reservoir and lid. No dangling parts are present, and typically require only drop-in assembly steps. Additionally, the reservoir can be located on top of the device, which can allow full and unobscured view of the drug reservoir through a transparent component, allowing view of the reservoir contents to the user or manufacturer.

Any number of the components provided in the above exemplary embodiments can be provided having additional functions and features to better achieve the desired results. Specifically, the use of improved materials, valve and Belleville spring constructions, safeties and packaging methods and materials, as described in greater detail below, can be provided with the exemplary embodiments to achieve the desired results. For example, returning to FIG. 1, the push button 105 engages the push valve 120, initiating flow between the now pressurized reservoir 150 and the manifold assembly 140. The push/pull valve assembly 120 of the embodiment shown in FIG. 1 is constructed to restrict flow between the reservoir 150 and the patient needle manifold 140 until pushed into an open position by the push button 105 and can be comprised of any number of improved valve assemblies as described in greater detail below.

Figure 61:
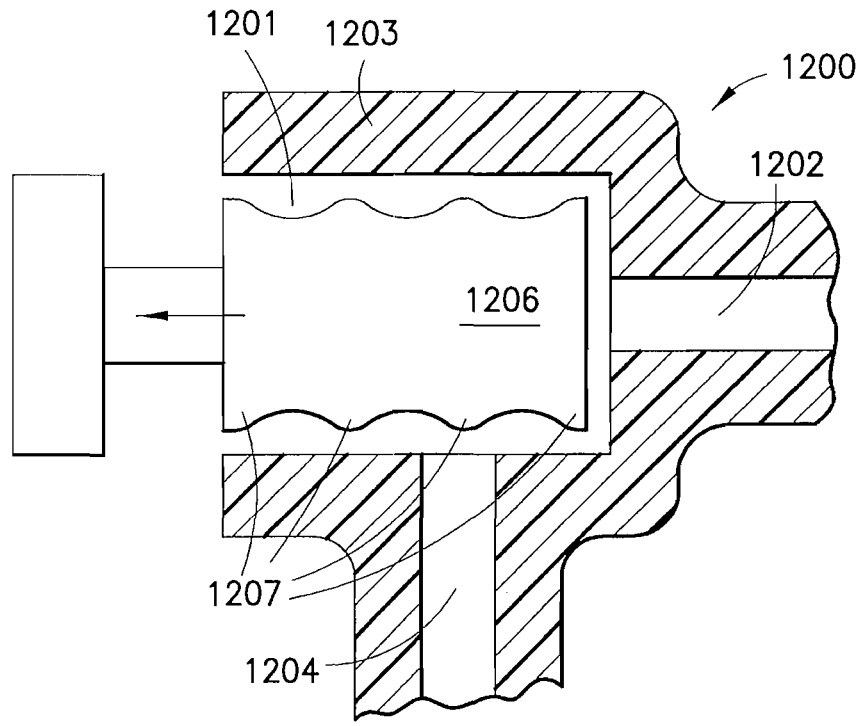
FIG. 61 is a cross-sectional view of a first variation of an improved valve embodiment in a closed position.
Figure 62:
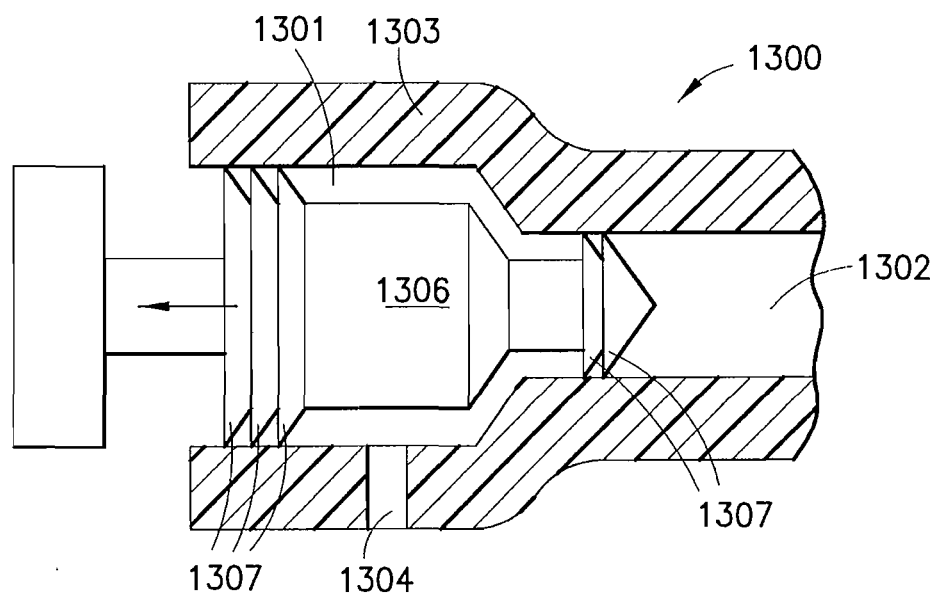
FIG. 62 is a cross-sectional view of a second variation of an improved valve embodiment in a closed position.

As shown in FIG. 61, an improved valve assembly 1200 can consist of a push/pull valve rod 1206 seated in an opening 1201 within a housing 1203 in fluid communication with the reservoir (not shown) via path 1202. FIGS. 61 and 62 illustrate a pull valve 1200 and 1300 in a closed position, and FIGS. 63 and 64 illustrate a push valve 1400 and 1500 in a closed position.

Conventional valve assemblies typically include a plastic member slidably engaged within a rubber stopper in fluid communication with the reservoir, and wherein the plastic member includes a proximal end seated securely within the rubber stopper to prevent any fluid escaping the reservoir. As the plastic member is engaged and displaced within the rubber stopper by a push button, an opening is created at the proximal end of the plastic member which allows fluid communication from the reservoir. However, such assemblies require a separate rubber plug or stopper, in which the proximal end of the plastic member is seated.

Figure 63:
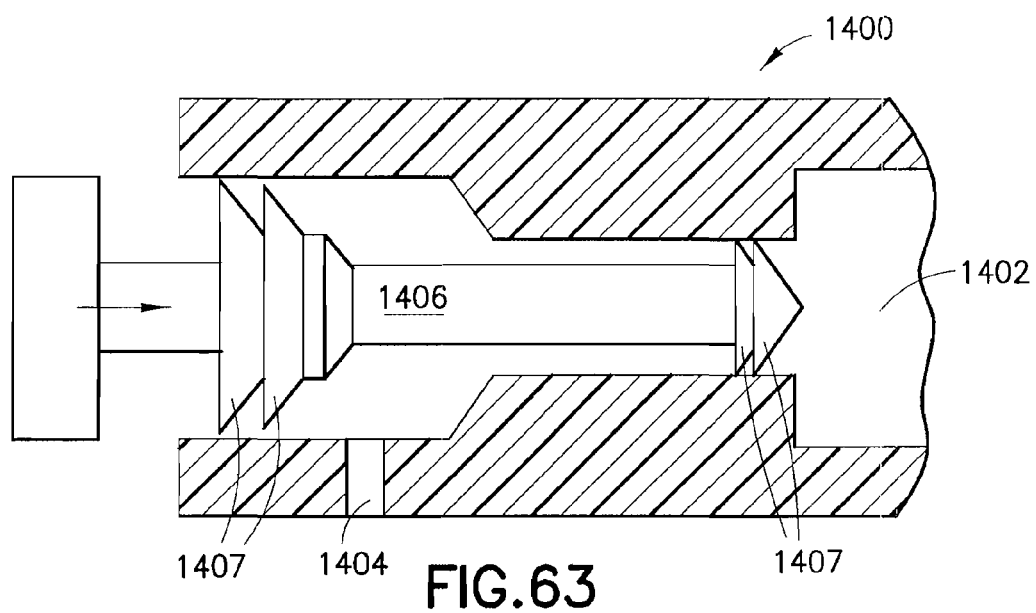
FIG. 63 is a cross-sectional view of a third variation of an improved valve embodiment in a closed position.
Figure 64:
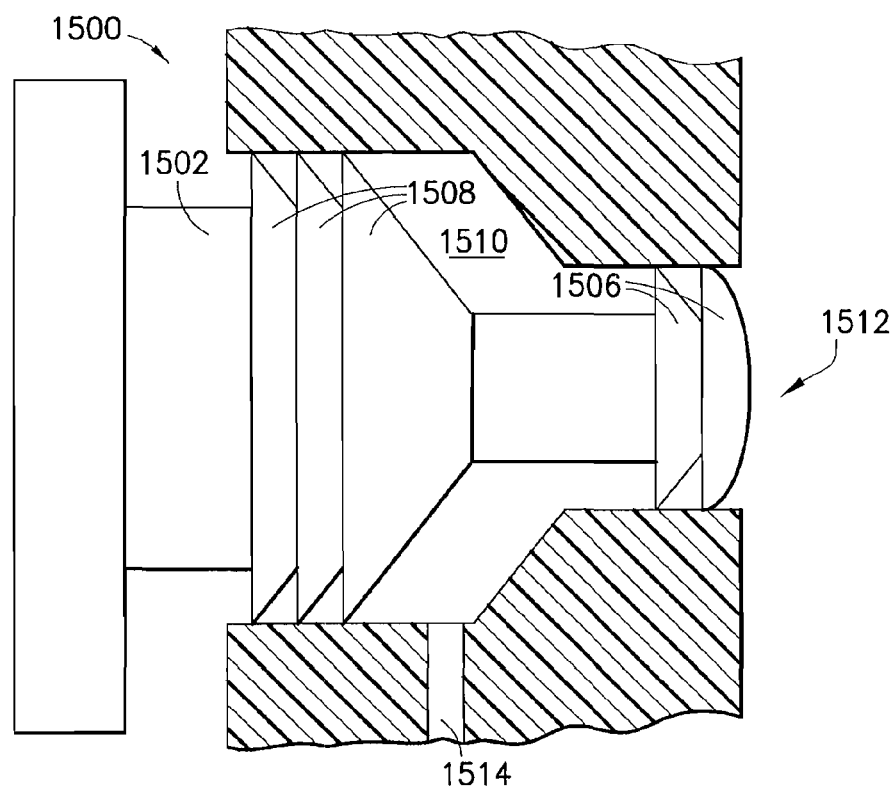
FIG. 64 is an enlarged cross-sectional view of a fourth variation of an improved valve embodiment in a closed position.

In FIGS. 61 through 63, valve embodiments 1200, 1300 and 1400 are shown wherein the valve body 1206, 1306 and 1406 are constructed of an elastomer. The valves and valve ribs 1207, 1307 and 1407 are constructed, in part, of an elastomer which allows the elimination of a separate rubber plug or seal (i.e. 224 of FIG. 6). Additionally, the valves of FIGS. 62 and 63 have a linear measurement sufficient to prevent the ribs 1307 and 1407 from contacting the fluid path escape opening 1304 and 1404, and possibly becoming damaged.

Specifically, in each of FIGS. 61 through 63, an opening 1202, 1302, and 1402 is provided in fluid communication with the reservoir (not shown). A second opening 1204, 1304, and 1404 is provided in fluid communication with the patient needle manifold (not shown). As the valve body 1206, 1306, and 1406 travels from a closed to open position, sealing members, or ribs 1207, 1307 and 1407, of the valve body 1206, 1306 and 1406, respectively, move to provide a fluid communication path between openings 1202 and 1204, 1302 and 1304, and 1402 and 1404, respectively. However, such sealing members are not allowed to contact the openings, specifically openings 1204, 1304, and 1404 in such a manner as to allow the openings edges to act in an abrasive manner against the valve body 1206, 1306, and 1406, or sealing members 1207, 1307 and 1407. This is prevented in each valve embodiment 1200, 1300, and 1400 by providing a sufficient clearance between the sealing members 1207, 1307 and 1407 and the openings 1204, 1304 and 1404 in either an open or closed valve position. For example, the ribs 1307 of FIG. 62, are sufficiently placed to avoid contact with the openings 1304 when the valve is closed, opened, or in between. Still further improvements and descriptions of these sealing members are provided by the valve bodies as described in greater detail below.

The valve assembly shown in FIGS. 64 through 68 further accomplishes the complex task of low pressure fluid sealing, high pressure fluid sealing, and anti-microbial ingress restriction, all in one part. The valve embodiment 1500 entails two components, which together form a fluid valve system. The first component is the valve plunger rod 1502, and the second component is the cylindrical body opening 1504 that the valve plunger rod 1502 is housed within. The entire fluid valve system is incorporated into a fluid reservoir such as might be used for holding drugs in liquid form within the infusion device 100 of FIG. 1.

The valve 1500 has as an initial state and an activated state, and includes a proximal and distal set of radially projecting fins, or ribs 1506 and 1508, respectively, as can be seen in FIGS. 64 through 68. In the initial state, the valve's proximal ribs 1506 create a seal to trap the drug safely within the reservoir (not shown), while the distal ribs 1508 serve to prevent microbial ingress into the fluid path 1510. Both sets of ribs 1506 and 1508 are performing critical tasks in preventing fluid loss from inside the reservoir over long periods of time as well as preventing contamination of the drug from outside the reservoir over the same period of time.

In use, the valve plunger rod 1502 will eventually be pushed into an activated state by the movement of the push button (not shown) and the functions of the ribs 1506 and 1508 change to accomplish new roles. When pushed in, the proximal set of ribs 1506 will be advanced into an enlarged cavity 1512 in fluid communication with the reservoir which permits the drug to flow from the reservoir, past the proximal ribs 1506 and into the valve fluid path 1510. At the same time, the distal set of ribs 1508 are by nature also pushed in and the location of the ribs 1508 themselves translate into a position such that they direct the fluid from the reservoir, through the valve fluid path 1510 out a side hole 1514, and down the final fluid path (not shown) to the patient needles (not shown).

Figure 65:
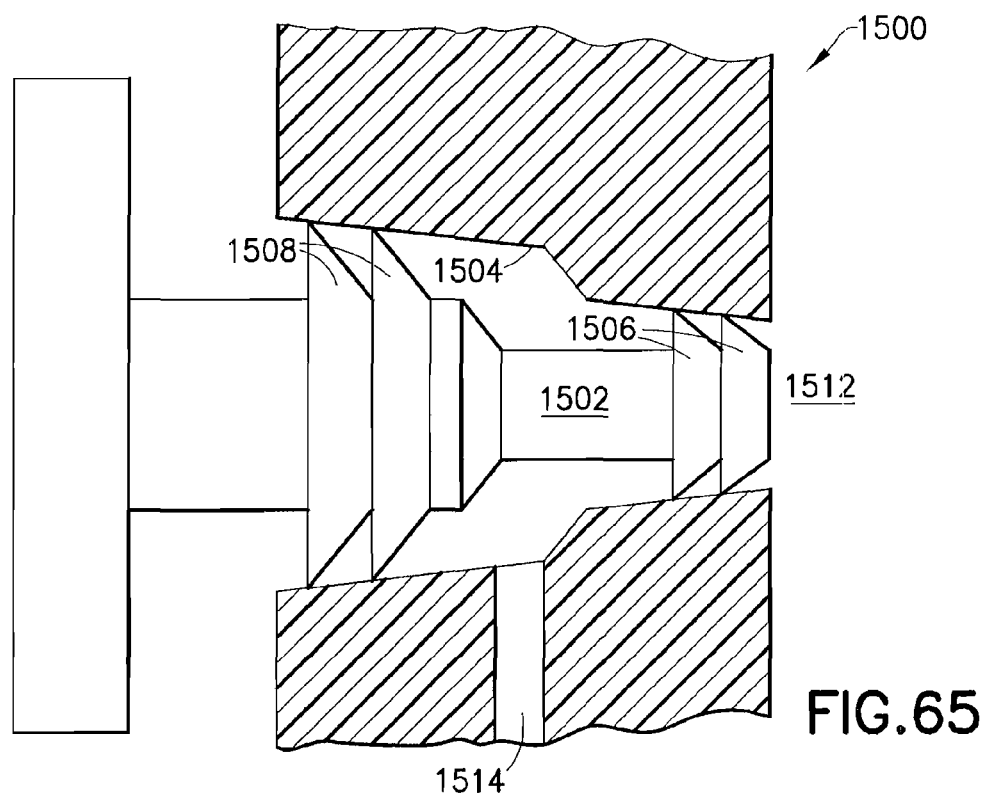
FIG. 65 is an enlarged cross-sectional view of a fifth variation of an improved valve embodiment wherein the opening includes tapered surfaces.
Figure 66:
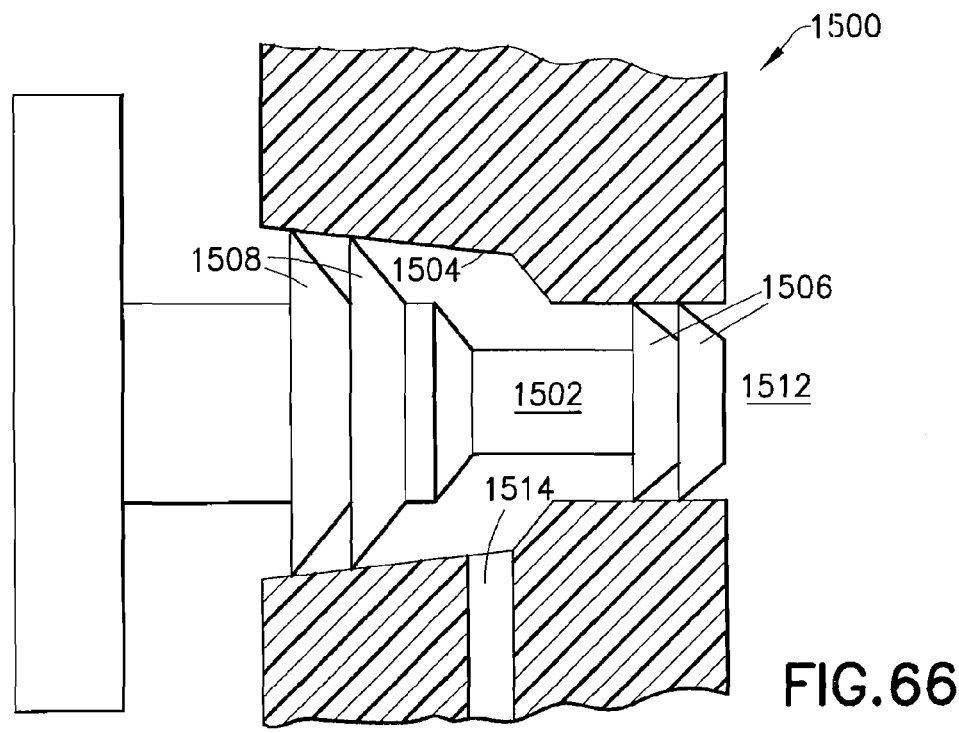
FIG. 66 is a cross-sectional view of the improved valve embodiment of FIG. 65 in a closed position.
Figure 67:
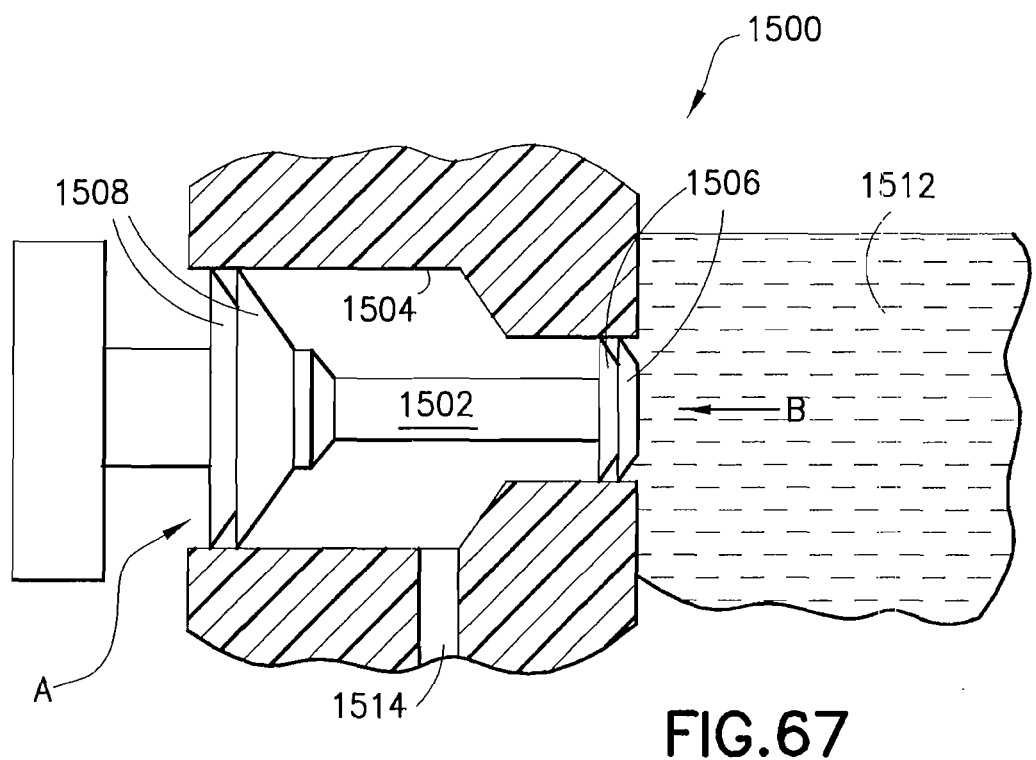
FIG. 67 is another cross-sectional view of the improved valve embodiment of FIG. 65 in a closed position.

As they direct the fluid out the side hole 1514, the distal set of ribs 1508 must now function as a high pressure seal to ensure the fluid correctly exits the appropriate side hole 1514, rather than escape past the distal ribs 1508 themselves, whereby the fluid would be lost. To ensure this is successfully achieved, the valve assembly can further incorporate a slightly tapered cylindrical valve body opening 1504 in which the valve plunger rod 1502 travels as shown in FIGS. 65 through 68. This tapered body opening 1504 permits the distal ribs 1508 which form the fluid seal, to safely "take a set" when in an initial, or closed state as shown in FIGS. 65 through 67. That is, the ribs 1508 of the plunger rod 1502 typically will relax over time within the inside diameter of the cylindrical valve body opening 1504 when in a closed position. Therefore, over time the ribs 1508 will lose some ability to exert a desired radial pressure on the body when finally moved into an open position.

Figure 68:
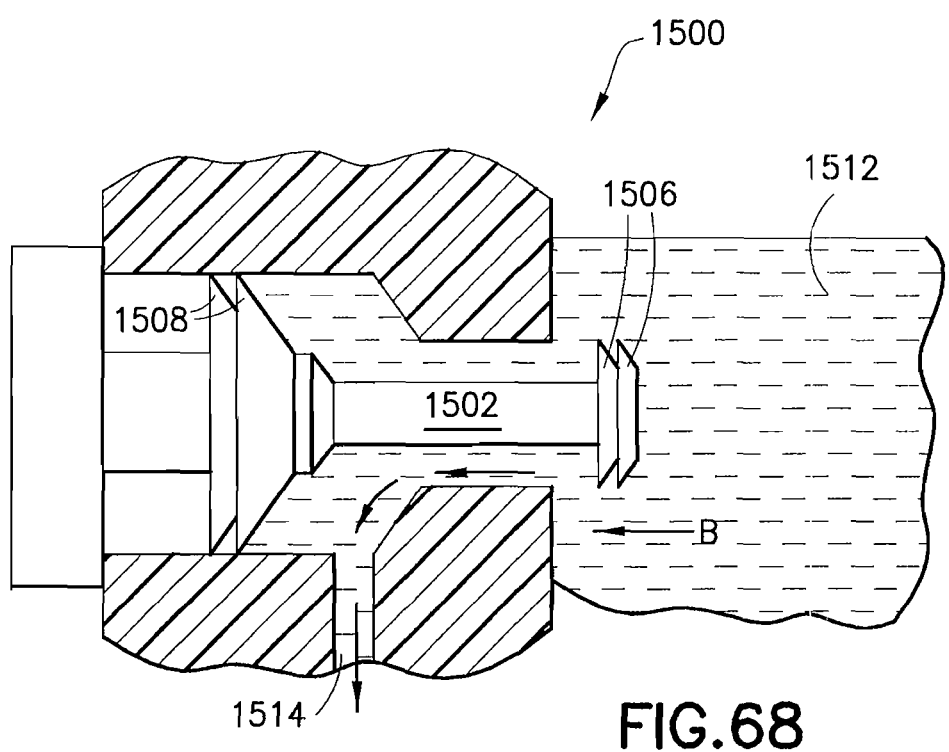
FIG. 68 is a cross-sectional view of the improved valve embodiment of FIG. 65 in an open position and wherein the opening includes both tapered and flat surfaces.

When the distal ribs 1508 are acting as microbial ingress barriers as shown by arrow A in FIG. 67, this reduced radial pressure is permissible and the valve will still function completely. However when the distal ribs 1508 are translated forward as shown in FIG. 68 and their primary function turns into that of high pressure seal against the flow of arrow B instead of microbial ingress barrier, the distal radial ribs 1508 are required to perform optimally as a fluid seal. Thus if the distal ribs 1508 have "taken a set" when closed, they would be less effective to accomplish this task when open if they are traveling in a non-tapered opening. Therefore, in the embodiment shown in FIGS. 65 through 68, a conically tapered body opening 1504 is further provided with the assembly 1500, therefore as the distal ribs 1508 move forward from the initial state to the activated state, they will be "re-pressurized" due to the reduced inside diameter provided by the conical tapered opening 1504, and the distal ribs 1508 can then work effectively regardless of "taking a set" during the period when the valve 1500 was closed.

The advantage of having a conically tapered body opening 1504 is that it accomplishes multiple sealing and fluid flow objectives with only a single molded part. Typical valves for use in systems such as this incorporate an elastomeric seal, or plug, in conjunction with a plunger rod to effect the same sealing characteristics that the embodiment shown in FIGS. 64 and 65 exemplifies. That is, in the embodiment shown in FIGS. 64 and 65, the seal or plug is eliminated, as the valve plunger rod 1502 used is comprised of a rigid portion, or member, and a softer overmold as described in greater detail below with reference to FIGS. 69 and 72. Since the embodiments of FIGS. 69 and 72 accomplishes all the required tasks with fewer parts, it exhibits significant cost savings due to reduced overall part counts, and provides for simplified manufacturing and assembly processes.

Figure 69:
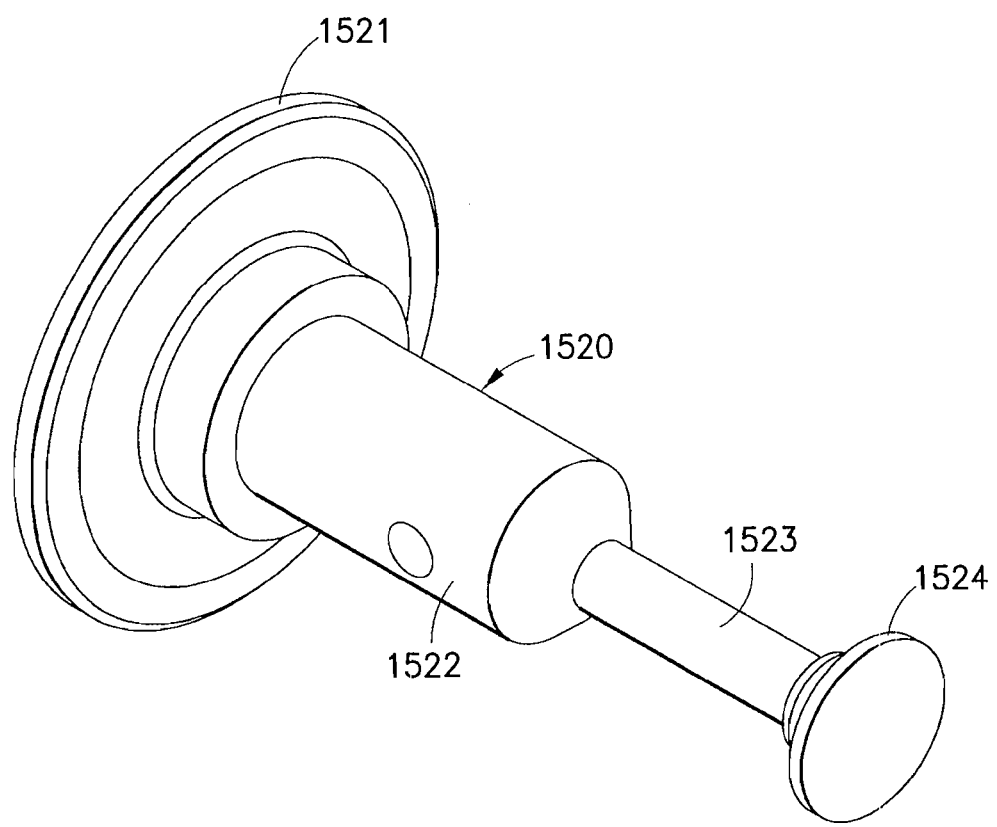
FIGS. 69 through 71 are views of an improved valve plunger rod embodiment.
Figure 70:
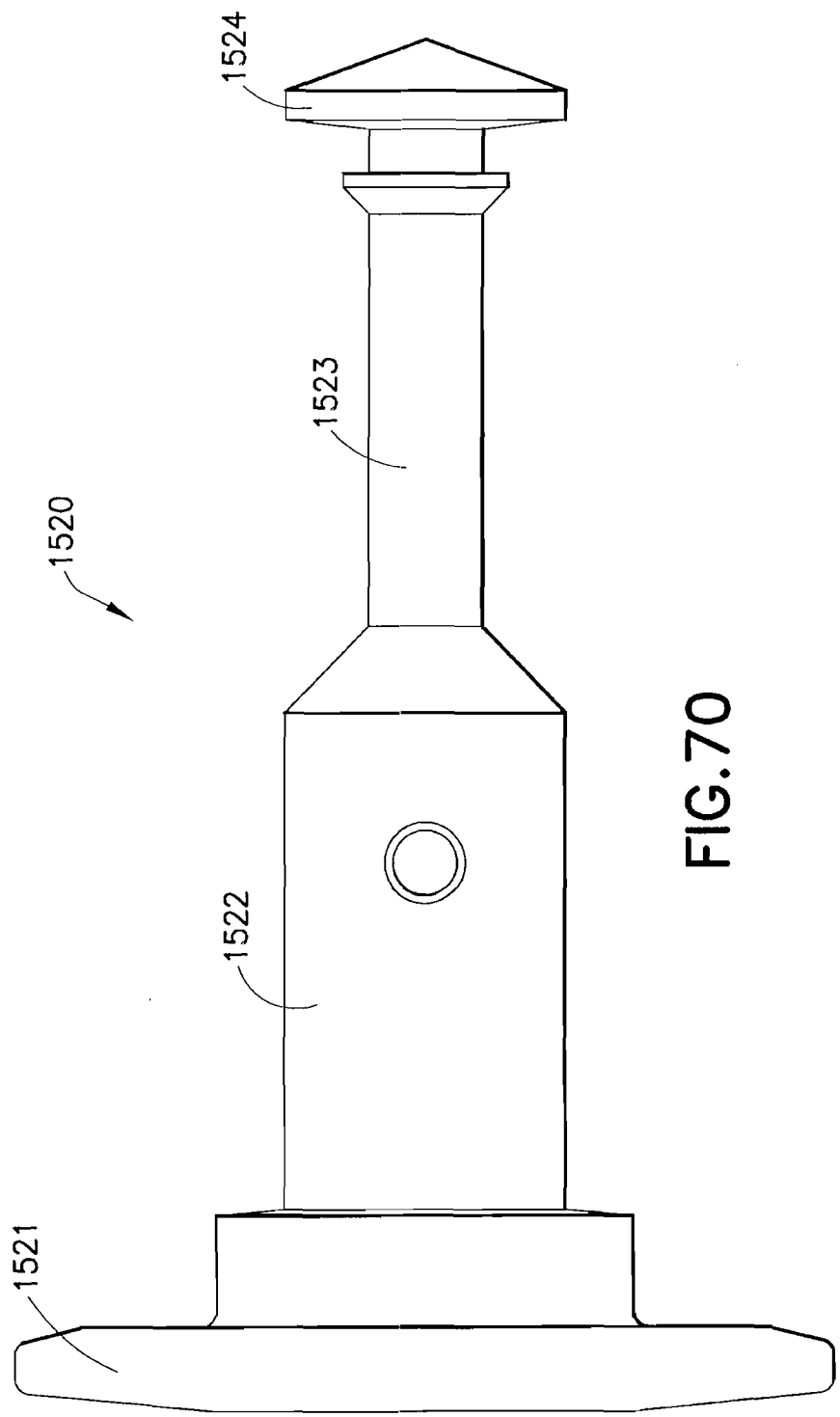
Figure 71:
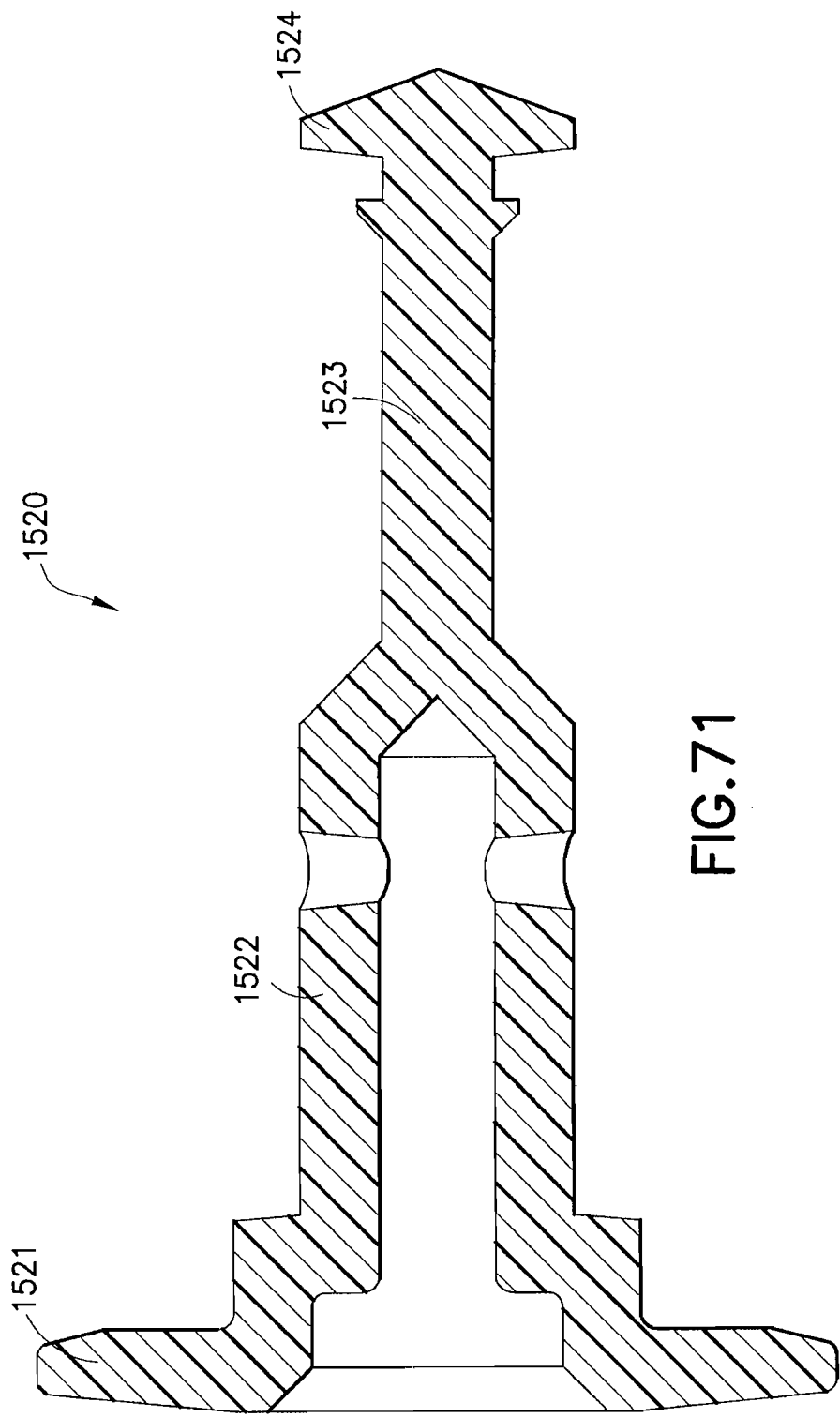

One method of constructing such a valve plunger rod 1502 to eliminate the need for an elastomer plug is with a one/two shot mold process as shown in FIGS. 69 through 74. In FIGS. 69, 70 and 71, a rigid polyethylene member 1520 is constructed as a core member of the valve 1502 and creates a rigid structure, and includes an enlarged distal end 1521, a body 1522 to later support a number of distal fins, a reduced diameter body 1523 to provided clearance for a flow path, and a minimally enlarged proximal end 1524 to later support a number of proximal fins. FIG. 69 shows a perspective view of the core member 1520, FIG. 70 shows a side view of the core member 1520, and FIG. 71 shows a cross-sectional view of the core member 1520. In an exemplary embodiment, the enlarged distal end 1521 has a diameter of approximately 0.288 inches and a thickness of approximately 0.030 inches. The body 1522 has a diameter of approximately 0.099 inches and a length of approximately 0.25 inches between end 1521 and body 1523. The reduced diameter body has a diameter of approximately 0.040 inches and a length of approximately 0.023 inches between end 1524 and body 1522. The enlarged proximal end 1524 has a diameter of approximately 0.10 inches and a thickness of 0.01 inches and having a 45° tapered end extending axially therefrom.

Figure 72:
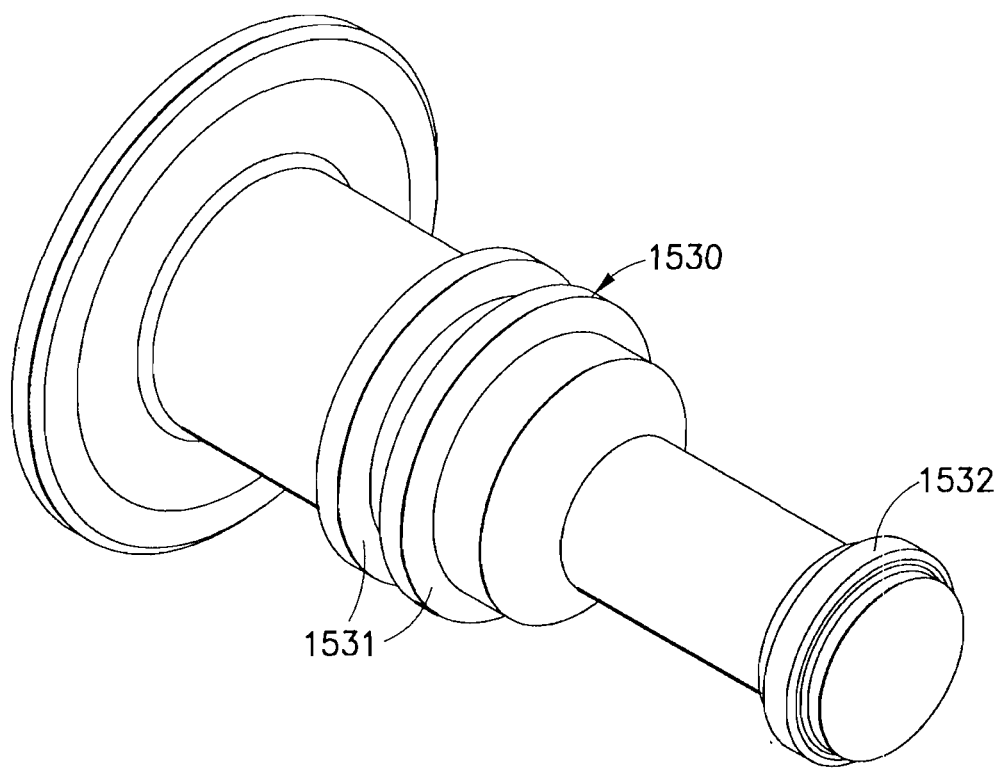
FIGS. 72 through 74 are views of an improved overmolded valve plunger rod embodiment.
Figure 73:
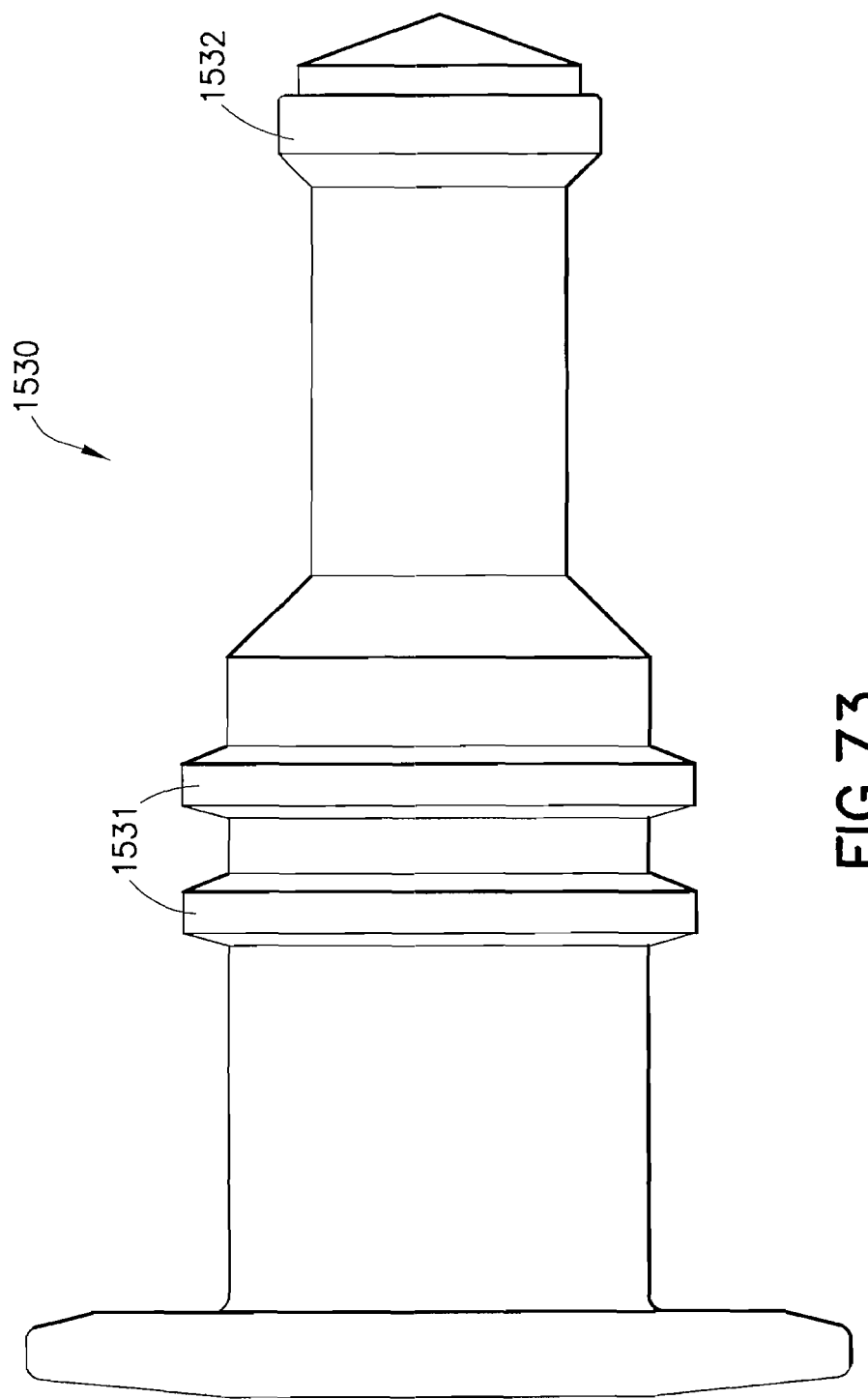
Figure 74:
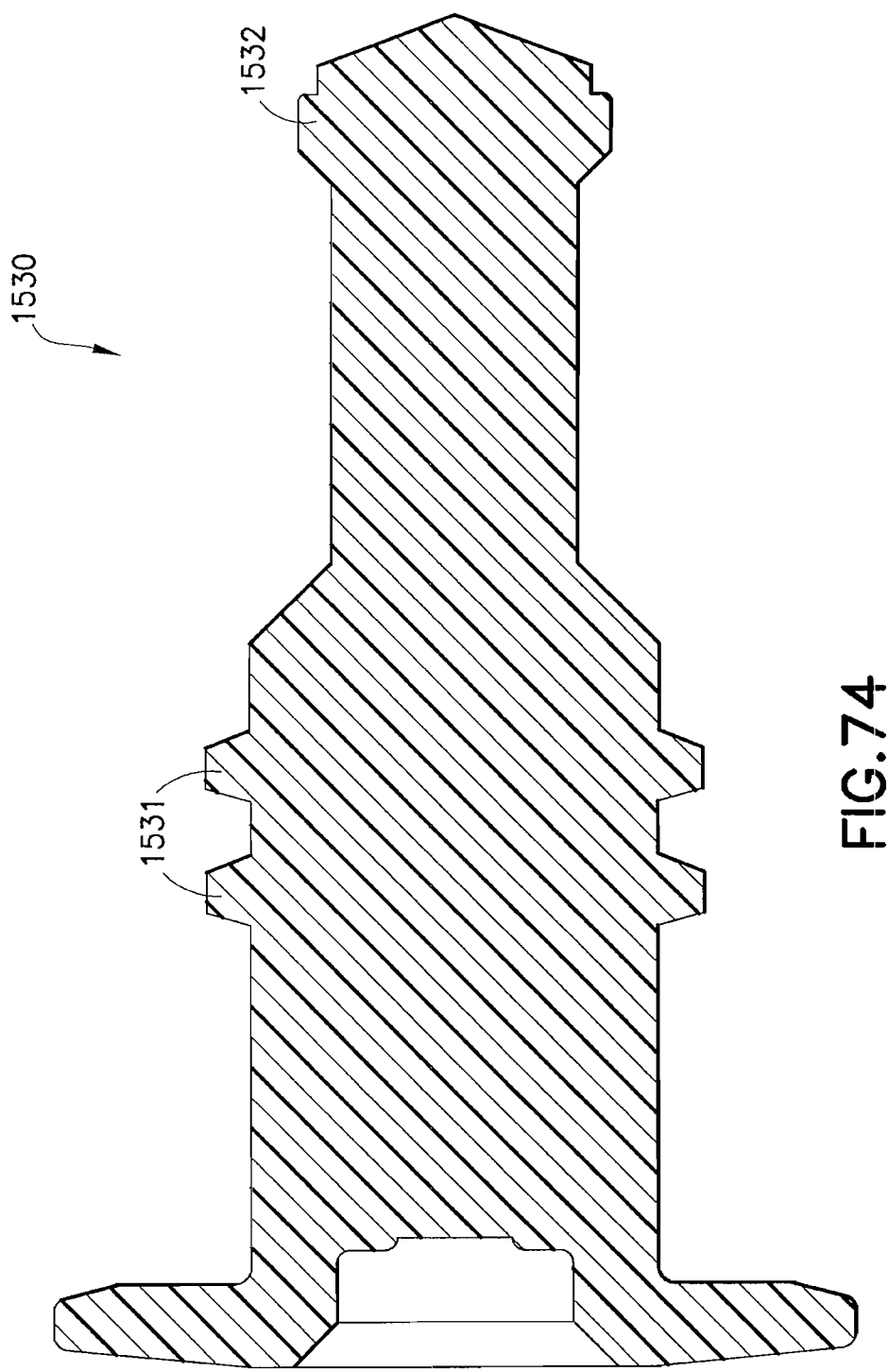

In a second shot mold process shown in FIGS. 72, 73 and 74, an elastomer overmold 1530 is provided over the core member 1520 of FIGS. 69 through 71. FIG. 72 shows a perspective view of the overmolded core member 1520, FIG. 73 shows a side view of the overmolded core member 1520, and FIG. 74 shows a cross-sectional view of the overmolded core member 1520. The resulting valve member or valve plunger rod includes distal sealing fins 1531 and proximal sealing fin 1532, which provide a surface which can create a seal within the valve opening equal to those provided by a separate plug. In doing so, the valve eliminates the need for a separate rubber plug or stopper in the valve. In an exemplary embodiment, the overmolded distal fins 1531 have a diameter of approximately 0.177 inches and a thickness of approximately 0.016 inches. The overmolded proximal fin 1532 has a diameter of approximately 0.114 inches and a thickness of 0.02 inches and having a 45° tapered end extending axially therefrom.

Figure 75:
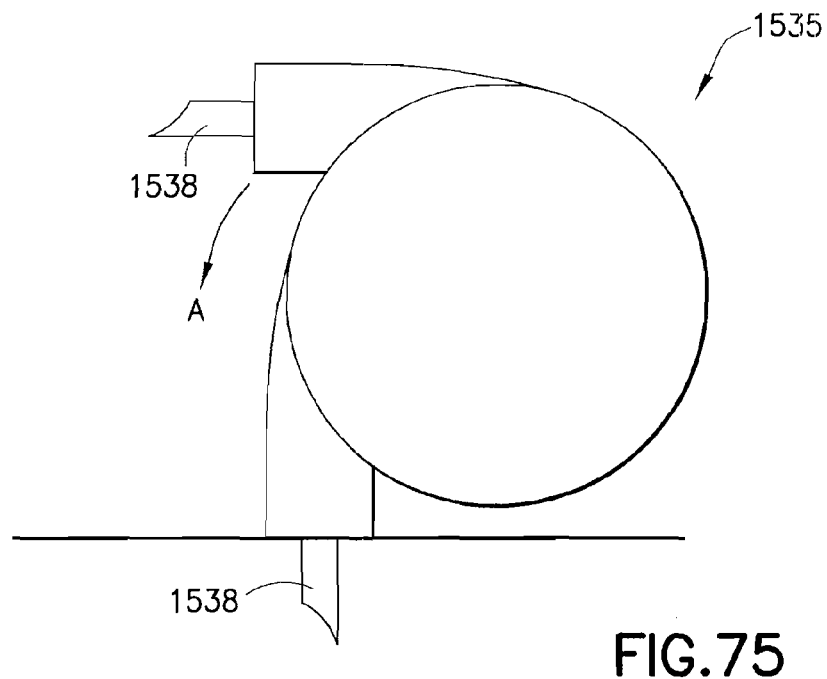
FIG. 75 is a view of an improved rotating valve embodiment.
Figure 76:
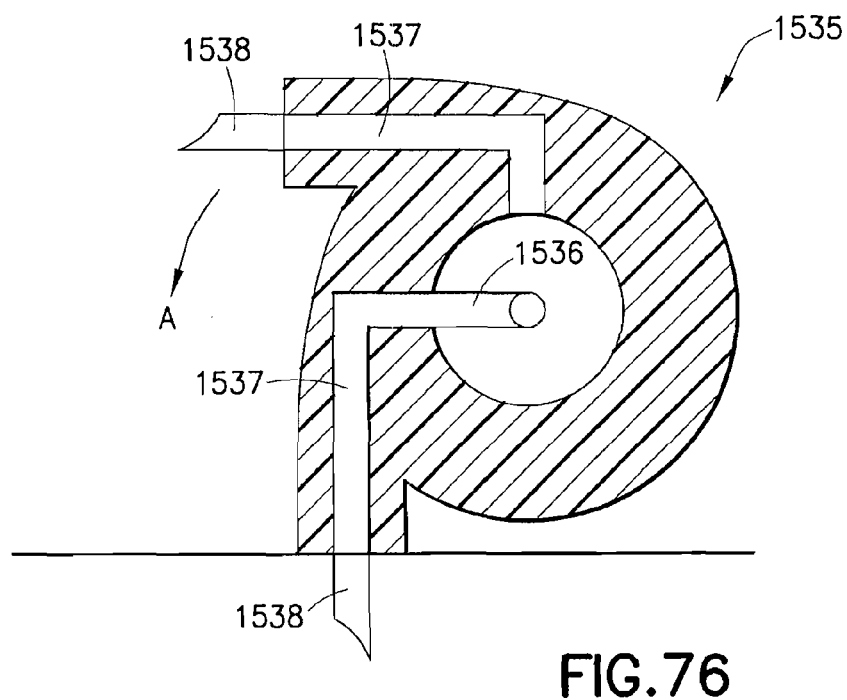
FIG. 76 is a detailed cross-sectional view of the improved rotating valve embodiment of FIG. 75.
Figure 77:
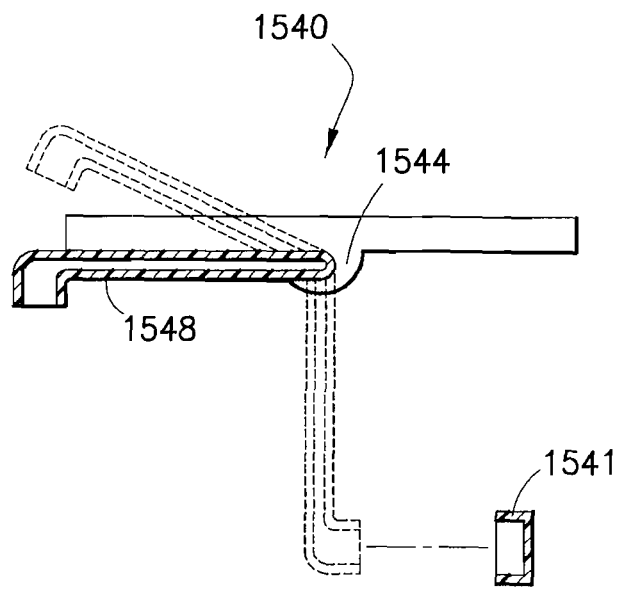
FIG. 77 is a cross-sectional view of another version of an improved rotating valve embodiment and fill cap.
Figure 78:
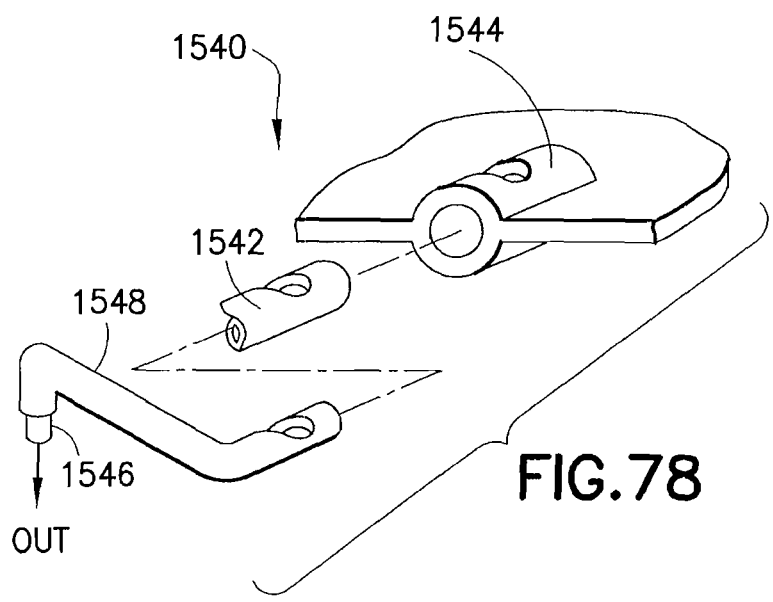
FIG. 78 is a perspective view of another improved rotating valve embodiment.
Figure 79:
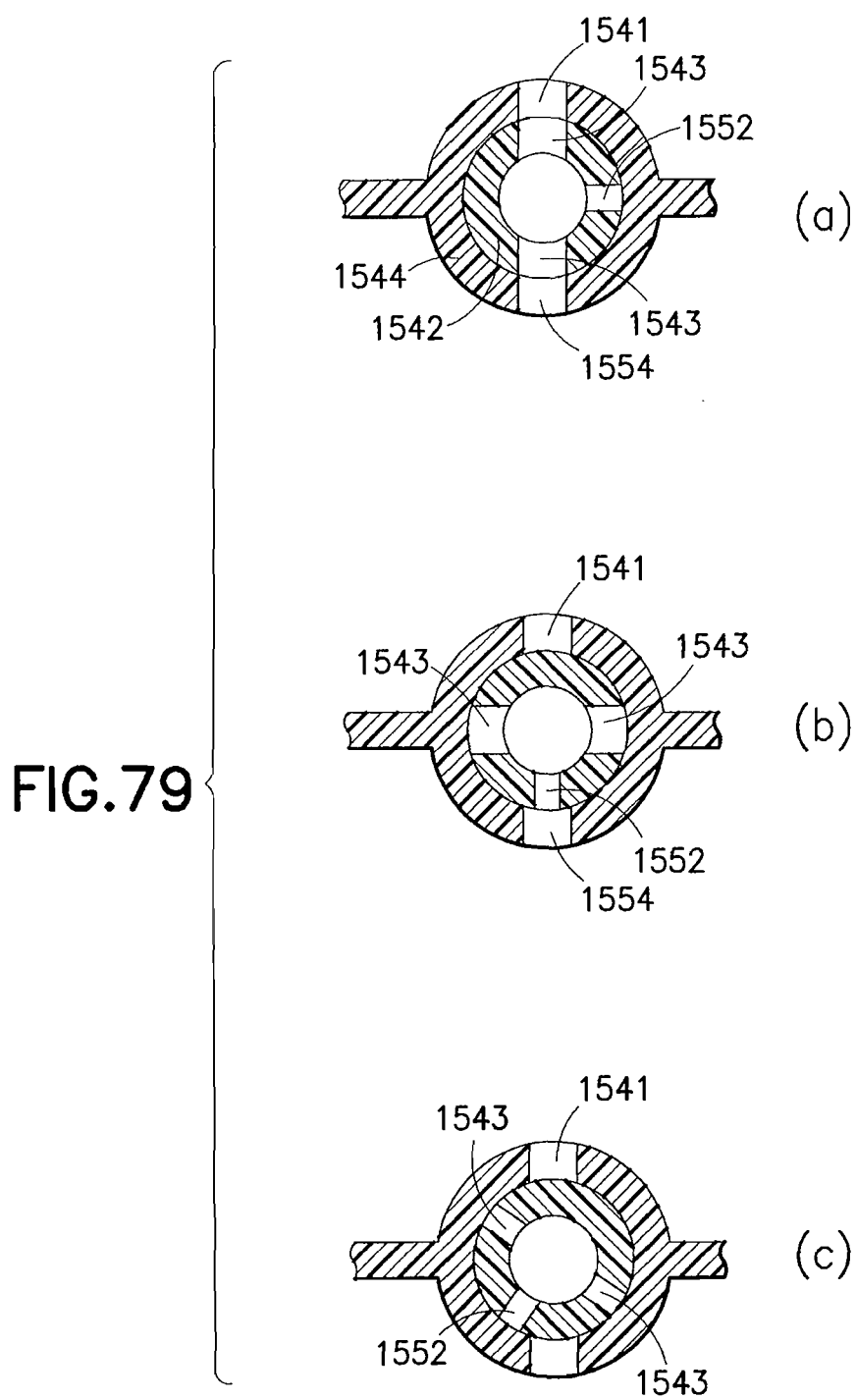
FIGS. 79(a) through 79(c) are cross-sectional views of a first, second and third stage of the fluid path of the improved rotating valve embodiment of FIG. 77.

The improved valve plunger rod and opening is only one improved mechanism provided by the embodiments of the present invention. In yet another improved valve embodiment, the infusion device can use a rotating valve 1535 to provide fluid communication for an infusion device. FIG. 75 is a side view of a rotating valve, and FIG. 76 is a cross-sectional view of a rotating valve in a pre-use and in-use position. The valve 1535 can have a simple valving alignment feature between paths 1536 and 1537, to permit fluid communication from a reservoir (not shown) to a needle 1538 when the valve is rotated as indicated by arrow A. Still another rotating valve embodiment 1540 is shown in FIGS. 77, 78 and 79, with distinct fill, injection and closed positions, or states. As shown in FIGS. 77 through 79, the rotating valve can include a first tube 1542 extending from arm 1548 and rotatably fit within a second tube 1544, and having the infusion needles 1546 attached to the first tube 1542 by a lever arm 1548. Each tube includes a number of openings for alignment to provide a fill position, a closed position, and an injection position, as described in greater detail below.

In a fill position, as shown in FIG. 79(*a*), a fill opening 1541 in the second tube 1544 is aligned with fill openings 1543 in the first tube 1542, thereby in fluid communication with the reservoir via a reservoir opening 1554 in the second tube 1544. This allows fluid communication between fill opening 1541 and the reservoir only. In an inject position shown in FIG. 79(*b*), the fill openings 1543 in the first tube 1542 are blocked, and an injection opening 1552 in the first tube 1542 is aligned with the reservoir opening 1554 in the second tube 1544. In a closed position shown in FIG. 79(*c*), all openings of both the first and second tubes are blocked.

When the device is armed and the valve is in the closed position as shown in FIG. 79(*c*), the fluid enters though the reservoir opening 1554 in the side of the second tube 1544 but is stopped by the side wall of the first tube 1542. In this position, the needles 1546 are attached to the first tube 1542 by a lever arm 1548, however, the fluid path between the needles and the inside of the first tube is closed from the fluid path of the second tube 1544, and the lever arm 1548 is positioned at an angle as to hold the needles 1546 above the skin of the user.

When the device is activated, the lever arm 1548 is rotated such that the needles 1546 enter the skin. This rotation turns the first tube 1542 inside the second tube until the injection opening 1552 in the first tube 1542 aligns with the reservoir opening 1554 in the second tube 1544 allowing fluid to flow. The fluid flows from the reservoir opening 1554 in the second tube 1544 through the injection opening 1552 in the first tube 1542 into the center of the first tube to the fluid path in the lever arm 1548, down the lever arm to and out the needles 1546 into the user's skin. The injection opening 1552 in the first tube 1542 is located such that it opens the fluid path only when the needles 1546 have entered the skin at the desired depth.

Because the rigid lever arm 1548 serves as the fluid path, the rotating valve embodiment does not require a flexible fluid path between the valve and the needles. Also, the timing of the opening of the valve is linked directly with the position of the needles in the skin, thereby eliminating the possibilities of the valve opening before the needles are properly positioned in the skin.

The fluid path and valving of the embodiments shown in FIGS. 75 through 79 are simplified and reduced into fewer parts by integrating the actions of opening the valve and inserting the needles into the same action and part. Additionally, the tubes 1542 and 1544 need not be complete circles but may be just arcs of circles. The fluid path may be a groove (not shown) down the outside of the first tube 1542 which aligns with the reservoir opening 1554 in the second tube 1544. The fluid path may also be a groove (not shown) down the inside of the second tube 1544 which aligns with the injection opening 1552 in the first tube 1542. The fluid path may further consist of a groove (not shown) in the inner wall of the second tube 1544 and the outer wall of the first tube 1542. In yet another variation, the lever arm 1548 could be attached to a rotating outer, or second tube 1544, with the inner, or first tube 1542 being stationary, such that the fluid flows from the first tube 1542 to the second tube 1544. In each variation, the valve type is one of aligning holes and/or grooves by integrating the movement of the needle insertion with the valve which opens the fluid path.

Figure 80:
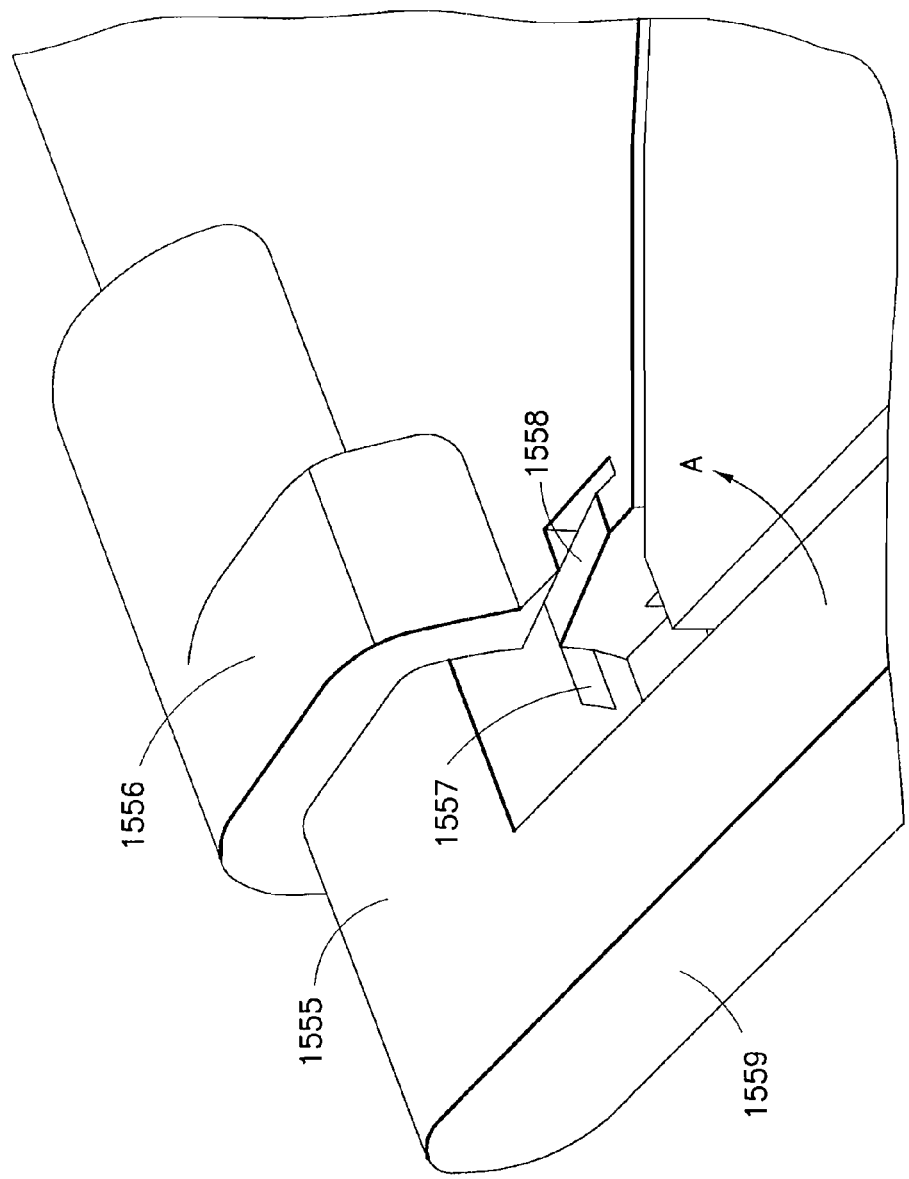
FIG. 80 is a cross-sectional view of an improved valve subassembly in a closed position.
Figure 81:
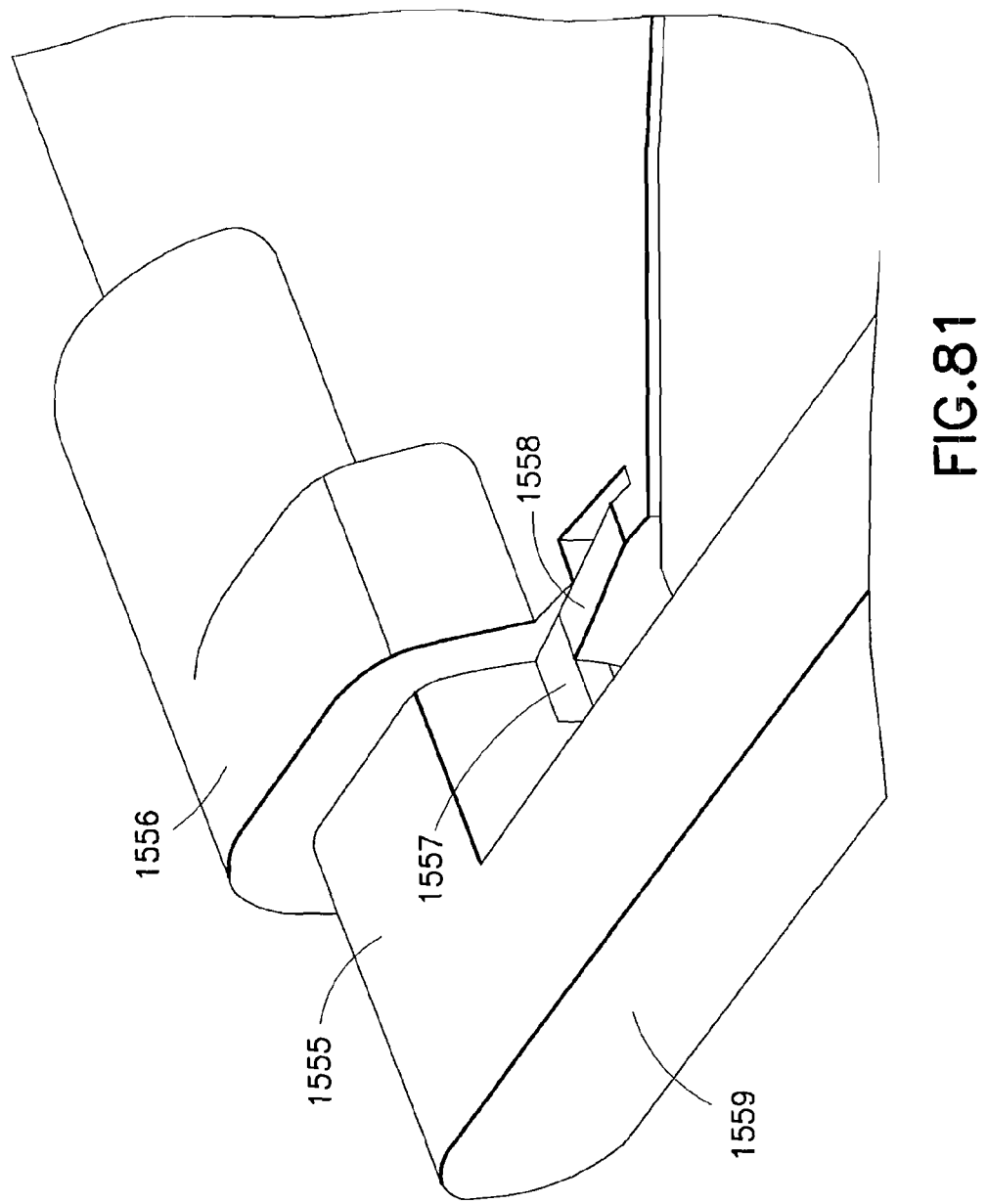
FIG. 81 is a cross-sectional view of the improved valve subassembly of FIG. 80 in an open position.

In yet another rotating valve embodiment shown in FIGS. 80 and 81, the infusion device can also use an improved rotating valve mechanism between a reservoir channel and a patient needle fluid path. FIGS. 80 and 81 illustrate the valve assembly in a closed and open position, respectively. In FIG. 80, the fluid path openings 1557 and 1558 are not aligned due to the rotational position of the arm 1559. As the arm 1559 is rotated in the direction of arrow A, member 1555 is rotated within member 1556 into the position shown in FIG. 81, such as when the patient needles are seated, and the fluid path openings 1557 and 1558 become aligned and allow fluid flow.

Returning to FIG. 1, a disk or Belleville spring 130 is also included in the device 100 for applying an essentially even, constant force to the reservoir to force the contents from the reservoir, and is therefore, referred to as a constant force spring. As noted above, the constant force spring 130 is used to store energy that when released by energizing the device, pressurizes the reservoir at the time of use. In FIG. 1, the Belleville spring is held in a flexed state by a retention disk, handle or pin 135, that is positioned at the center of a plurality of Belleville spring fingers. In doing so, the Belleville spring 130 is prevented from applying stress on the film 151 of the reservoir 150 or any remaining device components during storage.

When the retention pin 135 is pulled free of the Belleville spring 130, the fingers of the spring are released and exert a force on the film lid 151 of the reservoir 150. The edge of the Belleville spring 130 is typically trapped about an outer circumference of the reservoir 150 and can be configured to preferably create a pressure within the reservoir of from about 1 to 50 psi, and more preferably from about 2 to about 25 psi, and most preferably from about 15 to about 20 psi for intradermal delivery of the reservoir contents. For subcutaneous injection or infusion, a range of about 2 to 5 psi may be sufficient.

For these values, it is desirable to hold constant or near-constant infusion pressure for the duration of treatment. The Belleville spring mechanism 130 is one means of providing such a near-constant force, which can be translated to a near-constant pressure. As noted above, one method of loading a Belleville spring is to deflect the fingers of the spring and insert a pin through the enlarged inside diameter of the opening created. To return to a non-deflected position, the fingers must first travel a distance that reduces the inside diameter, which is not possible while the pin is in place, thus holding the spring in a loaded state. Triggering the Belleville spring is then simply a matter of removing the pin, but because the fingers of the Belleville spring induce a significant frictional load on the pin, the force required to pull the pin, even using a lever arm, can be substantial. If a "moment" is applied on the lever arm between the fingers and the pin, removal becomes much easier.

Figure 82:
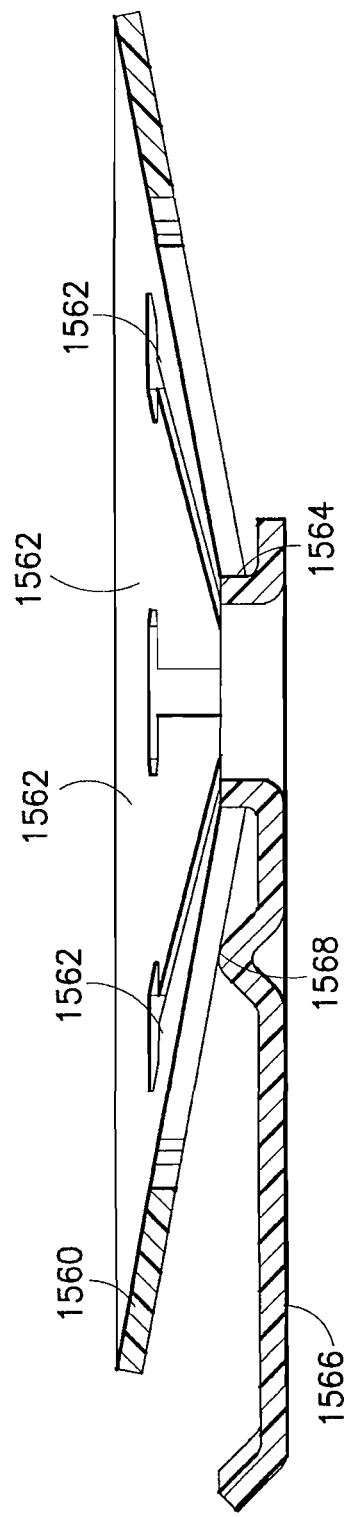
FIG. 82 is a cross-sectional view of an improved Belleville spring and pin embodiment in a secured position.
Figure 83:
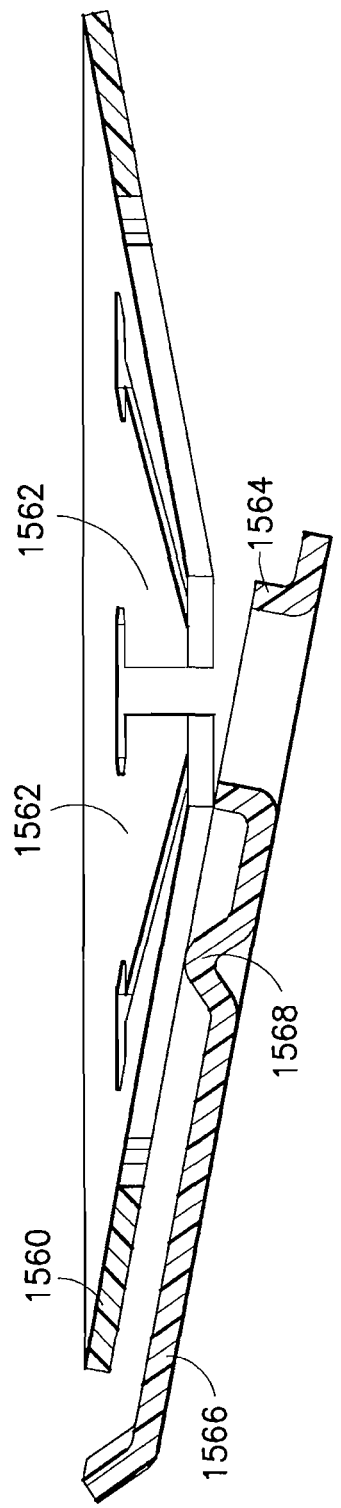
FIG. 83 is a cross-sectional view of the improved Belleville spring and pin embodiment of FIG. 82 in a released position.

In the improvement embodiment shown in FIG. 82, a Belleville spring 1560 is shown, including a number of fingers 1562, a pin 1564, a lever arm 1566 and a fulcrum 1568. When a force is applied to a distal end of the lever arm 1566, a reactionary force is induced on the Belleville spring fingers 1562 at the fulcrum 1568. Further application of the force will rotate the pin 1564 until it pops free of the Belleville spring 1560, removing the pin 1564 as shown in FIG. 83.

Figure 84:
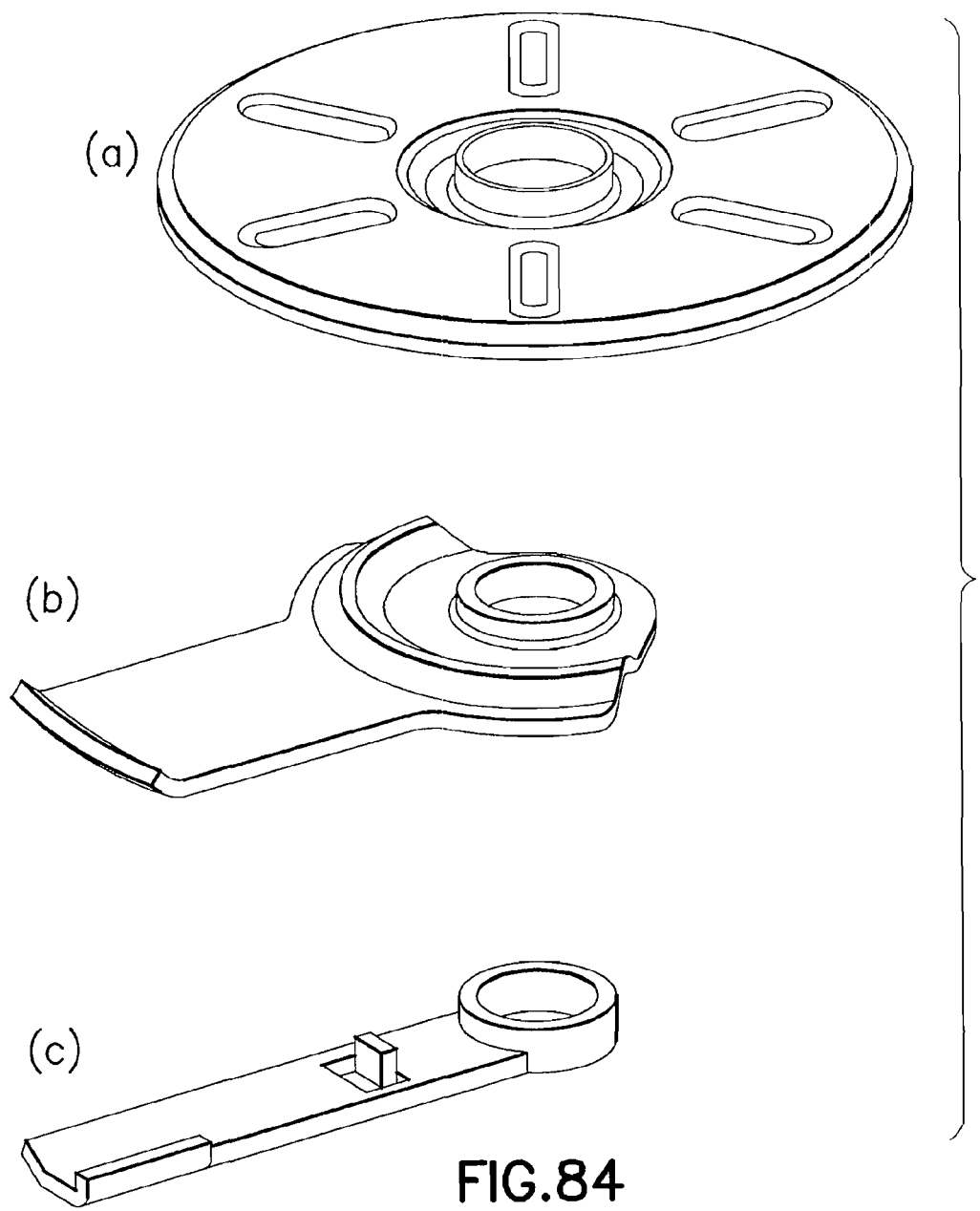
FIGS. 84(a) through 84(c) are perspective views of a first, second and third improved Belleville spring and pin embodiment configuration.
Figure 85:
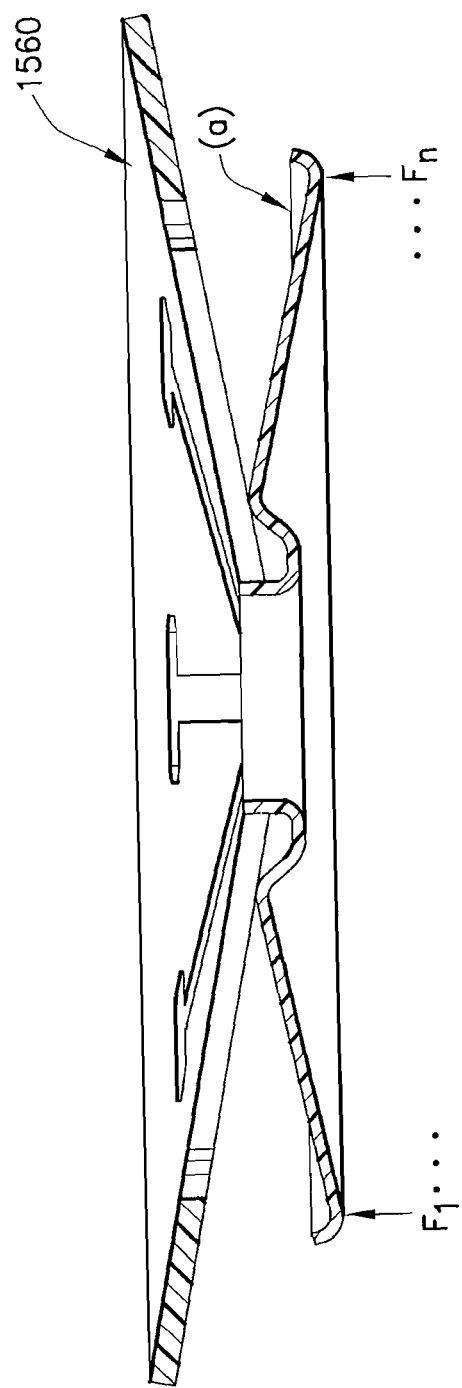
FIG. 85 is a force vector diagram of an improved Belleville spring and pin embodiment configuration.

A sample of several, but not all pin 1564 geometry configurations which can use this basic principle are shown in FIGS. 84(*a*), 84(*b*), and 84(*c*), and include a circular pin (a), a broad lever pin (b), and a narrow lever pin (c) to provide rotational lifting. The round geometry as shown in configuration (a), allows a releasing force $F_1 \ldots F_n$ to be applied anywhere around the outer perimeter of the part (a), top or bottom, as shown in FIG. 85, to release the pin 84(*a*). The broad lever geometry as shown in configuration (b), allows a releasing force to be applied at a substantially narrower perimeter of the part to release the pin (b), as typically provided by a push button. The narrow lever geometry as shown in configuration (c), allows a releasing force to be applied from the side of the lever (c), rather than the end. In regard to configuration (a) of FIG. 84, application of the releasing force at an extreme edge of the circular pin (a), as shown in the force diagram of FIG. 85, results in a longer effective lever arm, thus lowering the required force.

Figure 86:
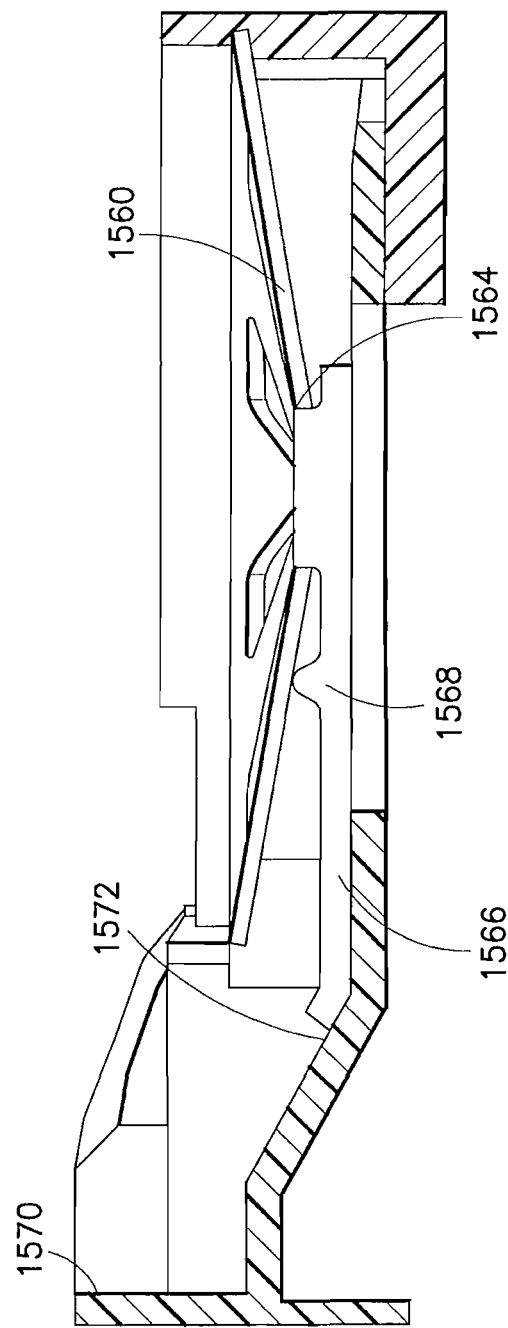
FIG. 86 is a cross-sectional view of an improved Belleville spring and pin embodiment in a secured position within an example infusion device to illustrate button induced pin release.
Figure 87:
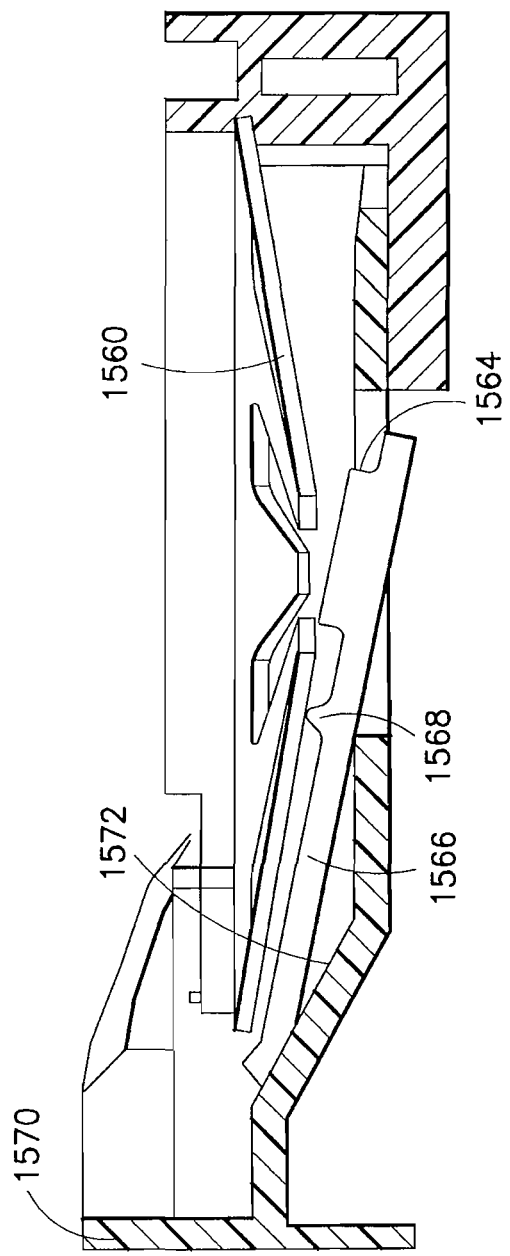
FIG. 87 is a cross-sectional view of the improved Belleville spring and pin embodiment of FIG. 86 in a released position.
Figure 88:
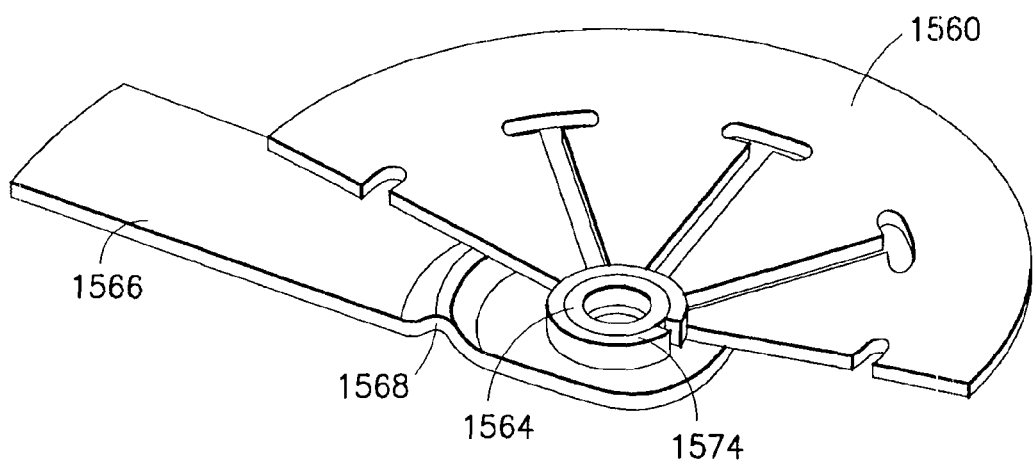
FIG. 88 is a cross-sectional view of an improved Belleville spring and split ring pin embodiment.
Figure 89:
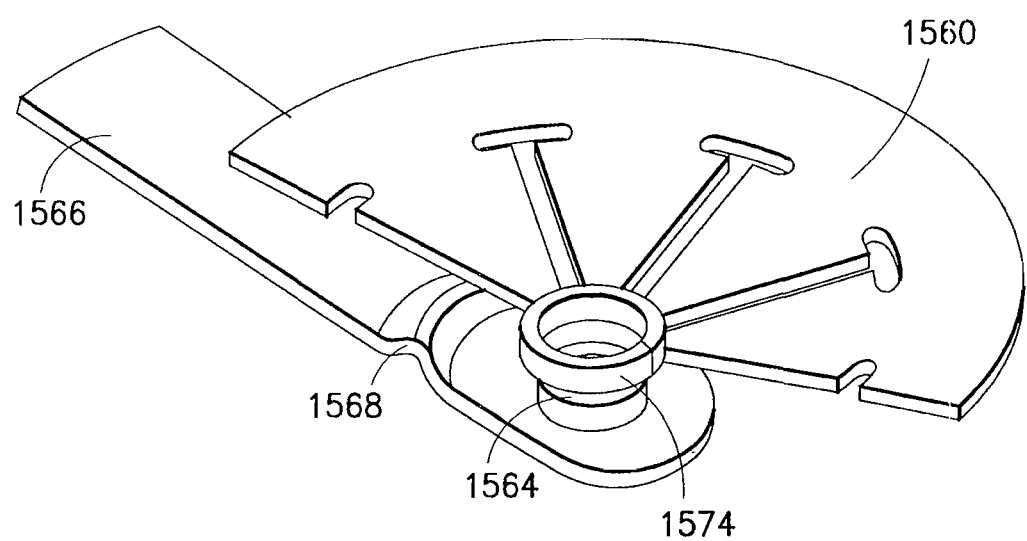
FIG. 89 is a second cross-sectional view of the improved Belleville spring and split ring pin embodiment of FIG. 88.

Two factors that can influence where the force is applied are overall height of the device, and ease of assembly in manufacturing. One method of applying the force and release the Belleville spring is shown in cross-sectional views of FIGS. 86 and 87. When in place within an infusion device that is button activated, the button 1570 is typically pushed to the right as shown, and the ramp 1572 applies the force on the pin 1564 via the lever arm 1566 to remove the pin 1564 from the Belleville spring 1560. Another version of this improved embodiment which can further reduce the required pull-out force, provides a split-ring 1574 on the outside of the pin 1564 as shown in a perspective view in FIGS. 88 and 89. The split-ring 1574 would necessarily have a low coefficient of friction to allow removal of the pin 1564 from the inside diameter of the split-ring 1574, and be compliant enough to collapse the split gap when the pin 1564 is removed as shown in FIG. 89, allowing the Belleville spring 1560 to activate.

In each of the above embodiments, the position and height of the fulcrum 1568, relative to the center line and height of the pin 1564, are critical to the function. In order to maximize the efficiency, the fulcrum 1568 should be positioned and scaled so that it will induce enough pin displacement such that the pin 1564 clears the Belleville spring 1560, but requires a minimum amount of releasing force. Placing the fulcrum 1568 farther from the centerline of the pin 1564 will provide more pin displacement, but increases the releasing force required on the lever arm to remove the pin 1564. Likewise, placing the fulcrum 1568 closer to the centerline of the pin 1564 will provide less pin displacement, but decrease the releasing force required on the lever arm to remove the pin 1564.

In order to assure reliable operation in some applications, especially those having very pliable spring fingers, the mechanism must be designed such that the fulcrum spans more than one of the fingers of the Belleville spring. Configurations (a) and (b) in FIG. 84 therefore, are better suited for these applications than configuration (c) in this regard. Conceptually, configuration (c) will work with a multitude of narrow, closely-spaced fingers, or it can be made to work by simply widening the fulcrum 1568 only. If more than one finger of the Belleville spring 1560 is not spanned in some cases, the single finger in contact may deflect independently of the other fingers and slide along the pin 1564 without inducing the sliding of the pin relative to the other fingers, resulting in a spring release failure.

Figure 90:
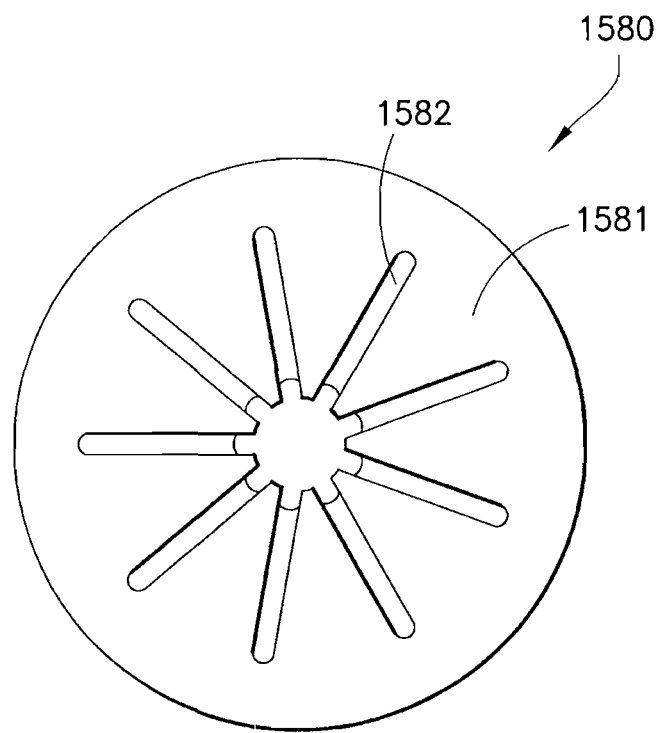
FIG. 90 is a perspective view of an overmolded Belleville spring in accordance with an embodiment of the present invention.

FIGS. 90 through 92 illustrate an improved embodiment of the Belleville spring 1580 which can be used in association with the improved pin release mechanisms described above and in place of the Belleville spring 1560. The improved Belleville spring 1580 is typically sized between about 1.15 to 1.50 inches in diameter, preferably 1.26 inches, and can further include a spring follower 1592 to allow for full reservoir content delivery substantially as described above with reference to FIGS. 55 through 60. In the improved spring embodiment 1580 described below, the Belleville spring includes a conventional spring body 1581, and an overmolded elastomer 1582 which covers the body 1581 and fills in the otherwise open spaces between the spring fingers, such that as the Belleville spring 1580 travels between a flexed and relaxed position, the spring exerts a substantially uniform and constant force over the entire reservoir film surface. The overmolded elastomer fills in the "dead spaces" between the fingers of the spring without compromising the performance of the Belleville spring.

The Belleville spring improvement embodiment 1580 shown in FIGS. 90 through 92 can be provided as the primary fluid chamber pressurization mechanism. The above infusion devices typically incorporate a Belleville spring suited for administering a desired pressure on a fluid filled chamber when the Belleville spring is allowed to flex upon the chamber and thereafter, expel the fluid in the chamber by displacement. As shown in FIGS. 91 and 92, inherent in the design of the chamber is a rigid side of the chamber 1598 to provide structure to the chamber, and a flexible film side of the chamber 1594 which is deformable to accept the arms of the Belleville spring biasing into the chamber to displace fluid in the chamber. Though the Belleville spring and the chamber may be suitable for pressurizing the chamber and delivering the fluid, the Belleville spring is ultimately unable to fully conform to the shape of the rigid side of the chamber 1598 due to the rigid nature of both the chamber and the Belleville spring. This lack of conformity results in some fluid not being fully pushed out of the chamber when the spring "bottoms out" into the chamber. Such fluid loss is undesirable.

The improved Belleville spring embodiment 1580 of the present invention includes an assembly that seeks to address this fluid loss to some degree by over-molding the Belleville spring 1580 with an elastomeric material, especially between the fingers of the Belleville spring 1580, such that the elastomer permits the Belleville spring 1580 to more fully conform to the chamber. This allows the Belleville spring 1580 to displace more fluid, as gaps between fingers are no longer present, and reduce fluid loss. An example of such a use of an overmolded Belleville spring 1580 is shown in FIGS. 91 and 92. The elastomer filled areas 1582 of the spring 1580 fill the "dead spaces" between the fingers of the spring without compromising performance.

The elastomer can be molded over the entirety of the Belleville spring 1580 to create a spring with a compliant surface capable of permitting the Belleville spring 1580 to both pressurize the chamber, and conform completely to the contours of the chamber to displace all the fluid in the chamber. As shown in reservoir cross-sectional FIGS. 91 and 92, the Belleville spring 1590 further includes an overmolded elastomeric follower 1592, similar to the followers of FIGS. 55 through 60, but provided as an overmolded surface to the Belleville spring 1590. The follower 1592 is provided and more closely conforms to the shapes in the reservoir, specifically the rigid side of the chamber 1598, such that dead spaces are prevented as they are filled by the follower 1592 as the Belleville spring 1590 travels.

Adjacent to the Belleville spring 1590, a flexible film seal 1594 is provided covering a fluid pocket 1596 positioned against a rigid chamber wall 1598. When released, the Belleville spring 1590 forces the contents from the chamber as shown in FIG. 91. In the embodiment shown in FIG. 91, the spring 1590 displaces the fluid in the pocket completely by "squishing" it out via the overmolded elastomeric follower 1592. The advantage of such an elastomer covered Belleville spring 1590 and spring follower 1592 described above is that it enhances the performance of the Belleville spring as a "squeegee" to ensure complete evacuation of the fluid in the chamber while not compromising its performance as a pressurizer of the same chamber.

Figure 93:
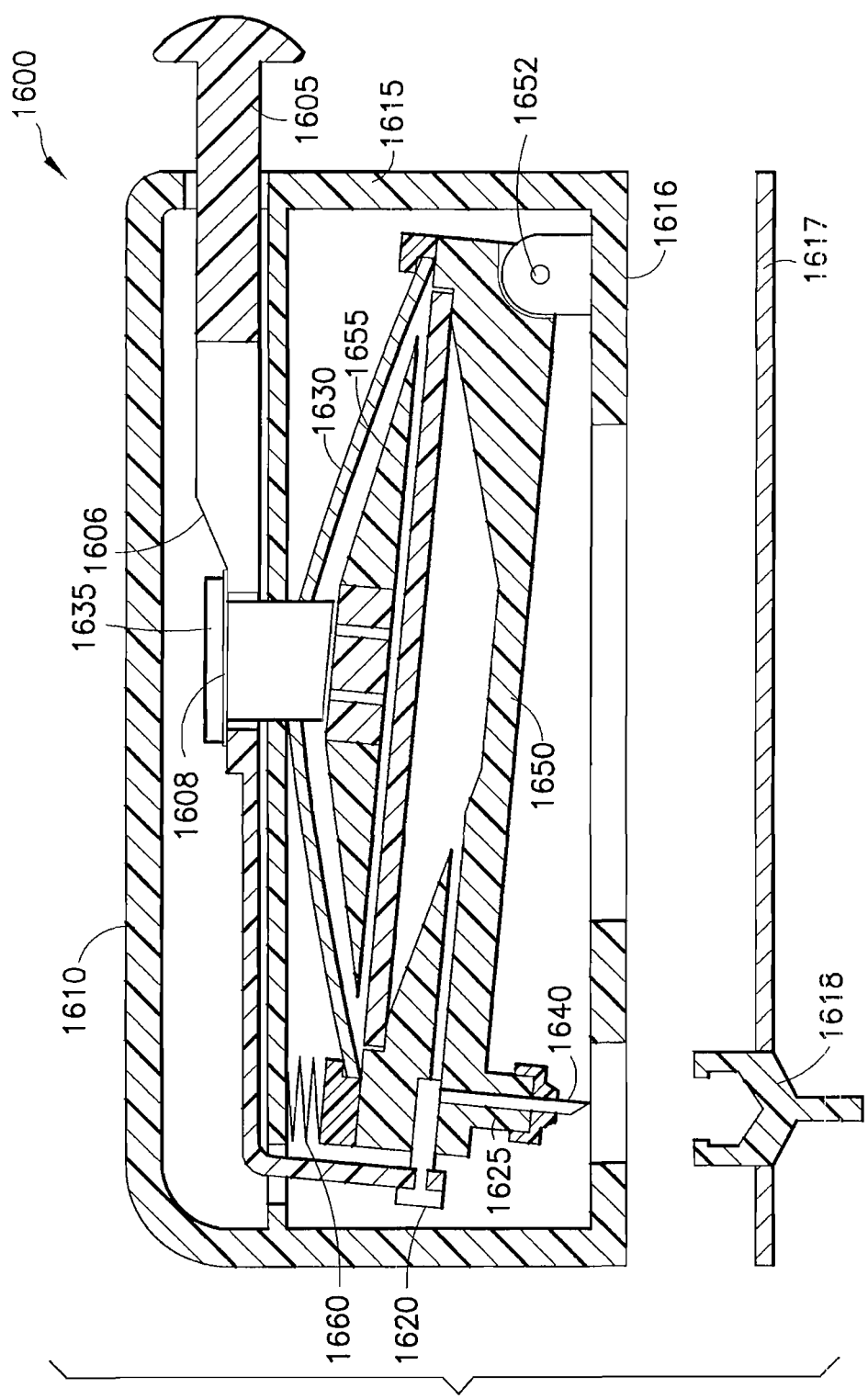
FIG. 93 is a cross-sectional view of a device embodiment using Belleville spring and pin friction to hold the device in a pre-activated state.

Another benefit associated with the use of a Belleville spring assembly is the ability to use friction created by the Belleville spring in a productive manner. For example, as shown in device cross-sectional FIG. 93, the friction between the retaining pin 1635 and the Belleville spring 1630 can be used to hold the device 1600 in an unreleased state. As shown in FIG. 93, an example device 1600 is shown having a pushbutton design wherein the activation and energizing of the device 1600 is accomplished in a single multi-function/step process. FIG. 93 is cross-sectional view of an example patch-like injector or infusor system that is activated using a side push button 1605.

The device of FIG. 93 includes the push button 1605, an upper housing 1610, a lower housing 1615, a reservoir pull valve assembly 1620, the Belleville spring 1630, the spring retention pin 1635, a manifold assembly 1625, and a reservoir 1650. The device further includes a flexible spring follower 1655. The device can further include an adhesive surface 1616 having a cover 1617, which is secured with a needle cap 1618 for one step removal. In the device shown in FIG. 93, as the push button 1605 is pushed, two functions are achieved in an ordered and/or simultaneous fashion, rather than the three functions of the device of FIG. 1. First, the movement of the push button 1605 opens the pull valve 1620 allowing fluid communication between the reservoir 1650 and the patient microneedles 1640 of the manifold 1625. The valve 1620 can be comprised of any number of pull valves as described above. Second, the movement of the push button 1605 dislodges the spring retention disk or pin 1635, releasing the Belleville spring 1630. However, the friction between the pin 1635 and the spring 1630 is also being used to hold the rotatable reservoir 1650 in a retracted position. When the push button releases the Belleville spring 1630, one or more manifold drive springs 1660 then rotate the reservoir 1650 downward about a hinge mechanism 1652, and drive the needles 1640 into the patient's skin.

The push button 1605 is provided with a tapered surface 1606 which further includes a slot 1608 (not shown) extending along a center of the tapered surface 1606 and through which the pin 1605 is allowed to travel. As the push button 1605 is pressed, the slotted tapered surface 1606 is forced to travel past the pin 1635, which forces the pin 1635 up the tapered surface 1606 and away from the spring 1630. The movement of the push button 1635 further serves to open the pull valve 1620. After a short distance, which is sufficient to open the pull valve 1620, the pin 1635 is lifted sufficiently to release the spring 1630 and the reservoir 1650.

Specifically, the Belleville spring 1630 is held under tension during storage by the pin 1635 that interferes with the inner fingers of the spring 1630, and keeps them from moving any closer (i.e., reducing the inside diameter of the center opening in the Belleville spring). The fingers must move closer as they pass through the center in order to relax. This allows a simple pin 1635 to be placed between the fingers (i.e., the inside diameter of the center opening in the Belleville spring 1630) when it is flexed past center to hold the tension of the spring 1630. However, the device must also automatically insert the infusion micro needles 1640 which are attached to the reservoir by way of one or more separate drive springs 1660. These drive springs 1660 are compressed for storage until the device 1600 is used, at which time the entire reservoir 1650 moves with the micro needles 1640 as they are being inserted.

In the embodiment shown in FIG. 93, the friction between the pin 1635 and the Belleville spring 1630 is used as the means of holding the drive springs 1660 under compression and the device 1600 in an unactivated state. The user activates the device 1600 by removing the pin 1635 from the Belleville spring 1630 via movement of the button 1605. The removal of the pin 1635 not only allows the released Belleville spring 1630 to pressurize the reservoir 1650, but it also releases the reservoir 1650 and needles 1640 to rotate downward under the force of the drive springs 1660, and the movement is sufficient to insert the needles 1640 into the patient's skin (not shown). The pin 1635 holds the tension on both the Belleville spring 1630 and the drive springs 1660, thus it requires only a single motion to set in motion two completely different actions.

In other devices, the user is required to perform two or more different steps to accomplish the pressurization of the reservoir and the release of the patient needles. Still other devices have the button perform the two steps with one push from the user, but require a more complicated button assembly to accomplish the correct timing of the actions. In the embodiment shown in FIG. 93, the timing is integral with the device. This is achieved by utilizing the Belleville spring and pin system as the reservoir drive spring release mechanism, utilizing the friction of the Belleville spring 1630 fingers on the pin 1635 as the means of holding the compression on the drive springs. The friction is eliminated when the pin 1635 is removed from the Belleville spring 1630 thereby allowing the drive springs 1660 to push the needles 1640 into the patient.

As noted above, the Belleville spring is allowed to flex upon a reservoir to expel the fluid in the reservoir by displacement. As noted above, the reservoir itself can include a rigid side and a flexible film side which is deformable to accept the arms of the spring. However, reservoir improvements to materials and construction techniques can be provided, as described in greater detail below.

Figure 94:
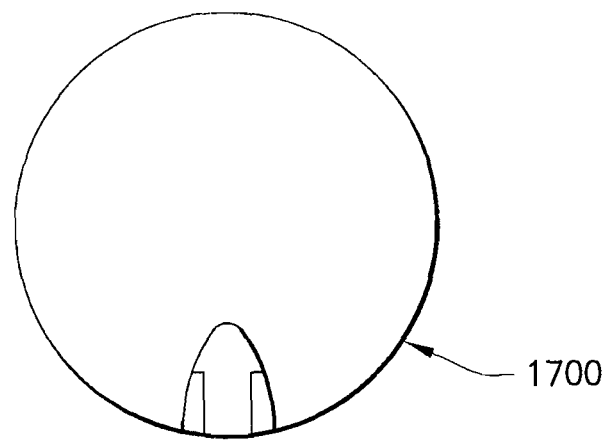
FIG. 94 is a top view of an improved reservoir embodiment of a device.
Figure 95:
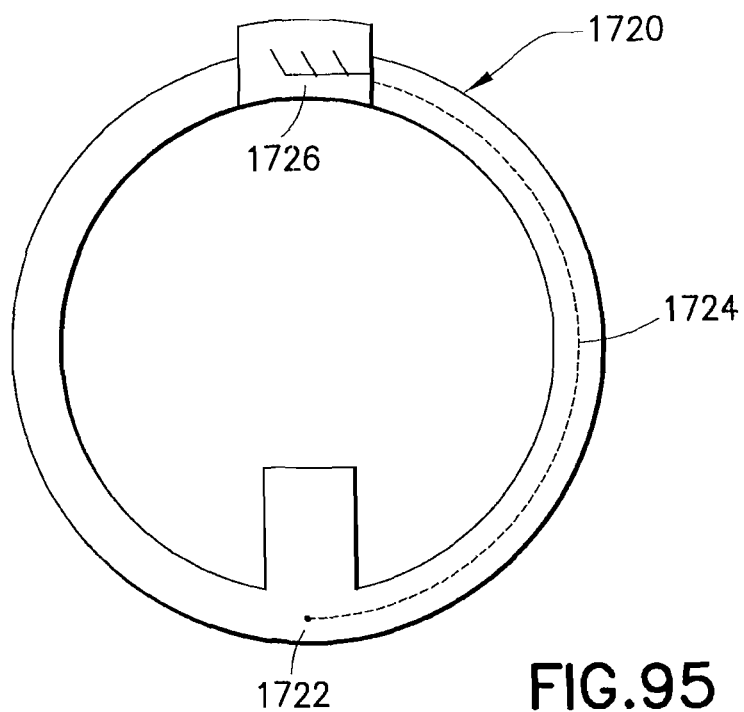
FIG. 95 is a top view of an improved arm/fluid path embodiment of a device.
Figure 96:
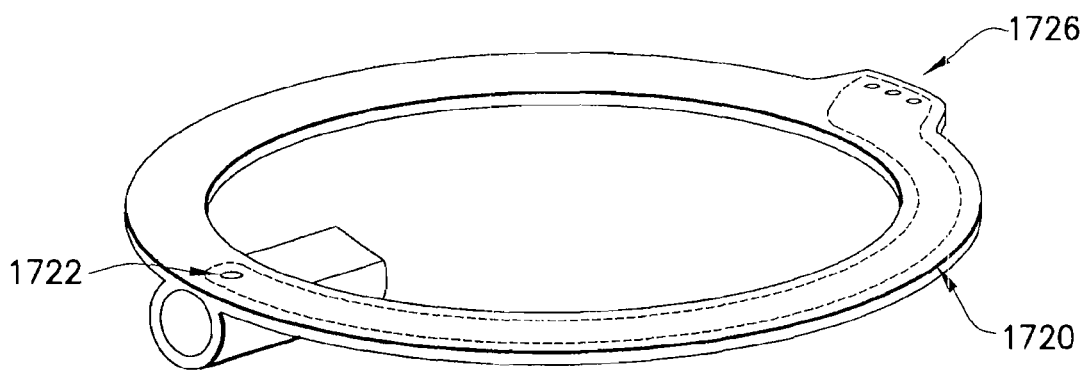
FIG. 96 is a perspective view of the improved arm/fluid path embodiment of FIG. 95.
Figure 97:
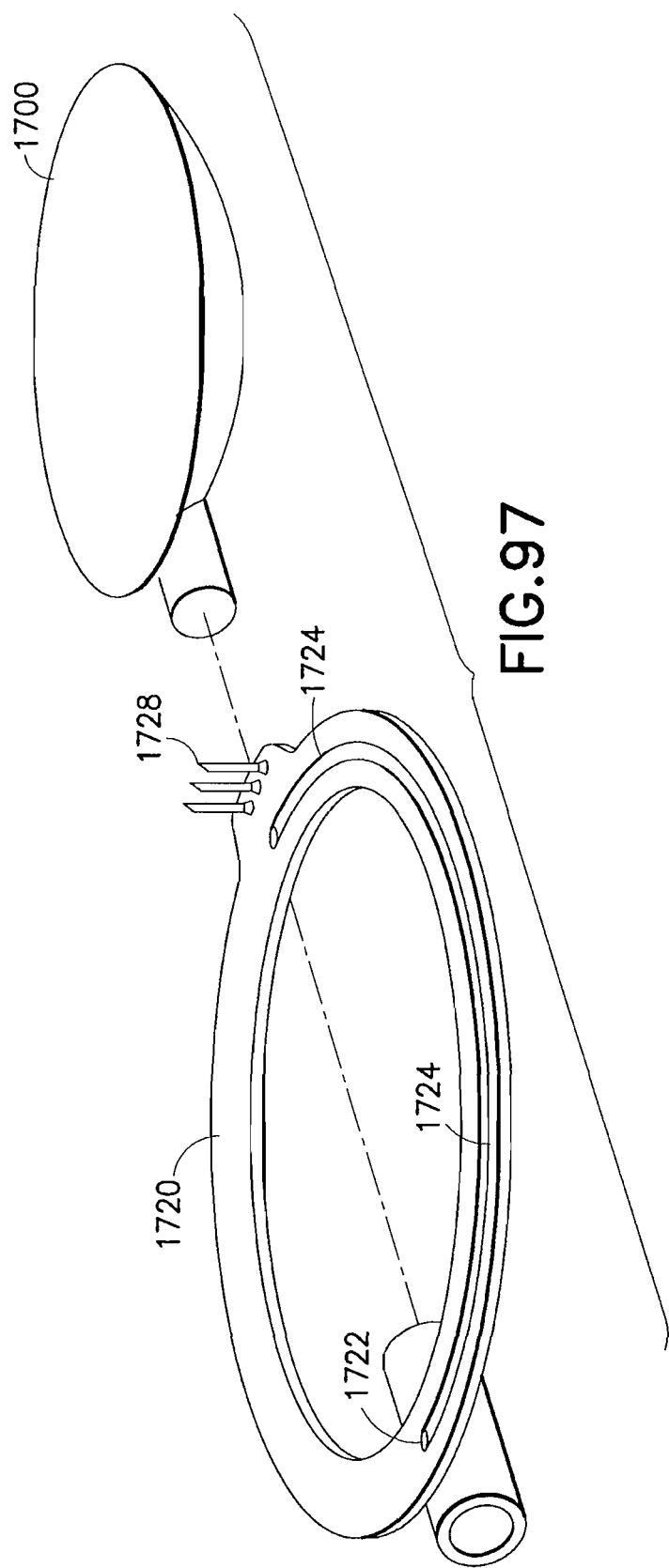
FIG. 97 is an assembly diagram of the improved reservoir and arm/fluid path embodiment of FIGS. 94 and 95 in a disassembled position.

In the typical infusion device, the reservoir is typically made of a material that has strong chemical and/or drug resistant properties. This material unfortunately does not bond well with other materials. The improved reservoir embodiments of the present invention shown in FIGS. 94 through 100, introduces at least one other material which will bond well to other materials, such as needles, and then includes a means to mechanically lock the non-bondable materials to this new material. This separates the non-bondable materials, such as the reservoir 1700, which contains the strong drug resistant properties, from the bondable materials, such as the needle hub/spring arm 1720 of FIG. 95. The two separate pieces then interface and act as one with each other via a sealing interlock, such as an O-ring sealed lock 1730, or an elastomeric sealed lock 1740 as shown in FIGS. 99 and 100, respectively. FIG. 94 is a view of a reservoir, and FIG. 95 is a view of a reservoir arm providing a fluid path. FIG. 96 is a perspective view of the reservoir arm of FIG. 95. FIG. 97 is an assembly illustration of the reservoir and arm of FIGS. 94 and 95, and FIG. 98 illustrates an assembled component.

The improved reservoir embodiments of the present invention include providing a reservoir 1700 and fluid path containing needle hub/spring arm 1720, each being constructed of two separate molded parts. The reservoir 1700 of FIGS. 94, 97 and 98, can be made of a material that has strong chemical and/or drug resistant properties. The needle hub/spring arm 1720 and resulting fluid path 1724 of FIGS. 95, 96, 97 and 98 can be made of any number of plastic materials, and can include a single film seal along the fluid path 1724 between the valve exit hole 1722 and the needle openings 1726. The reservoir 1700 can then be assembled with the needle hub/spring arm 1720 via a compatible valve mechanism 1730 or 1740, shown in FIGS. 99 and 100. FIGS. 99 and 100 illustrate a first and second valve 1730 and 1740 for use with the assembly of FIGS. 94 through 98.

In the typical infusion device, the configuration of the reservoir and needle hub/spring arm includes a reservoir and fluid path constructed of one part. However, as noted above, the reservoir 1700 is typically required to be made of a material that has strong chemical and/or drug resistant properties. This material unfortunately does not bond with other materials (i.e., the needles) very well. The advantage of separating the two pieces as shown in FIGS. 94 through 97, allows for easier assembly of the needles 1728 to the spring-arm hub. They can be insert-molded or bonded, instead of mechanically fixed into a non-bondable material.

Figure 98:
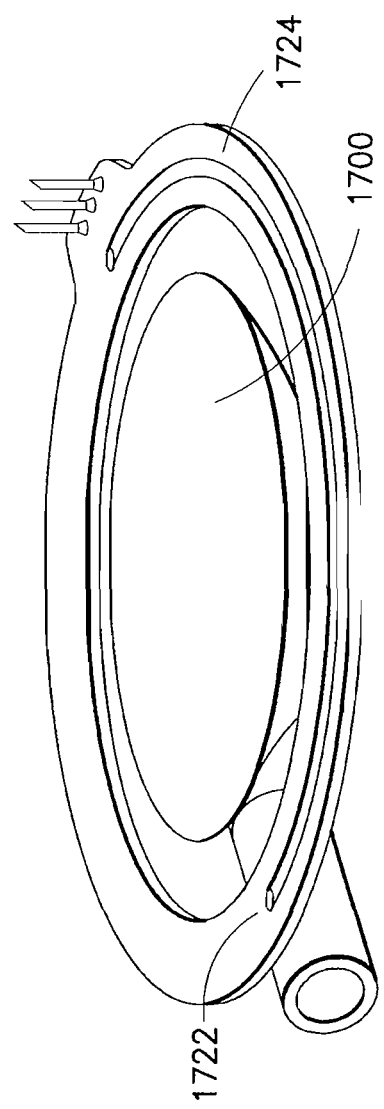
FIG. 98 is an assembly diagram of the improved reservoir and arm/fluid path embodiment of FIGS. 94 and 95 in an assembled position.
Figure 99:
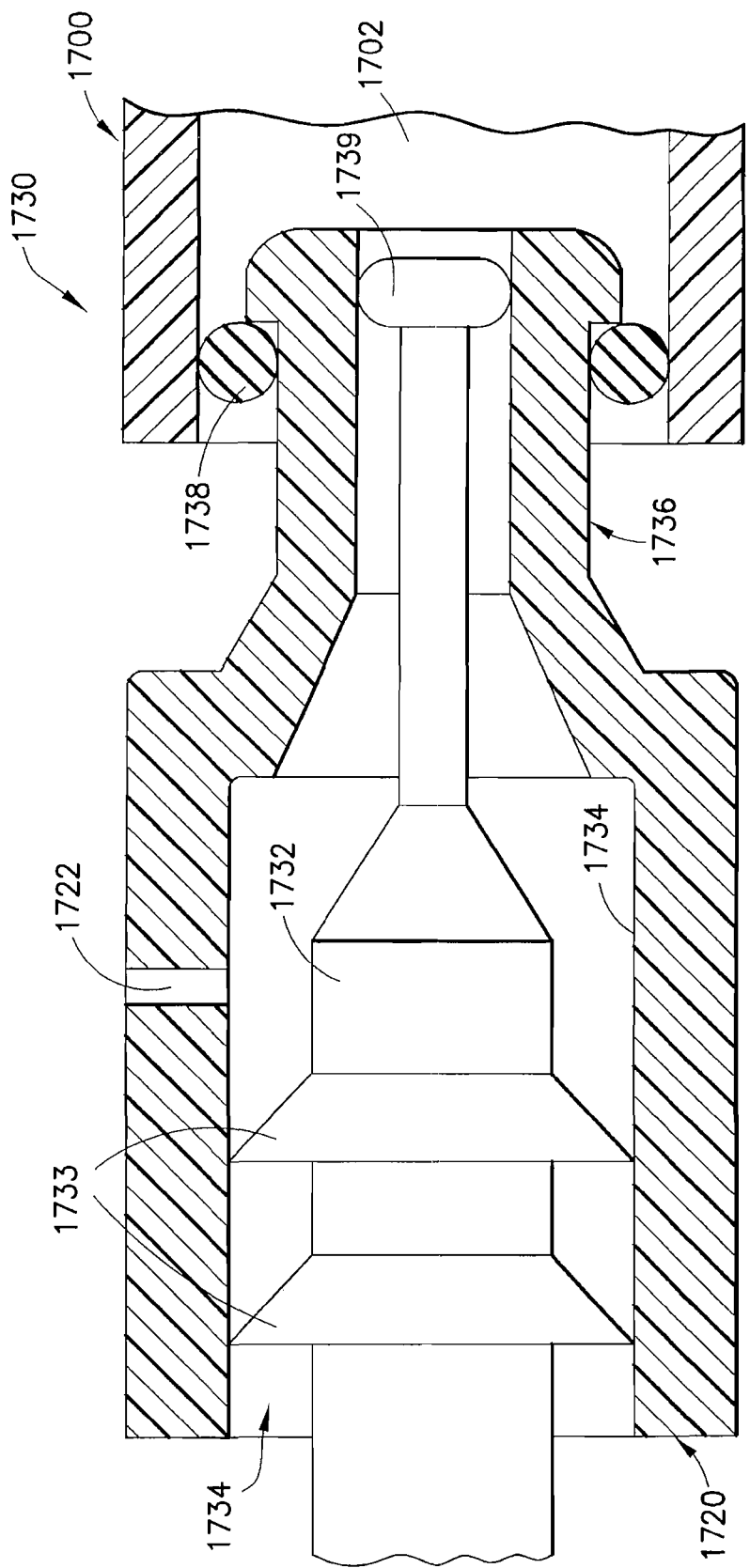
FIG. 99 is a cross-sectional view of a first sealing device for the reservoir and arm/fluid path assembly embodiment of FIG. 98.
Figure 100:
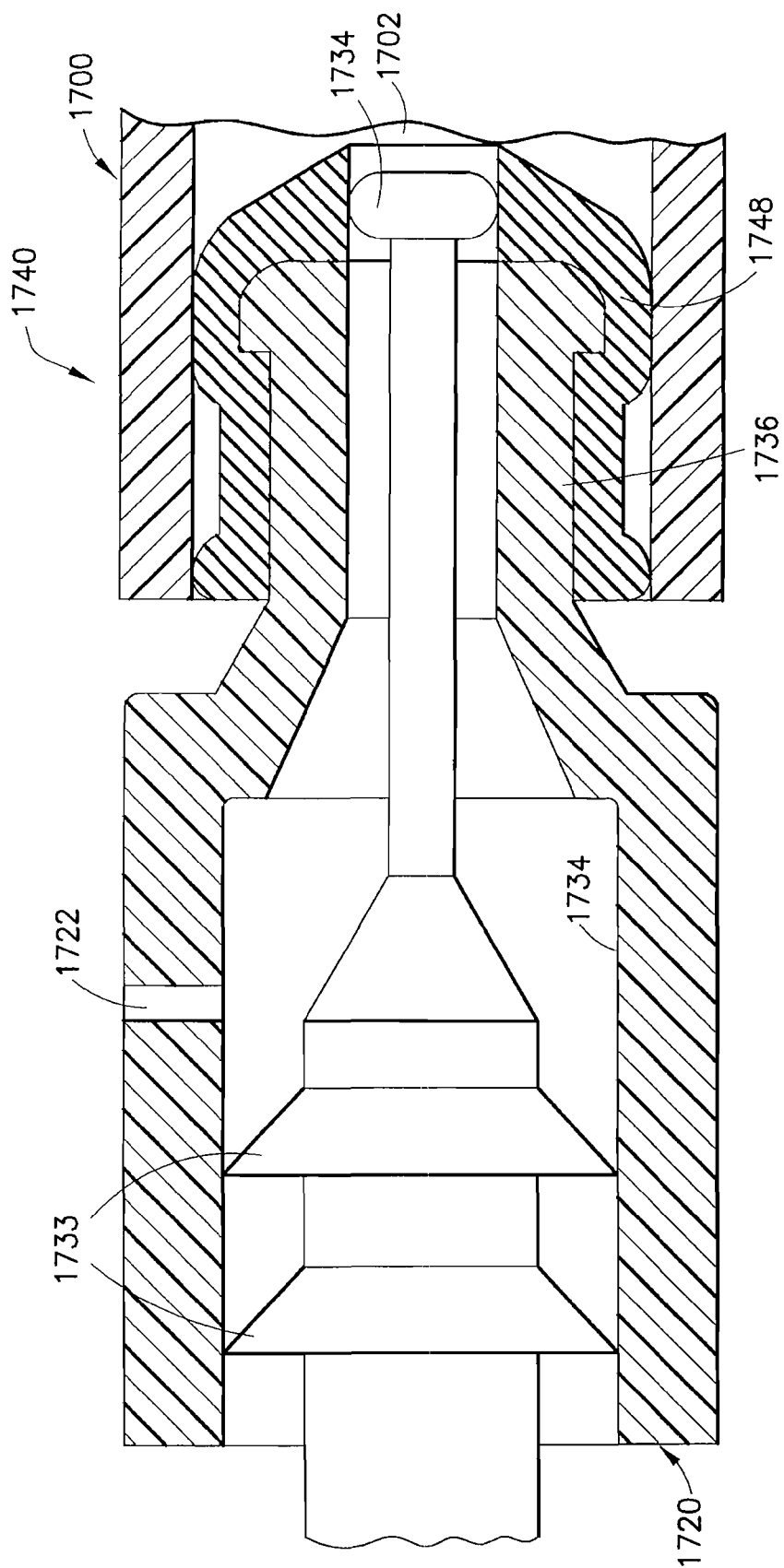
FIG. 100 is a cross-sectional view of a second sealing device for the reservoir and arm/fluid path assembly embodiment of FIG. 98.

Sealing interlock examples for completing the assembly shown in FIG. 98 are shown in FIGS. 99 and 100. In FIG. 99, a valve plunger rod 1732 is positioned within a cylindrical opening 1734 in the spring arm/fluid path housing 1720. The spring arm/fluid path housing 1720 includes a reduced diameter member 1736 which is mated with an opening 1702 in the reservoir 1700, and sealed with an O-ring 1738. The rod 1732 includes a number of ribs 1733 and an enlarged proximal end 1739 which functions substantially similar to those described above with reference to FIGS. 5 and 6. In FIG. 100, the O-ring seal 1738 is replaced with an elastomeric exterior seal 1748 about the outside surface of the reduced diameter member 1736. The remaining valve functions are substantially as described above in regards to FIG. 99.

This use of non-bondable and bondable material engagement is further incorporated in the following additional improved needle hub embodiments of the present invention. The embodiments use a two shot molding process which has the ability to have two or more thermoplastics of dissimilar nature create a fluid seal. Since the materials in question are dissimilar, they inherently resist being bonded to each other. In a normal two shot molding process, a seal is typically created via the adhesive nature of the plastics being used. In the case of the improved hub embodiments described below, there is no adhesive nature between the plastics, therefore a number of unique designs are utilized to create a pressure fit, and thus a fluid seal.

Figure 101:
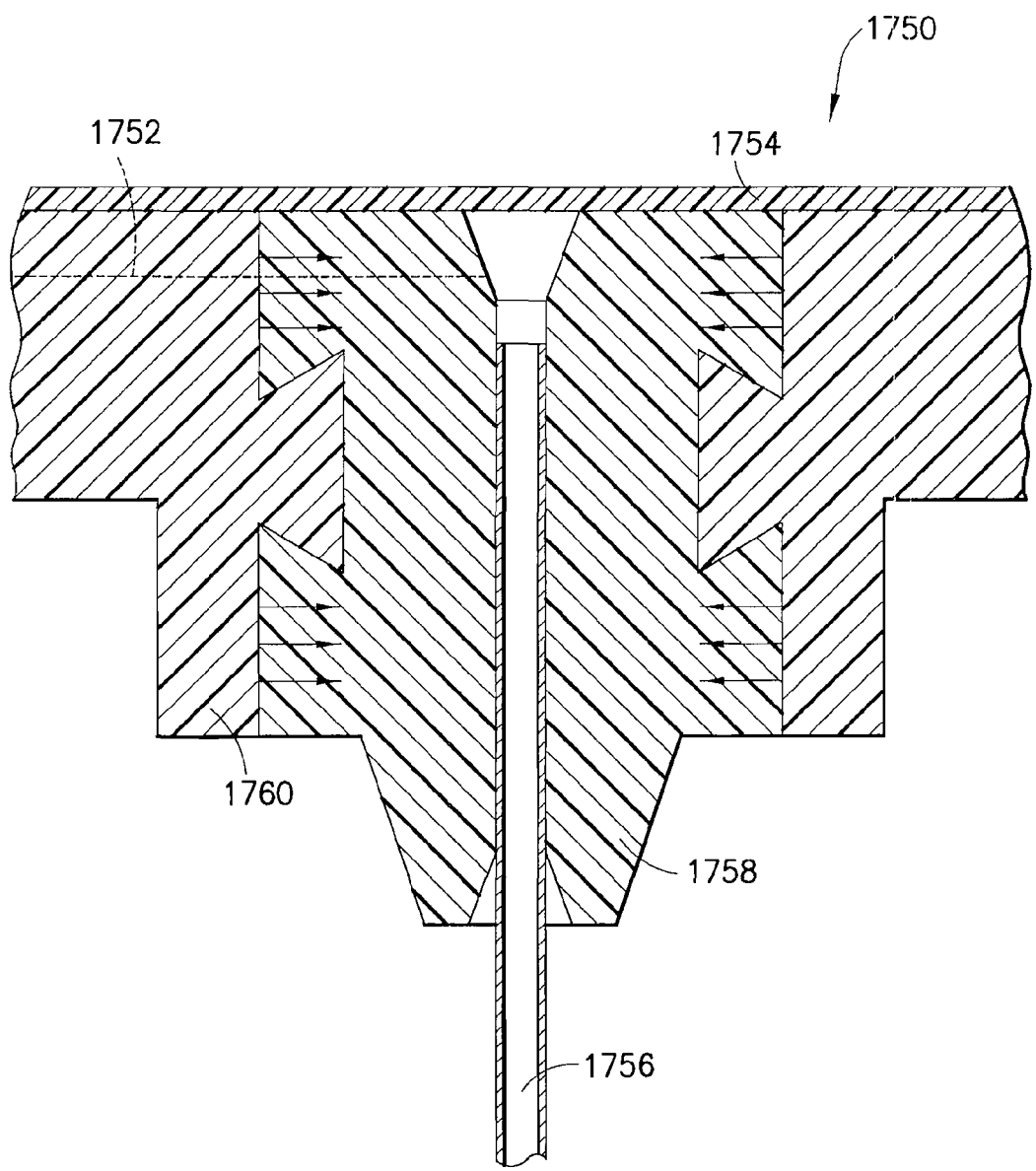
FIGS. 101 through 105 are cross-sectional views of construction examples of a patient needle manifold.
Figure 102:
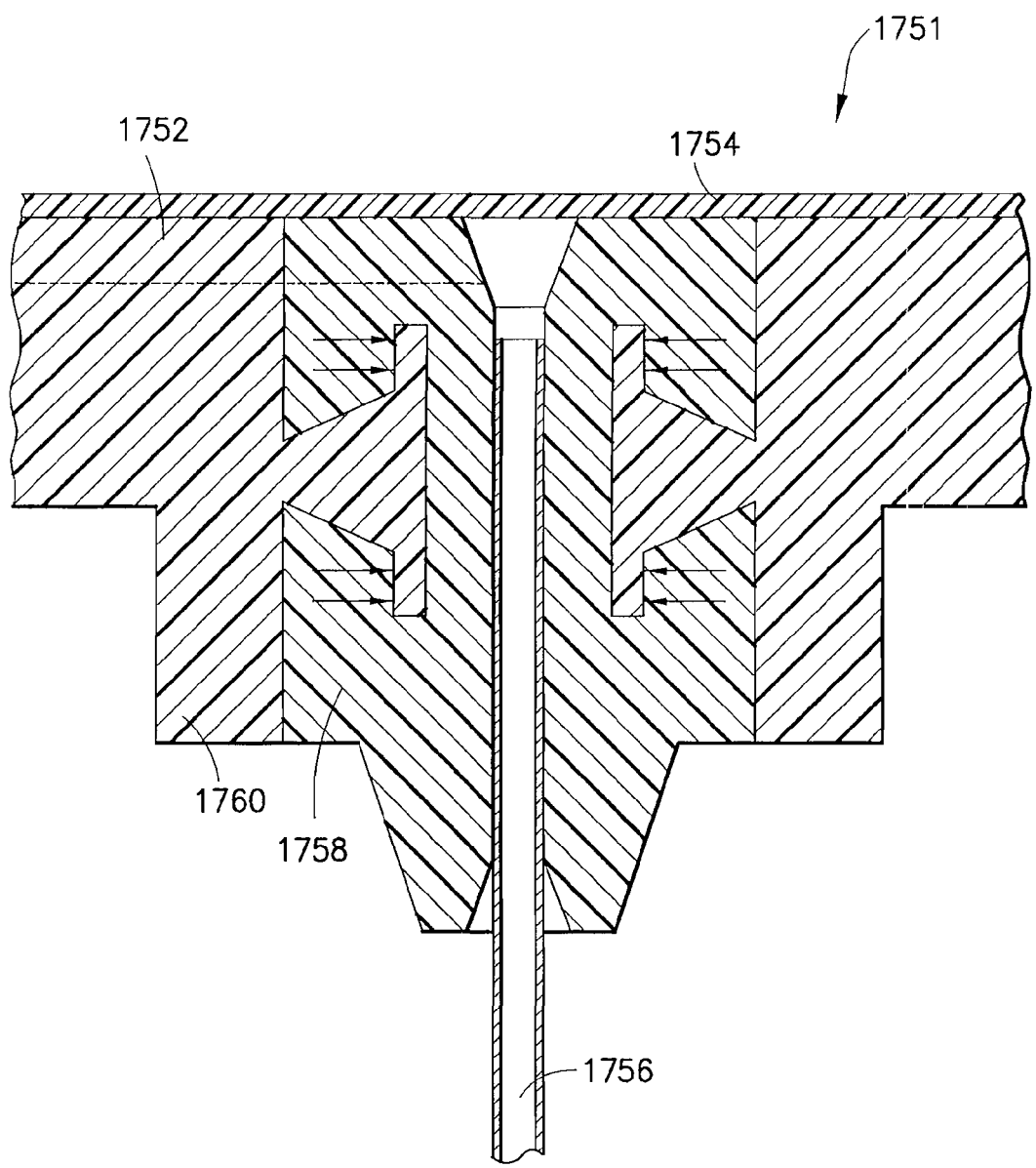

In FIG. 101, a cross-sectional view of a completed bond 1750 is shown, and includes a fluid path 1752, a film seal 1754, and a first shot mold 1760. A second shot mold 1758 is then disposed about the first shot mold 1760 and secures the needles 1756. The first shot mold 1760, as shown in FIG. 101, is molded having protruding dovetail configurations to provide a mechanical lock with the second shot mold 1758 as the second shot mold cools and shrinks about each dovetail.

Specifically, following appropriate cooling and standard multi-shot molding procedures, the second shot mold 1758 is done in a material with desirable processing characteristics such as polycarbonate. The first shot is done, in this case, in a transparent, clear plastic material. The transparent, clear plastic material is preferably a cyclic olefin copolymer (CCP) that is characterized by high transparency and clarity, low extractables and biocompatibility with the substance contained in the reservoir. This material is by nature incapable of bonding adhesively to another material such as polycarbonate and the like.

The geometry for the CCP first shot, as shown in FIGS. 102 through 105 which are cross-sectional views of completed molding assemblies 1751, 1753, 1755 and 1757, can include any number of dovetail and locking configurations. In each case, after appropriate cooling of the first shot, the second shot is done in a material, such as polycarbonate, and is injected around the dovetails such that they encompass each dovetail. When the second shot material shrinks, as all plastics do to some degree, it will put pressure on the sloped surfaces of the dovetail and have the effect of "pinching" the dovetail. This pinching creates the tight fluid seal between the two dissimilar materials that would otherwise be incapable of creating a fluid seal between them.

The improved embodiment of the present invention described above is further capable of creating a continuous fluid path in a single part over two different material types (i.e., 1760 and 1758). This reduces part count which reduces cost, as it would otherwise have to be done with a snap fit and potentially a sealing member, such as an O-ring. This would not only increase the cost due to part count, but further increase the manufacturing complexity as well. Additionally, the construction can take advantage of the desirable characteristics of two or more different materials and reduce compromises that would otherwise have to be made if construction was done in only one or the other material.

For example, by molding the first shot (i.e., 1760) in a material such as CCP, the embodiment can capitalize on the beneficial drug carrying capabilities of the material. Unfortunately, the material does not exhibit practically any other common, positive manufacturing or processing attribute. For example, CCP is difficult to bond with needles. Therefore, the second shot (i.e., 1758) can be done in a material such as a polycarbonate, which readily bonds needles to the polycarbonate, and further does not have adverse effects on the drug which is contained in the parts made of CCP.

Figure 103:
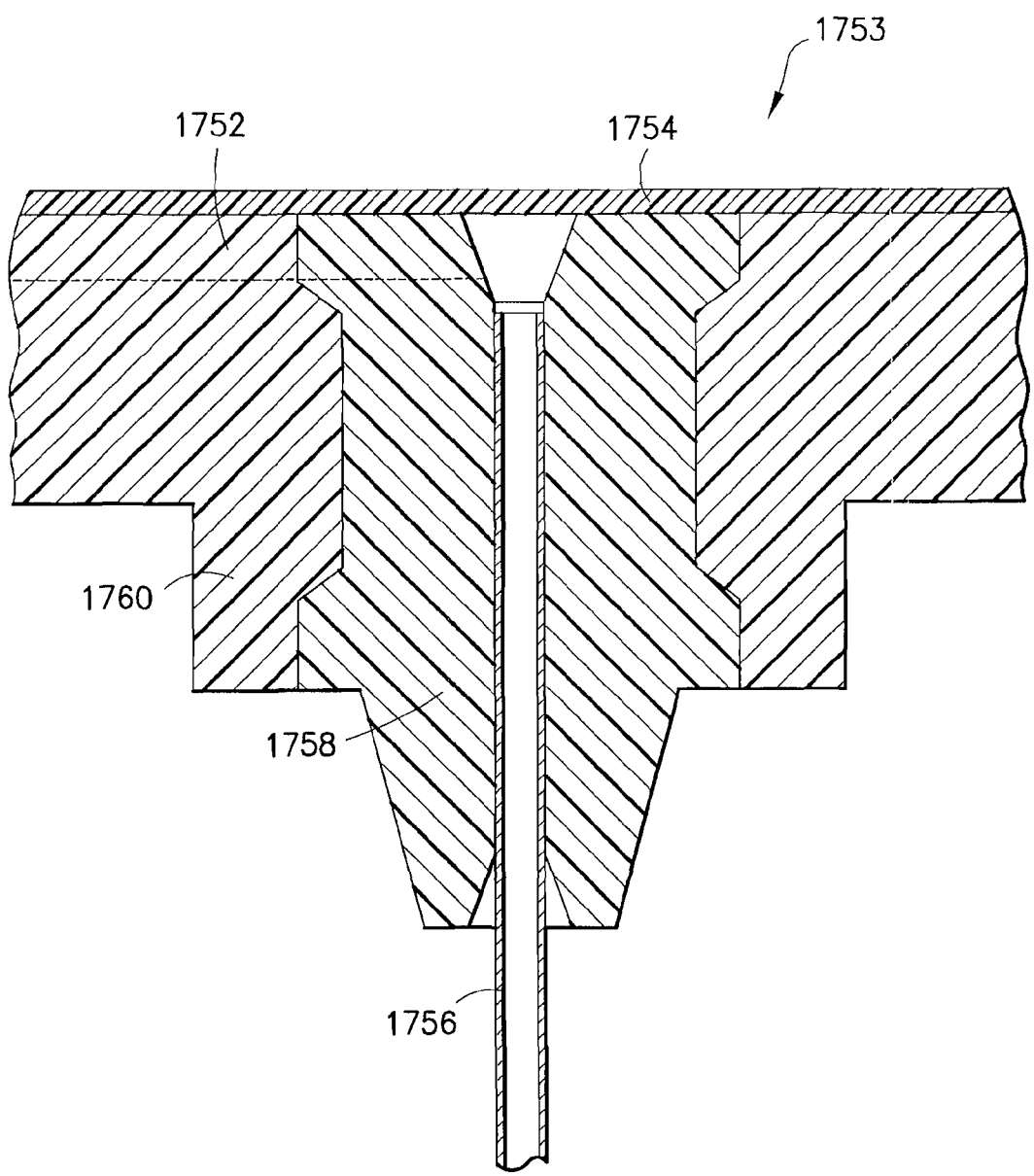
Figure 104:
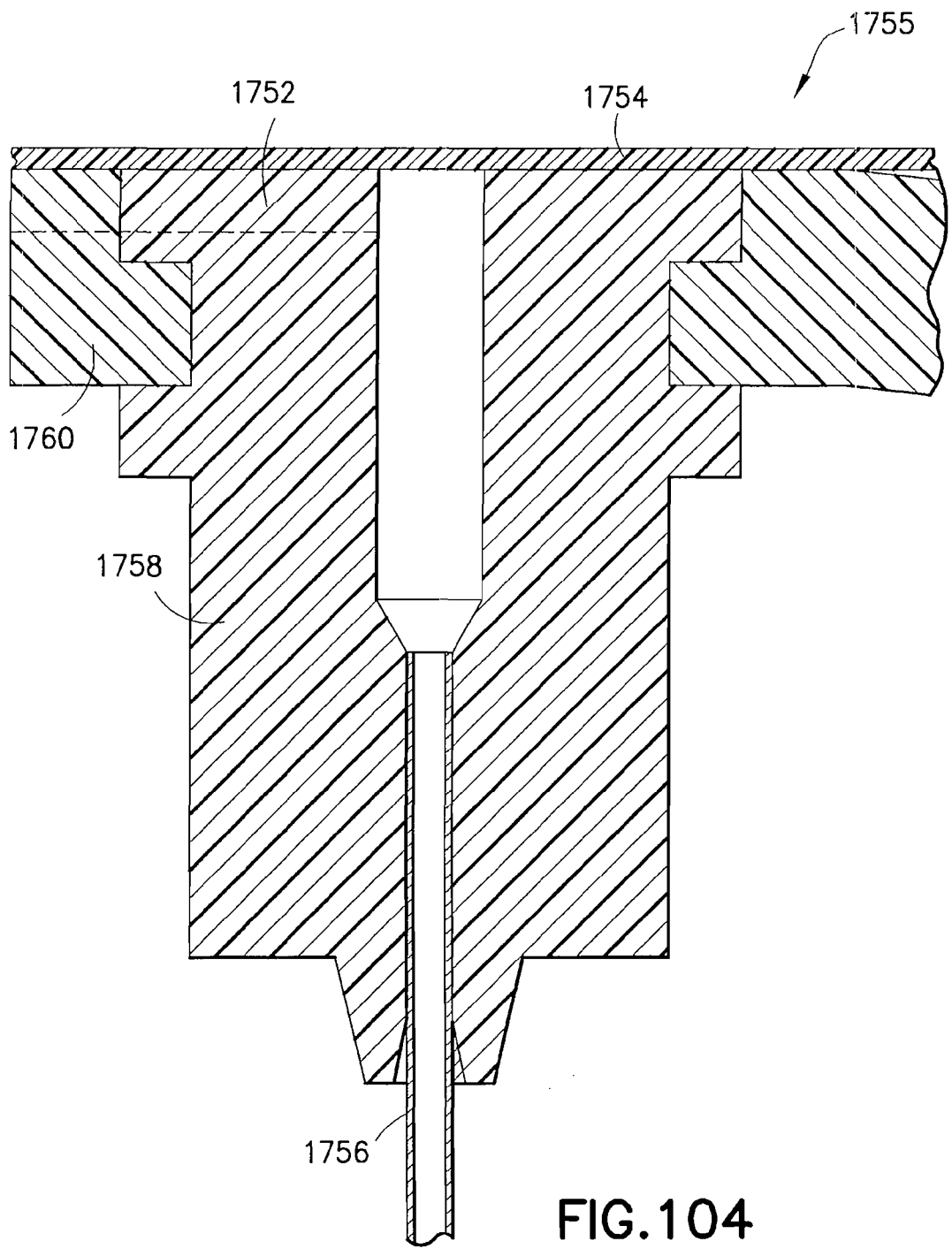
Figure 105:
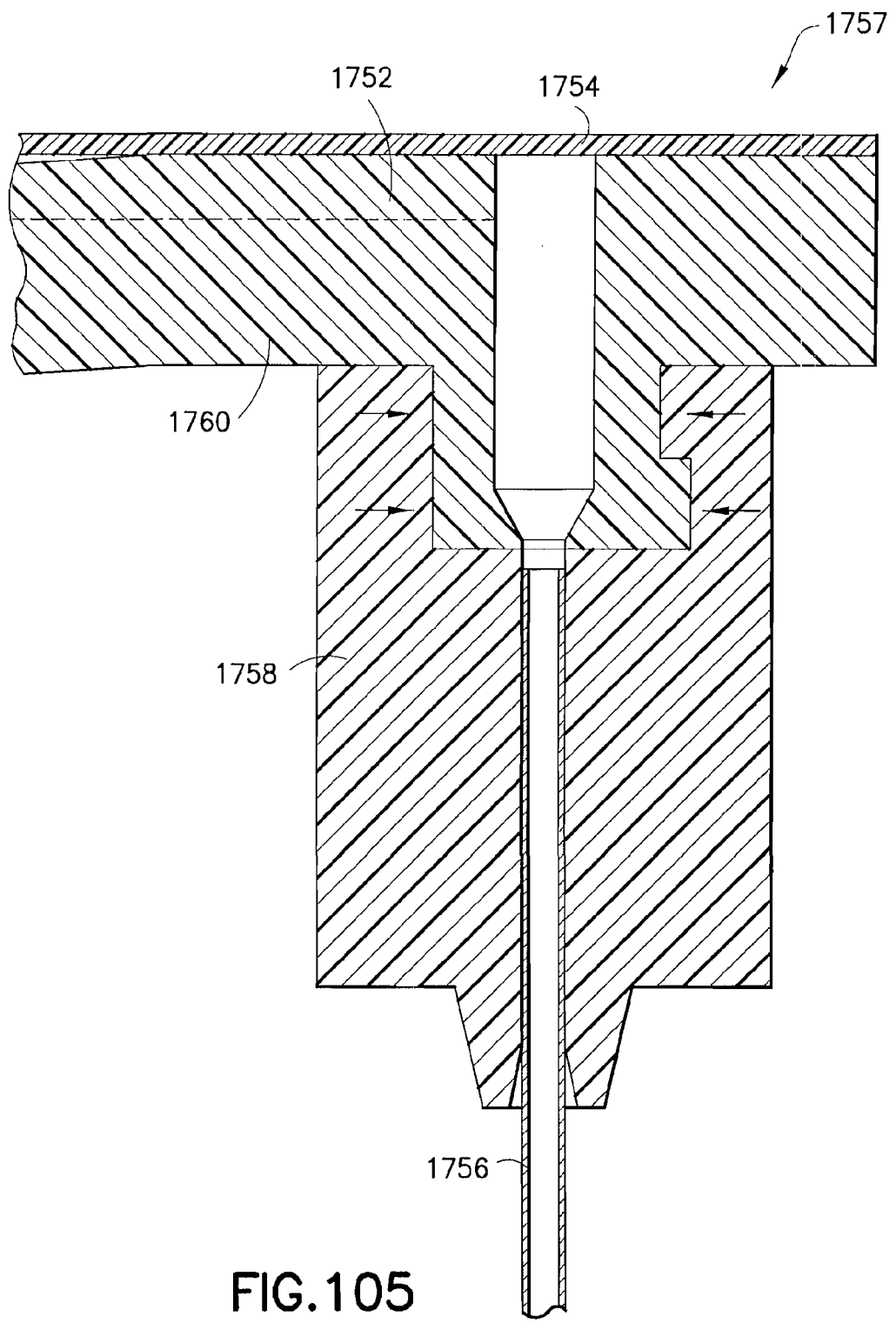

It will be appreciated that this concept of creating a fluid seal between two somewhat dissimilar materials can be accomplished in several ways. The underlying principle is channeling or harnessing the shrinking of one material against a surface of a second material in such a fashion as to induce a tight, pressure induced seal between the materials. This is achieved in the embodiments of the present improved feature invention by using variants on the dovetail concept. As shown in FIGS. 103 through 105, in the modified locks, shrinkage against vertical and perpendicular surfaces also can be used to create a sufficient fluid seal.

The concept can be further refined to include improvements for high volume molding, assembly, and automation processes. The dovetail arrangement represents an improvement over earlier concepts in several ways, including the simplification of the molding process and using the shrink in thermoplastic molding operations to create a pressure seal between dissimilar materials. The ability to bond with patient needles is further developed in the improved hub embodiments described in greater detail below.

Each embodiment of the infusion device described above contains at least one or more patient needles, or microneedles. Each microneedle is preferably at least 31 gauge or smaller, such as 34 gauge, and is anchored within the patient needle manifold and can be used to target either an intradermal or subcutaneous space as required by the specific application.

The patient needles are positioned in the patient needle manifold, which includes at least one fluid communication path to each patient needle. The manifold may simply have a single path to one or more patient needles, or may provide multiple fluid paths routing contents to each needle separately. In the embodiment of the improvement shown in FIG. 106, a mini needle hub 1770 is constructed to secure a needle 1772 and to then be snap fit into a corresponding needle manifold 1771.

In a micro infusion device, a drug reservoir typically has attributes suitable for storing and sustaining drugs in liquid form. The same reservoir, however, due to the drug storing attributes, has characteristics not well suited for peripheral manufacturing processes necessary to create a robust drug delivery device. Although it is desirable to have the fluid reservoir have direct communication with the needles which will eventually deliver the drug to a patient, the thermoplastic which is used to store the drug is not easily bonded to other materials. Thus, as noted above, it is nearly impossible to bond needles to the same reservoir material and create the desired fluid path without the needles potentially falling out due to the lack of a strong bond.

Figure 106:
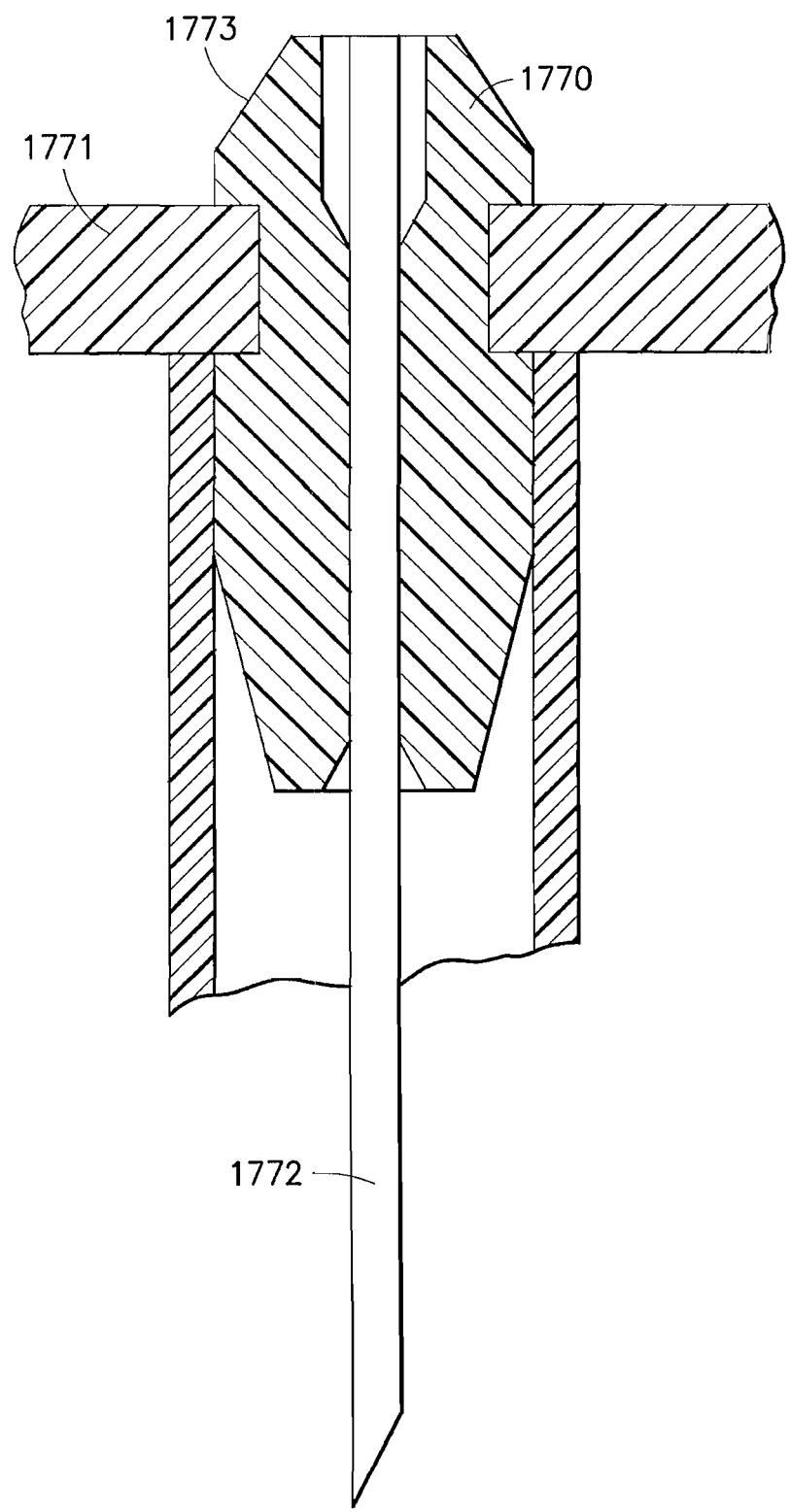
FIG. 106 is a cross-sectional view of an improved patient needle hub and manifold.

The improved hub embodiment of the present invention shown in FIG. 106, solves this problem by isolating the needle hub portion 1770 of the reservoir as a separate part. By doing this the separated hub 1770 can be configured to function properly (i.e., as a secure needle manifold), as can be the drug reservoir (i.e., as a biocompatible reservoir) (not shown). Unfortunately, when a single complex part is constructed as two simpler parts, this actually adds overall cost due to the increases in tools, handling, storage (i.e., stock keeping units or SKUs), and the like. However, the improvement embodiment shown in FIG. 106, by its simple manufacturing attributes, can save resources in the long run.

The hub 1770 can be molded in standard, uncomplicated mold tools at high cavitation. It can be automated at high speeds and can be molded in a material suitable for bonding with needles, such as needle 1772. The hub 1770 is further independent of large amounts of handling due to orientation requirements, and can be mechanically attached to the manifold 1771 with snap fits provided by a tapered surface 1773, eliminating costly materials and processes. Additionally, the embodiment permits easy testing of the continuity of the fluid path prior to actual insertion of the hub 1770 into the manifold 1771.

As noted above, the microneedles of the devices can be of differing lengths or gauges, and can contain one or more ports along a body length, needle tip, or needle bevel. As such microneedles are used for delivery of medicine, they can occlude for a variety of reasons. In yet another improved needle embodiment of the present invention, a microneedle is provided which can assist in delivery of the medicine despite possible occlusion.

Figure 107:
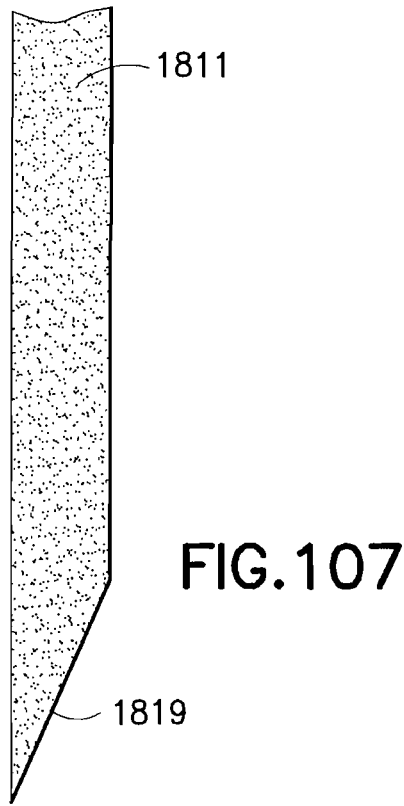
FIG. 107 is a view of a porous patient microneedle.
Figure 108:
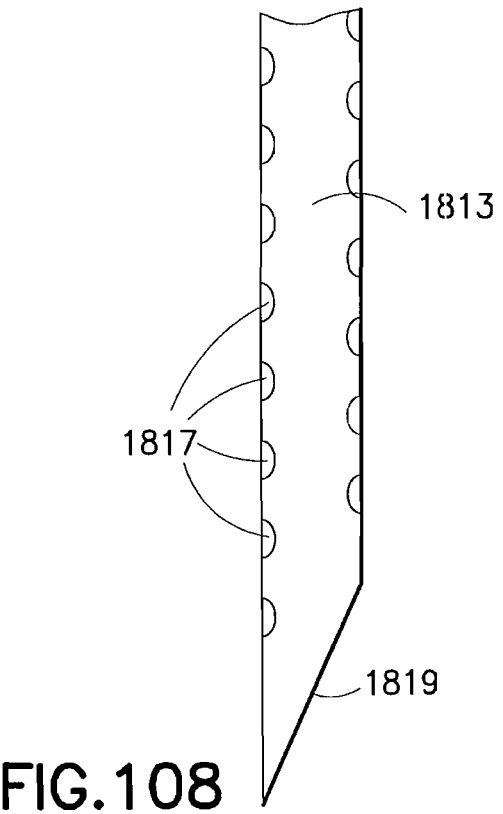
FIG. 108 is a view of a patient microneedle having a number of side holes.

A first variation of the improvement embodiment is shown in a needle side view in FIG. 107, wherein the needle 1811 is constructed using a porous material along at least a portion of the needle body, providing fluid communication between the inside and outside of the needle to a desired degree. Therefore if the needle 1811 tip is plugged, flow can still occur through the porous material. A second variation of the improvement embodiment is shown in FIG. 108, wherein the needle 1813 uses a number of tiny holes 1817 along at least a portion of the needle body, preferably around the tip of the needle 1813, aside from the main exit orifice 1819. This allows flow via the tiny holes 1817 if the tip becomes plugged. Each variation can be accomplished by using either a porous material in construction, or by adding the holes later.

Figure 109:
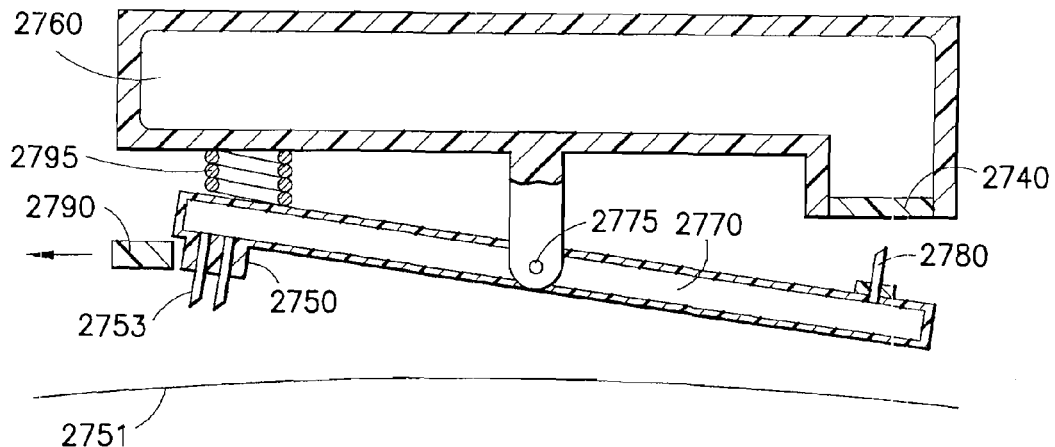
FIGS. 109 and 110 are cross-sectional views of a device having a pivot arm assembly.

Needle improvements, Belleville spring improvements, and material usage improvements can also be applied in devices having activation improvements as described in greater detail below. In a further device improvement shown in FIGS. 109 and 110, improved activation and energizing of the device is accomplished in a single multi-function/step, and timing is precisely controlled by using a pivot arm 2770 to both access the reservoir and a patient skin surface at substantially the same moment. FIG. 109 is cross-sectional view of a first embodiment of such a patch-like injector or infusor system in an unactivated state, and FIG. 110 is cross-sectional view of the embodiment shown in an activated state.

The device of FIG. 109 includes an upper and lower housing (not shown), a reservoir septum assembly 2740, a patient needle manifold assembly 2750, and a reservoir 2760. The pivot arm 2770 is also provided, extending between the manifold 2750 and a valving needle 2780. An activation mechanism 2790 is shown, which can consist of any number of devices such as the push button of FIG. 1.

Figure 110:
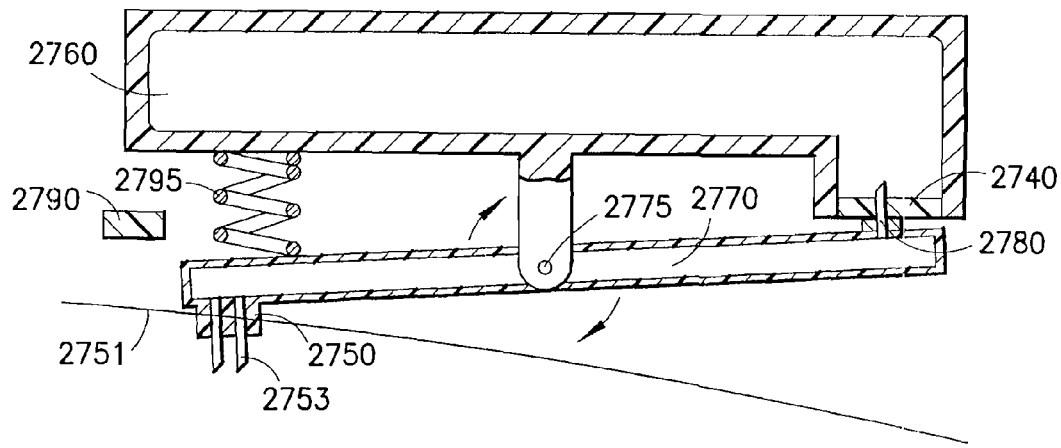

In the embodiment shown in FIGS. 109 and 110, as the device activates, two functions are achieved in a sequenced and/or simultaneous fashion. First, the activation mechanism 2790 releases the manifold 2750 which is then driven by one or more manifold springs 2795, allowing the pivot arm 2770 to rotate about the pivot 2775. Second, the rotating pivot arm 2770 seats the patient needle manifold 2750 against the patient's skin 2751, and also drives the valving needle 2780 into the reservoir septum 2740. In doing so, the rotating pivot arm serves as a fluid communication path between the reservoir 2760 and the patient needle manifold 2750. This embodiment therefore penetrates the microneedles into the patient's skin 2751 and opens a valve to inject the drug all with a single action, such as the simple push of a device button (not shown), and additionally provides the transfer of the fluid between the reservoir and the patient.

The improvement embodiment shown in FIGS. 109 and 110 includes the pivot arm 2770, or tube, which includes a number of injection needles 2753 at a substantially perpendicular angle at one end, and the single valve needle 2780 pointing in the opposite direction at the other end. The tube of the pivot arm 2770 has the pivot point 2775 between the two ends that allows the infusing needles 2753 a range of movement necessary to penetrate the patient's skin 2751, while also allowing the valving needle 2780 to penetrate the septum assembly 2740 leading into the reservoir 2760. The pivoting action is powered by one or more springs 2795 and is held in the armed position by the activation mechanism 2790.

As shown in FIG. 110, when the activation mechanism 2790 is activated, the spring 2795 starts to rotate the tube of the pivot arm 2770 about the pivot point 2775. As the tube of the pivot arm 2770 pivots, the end of the tube with the infuser needle manifold 2750 moves down, pushing the needles 2753 into the patient's skin 2751. The other end of the tube of the pivot arm 2770 moves up, pushing the valving needle 2780 through the septum 2740. When the valving needle 2780 penetrates the far side of the septum 2740, the drug is released from the reservoir 2760 and passes through the valving needle 2780, down the tube of the pivot arm 2770 and out the infusion needles 2753 of the manifold 2750 into the patient. The drug will flow because the reservoir 2760 is pressurized at some point before, or at the same time, the activation mechanism 2790 is pushed, using any of the pressurization techniques described above.

This improved activation embodiment of the present invention is a simpler device and includes a reduced number of parts relative to conventional devices and as such, is easier to assemble. For example, in conventional devices the infusion needles and the valving needle move perpendicular to each other and are typically connected by a tube. This improvement embodiment replaces the three commonly found moving parts of the fluid path in other embodiments, that is, two pieces sliding at right angles and a flexible piece, with one moving part consisting of the single continuous rigid rotating piece 2770. The flexible tubing, which can be hard to assemble, is replaced with an easier to assemble rigid part.

In yet another improved activation embodiment shown in FIGS. 111 through 115, the device can use the attractive or repelling forces of magnets to apply a force on a fluid and drive it through a fluid path. These embodiments can also be used to magnetically apply the force required to drive the needles into the skin. Potential energy of the magnets inside the system does not dissipate over time, and the magnets can be separated sufficiently to reduce their attractive force on each other and their force exerted on the polymer that contains them, thereby reducing creep. The magnet separation distance and the strength of the magnets can be adjusted in strength to optimize the mechanism.

Figure 111:
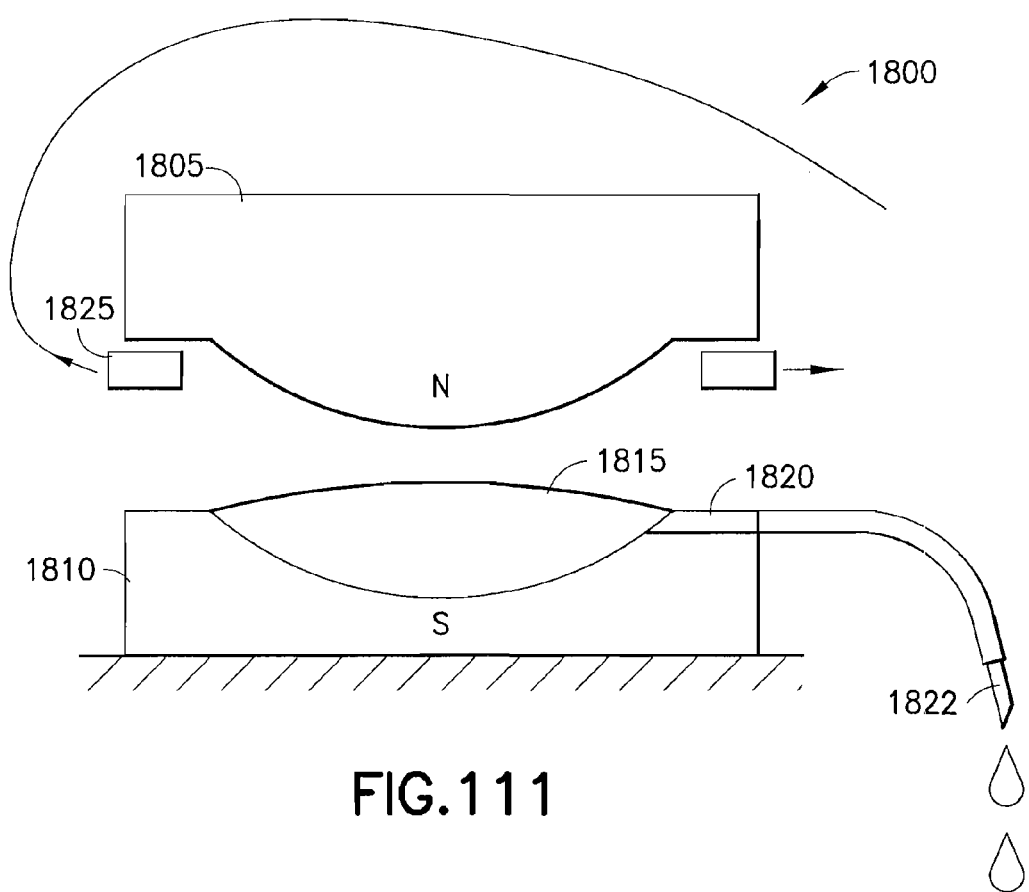
FIGS. 111 through 115 are cross-sectional views of a device having a magnetic activation assembly.

As shown in the cross-sectional device view of FIG. 111, the device 1800 has an upper housing 1805, a lower housing 1810, a film-covered fluid reservoir 1815, a fluid path 1820, and an activation mechanism 1825. When activated (i.e., the mechanisms 1825 moved free of magnet 1805 via a button or similar means), the attractive forces of the magnetic upper and lower housings 1805 and 1810, respectively, coming together forces the contents from the reservoir 1815 via the fluid path 1820 and into a patient via needle 1822. In the cross-sectional device view of FIG. 112, the repellent forces of a first and second magnet are used to force the contents from a reservoir positioned above the engaged magnets.

Figure 112:
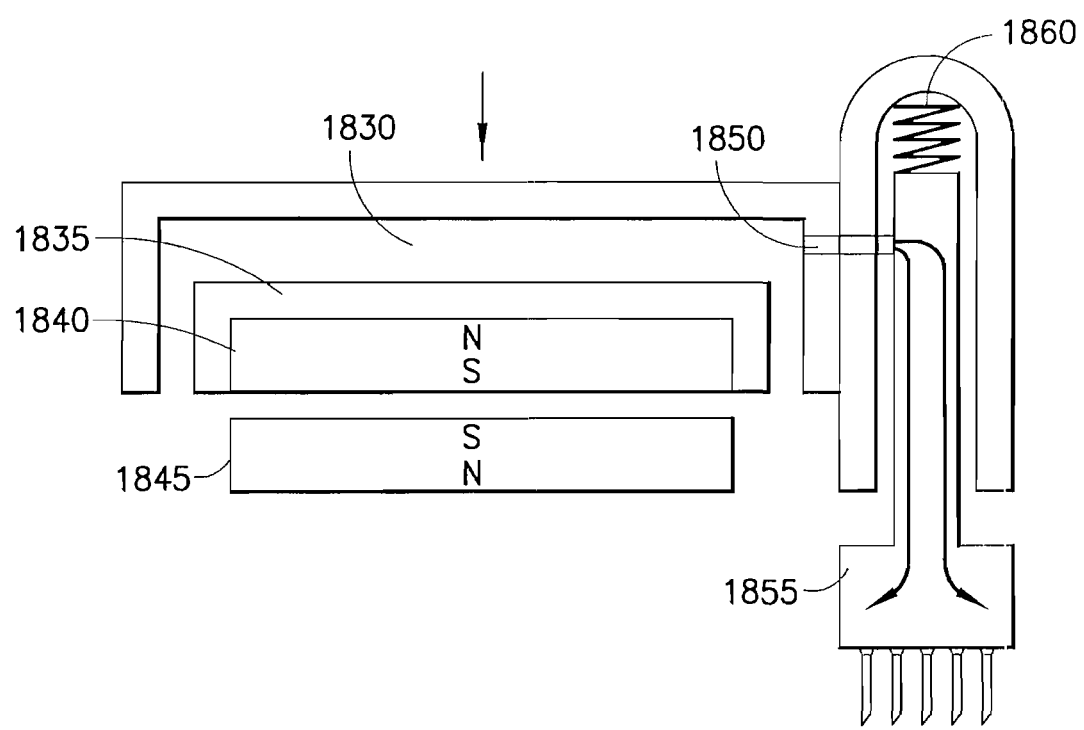

As shown in FIG. 112, a clear-covered fluid chamber 1830 is positioned above a piston 1835 engaged with an upper magnet 1840 (in this example, having an N pole above and an S pole below). The upper magnet, when activated, is repelled by a lower magnet 1845 (in this example, having an S pole above and an N pole below), forcing the piston 1835 into the contents of the chamber 1830. The contents are forced through an opening 1850 (which can be furthered valved as described above) and to a manifold 1855. The manifold can be constructed of a material with a low resistance to movement when driven by the manifold spring 1860, such as polypropylene or polyethylene.

Figure 113:
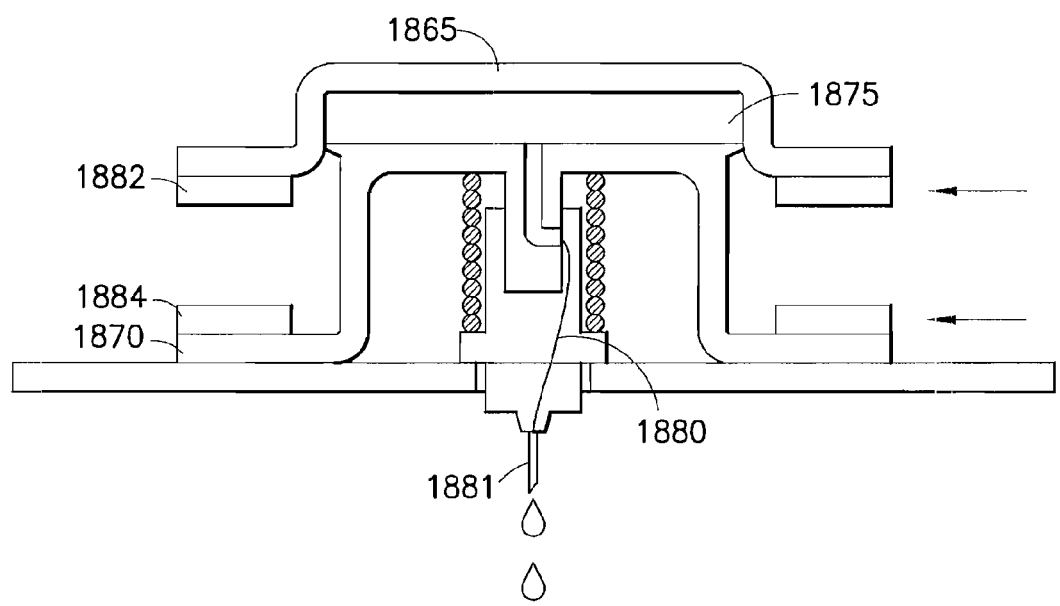

In yet another activation improvement embodiment shown in a device cross-sectional view in FIG. 113, the device includes an upper housing 1865, a lower housing 1870, a fluid reservoir 1875 (i.e., clear fluid chamber), a fluid path 1880, and an upper and lower magnet 1882 and 1884, respectively. The magnet of 1882 or 1884 can be replaced with a steel plate (not shown) which would also achieve the attraction force required. When activated (i.e., via a button or similar means), the attractive forces of the upper and lower magnets 1882 and 1884, or magnet and plate, coming together forces the contents from the reservoir 1875 via the fluid path 1880 and into a patient via a needle 1881. A center-fired patient needle mechanism incorporating any number of mechanisms described above can be used to seat the needles 1881 during activation and results in a minimum of dead space.

Figure 114:
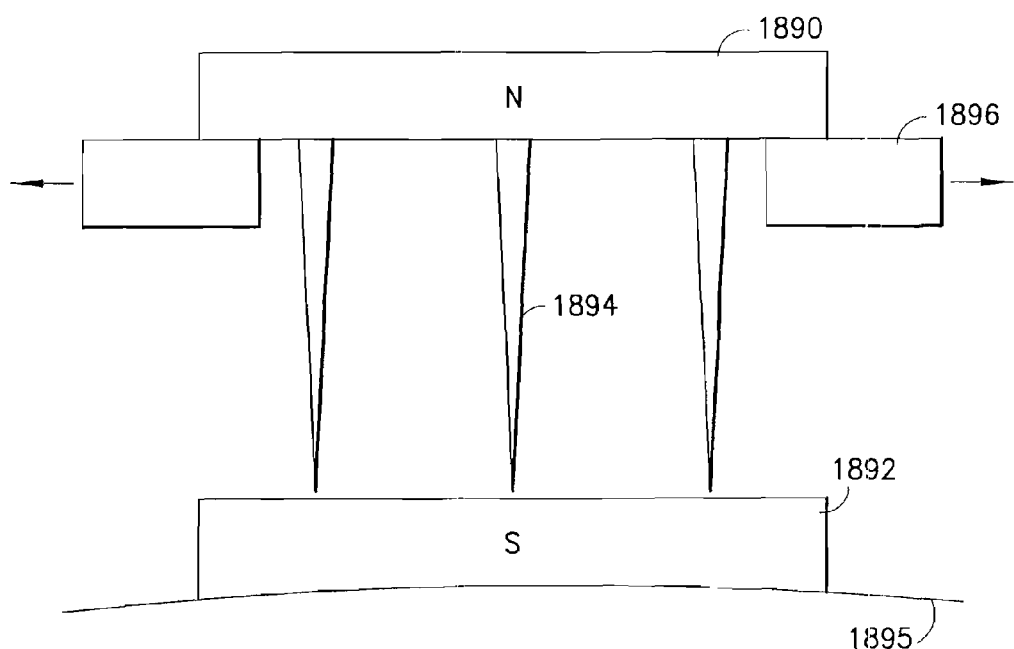
Figure 115:
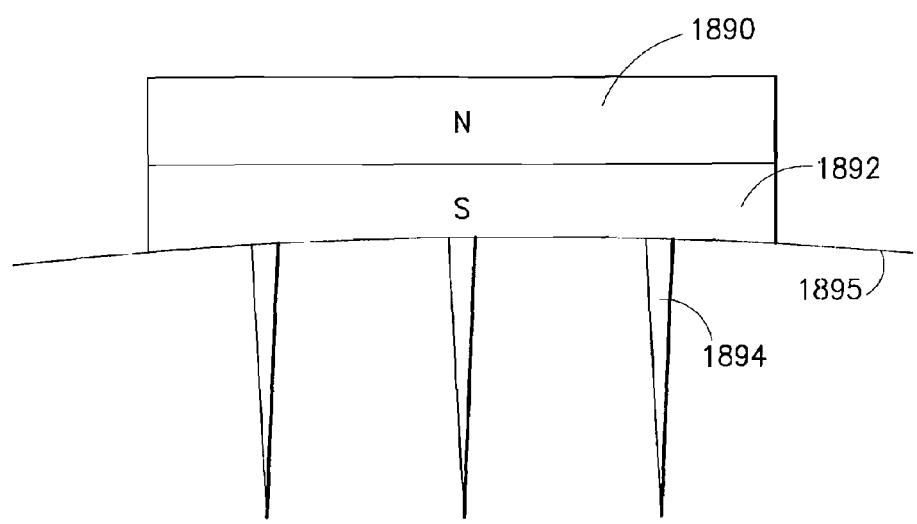

In yet another activation improvement embodiment shown in the pre-use and post-use side view FIGS. 114 and 115, the device includes a magnetic upper housing 1890 that includes a number of needles 1894, and a magnetic lower housing 1892 having a number of openings (not shown) concentric with the needles 1894 and each having a diameter sufficient to allow each needle 1894 to pass. Once again, the magnet of 1890 or 1892 can be replaced with a steel plate which would also achieve the attraction force required. When activated using a mechanism 1896 (i.e., displaceable via a push button or similar means), the attractive forces of the upper and lower magnets 1890 and 1892, or magnet and plate, force the needles 1894 through openings in the lower housing 1892 and into the patient skin surface 1895 as shown in FIG. 115.

The devices above each function to infuse a substance via the patch-like device. Once positioned on a user and activated, the user typically leaves the device in position, or "wears" the device, for some period of time, and then removes and discards the device with no damage to the underlying tissue. However, upon intentional or accidental removal, one or more safety features can deploy as described in greater detail below to shield the exposed needles resulting from activation.

In general, a passive safety system is most desirable. This allows the device to be self-protected in case of accidental removal or if the user "forgets" that there is a safety step. Since a typical use for this device is for providing human growth hormone, which is usually given in the evening, it can be expected that users such as children that wear the device may actually wear them overnight, even though the delivery in this case is only expected to take less than 10 minutes, if the device falls off during this time, without a passive system, the needles could re-stick the user or caregiver. The solution is to either limit the activities during use, or include a passive safety system.

With respect to safety systems there are typically three options. A first option is to retract the needles into the device. A second option is to shield the needles to remove access, and a third option is to destroy the needles in a way that prevents needlestick. Although versions of each can be constructed, no substantially viable method or device exists to destroy the needles that does not substantially risk breaking a needle and exposing the user to needlestick. Other systems, such as active systems, explore a manual shielding and/or destruction, or manual release of safety features with an additional button push or similar action. A detailed description of passive embodiments of the present invention is outlined below, followed by a detailed description of active embodiments of the present invention.

To prevent inadvertent or accidental needle sticks, intentional re-use of the device, and to shield exposed needles, a locking needle safety mechanism can be provided and activated automatically upon removal of the device from the skin surface. The improved safety mechanism embodiments can be provided in a number of versions, including a "mouse-trap" type safety (passive), a needle lift-and-cover type safety (active or passive), and a rotating needle manifold type safety (active or passive).

Still other improved safety mechanism embodiments described below include spring loaded, pivoting transverse barrier mechanisms with and without a "ratchet" style lock feature (passive), manual flip top, snapped or glued down transverse barrier mechanisms (active), pull out and lock shield mechanisms (passive), spring loaded lift converting to transverse barrier (passive), spring assisted, slotted needle retraction "sled" (passive or active), torsion spring to lift the needles out (passive), hinged flat shield with and without adhesive (passive), and bending needles following use safety (active or passive) and a bi-stable leaf spring (active or passive).

The first improved safety embodiment of the present invention, or mouse-trap safety, is shown in FIGS. 37 through 41. In this safety device embodiment in a ready, or biased state, a sleeve which is integral to a spring (i.e., a safety spring), is retracted and permits exposure and use of the needles. When the device is removed from the skin the spring deflects to its unbiased state, and extracts and positions the sleeve about the needles in such a way as to encase and shield the needles.

Figure 37:
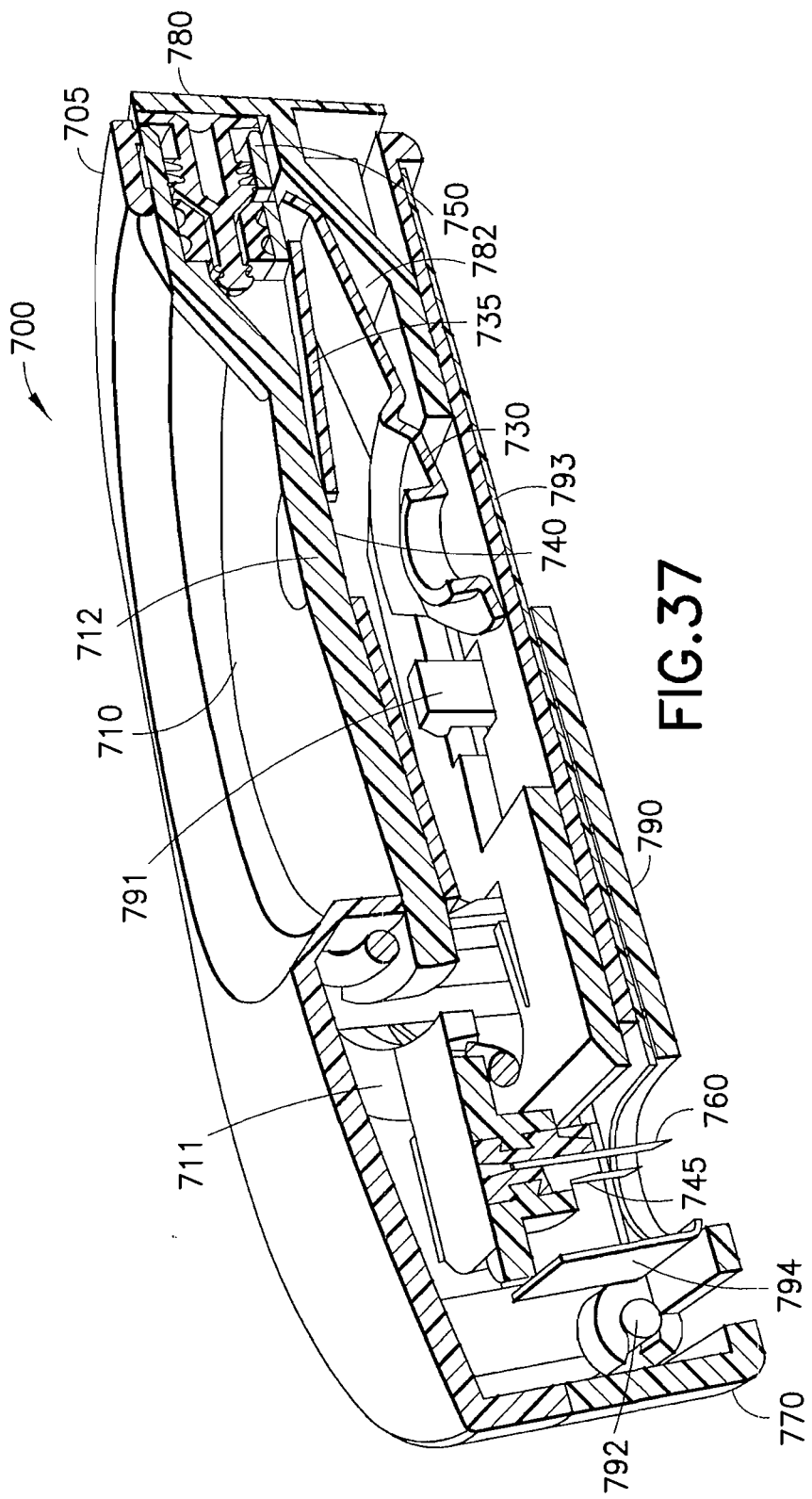
FIG. 37 is a cross-sectional view of a fifth embodiment of a patch-like injector or infusor system.
Figure 38:
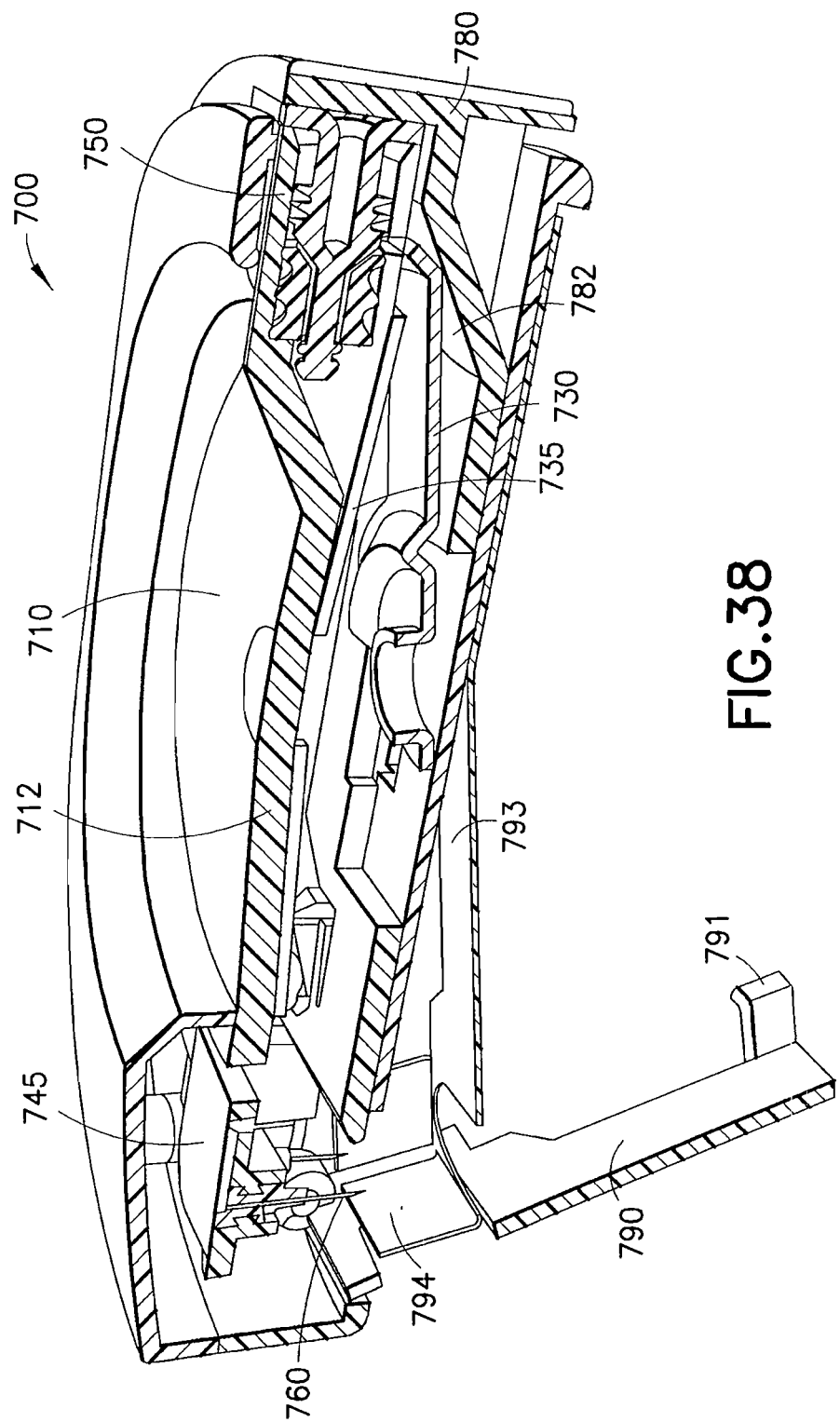
FIGS. 38 through 41 are cross-sectional views of the patch-like injector or infusor system of FIG. 37 with extended safety.
Figure 39:
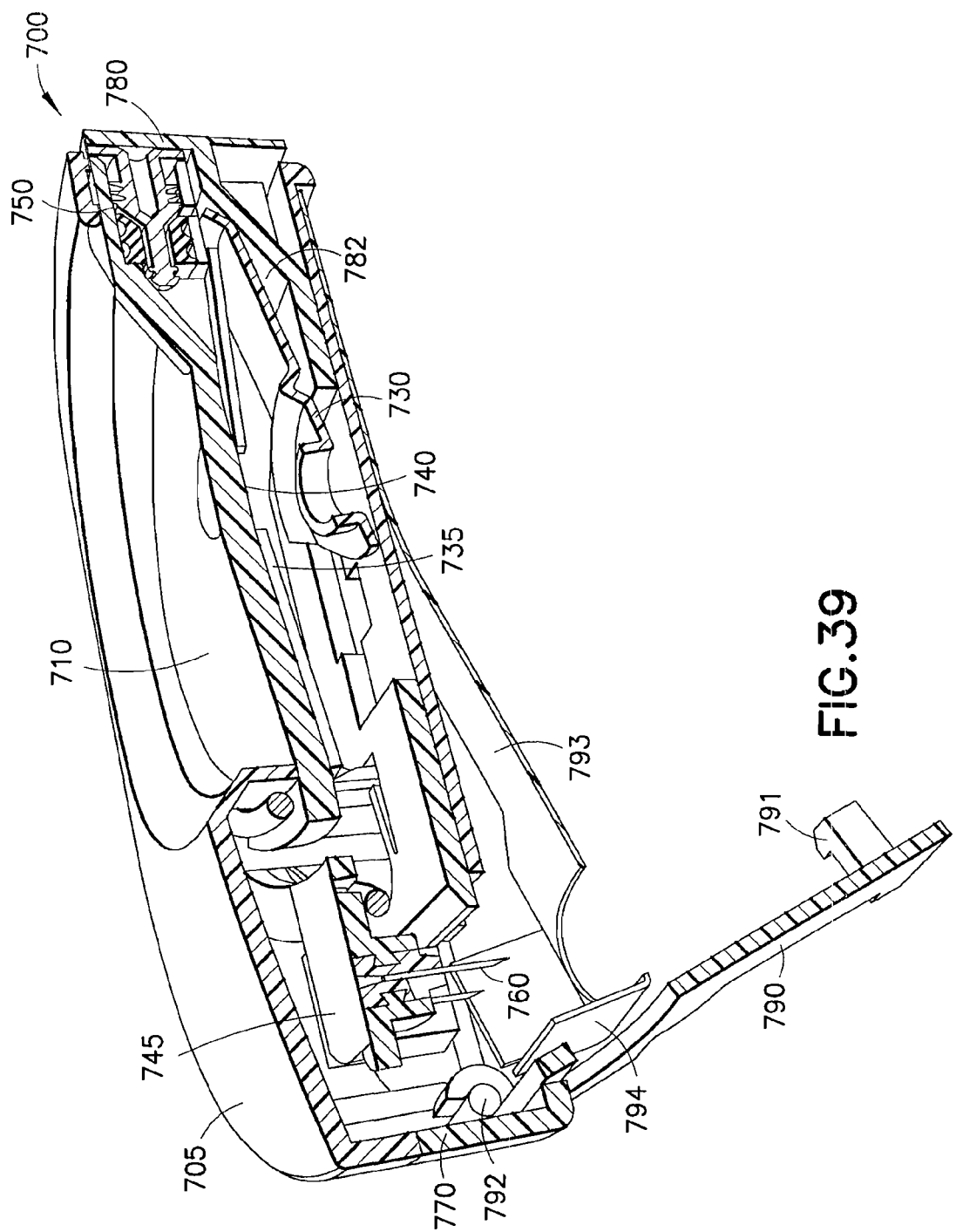
Figure 40:
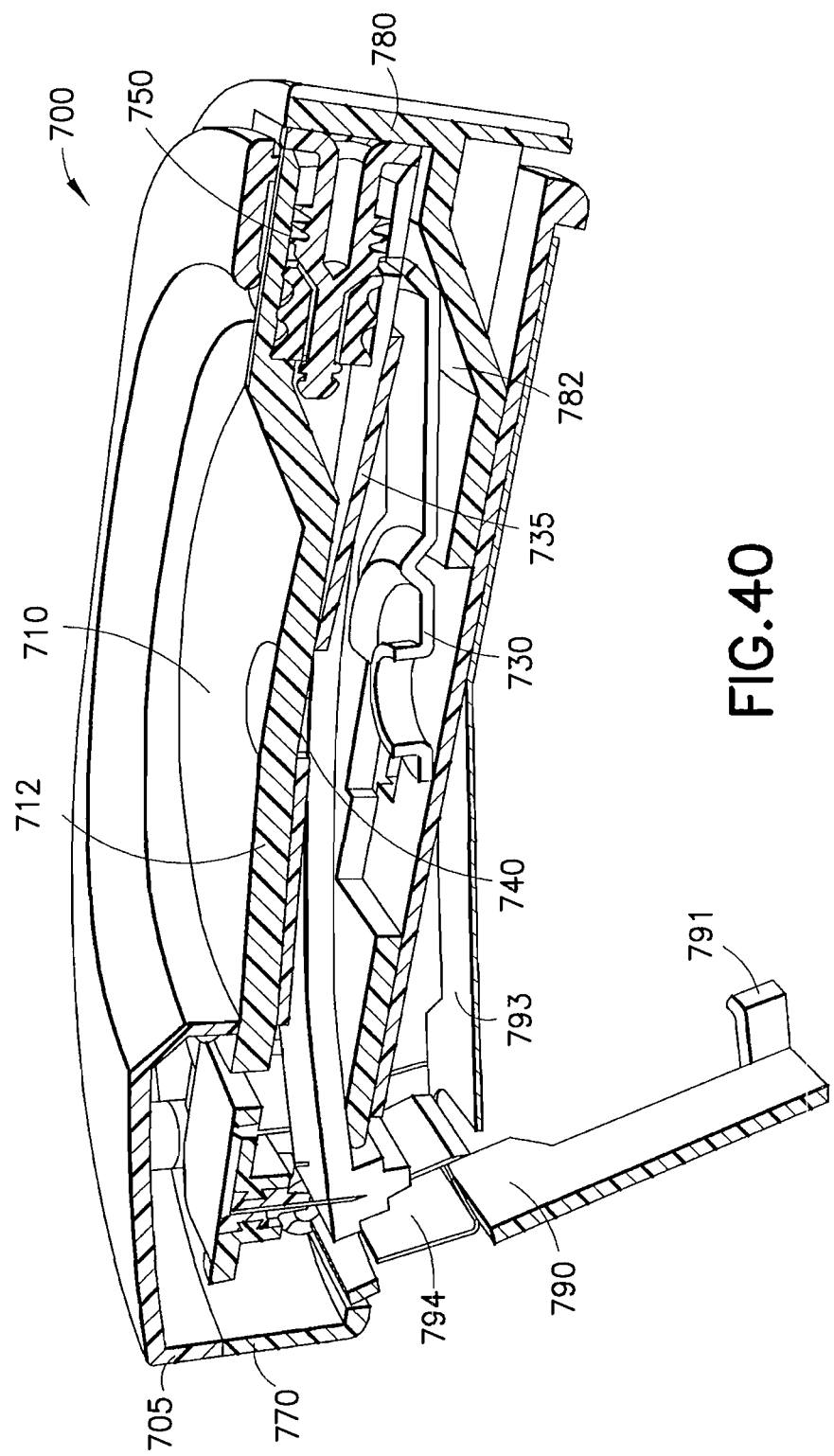
Figure 41:
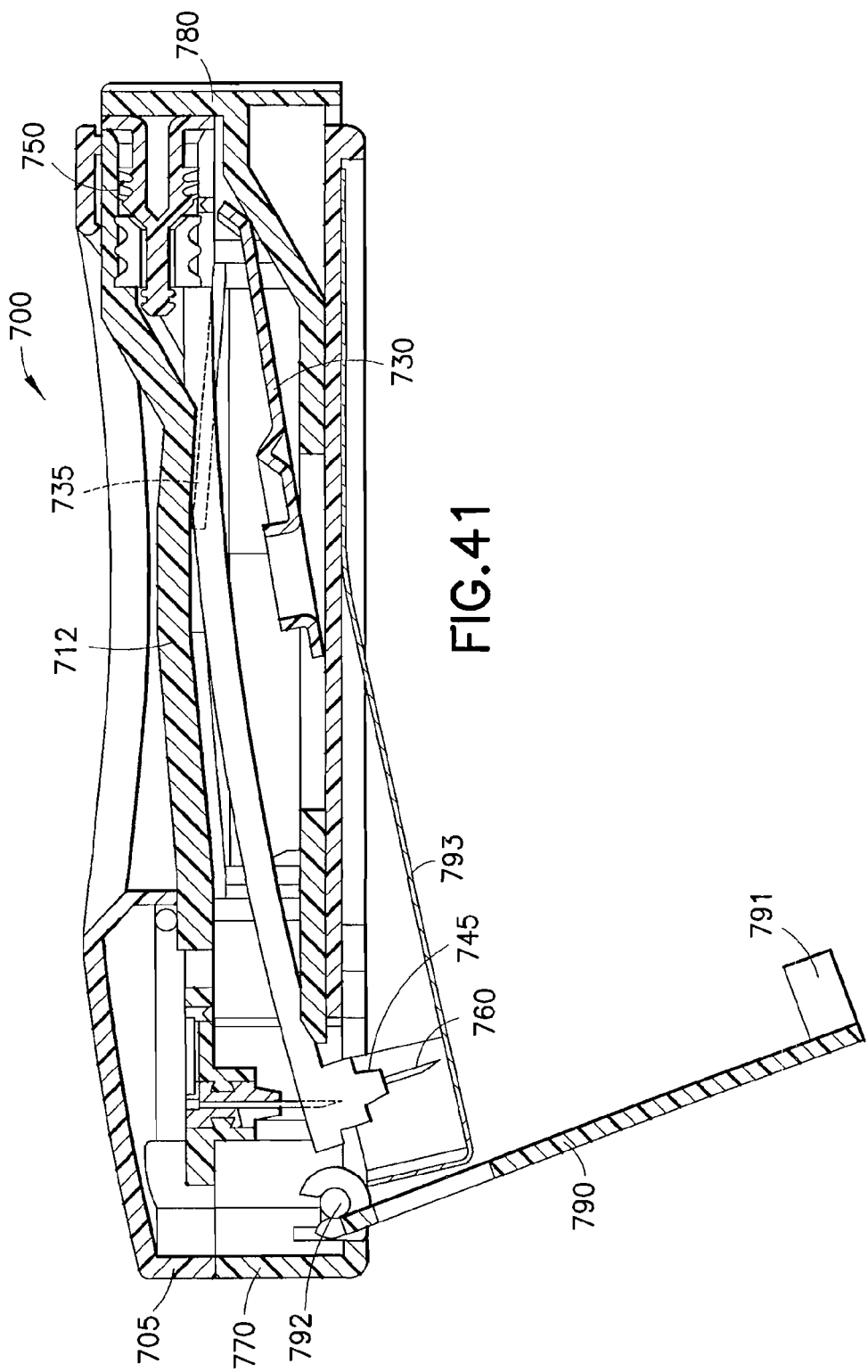

In a first example mouse-trap safety device shown in FIG. 37, the push-button device 700 is shown wherein the activation and energizing of the device is accomplished in a single multi-function/step process as described above. FIG. 37 is cross-sectional view of an example patch-like injector or infusor system that is activated using a side push button and including the first improved safety embodiment of the present invention.

The device of FIG. 37 includes the push button 780, the upper housing 705, the lower housing 770, a mouse-trap door 790, a door latch 791, and a door pivot point 792. According to one embodiment, the door pivot point 792 comprises a barrel hinge. A flat spring 793 and a shield 794 are also provided and more clearly shown in FIG. 38. As the push button 780 is pushed, the movement of the button 780 opens at least one valve 750, dislodges the spring retention disk or pin 730, and removes a support member (not shown) from the patient needle manifold 745 allowing the manifold 745 to travel. The movement of the push button 780 also releases the door latch 791, however, as the device is adhesively positioned against a user's skin, no movement of the door 790 is allowed.

One aspect of this embodiment of the present invention is that in this state, the safety spring 793 is in a constant state of exertion towards an unbiased state (i.e., the state shown in FIGS. 38 through 41). This constant exertion is countered by the surface upon which the device is attached (i.e. the skin of the patient) and the adhesive used to attach it. Therefore, the safety spring 793 is known to be working in a manner counterproductive to embedding needles 760 in a patient and keeping them embedded for a desired amount of time. This force however, is necessary to the functionality of the mechanism, since it is this exerted spring 793 force which ensures eventual shielding of the needles 760 when the device is removed from the skin surface. Therefore to counter this force, a further aspect of the embodiment of the present invention is the inclusion of what could best be described as the mouse-trap door 790.

The mouse-trap door 790 acts to trap the safety spring 793 in such a way as to reduce the amount of force actually transmitted to the skin surface by the safety spring 793. The trap door 790 uses principles of leverage (such as those found in a common mouse trap) to produce a mechanical advantage of the door 790 over the safety spring 793. Thus, when the door 790 is folded over the safety spring 793, the safety spring 793 puts pressure at a predetermined spot on the door 790 which is at a predetermined distance from the door hinge 792, which reduces the force of the safety spring 793 by a multiplier of the ratio of the distance between the pressure point of the safety spring 793 and the hinge 792 of the door 790. When in use, the skin surface will then see only a fraction of the actual force of the safety spring 793 rather than its full force.

When the device is removed from the skin surface however, the trap door 790 is urged away from the device by the safety spring 793 as it travels to its fully deployed state as shown in FIGS. 38 through 41. The initial force of the safety spring 793 on the door 790 is light due to the mechanical advantage of the door 790 being hinged at 792. However, as the door 790 is urged and pivots away from the device, the mechanical advantage is proportionately reduced. The safety spring 793 will, as a result, accelerate such that the full strength of the safety spring 793 is realized at or near the end of its length of travel. This safety spring 793 strength is necessary to ensure that any locking mechanism, such as a first detent means (not shown) on the safety spring sleeve 794 and any second detent means (not shown), can be engaged and locked using the safety spring 793 force to overcome the resistance of the detent means. In the end, when the safety spring 793 is fully deployed, the spring sleeve 794 will be shielding the needles 760 and the detent means will not permit retraction, and subsequently prevent access or reuse of the needles 760.

Figure 116:
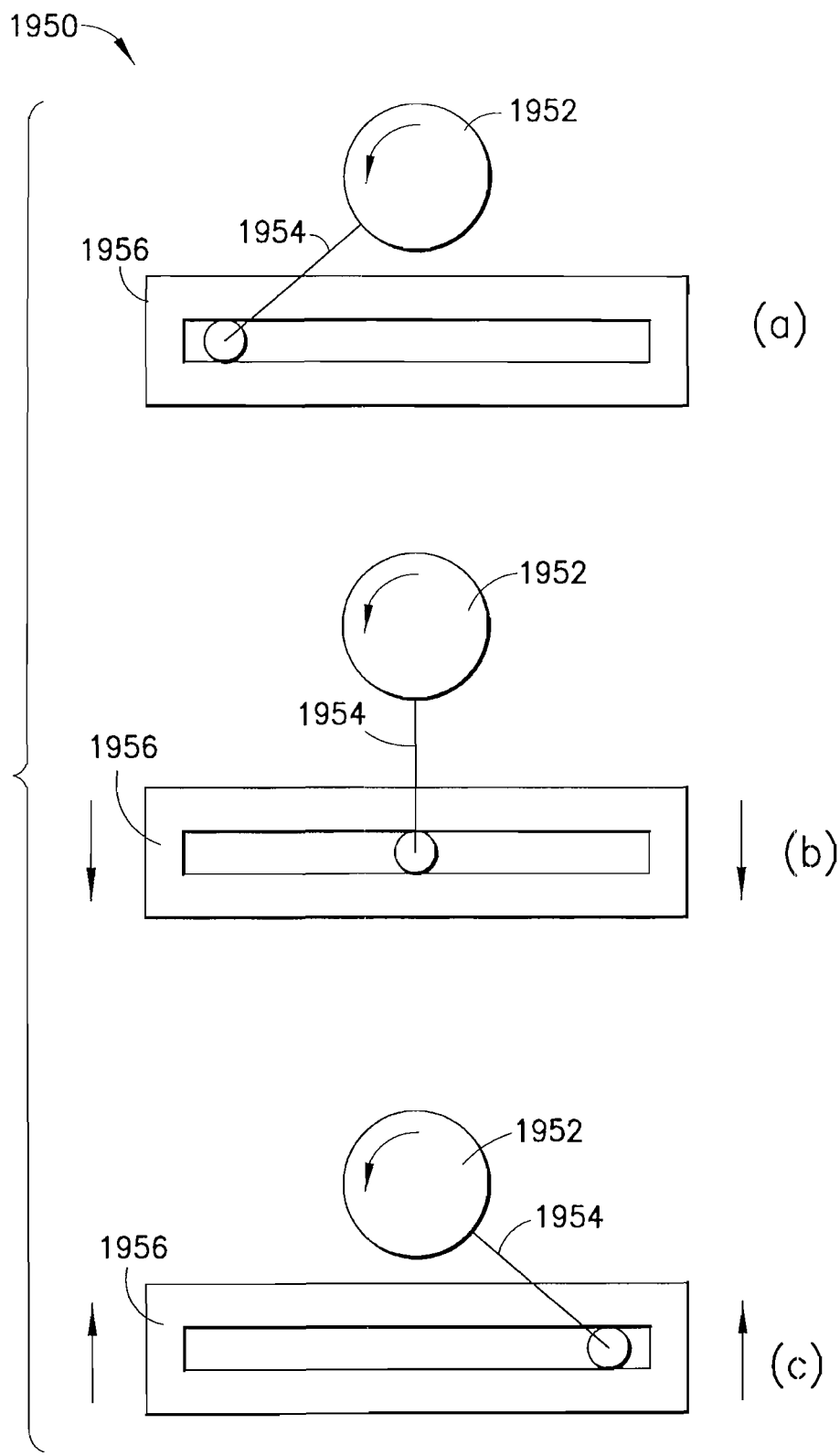
FIGS. 116(a) through 116(c) are illustrative views of a scotch-yoke function safety embodiment.

The second improved safety mechanism embodiment, or needle lift-and-cover, is shown in FIG. 116 and can incorporate what is commonly known as a scotch-yoke 1950 or a "crank and slotted cross head". Additional details of such a method are disclosed in a text entitled *Ingenious Mechanisms for Designers* (Industrial Press), page 251, the relevant contents of which are incorporated herein by reference. In this embodiment, the needle manifold 1956 is coupled with a spring loaded crank 1952. The crank 1952 has a pin 1954 in communication with the manifold 1956 such that as the crank 1952 rotates, the manifold 1956 is driven downward to embed the needles (not shown). The crank 1952 is stopped in rotation coincident with a point representing the full embedded depth of the needles to allow the fluid to be delivered. Upon removal of the device from the users skin which allows a slight further manifold 1956 travel downward, the crank 1952 is "released" and allowed to continue rotation which, according to the principles of the scotch-yoke, will withdraw the needle manifold 1956 back out of the skin to a safe position.

As shown in FIG. 116, the lifting is achieved using a scotch-yoke mechanism which is engaged with the patient needle manifold 1956, and is shown in a pre-use position (a), a substantially in-use position (b) and a post-use position (c). A torsional spring 1952 is provided with a pin or cam arm 1954 having a cam driven through a slot of the manifold member 1956. As the spring 1952 exerts a rotational force, the arm 1954 drives the manifold 1956 into the skin surface (not shown) which also blocks further travel of the arm 1954. When removed, the arm 1954 is free to travel and in doing so, lifts and retracts the manifold 1956.

The mouse-trap and scotch-yoke type embodiments of a safety mechanism are passive systems, which require no additional steps by the user to render the needles safe. Such passive systems must use some means to trigger the deployment of the safety mechanism, and the most effective passive systems are those that sense proximity to the skin surface and when removed from the skin surface, deploy the safety mechanism. This "sensing" of the skin implies a direct relationship between the element that senses, and the element that is deployed. The embodiments described above improve upon conventional passive safety designs by reducing the forces of the safety mechanism realized on the skin by the user to imperceptibly low values.

Yet another embodiment of the present invention which includes lifting the needle or needles back out of the skin after they have been deployed uses a ramp mechanism as shown in FIGS. 117 through 122. As noted above, the microinfusor includes at least one drive spring which acts to embed a needle or an array of needles into the skin of the user. The drive spring, by design, is positioned in such a manner that it can drive the needles into the skin. In the embodiment shown in FIGS. 117 and 118, when the infusion is complete, a mechanism such as a ramp 1004 can be provided and positioned to allow the user to engage the ramp 1004 with the manifold 1000 or head of the needle or needle array, and by pushing the ramp 1004 toward the manifold 1000 the needles (not shown) can be ramped up or lifted back out of the skin of the user. If the drive spring (not shown) however, is allowed to stay in position exerting force on the manifold 1000 of the needles, then this lifting of the needles is done against the force of the drive spring.

Figure 117:
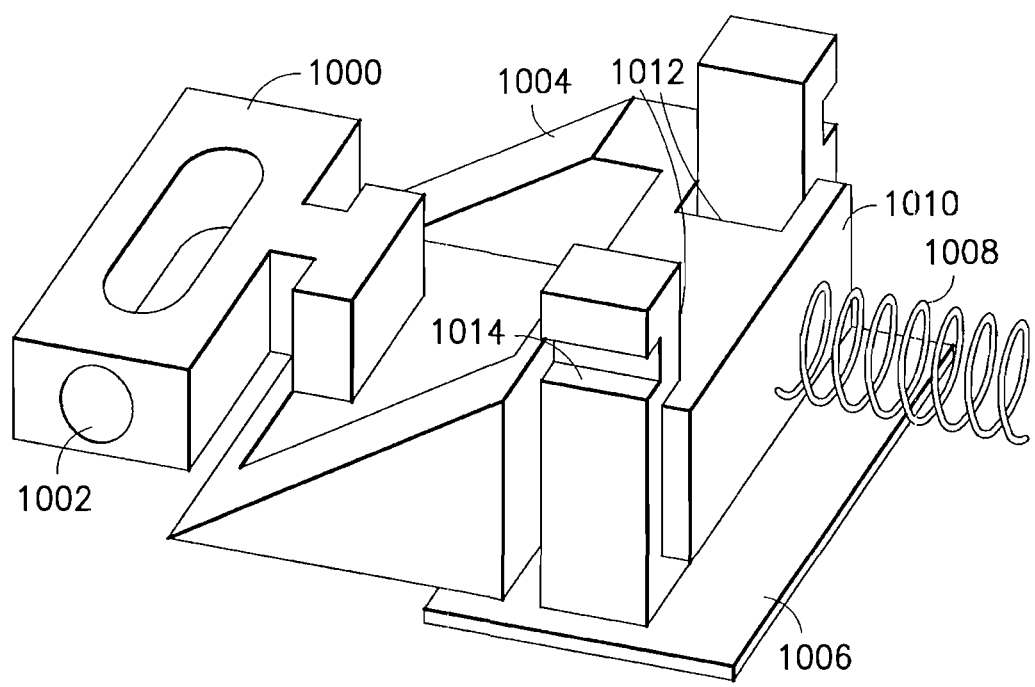
FIG. 117 is a perspective view of a retraction wedge shield in a retracted state.
Figure 118:
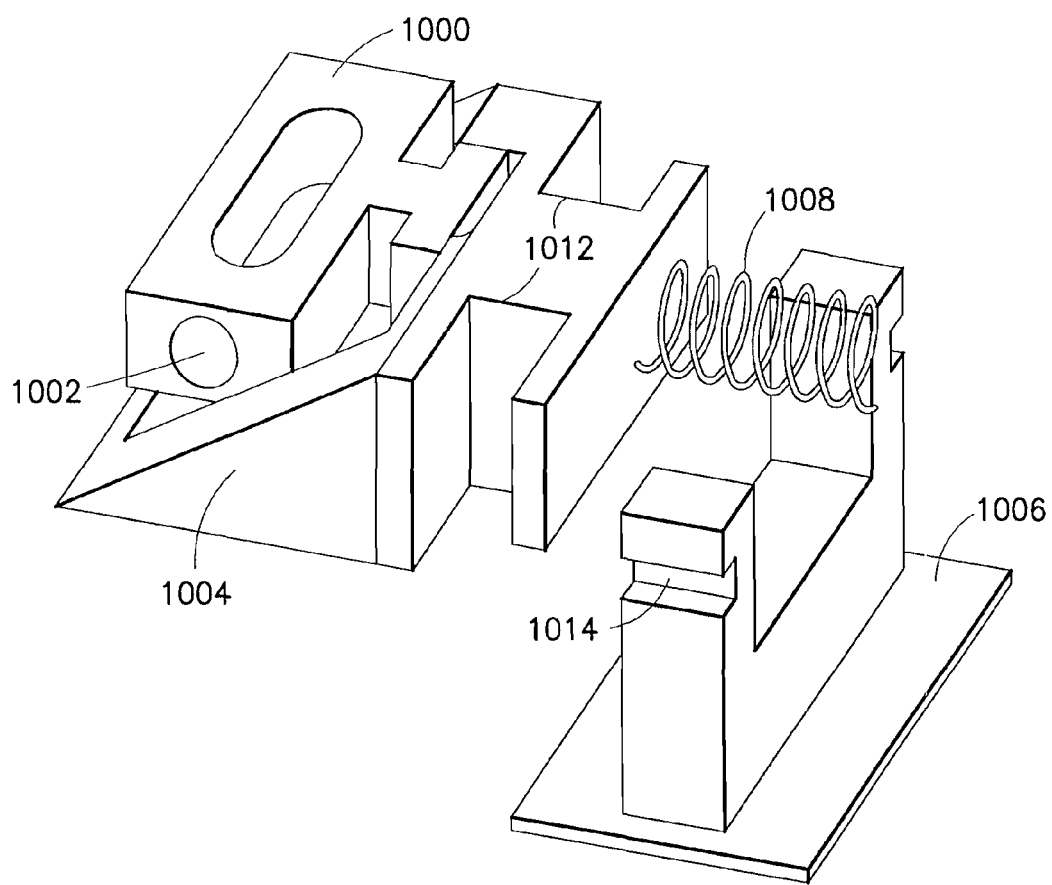
FIG. 118 is a perspective view of the retraction wedge shield of FIG. 117 in an extended state.

As shown in FIGS. 117 and 118, a passive retraction wedge design is shown having the patient needle manifold 1000 having a substantially round pin 1002 extending from opposite sides thereof to engage an incline of the ramp 1004 when the ramp is driven toward the manifold 1000 by a spring 1008. The ramp 1004 is secured from prematurely lifting the manifold 1000 by slots 1012 secured by an adhesive skin sensing pull-out member 1006. The entire assembly is disposed within an infusion device as described above. After use, the device is removed from the skin and the adhesive pull-out member 1006 is pulled downward out of the device as it is stuck to the skin surface (not shown). When this occurs, the slots 1012 of wedge 1004 are released from the pull-out member 1006 and the wedge 1004 is driven against the pins 1002 of the manifold 1000 as shown in FIG. 118. This lifts the manifold 1000 and the needles (not shown) are retracted into the device and the needle opening is covered internally by the wedge 1004.

In this embodiment, the wedge 1004, or shield, is a molded part and is positioned between an activation button (not shown) and the manifold 1000. The spring 1008 is also positioned between the wedge 1004 and the button. The spring 1008 is preloaded only enough to compensate for the difference in travel between the button and the necessary travel for retraction. The wedge 1004 is held in place by the skin-sensing pull-out member 1006. The skin-sensing pull-out member 1006 is held by a slidable button component (not shown) in the side notches 1014 of the pull-out member 1006.

When the button is pressed, it moves until there is a gap that releases the side notches 1014 of the skin-sensing pull-out member 1006 component and simultaneously compresses the spring 1008 to its full displacement. The skin-sensing pull-out member 1006 stays in place due to the presence of the skin. The manifold 1000 is released and seats the needles in the skin. Upon removal from the skin the adhesive on the large surface area of the skin sensing pull-out member 1006 pulls outward and this in turn, releases the wedge 1004, which is now under spring load. The wedge 1004 moves forward, lifting the manifold 1000, retracting the needles and covering the access hole.

In this embodiment, there is a force-balance issue, which can be controlled. The spring 1008 that drives the wedge 1004 loses force as it expands. The manifold drive spring (not shown) disposed above and pressing down on the manifold 1000 is increasing in force as it is compressed by the lifting of the manifold 1000 by the driven wedge 1004. This can be overcome with a very strongly biased wedge spring 1008, however this negatively impacts the force required to press the push button.

Figure 119:
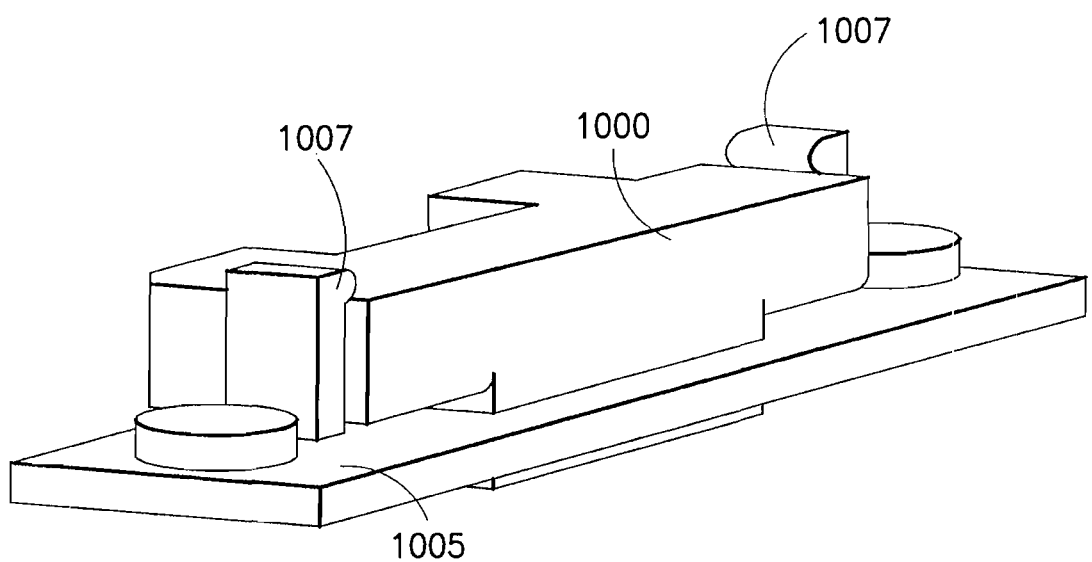
FIG. 119 is a perspective view of the carriage return mechanism of the shield of FIG. 117.

Therefore, another version of the above embodiment is shown in FIG. 119. The concept of this embodiment includes the manifold 1000 and a carriage 1005 that are launched forward together. The manifold drive springs (not shown), drive the carriage 1005 directly, and the manifold 1000 is coupled with the carriage 1005. The wedge 1004 in this case, is used to then separate the manifold 1000 from the carriage 1005 upon safety release by pushing the manifold free of detents 1007. Thus the drive springs of the manifold do not need to be overcome, as they remain exerted against the now independent carriage 1005.

Yet another version of an improved design is to use the initial travel of the wedge 1004 to push the drive springs of the manifold 1000 out of line so that they are buckled and can no longer exert a normal load on the manifold 1000 during retraction. Both of these versions also have a benefit in that the manifold 1000 can not be re-fired and reused.

In the embodiments of FIGS. 117, 118 and 119, the shielding is passive and completely covers the needles with material. It is constructed of molded parts with a high degree of strength and does not apply force to the skin surface during injection or affect adhesive presence at the needle area. The needles are held internally after use and the spring 1008 is minimally loaded over life. The embodiment does require a force balance such that the expanding spring 1008 compresses the drive spring and a skin adhesion area is required to release the safety shield. Therefore, low skin adhesion or high friction can be of concern. Additionally, three parts are included, contributing to assembly complexity and the need for a long throw to work (i.e., increased device size). Also, as with most compressed spring mechanisms, such springs can be subject to creep.

The ramp element 1004 included in this embodiment of the present invention includes a ramp profile which is shallow enough to overcome both the friction on the ramp (i.e., friction between pins 1002 and ramp 1004 while lifting manifold 1000), and the force of the drive spring (i.e., force urging the manifold 1000 downwards), without being so shallow that the "throw", or translation of the button is adversely long. As noted above, a further aspect of this embodiment is the use of the translation of the ramp to affect the manifold spring, such as to "knock the drive spring of its perch" above the manifold 1000. This embodiment employs structures (not shown) necessary to not only lift the needles out of the skin, but to also dislodge the drive spring (not shown) from its engagement with the needle manifold 1000, thus eliminating the force exerted by the drive spring and making the corresponding lifting of the needles easier.

A further aspect of this embodiment is the inclusion of structures which would provide a transverse barrier over the needles when they have been successfully lifted out of the skin and are back in the device. These needles are typically small enough that they require special features to ensure they embed properly into the skin of the user. These needle features, by nature extend beyond the bottom of the device and unless fully retracted, would be difficult to cover with a simple transverse barrier which could otherwise bend and break off the needles. This embodiment of the present invention therefore, provides for lifting the needles such that a transverse barrier, in this case the ramp itself, can be deployed without breaking the needles off, as broken needles could be harmful in the environment.

Figure 120:
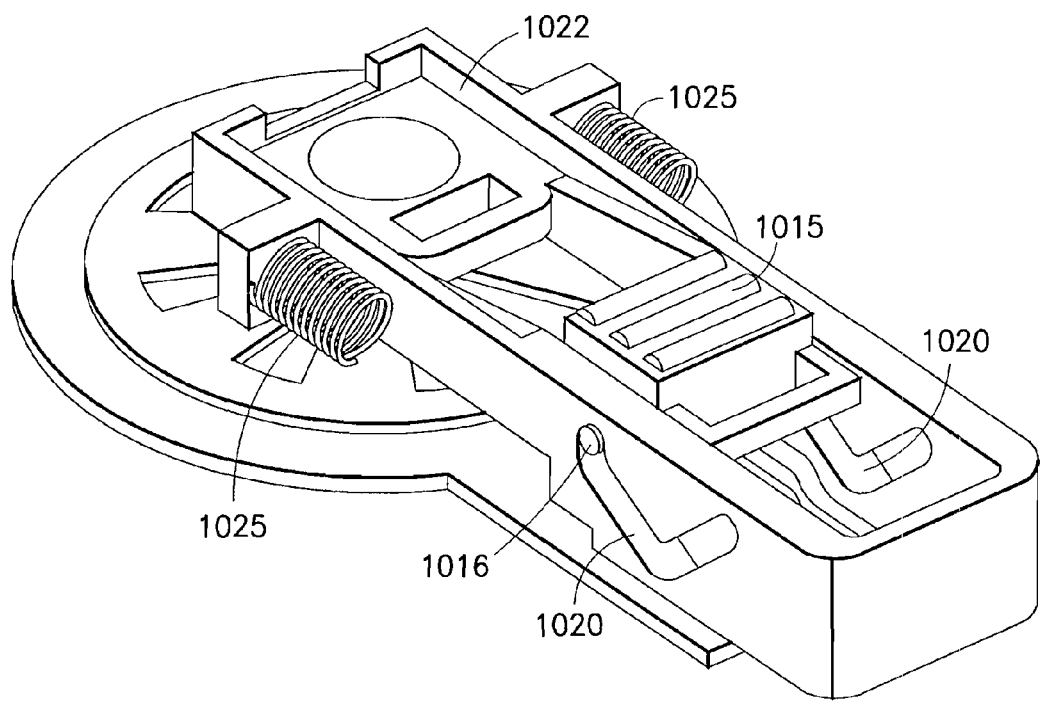
FIG. 120 is a perspective view of a retraction-slot shield in an initial position.
Figure 121:
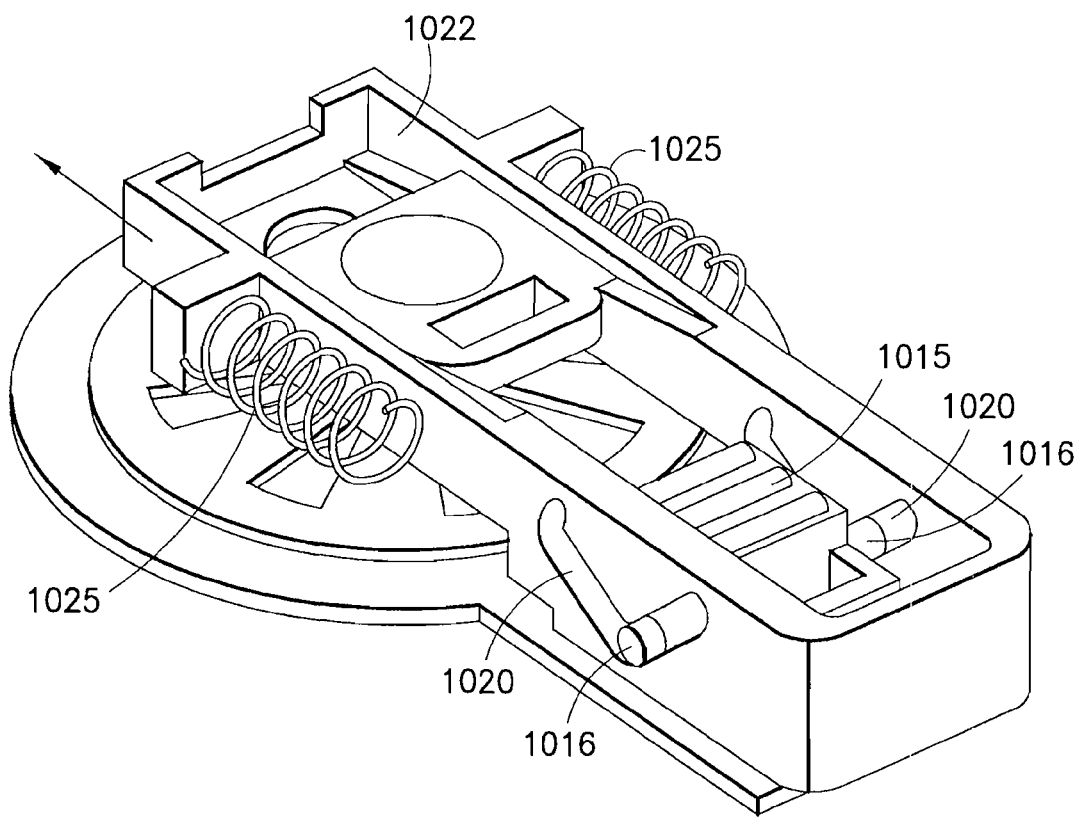
FIG. 121 is a perspective view of the retraction-slot shield of FIG. 120 in an in-use position.
Figure 122:
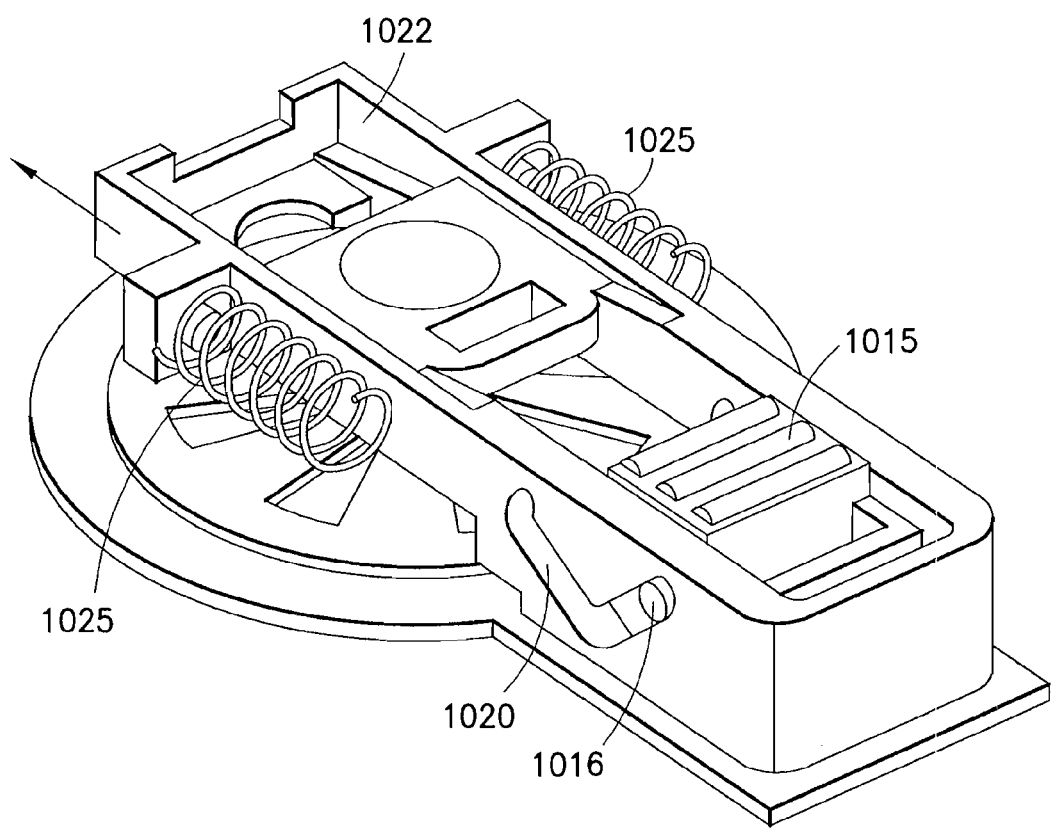
FIG. 122 is a perspective view of the retraction-slot shield of FIG. 120 in a retracted position.

Still another embodiment of the present invention similar to the scotch-yoke type, includes a mechanism for lifting the needle or needles back out of the skin after they have been deployed using V-slot mechanism as shown in FIGS. 120, 121 and 122. In the passive retraction slot design of this embodiment of the present invention, the user begins operation of the device by pressing the manifold to activate the device. After delivery, the user removes the device from the skin and the adhesive pulls a small lock out of the path of the main slide. The manifold is then retracted into the device and the hole through which the needles protruded is covered by the slide.

As shown in FIG. 120, a passive retraction slot design is shown having a slide 1015 having a pin 1016 extending from opposite sides thereof to engage a V-slot 1020 formed in a member 1022, and is driven within the slot 1020 by a pair of springs 1025. The entire assembly is disposed within an infusion device as described above. As noted above, the user begins operation of the device by pressing a means, such as the manifold or a button (not shown) substantially as described in the above embodiments to compress the springs 1025 as shown in FIG. 120. Once the device is activated by a release means, such as a user push button, the springs 1025 are released and drive member 1022 forcing the slide 1015 toward the skin surface as guided by slots 1020. The slide 1015 travels to the point of maximum needle insertion and is stopped from further downward travel by the skin surface (not shown), stopped from rearward travel by the springs 1025, and stopped from further forward travel by the ramped protrusions of the slots 1020. When the device is no longer in contact with the skin, the slide 1015 is pushed down freely and travels further forward into the upward slope of slots 1020. The travel of the slide 1015 then exerts upward force on the manifold disposed beneath the slide 1015 (not shown) and retracts the needles back into the device and covers the hole, completely enclosing the needles.

This embodiment provides complete covering of needles with material and can be molded having very high strengths. Very little force is applied to the skin during injection and the mechanism does not affect adhesive presence at needles. The needles are safely held internally after use, such that the embodiment clearly provides visual feedback of "in use" or "used" states, and requires no extra parts. However, skin adhesion is required to release the safety, therefore low stick or high friction can present difficulties. Additionally, as with the above embodiment, the need for a long throw to work (i.e., increased device size) is present. Also, as with most compressed spring mechanisms, such springs can be subject to creep, and there can be concerns about high forces held over the device life and the rate of deployment.

Figure 123:
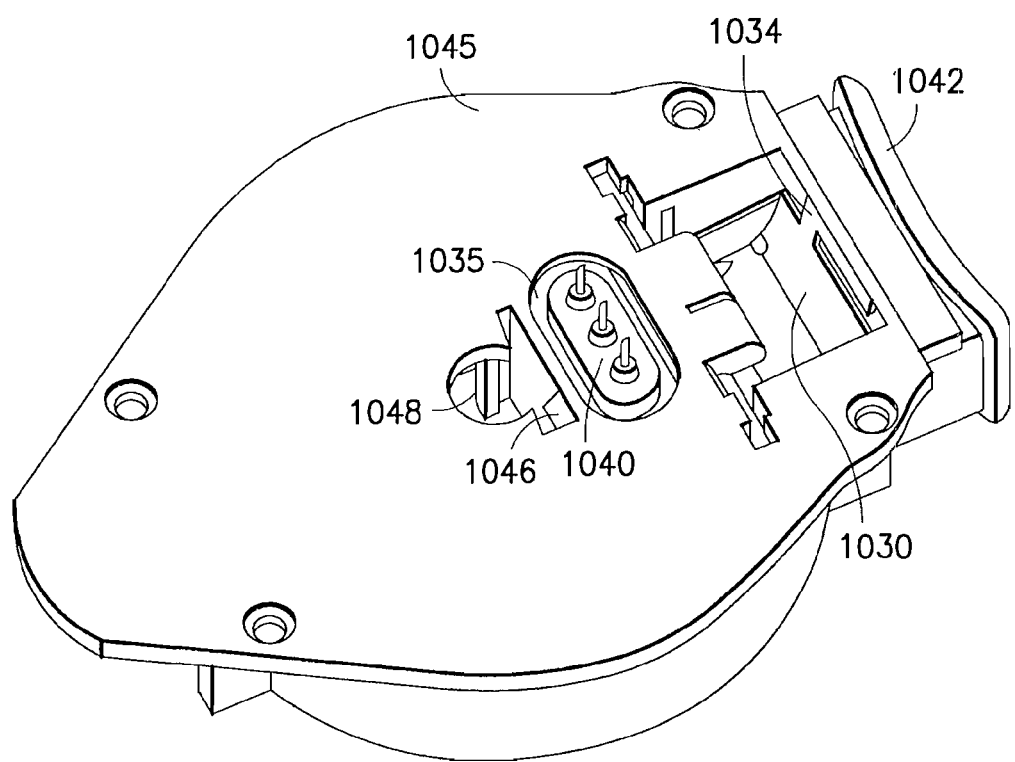
FIG. 123 is a perspective view of a bucket shield in a retracted state.
Figure 124:
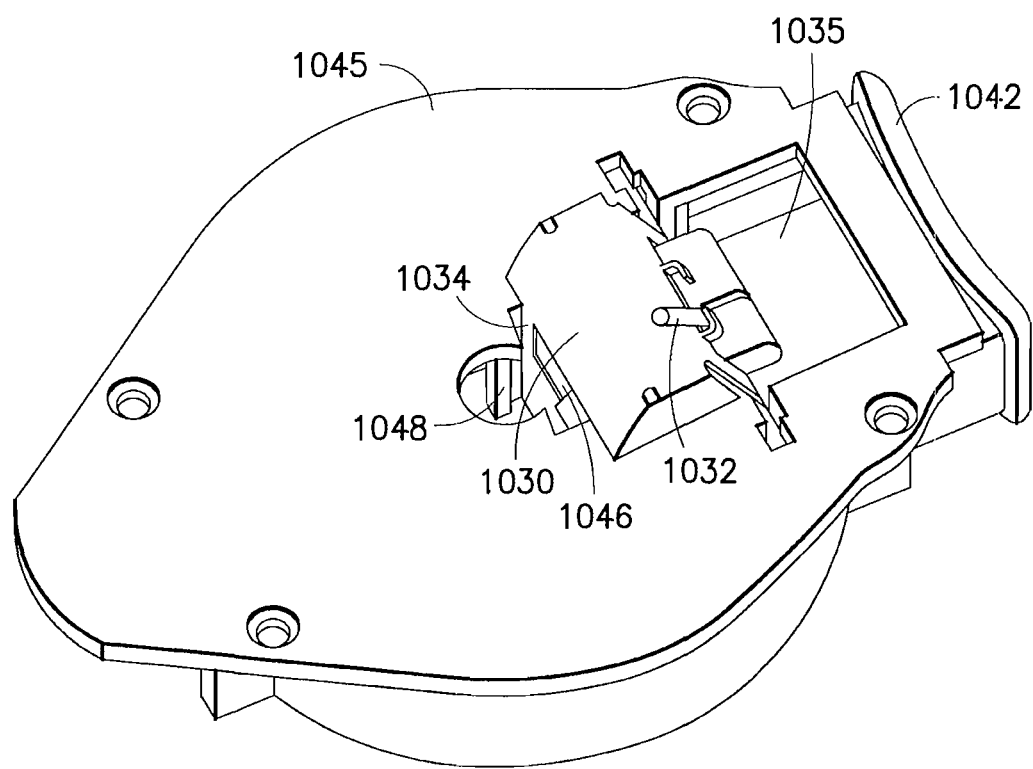
FIG. 124 is a perspective view of the bucket shield of FIG. 123 in an extended state.

Another improved safety embodiment of the present invention is a passive fully enclosed shield as described below. FIG. 123 is a perspective bottom view of a device, illustrating a view of an embodiment of a bucket-type safety shield feature of an infusion device before activation, and FIG. 124 is a perspective bottom view of a device illustrating a view of the bucket-type safety shield feature after activation.

The rotating shield 1030 can be powered by a preloaded torsion spring 1032 and remains loaded in an "up" rotated position until the push button 1042 is pressed. The shield 1030 is then released and free to rotate, but is prevented from rotating to a full deployment position by the presence of the user's skin against the adhesive covered surface 1045 of the device. When the device is no longer against the user's skin, such as when the device is removed or falls free, the shield 1030 is no longer obstructed by the skin surface and rotates about 180 degrees, and is thereafter locked into place, fully covering the patient needles 1040 and preventing needle stick injuries.

As shown in FIG. 123, the needles 1040 are originally recessed within an opening 1035 on the lower, adhesive covered surface 1045 of the device. The user secures the device on the skin with the adhesive surface 1045 and then presses the activation button 1042 to activate the infusion device. When the device is removed, the shield 1030 flips down and locks in place over the needles 1040 to prevent the user from seeing or touching the needles.

Figure 125:
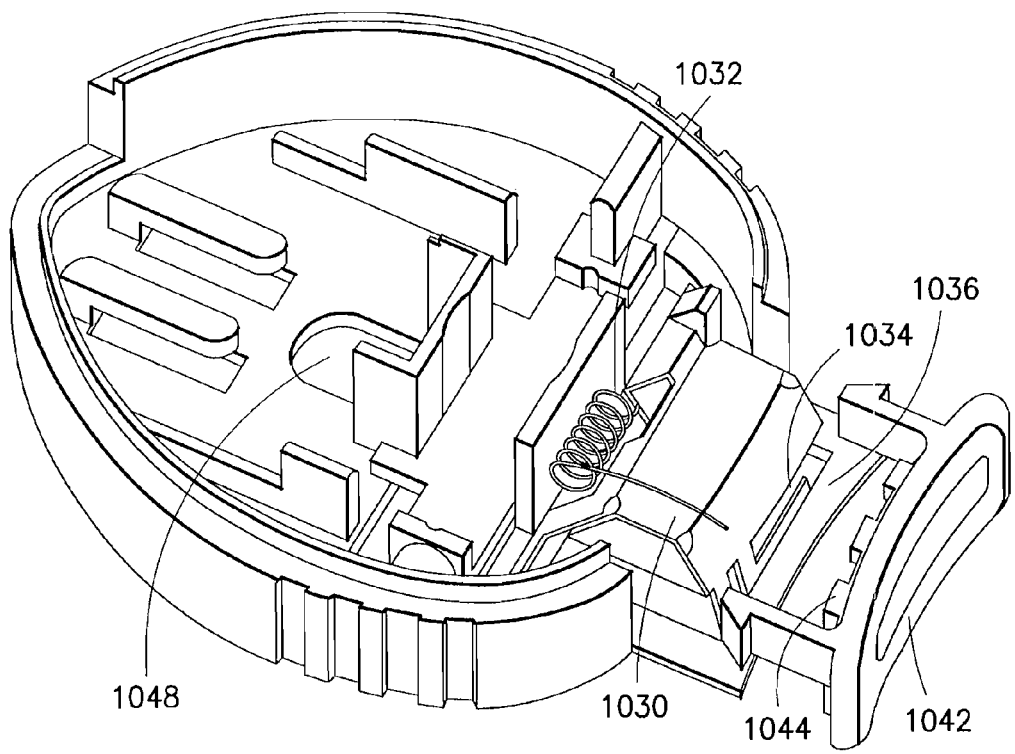
FIG. 125 is a perspective internal view of the bucket shield of FIG. 123 in a retracted state within an unactivated device.
Figure 126:
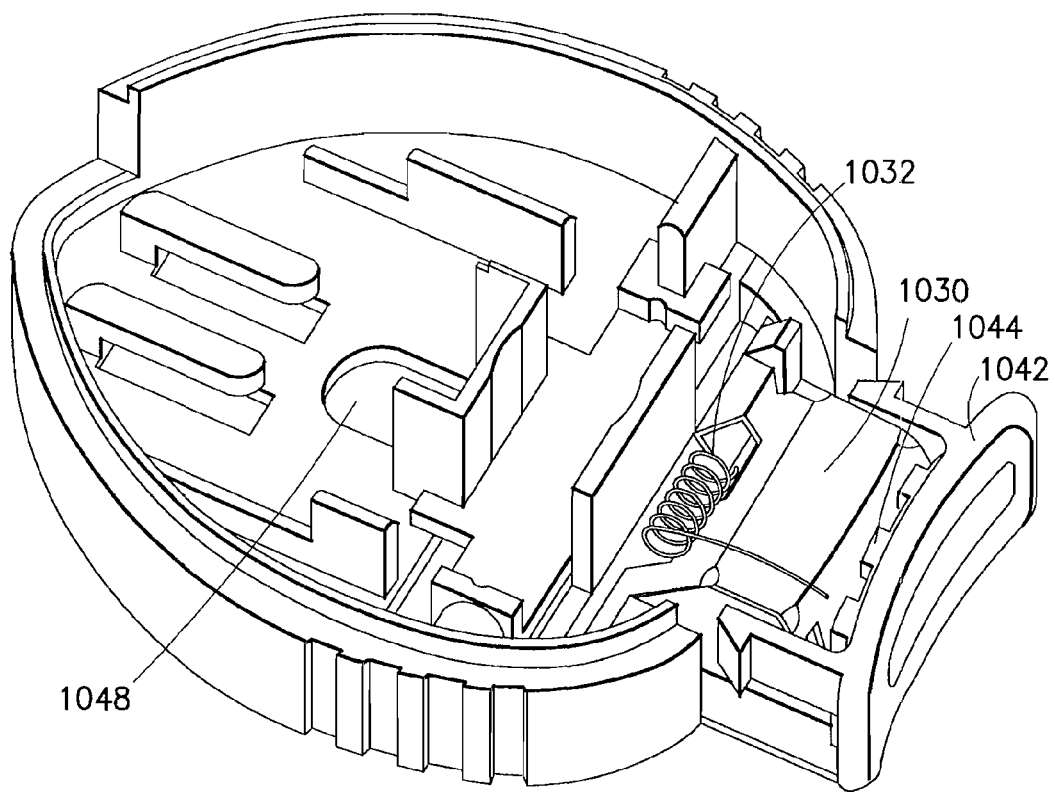
FIG. 126 is a perspective internal view of the bucket shield of FIG. 123 in a retracted state within an activated device.
Figure 127:
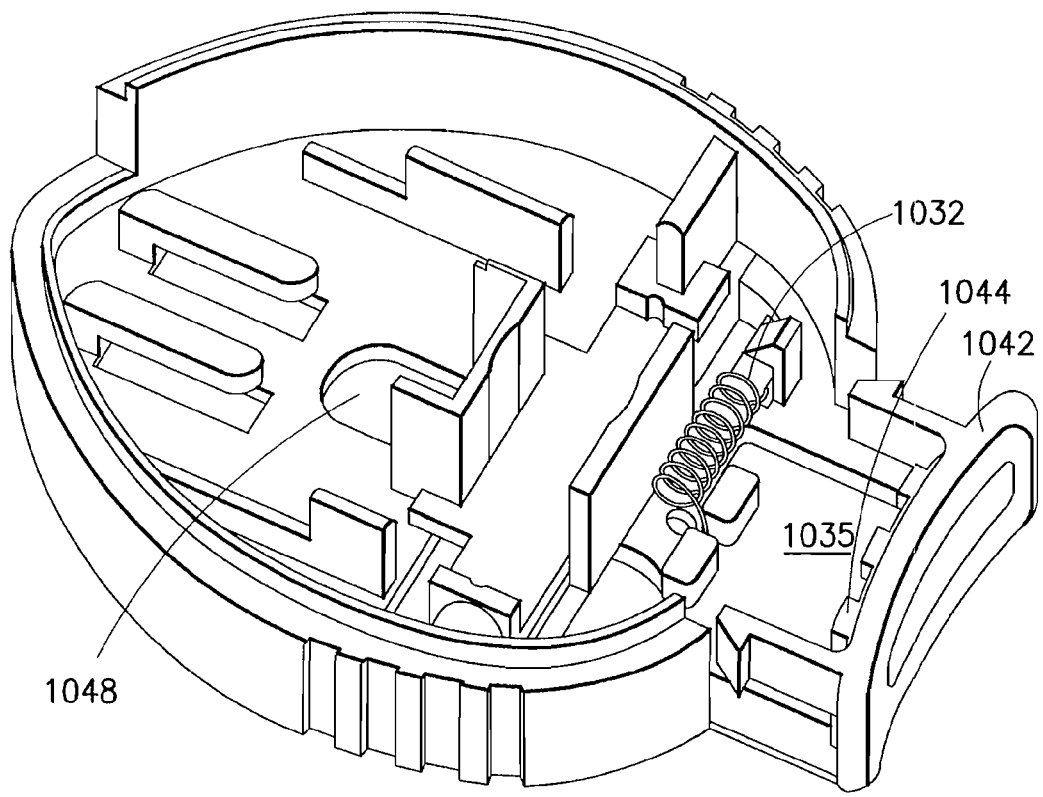
FIG. 127 is a perspective internal view of the bucket shield of FIG. 123 in an extended state within an activated device.

The shield 1030 is a stamped and formed sheet metal part that is pre-loaded with the torsion spring 1032. As can be seen in FIG. 125 illustrating a perspective view of the opened lower housing of the device showing the shield 1030 retracted within the device, the front edge of the shield 1030 includes a lock arm 1034 that rests on a cross bar member 1036 of the device, thus holding it fixed. When the button 1042 is activated as shown in FIG. 126 illustrating a perspective view of the opened lower housing of the device showing the shield 1030 ready to rotate, the tabs 1044 on the button 1042 push the lock arm 1034 off the cross bar member 1036 to allow the shield 1030 to rotate under the load of the spring 1032 when clear of the skin surface. FIG. 127 illustrates a perspective view of the opened lower housing of the device after the shield 1030 is rotated. The tabs 1044 extend from the push button 1042 to also help prevent pinching of the skin between the push button and the cross bar member 1036 during activation.

In yet another release embodiment, an additional arm (not shown) is provided at substantially 90 degrees to the lock arm 1034. This arm would point along the axis of movement of the button and hold the shield 1030 fixed before use. When the button 1042 is pressed, cam feature(s) (not shown) on the button 1042 push the additional arm sideways so that it can drop through a slot and release the shield 1030 with only a small force applied. This also helps remove the tolerance sensitivity of button 1042 position while allowing the shield 1030 to rest lower in the device. This also can provide more room for the torsion spring 1032 and require less device height.

While the infusion device is administering the dose, the shield 1030 of FIGS. 123 through 127 rests on the skin surface. When the device is removed, purposely or accidentally, the bucket-type guard 1030 flips through the opening 1035 due to the torsion spring 1032 and locks over a tab 1046 in the hole 1048 where the spring pin was removed during activation.

In this embodiment, locking is achieved with the lock arm 1034 and/or snap configuration located at the front of the shield 1030. The force to engage the shield lock pushes the lock arm 1034 outward across the small dimension of the cross-section thus keeping the force low. The force to defeat the shield 1030 is applied across the large dimension of the cross-section normal to the movement of the lock. This allows the force to engage the lock to be low while requiring a much higher force to defeat the lock.

The torsion spring 1032 can be loaded onto a pin (not shown) on the shield 1030, and a spring arm can be locked under tabs (not shown) on the back of the spring, thus preloading the spring and creating a stable sub-assembly. The shield assembly would be top down assembled into the bottom housing of the infusion device prior to the button sub-assembly by pressing a pivot means, such as a main bar (not shown) of the shield 1030 into two sets of snaps (not shown) within the lower housing to create the pivot. One arm of the spring can be released to press on the bottom housing, and one arm of the spring can be locked under tabs on the back of the spring, thus "energizing" the safety shield.

The safety embodiment shown in FIGS. 123 through 127 is another example of a passive safety system that completely covers the needles 1040 with material. The material is constructed as a metal stamping, which allows smaller wall thickness. In doing so, the embodiment requires only two additional parts having a high strength to fail. Also, the minimal force applied to the skin by the shield is farther away from the needle contact point than other embodiments. The shield 1030 however, requires a degree of space within the device, which can make the device longer, and the shield 1030 presses on the skin during delivery. The shield opening 1035 further removes a large adhesive surface near the needles 1040. Also, as with most compressed spring mechanisms, such springs can be subject to creep, and there can be concerns regarding spring selection and the ability to construct pivot tubes as required.

Figure 128:
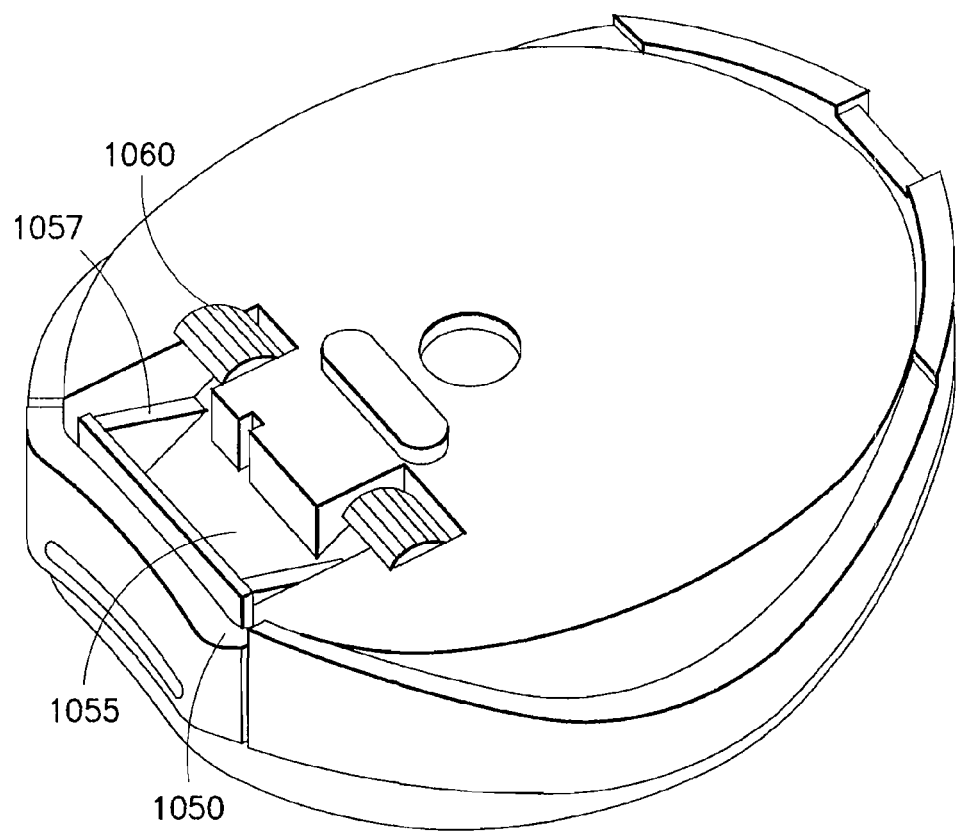
FIG. 128 is a perspective view of a ratchet-lock shield in a retracted state.
Figure 129:
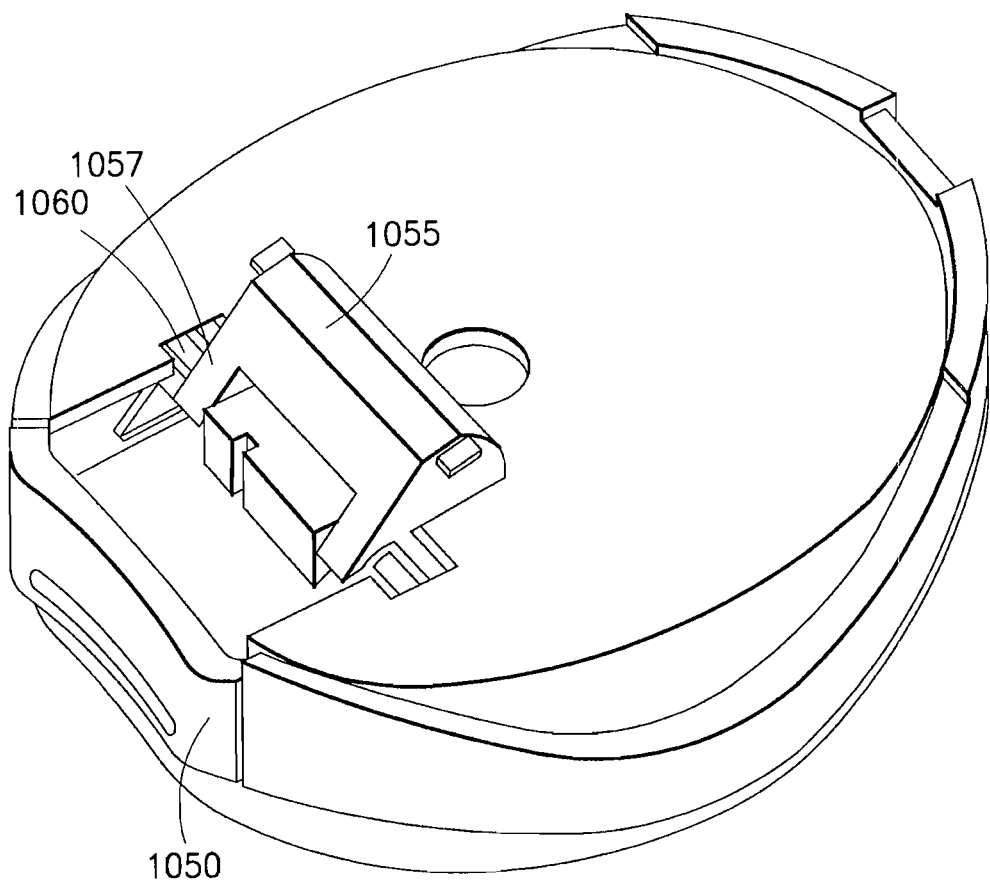
FIG. 129 is a perspective view of the ratchet-lock shield of FIG. 128 in an extended state.

The above embodiment can be further provided with an improved locking mechanism as the bucket, or shield 1030 travels from retracted to extended positions. The shield in this case, is a molded part and instead of having a flexible lock, the pivot of the shield can "ratchet" around and thereby prevent reverse rotation. FIG. 128 is a perspective view of an improved safety shield embodiment of an infusion device before activation, and FIG. 129 is a perspective view of the safety shield feature after activation.

Figure 130:
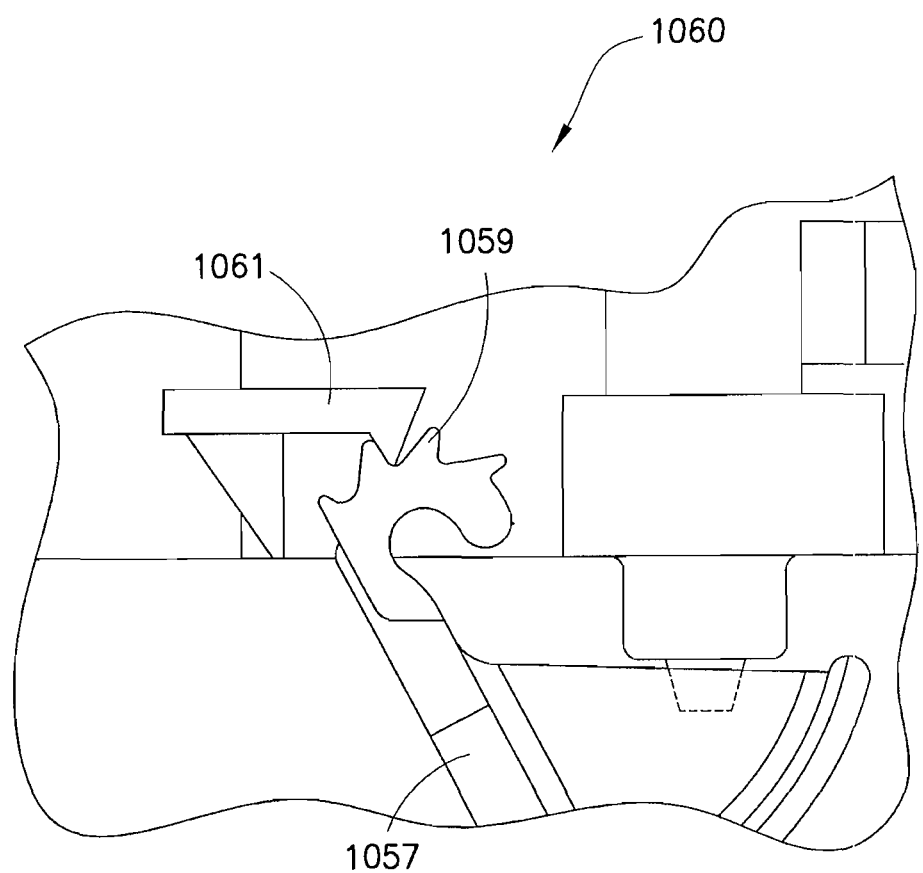
FIG. 130 is a perspective view of the ratchet-lock mechanism of the shield of FIG. 128.

As shown in FIG. 128, a button 1050 and not the housing holds a shield 1055. When the button 1050 is pressed, the shield 1055 is released and rests on the skin substantially as described above. As the device is removed from the skin surface, the spring (not shown) flips the shield 1055 and a ratchet mechanism 1060 at the pivot point engages a catch 1061 on the device body as it rotates, such that the ratchet mechanism 1060 holds the shield 1055 in place. FIG. 130 illustrates the ratchet mechanism 1060 in greater detail. Ratchet teeth 1059 are present on the shield 1055 arm 1057, and a corresponding wedge, or catch 1061 is located on the device. Any partial rotation is now locked.

The ratchet can provide teeth 1059 sufficiently large enough to resist a defeating load however they are not so large as to protrude from the bottom of the device and into the user. Additionally, to achieve these goals, the ratchet 1060 does require recessing the shield 1055 into the device, thereby adding to the height of the device. A sufficient spring force is provided to drive the shield 1050 incrementally over the ratchet 1060, however care must be given to force balance between full travel and creep issues. Also, final assembly is somewhat more intricate as the spring has no natural place to be held and must be loaded in the device at the time of assembly, which also requires interleaving the button between the manifold and shield.

The ratchet lock provides yet another passive safety embodiment which completely covers the needles with material and can be molded of high strength parts. The embodiment requires only two additional parts and will lock on full or partial deployment for robust safety. The force applied to the skin surface is further away from the needle site than with other embodiments however, the embodiment requires a degree of space within the device which can make the device longer. As with the above embodiment, the shield 1055 presses on the skin during delivery and the shield opening removes a large adhesive surface near the needles. Also, as with most compressed spring mechanisms, such springs can be subject to creep and the spring must be loaded during assembly into device. A ratchet lock so close to the pivot point also requires very high strength.

Figure 131:
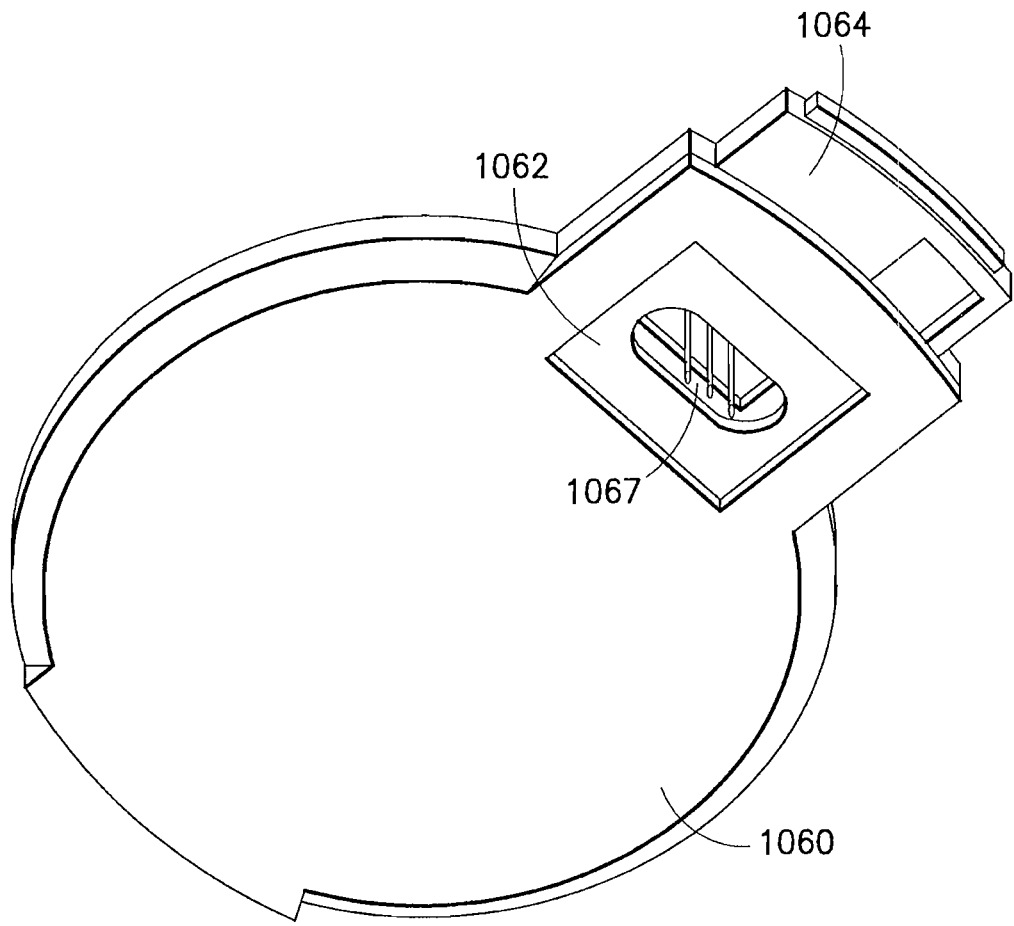
FIG. 131 is a perspective view of a pull-out shield in a retracted state.
Figure 132:
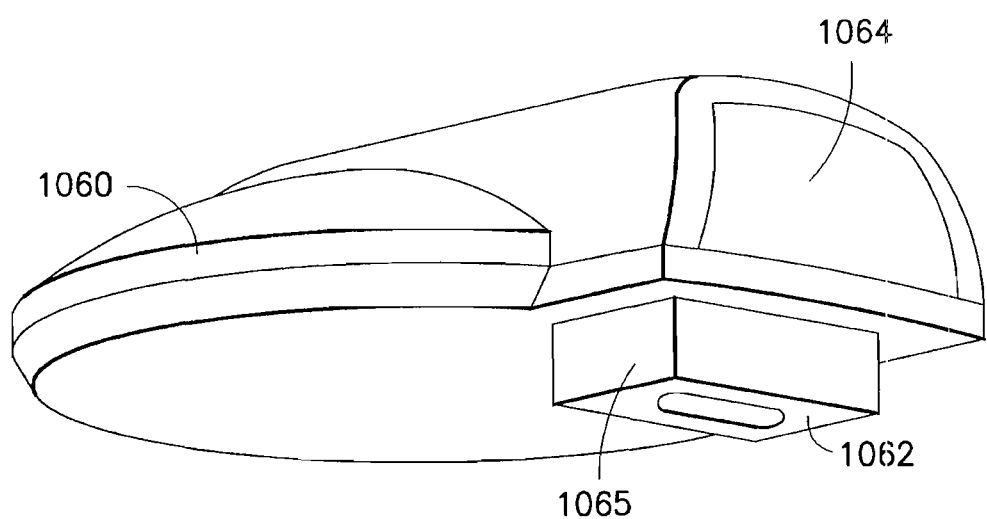
FIG. 132 is a perspective view of the pull-out shield of FIG. 131 in an extended state.
Figure 133:
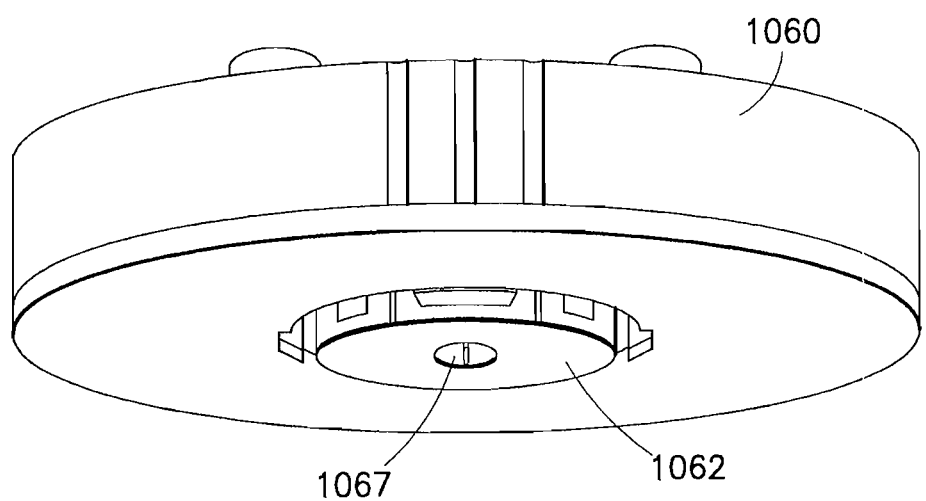
FIG. 133 is a perspective view of another pull-out shield in a retracted state.
Figure 134:
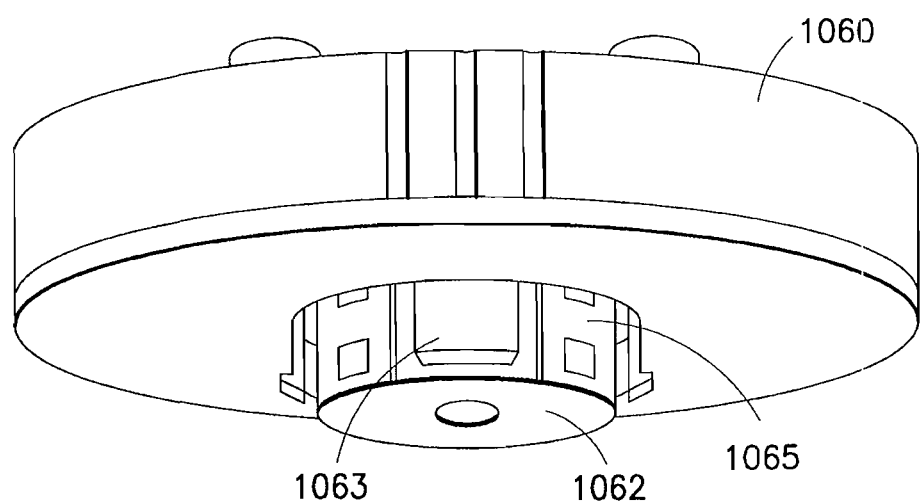
FIG. 134 is a perspective view of the pull-out shield of FIG. 133 in an extended state.

Another improved safety embodiment of the present invention is a passive fully enclosed pull out design embodiment as described below. FIGS. 131 and 133 are perspective bottom views of a device illustrating an embodiment of a safety shield feature of an infusion device before activation, and FIGS. 132 and 134 are perspective bottom views of a device illustrating the safety shield feature after activation.

In the use of the embodiments of FIGS. 131 through 134, the user prepares and uses an infusion device 1060 substantially as described above. When the device is removed from the skin, an adhesive patch 1062 attached to a shield 1065 will pull the shield 1065 out and lock it into place before the adhesive patch 1062 releases the skin surface. The safety housing, or shield 1065, is provided which includes a flat surface portion that is in contact with the patient's skin. The flat surface includes the adhesive patch 1062 disposed thereon such that when the device is removed by the patient from the skin, the adhesive patch 1062 will act to deploy (i.e., retract or extract) the shield 1065 from the interior of the device, thereby shielding patient needles 1067 which otherwise would be exposed upon removal of the device from the patient. The extended safety shield 1065 is then locked into place and prevents accidental injury or exposure to the patient needles.

The shield 1065 is a stamped metal part that fits within the device 1060 and is held in place by a button 1064 to prevent the shield 1065 from activating prior to use when the adhesive liner and needle cap (not shown) are removed. The adhesive patch 1062 is provided in substantially two parts, one on the bulk of the bottom surface of the device 1060, and one on the bottom surface of the shield 1065. When the device 1060 is removed, the two patches move independently and the shield 1065 is now mobile since the button 1064 has been pushed. In the embodiment shown in FIGS. 133 and 134, a number of guide slots and tabs 1063 are provided with the shield 1065. The shield 1065 is pulled out until it becomes trapped between the top of the slots and the tabs 1063, and is thereby locked into position by the angled tabs on the shield 1065.

The assembly of this embodiment can be snap fit into the device from the bottom. The button is also snap fit into place, as it is required to engage the initial lock. The pull out embodiment is yet another passive safety embodiment that is provided as a single part and provides a good lock which will not crush under human loads. However, the embodiment requires a degree of space within the device, and can be difficult to expose as it requires a large adhesive area that floats at the needles and which includes at least one non-adhesive covered hole at the bottom. This also results in a large travel required, and yet provides limited coverage on the backside. Also, interference such as a finger could prevent deployment upon removal.

Figure 135:
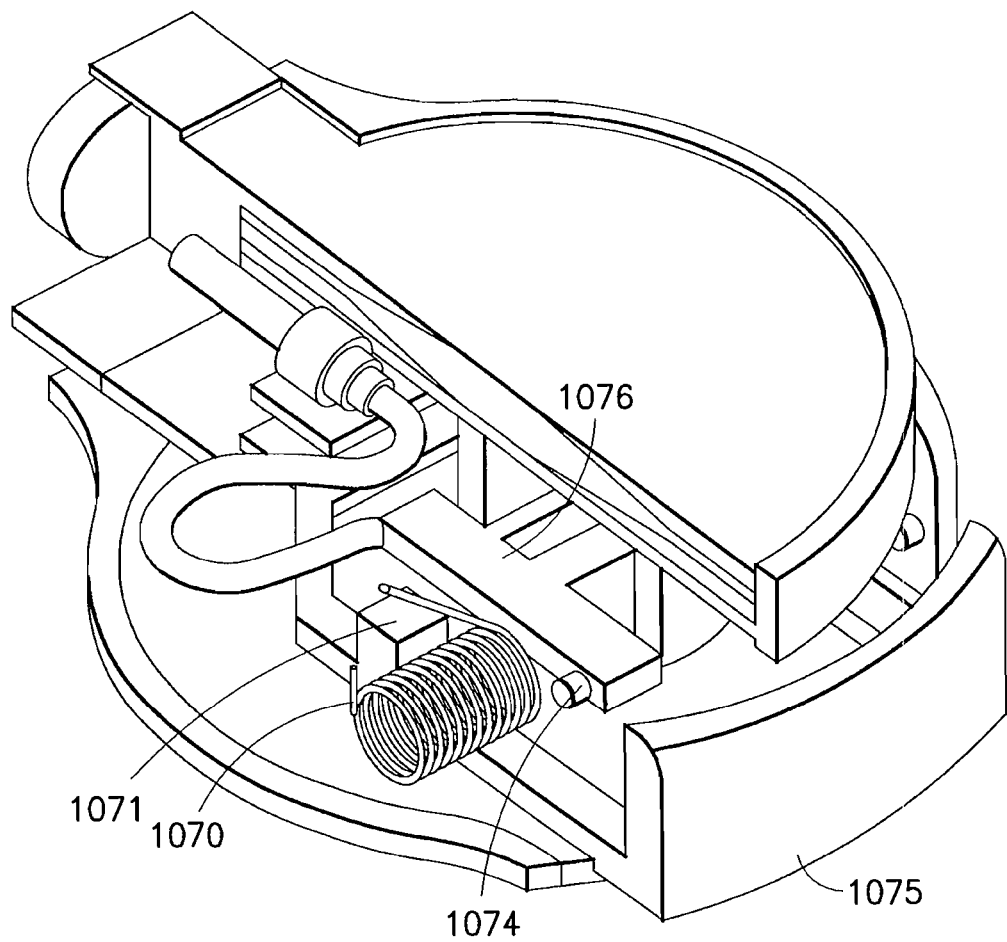
FIG. 135 is a perspective view of a torsion-spring shield in an initial position.
Figure 136:
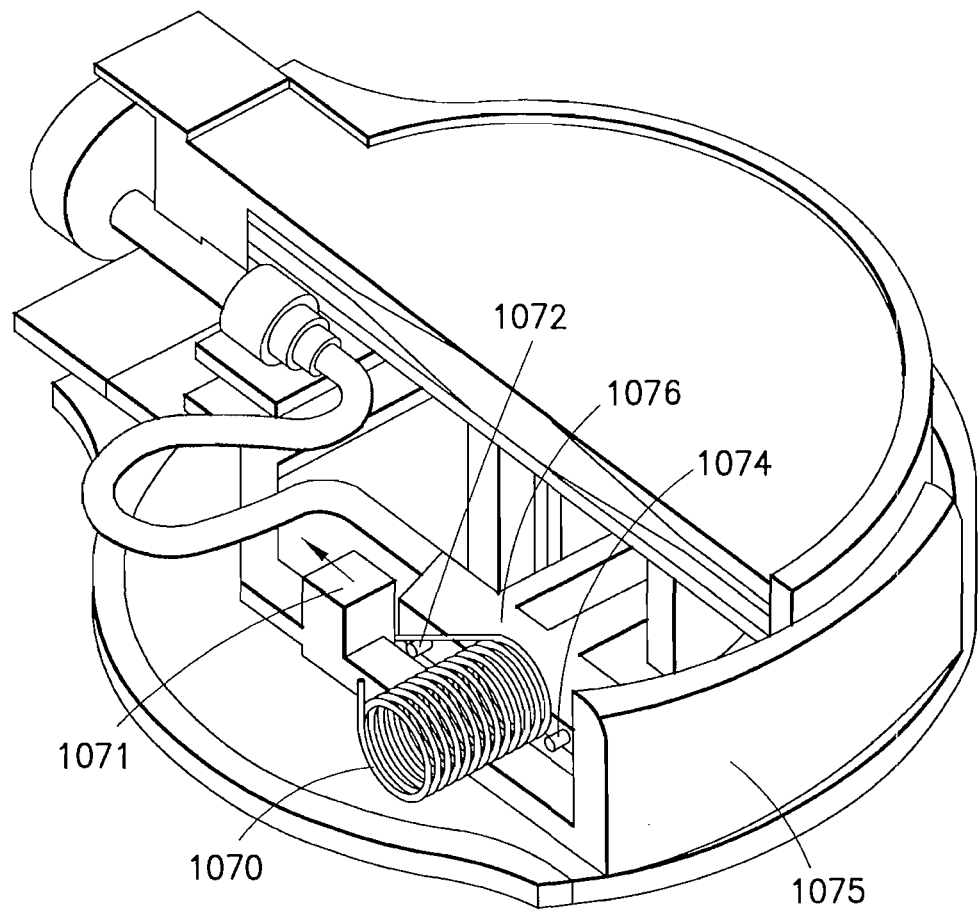
FIG. 136 is a perspective view of the torsion-spring shield of FIG. 135 in an in-use position.
Figure 137:
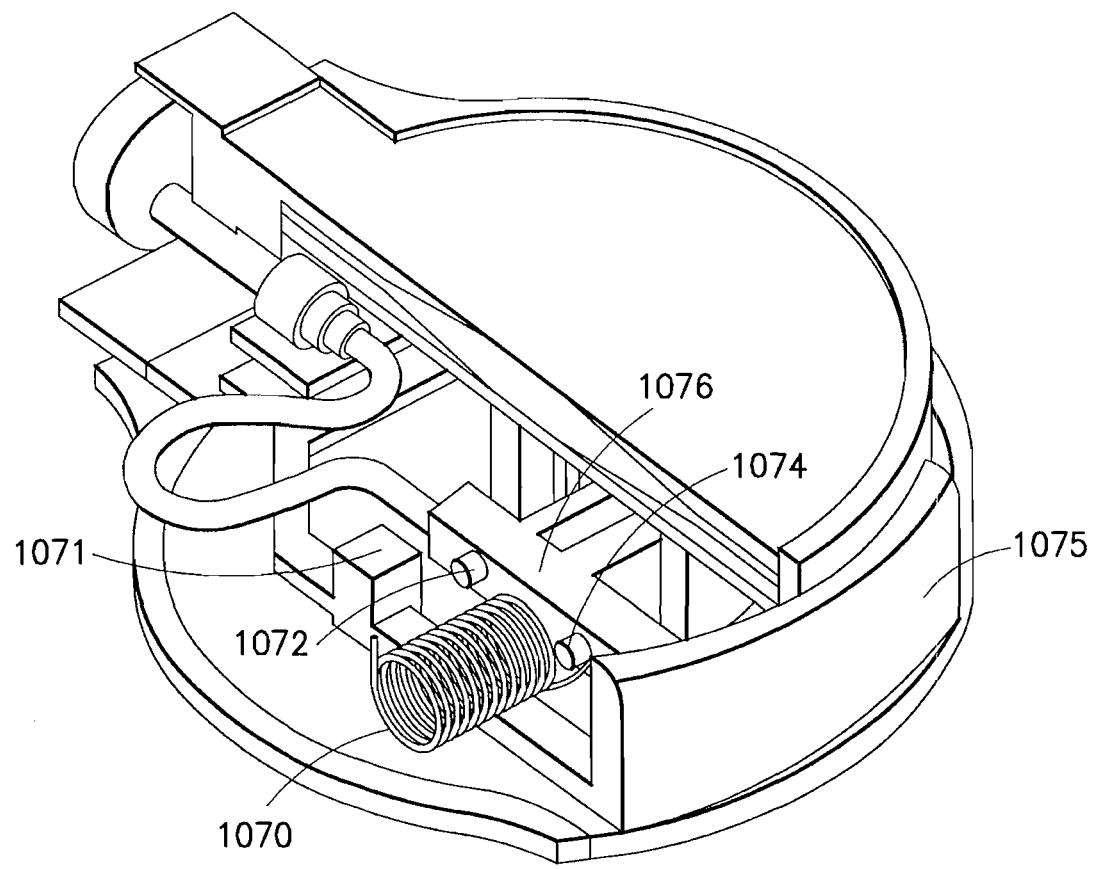
FIG. 137 is a perspective view of the torsion-spring shield of FIG. 135 in a retracted position.

Another improved safety embodiment of the present invention is a passive torsion spring retraction design as described below. FIG. 135 is a perspective view of an embodiment of a safety shield feature of an infusion device in an initial position, FIG. 136 is a perspective view of the safety shield feature in an in-use position, and FIG. 137 is a perspective view of the safety shield feature in a final retracted position.

The embodiment includes a preloaded internal torsion spring 1070 which rests on a peg 1074 on a manifold 1076. Two springs could be used if necessary. When a button 1075 is pushed, the manifold 1076 is released and the spring falls off block 1071 and pushes a drive peg 1072 on the manifold 1076 to push the manifold 1076 downward to a seated position at the appropriate velocity. When the device is exhausted and it is removed from the skin, one of two things can occur. First, the manifold 1076 which is designed having extra overtravel, continues forward and the spring 1070 slips off the drive peg 1072, flips through 180 degrees, and catches a retraction peg 1074 on the manifold 1076, lifting the manifold 1076 thus retracting the needles (not shown). In an alternate version of the embodiment, the manifold 1076 is allowed to move sideways slightly, thus releasing the spring 1070 from the drive peg 1072 (which is somewhat shorter than the retraction peg 1074) to flip to the retraction peg 1074 on the manifold 1076, lifting the manifold 1076 thus retracting the needles.

The moving end of spring 1070 should have sufficient clearance to make the 180° rotation but avoid the risk of causing injury as the arm of the spring passes from the drive peg 1072 to the retraction peg 1074. However, once retracted the spring 1070 holds the manifold 1076 and needles up and disables the device. The embodiment also requires no additional parts.

As with the embodiments described above, this is a passive safety mechanism in which the manifold is the trigger and no additional parts are required. No additional forces are applied to the skin during injection, and the needles are safely held internally after use. Unlike the pull out designs, this embodiment does not affect adhesive presence at needles. However, clearance is required to avoid possible injury to the user due to the moving arm of spring 1070. Also, as with most compressed spring mechanisms, such springs can be subject to creep, and there can be concerns regarding spring dimensions and force profiles.

Figure 138:
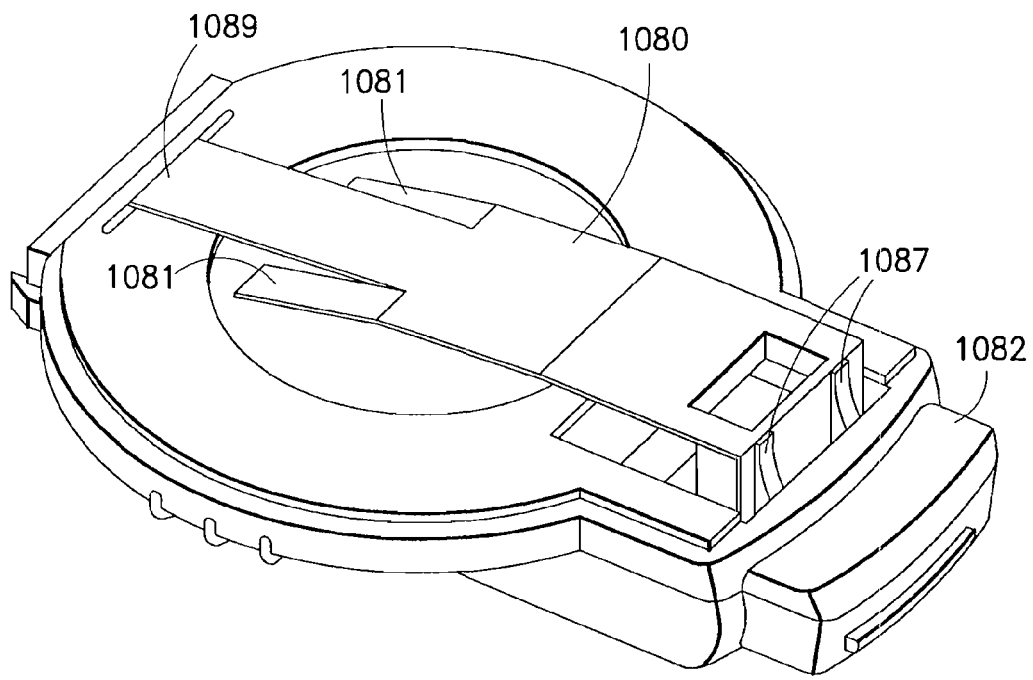
FIG. 138 is a perspective view of a hinged shield with an integral spring.
Figure 140:
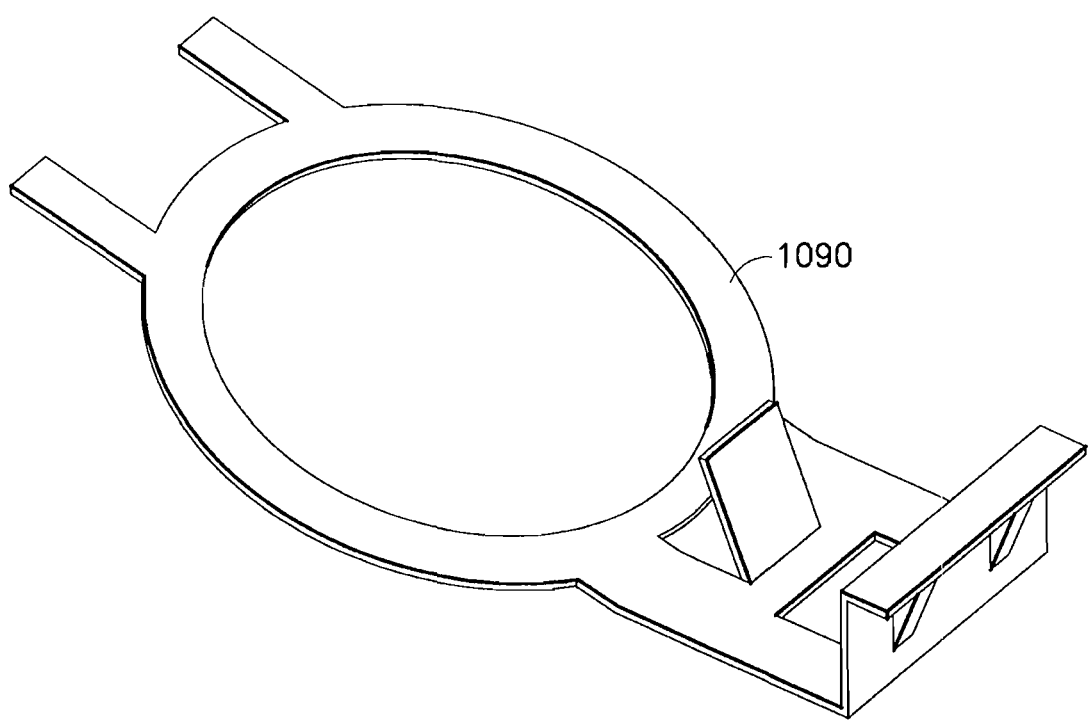
FIG. 140 is a perspective view of a spring shield with a circular integral spring.
Figure 141:
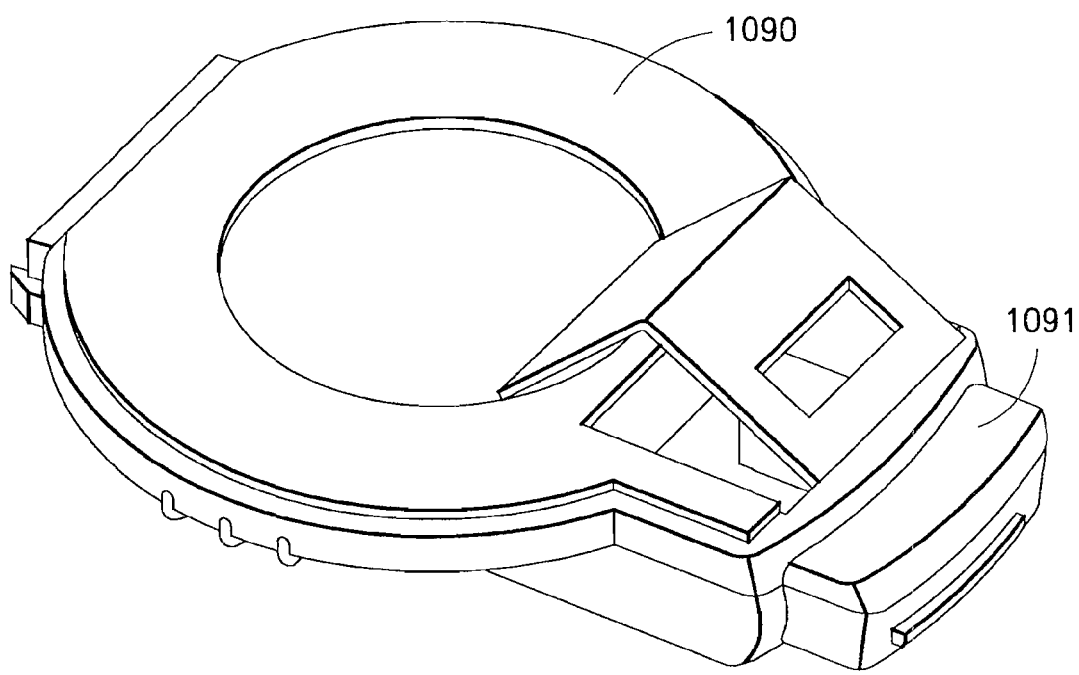
FIG. 141 is a perspective view of a spring shield with a buckle-type integral spring.

Other improved safety embodiments of the present invention include passive hinged shield design embodiments as described below. FIG. 138 is a perspective view of an embodiment of a safety shield feature of an infusion device in a spring-driven hinged position, FIG. 139 is a perspective view of a safety shield feature in an adhesive-driven hinged position, FIG. 140 is a perspective view of a safety shield with a circular integral buckle spring held in a retracted position, and FIG. 141 is a perspective view of the buckle spring in an activated position.

Figure 139:
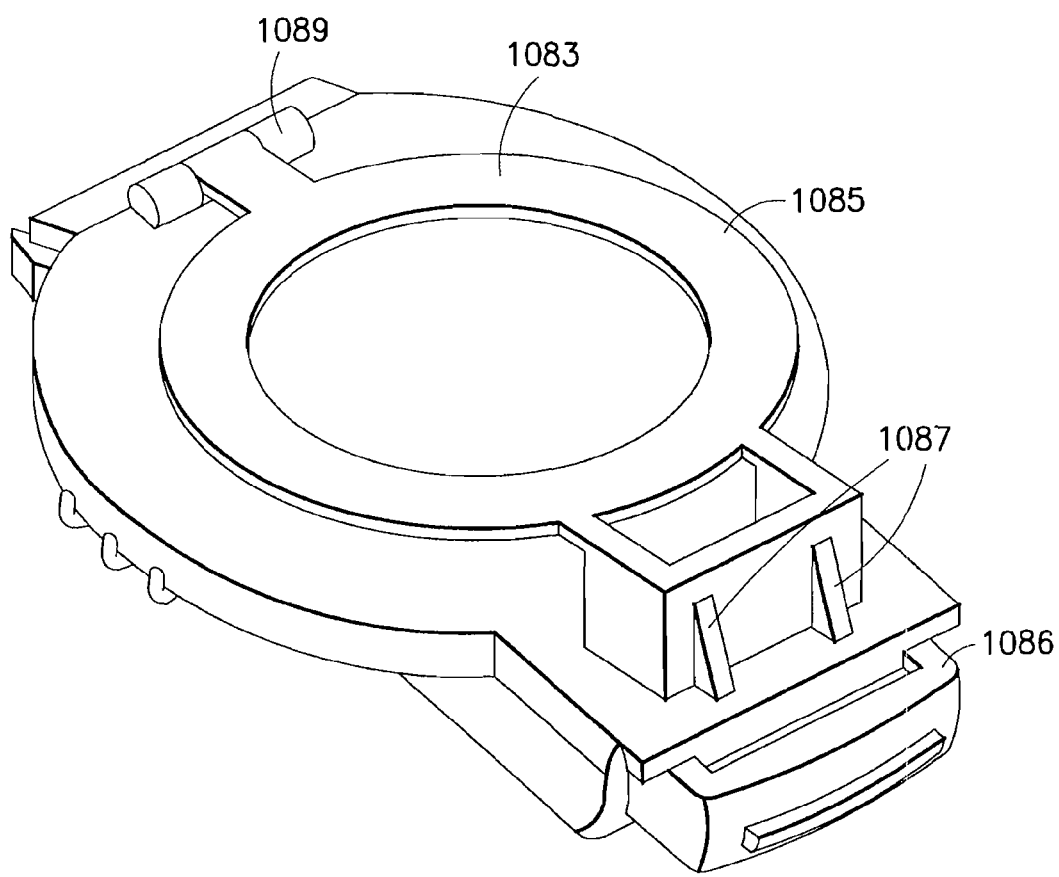
FIG. 139 is a perspective view of a hinged shield with an adhesive driven hinge.

In FIGS. 138 and 139, a hinged shield 1080 and 1085 is shown, respectively. When on the device, the hinged shields 1080 and 1085 are flat. The shields 1080 and 1085 are locked flat until buttons 1082 and 1086 are pushed, respectively, in which case, the shields 1080 and 1085 are released but an adhesive holding the device to the body secures the shields 1080 and 1085 in a flat position against the skin. When the device is removed from the skin, the shields 1080 and 1085 "pop" up as urged by spring elements 1081 and/or an adhesive surface 1083, respectively, and are locked into place by tabs 1087.

In each of these embodiments, the shields 1080 and 1085 can be a metal part sufficiently hinged at one point 1089 to secure rotation from the device. The hinged metal shield 1080 is driven by spring elements 1081 to an extended and locked position. Specifically, the shield 1080 can be constructed having a number of bent arms of the spring elements 1081 that act as springs against the surface of the device. The bent arms of the spring elements 1081 are loaded against the bottom housing of the device and the button 1082 locks the front of the springs, typically at a point farthest from the hinge 1089, in the retracted position. When the button 1082 is pushed, the shield 1080 is free to rotate about the hinge 1089 but the skin keeps the shield flat. Upon removal of the infusion device from the skin, either the bent arms of the spring elements 1081 alone or in combination with the adhesive 1083 as provided with spring 1085, pulls the shields 1080 and 1085 outward and locks it into place with a number of tabs 1087 at the front of the device.

The spring embodiments described above are typically constructed with an ability to resist a defeating load, since each can be a long and/or thin part. Additionally, the springs 1080 and 1085 are adapted to provide a suitable amount of protection, even with a long term load and a long travel. Once engaged, the springs 1080 and 1085 are also sufficient to hold on the hinge 1089 after engagement as required.

As shown in FIG. 140, an alternate version of the above embodiment includes a shield 1090 having a natural hinge which acts as the spring. The shield 1090 is held in the position shown in FIG. 140 by a push button 1091. Once released, the shield 1090 is biased to the shape shown in FIG. 141. Therefore upon activation and removal of the device, the spring 1090 is activated into the shape shown in FIG. 141 through the action of a natural hinge, covering the needles (not shown). The base of the device can further include at least one notch that can lock the rear edge of the shield 1090 as it travels.

The hinged shield embodiments described above provide another entirely passive, single piece safety shield, which is simple to assemble and activate with a snap of the button. The features also ensure the device maintains a low profile. However, the embodiments include flex elements and require a balance between obstructed views and part stiffness. Access to the needles still exists somewhat through an opening, and the spring can be easy to defeat in some cases. Also, the embodiments apply loads to the skin at the needles during delivery and rely to a great degree upon hinge integrity.

Figure 142:
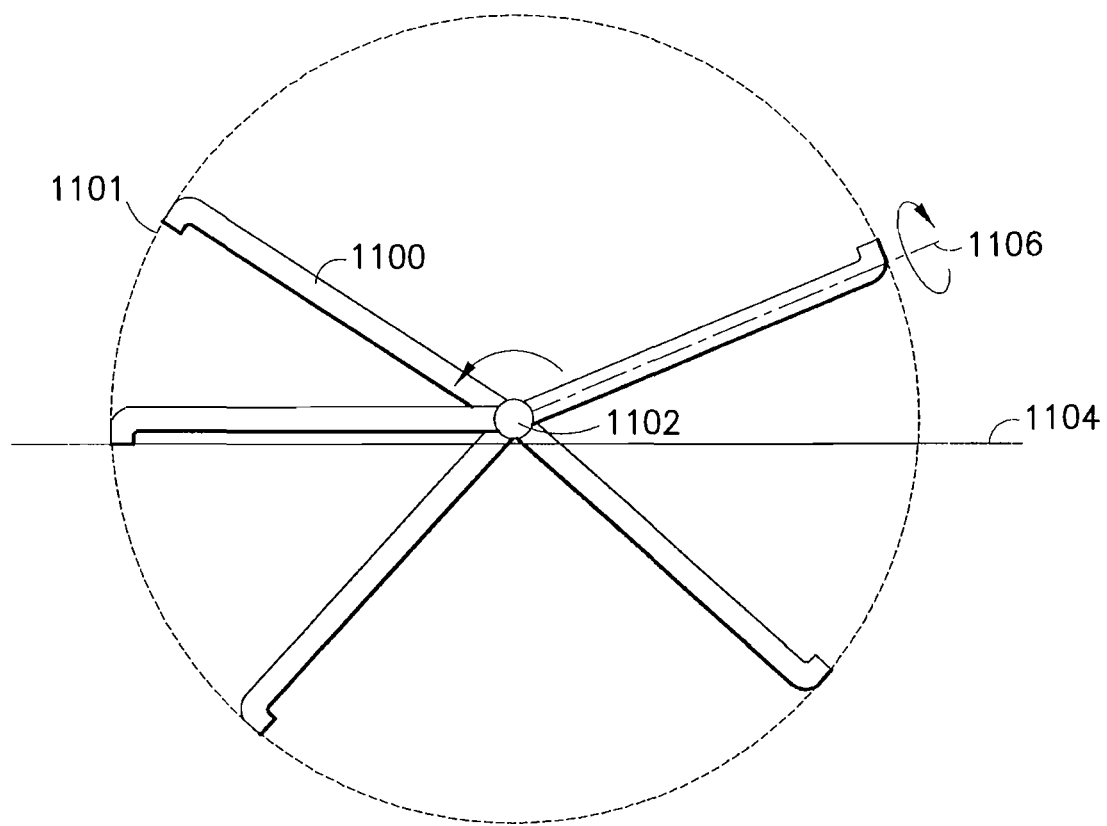
FIG. 142 is a view illustrating an over-rotating shield.

Still another passive design for shielding needles in a micro infusion device is that of rotating the needles either back out of the user or allowing the needles to "over rotate" to a safe position when the device is removed from the skin by the user. In the improved rotational shield embodiment shown in FIG. 142, the primary feature is the use of rotation to embed needles 1101, and the use of the same or similar rotation "path" to remove the needles 1101 once a skin surface 1104 is removed. In the embodiment shown in FIG. 142, a single needle-securing arm 1100 is rotated about a first axis 1102. As the needles 1101 contact the skin surface 1104, the needles 1101 are seated and travel about the axis 1102 is stopped. Upon completion and removal of the device from the skin surface 1104, the travel about the axis 1102 resumes, carrying the needle-securing arm 1100 back into the device (not shown). The needle-securing arm 1100 can also be rotated about a second axis 1106 to further shield the needles 1101 after use.

As noted above, one desirable feature of an infusion device is that of a continuous fluid path, which is preferred since it has the potential to reduce the number of sterile barriers and simplifies the manufacture of the device. Thus, an embodiment that includes rotating the needles 1101 into the user's skin 1104 via the needle-securing arm 1100 facilitates these advantages. This embodiment further provides the rotation of the needles 1101 into the skin 1104 to embed them, and then allows the needles 1101 to "over rotate" to a safe position when the device is removed from the user's skin 1104. This over-rotation capitalizes on the single path the needles 1101 are traveling and can be employed either as a passive or an active safety system. Additionally, the mechanism has the potential to provide safety while not compromising the integrity or manufacturability of the fluid path from the drug reservoir to the needles 1101.

Another embodiment of a passive safety mechanism for a micro infusion device provides for the unloading of the activation spring upon removal. As noted above, such an infusion device uses an array of needles to deliver subcutaneous injections. These are fired by means of a spring into the patient at the velocity necessary to penetrate the skin layer. After the infusion has taken place, it is desirable upon removal of the device from the patient to shield the now-exposed needles in some fashion in order to prevent needle-stick injuries during subsequent handling. If the driving spring can be unloaded or altered in some way, the needles can easily return back inside the housing of the device where they will no longer pose a threat. In this embodiment, an arm is provided, comprised of a bendable beam which can be loaded by means of a cam and made to function as the spring for firing the needles. FIGS. 143 through 146 illustrate an embodiment for accomplishing this task with a single additional part.

As shown in FIGS. 143 through 146, a cross-sectional view is provided of the device including the cam-arm mechanism. The mechanism includes an arm 1110 having at least one follower 1112 extending from the arm and slidably coupled with a cam opening 1114. The arm further includes a patient needle manifold 1116 at a distal end, which is releasably held in place by a trigger mechanism 1118. The cam opening 1114 is provided within a slidable member 1124. There are four basic states that the embodiment will see in use, all of which are depicted and described in greater detail below.

Figure 143:
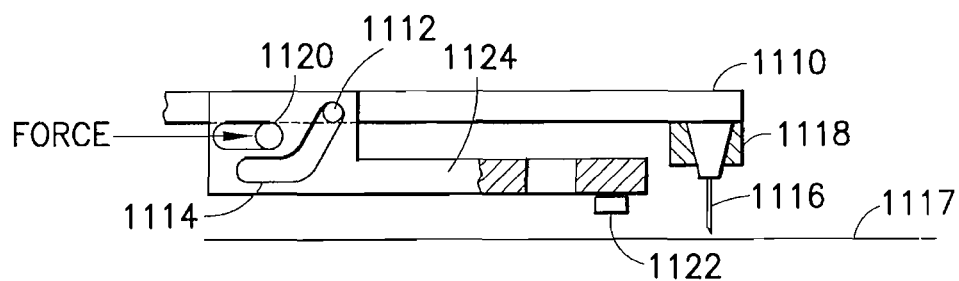
FIG. 143 is a cross-sectional view illustrating a cam-action safety in a ready state.
Figure 144:
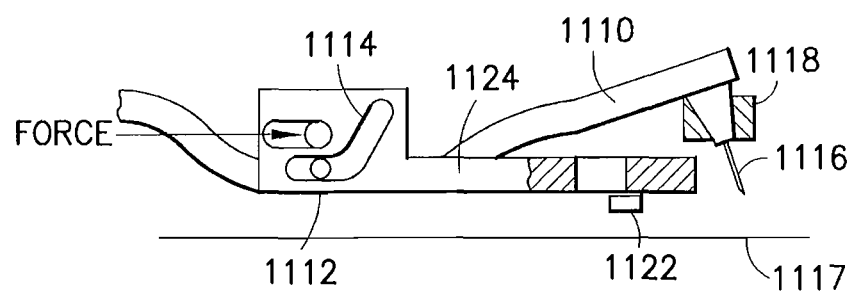
FIG. 144 is a cross-sectional view of the cam-action safety of FIG. 143 in a cocked state.

In a first or ready position shown in FIG. 143, the arm 1110 is at rest and the assembly is ready for activation by the user. This is typically the assembled and shipped configuration of the product. In a second, or spring cocked position shown in FIG. 144, a button (not shown) is activated by the user and moves the member 1124 to the right. As the member 1124 is moved to the right by a force applied to pin 1120, the arm 1110 remains stationary and is driven into a deflected position by the movement of the cam opening 1114 about the stationary follower 1112. Since the pin 1120 and trigger 1118 are both attached to the button, each shift, placing the arm 1110 into this bent state by means of the cam opening 1114 and follower 1112. The spring is armed in this manner by the user at the time of use, which has the advantage over a pre-loaded assembly of eliminating the stresses and creep associated with a loaded spring. In this state, the trigger 1118 and latch 1122 are engaged and ready to fire by the user shortly before use.

Figure 145:
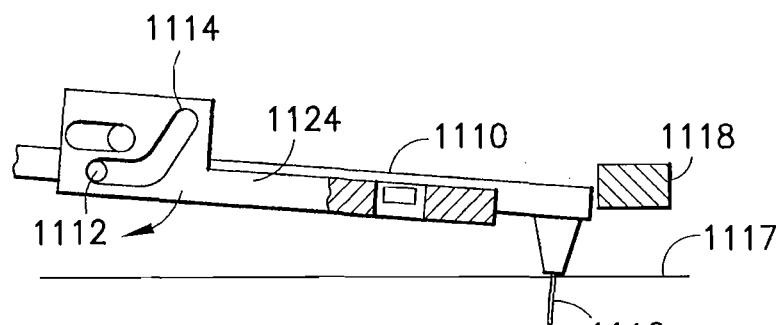
FIG. 145 is a cross-sectional view of the cam-action safety of FIG. 143 in a fired state.

In a third, or fired position shown in FIG. 145, further movement of the button has now moved the trigger 1118 far enough forward to unload the spring (i.e., release the arm 1110), driving the needles 1116 into the skin surface 1117. The latch 1122 has also now triggered via an opening provided in the member 1124, allowing the arm 1110 and member 1124 to both rest upon the skin surface 1117. The moment coupling of the follower 1112, cam opening 1114, and residual spring in the arm 1110 apply light pressure to the skin surface 1117.

Figure 146:
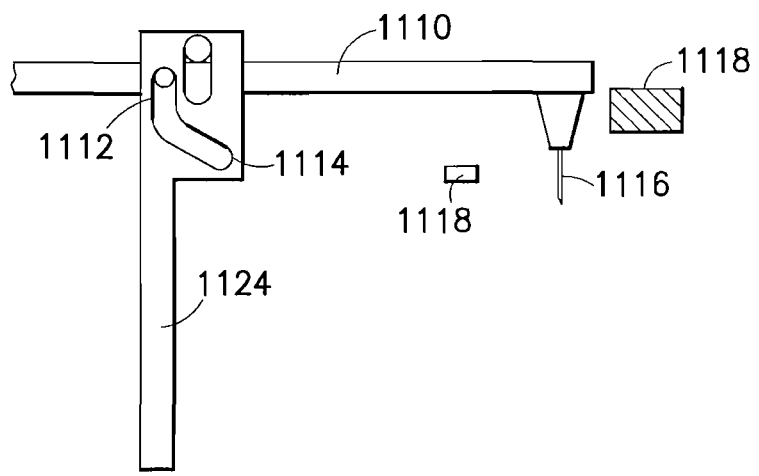
FIG. 146 is a cross-sectional view of the cam-action safety of FIG. 143 in a safe state.
Figure 147:
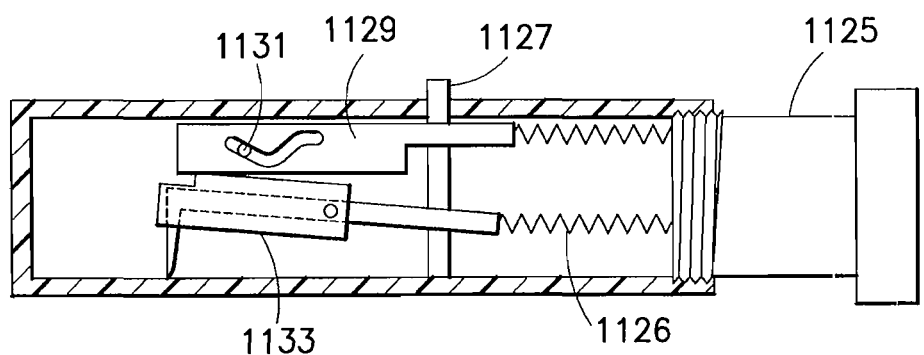
FIG. 147 is a cross-sectional view of another cam-action mechanism.

In a fourth, or safe position shown in FIG. 146, the device has been removed from the skin surface 1117 and the member 1124 has rotated due to the coupling of follower 1112 and cam opening 1114. This allows the arm 1110 to relax again to its original state, with the needles 1116 retracted into the housing. The entire above mechanism can be disposed within an infusion device. An additional use of a cam/follower action is shown in FIG. 147. FIG. 147 illustrates an example wherein a threaded member is used to load the springs used to cam the patient needles into and out of the patient, as well as pressurize the reservoir contents.

Specifically, FIG. 147 illustrates an embodiment having a twist, or threaded member 1125 to load spring(s) 1126 within the device. The springs 1126 are secured by a pin or button 1127 and when released, forces element 1129 forward, wherein a pin 1131 riding in a slot within element 1129, is forced downward and subsequently upward, corresponding to the slot within element 1129. Forcing the pin 1131 downward further forces a pivoting reservoir and needle assembly 1133 downward. Further movement of element 1129 forces pin 1131 upward and, with assistance from spring 1126 in contact with the assembly 1133, forces the assembly 1133 upward.

As noted above, a passive safety system is most desirable however active safety systems are also functional and can be used in several applications. Also as noted above, with respect to safety systems there are typically three options, including retracting the needles into the device, shielding the needles to remove access, and destroying the needles in a way that prevents needlestick injuries. A number of passive safety mechanisms have been described in detail above. A number of active safety mechanism embodiments of the present invention are now described in greater detail below.

Figure 148:
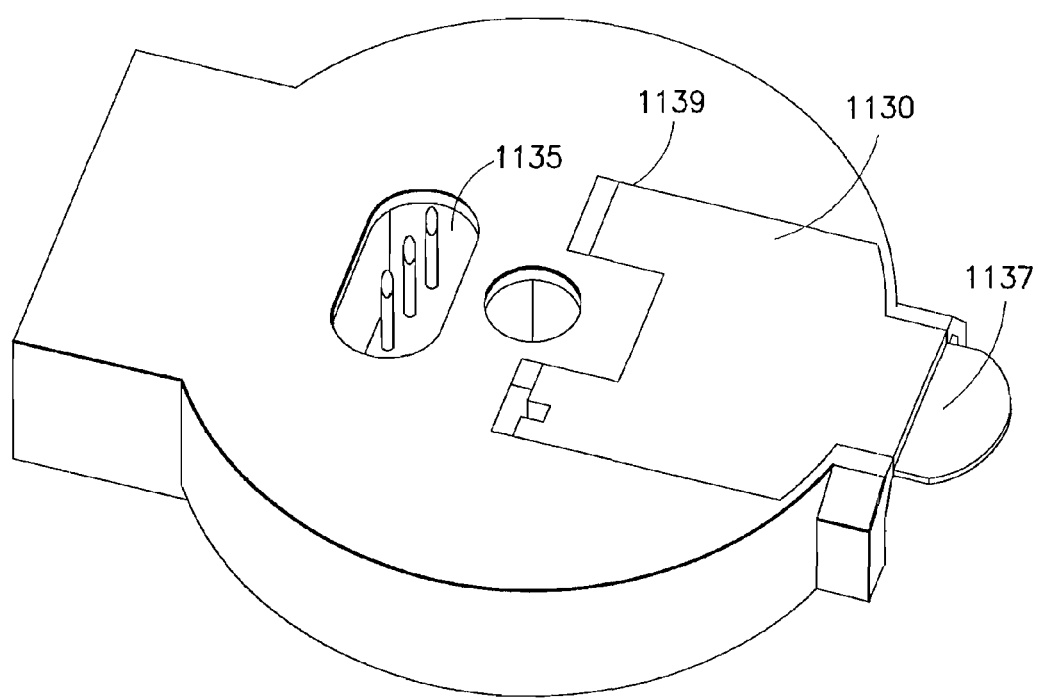
FIGS. 148 and 149 are perspective views of a flip shield.
Figure 149:
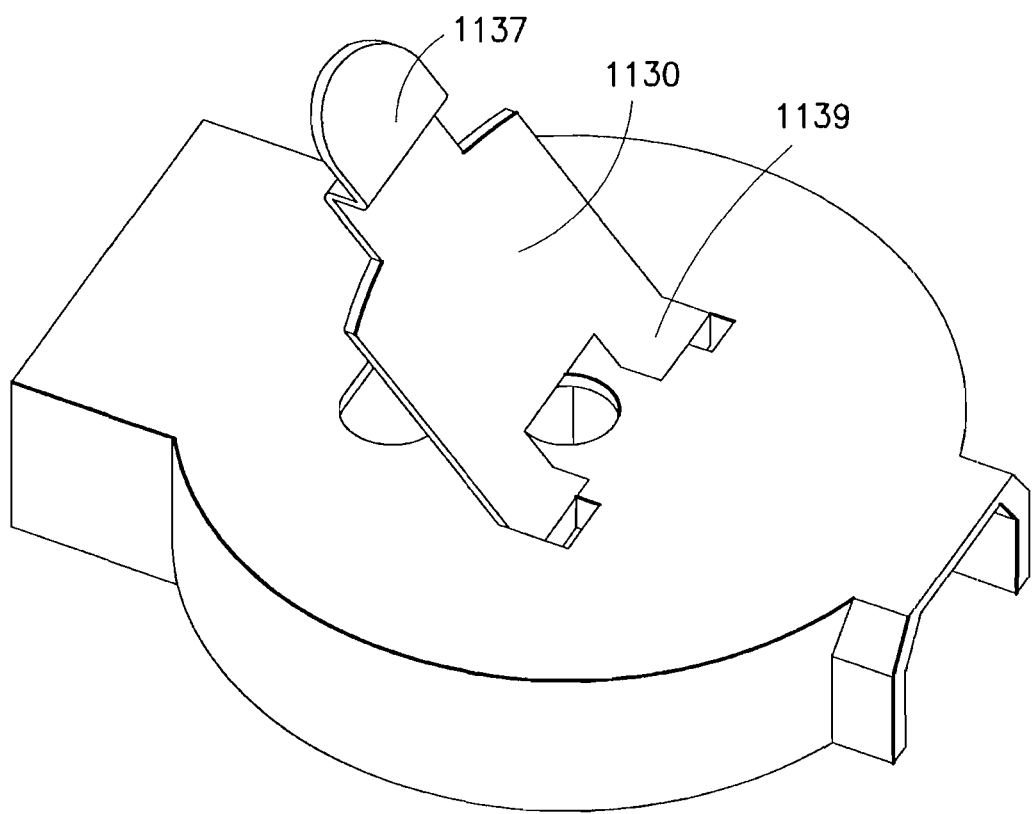

An improved flip-shield safety mechanism embodiment of the present invention is shown in FIGS. 148 and 149. The function of the device is substantially the same as above except when the device is removed, the user flips a shield 1130 down and locks the shield 1130 in place to prevent needles 1135 from being accessed.

As shown in FIGS. 148 and 149, the shield 1130 is a substantially flat piece of either plastic or metal, which is held in place by a press using a detent 1137 at the edge of the device. When the device is on a skin surface during use, the shield 1130 is essentially flat. After removal, the user grasps an extended tab of the detent 1137 on the shield 1130 and flips the shield 1130 about hinge 1139 to "crush and cover" the needles 1135. A lock (not shown) can also be provided such that the shield 1130 is irremovably secured with the device when closed after use. When the shield 1130 is locked in place, both the needles 1135 and needle opening are completely covered and locked.

The assembly of this embodiment can include a snap fit over the pivot, and press fit into an initial position. This can be done very early in manufacture, such that it is in place and on the bottom of the device while the rest of the device is assembled. An adhesive can also be disposed on top of the shield 1130. Such an active safety mechanism is provided by a single part, and has a simple assembly having a low profile and providing robust protection. However, the mechanism is active, which requires an extra user step. Also, adhesive on the shield 1130 can cause the device to float, and crushing the needles 1135 can be problematic. Additionally, the pivot 1139 must be carefully placed to get full rotation and avoid incomplete locks.

As noted above, the improvement embodiments of safety mechanisms can be provided in a number of versions, including a mouse-trap type safety, a needle lift-and-cover type safety, and a rotating needle manifold type safety. Both passive and active mechanisms are described in detail above, however, several mechanisms can be provided as either active or passive. A number of active/passive safety mechanism embodiments of the present invention are described in greater detail below.

In regard to the passive safety embodiments described above, several embodiments, such as the needle lift-and-cover embodiments can also be provided as active systems that the user employs, but which are inexpensive to manufacture and are very robust in use. For example, in the needle lift-and-cover embodiments the force needed to embed the needles by the drive spring is potentially high. Hence, overcoming these forces by the user in an ordinary active safety system may likewise be high and the potential for incomplete shielding of the needles is a possibility. However, several of the lift and cover embodiments described above as passive safety embodiments are advantageous in that each offers a ramp. Therefore, where applicable as active safety mechanisms, lift and cover embodiments can each offer a ramp to gain a mechanical advantage over the drive spring to lift the needles out, and also includes the potential to dislodge the drive spring completely which greatly eases the forces required by the user to shield the device. A final advantage in both the active and passive mechanisms is that these concepts can facilitate deployment of a transverse barrier which is integral to the ramp structure, and therefore inexpensive to manufacture, simple to use, and robust in use.

In another improved safety embodiment which can be provided as either an active or passive mechanism, a needle bending safety mechanism can be provided. In this embodiment (not shown), the mechanism can include a plate with a hole in which the needles are passed through during use and delivery. After use, either in an active or passive manner, the plate can be moved such that the edge of the hole in the plate would exert a shearing load on the very small gauge needles and bend them sideways, while at the same time covering them.

However, care must be taken to avoid breaking the needles and varying degrees of force can be required to bend the needles, as they should be bent very close to the mounting point where there is very little moment arm. This embodiment can be provided as either an active or passive mechanism, and include a simple single piece assembly with a low profile.

In still another improved safety embodiment which can be provided as either an active or passive mechanism, a bi-stable leaf spring mechanism can be provided, having a single spring which can both drive and retract the needles. By using either a thin piece of plastic or metal, a biased system can be created that would work in either direction. With a bi-stable spring, the user would only need to overcome the stable resistance, then the "snap" to the other stable state would provide high velocity seating. Conversely when the device was exhausted, the user would only need to exert the same small force and the device would retract the needles.

In yet another version of this embodiment, a thin plastic component (not shown) can be provided and supported on one end and compressed slightly from the other. When a moment is applied to the compressed end, the plastic will snap through to the more stable configuration. When the moment is released, the plastic component flips back. Such bi-stable springs can be provided as active or passive mechanisms, and can be constructed as a simple single piece assembly having a low profile and providing high velocities.

Most of the previous design embodiments can be made into an active version, which could simplify them in that the need to sense the skin with a trigger would be obviated by the application of a deployment force by the user. There are also a myriad of concepts in which retraction is accomplished via a direct force from the user on a button or other such component, which then moves the manifold with no intermediate spring or other component.

In addition to the improved safety embodiments described above, further improvement embodiments of the present invention include improved manifold springs, improved fill mechanisms, improved packaging mechanisms, and improved end-of-dose indicator mechanisms.

As noted above, the patient needle manifold is typically urged forward when released by one or more patient needle manifold springs disposed within the infusion device. An exemplary device is shown and described in relation with FIGS. 37, 38 and 39. However, the manifold springs of FIGS. 37, 38 and 39 can further include the improved springs of FIGS. 150 through 156, described in greater detail below.

Figure 150:
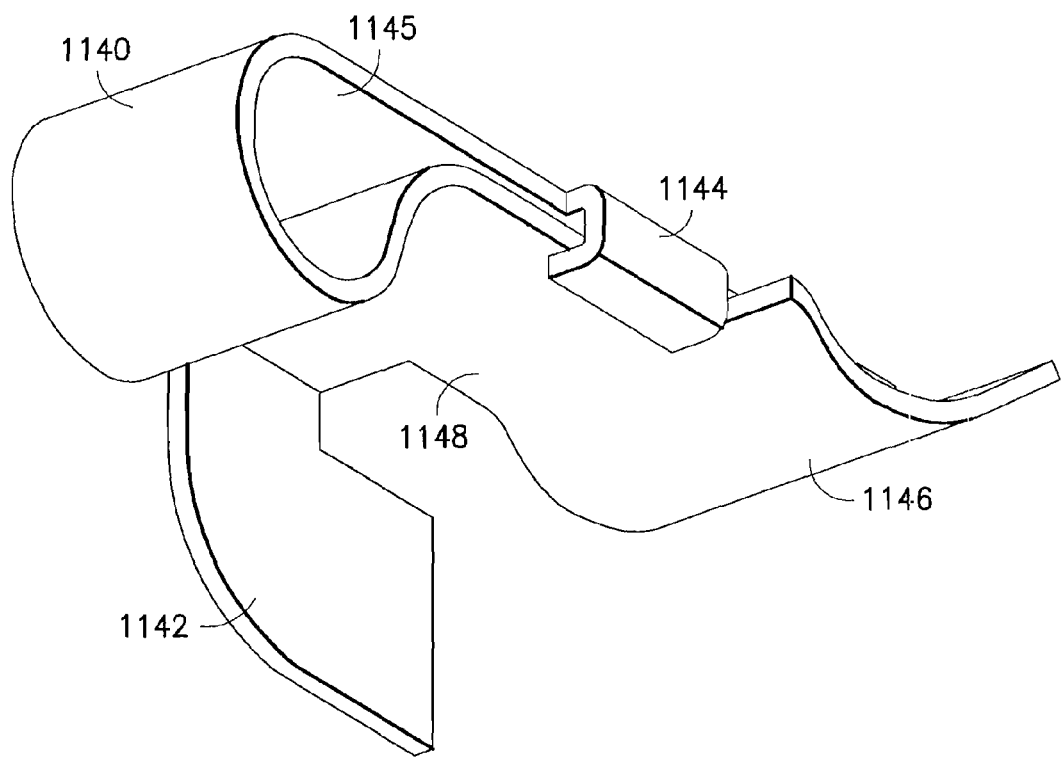
FIG. 150 is a perspective view of an improved manifold spring in an unactivated position.
Figure 151:
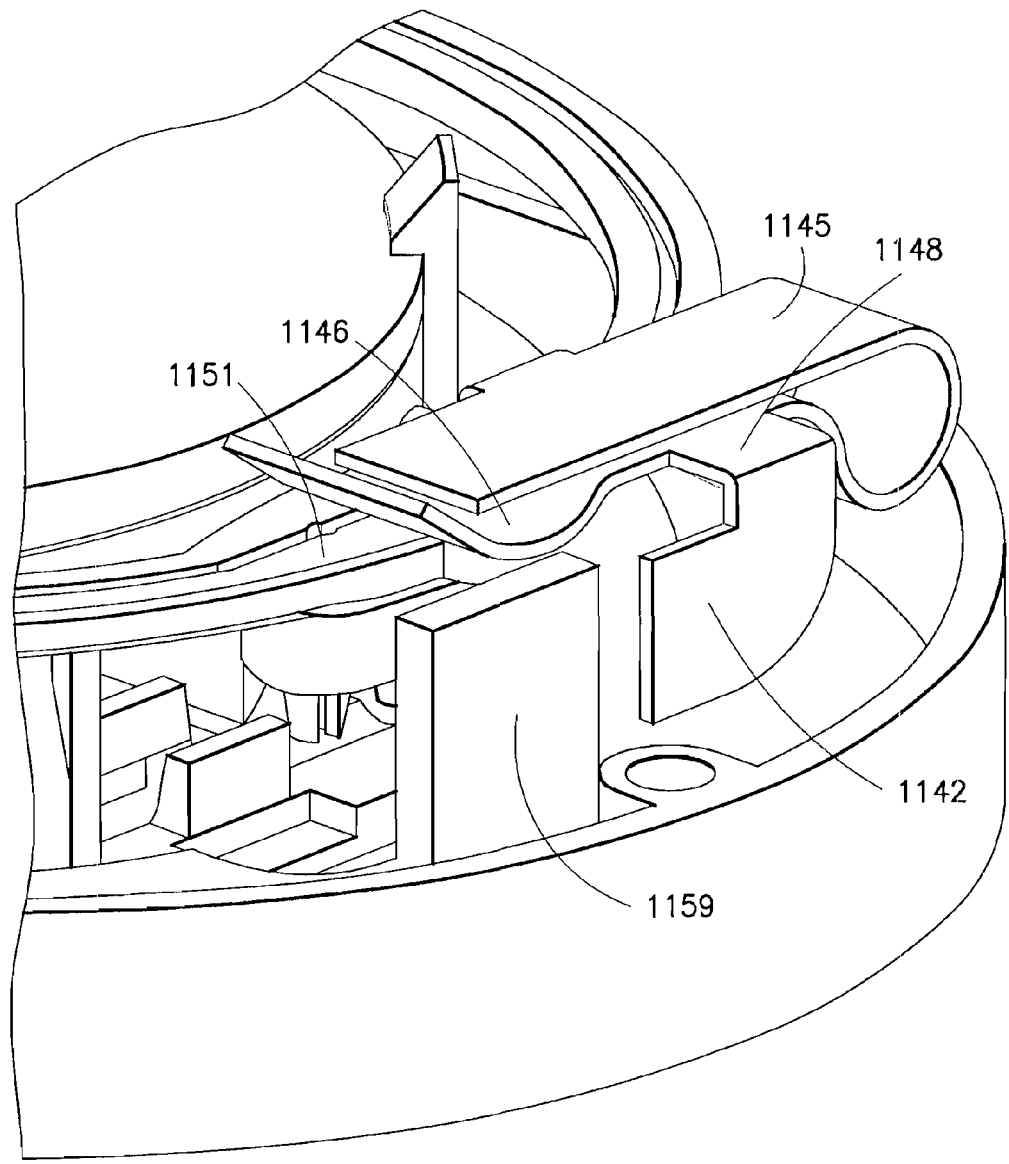
FIG. 151 is another perspective view of the manifold spring of FIG. 150 in an unactivated position installed within an exemplary device.
Figure 152:
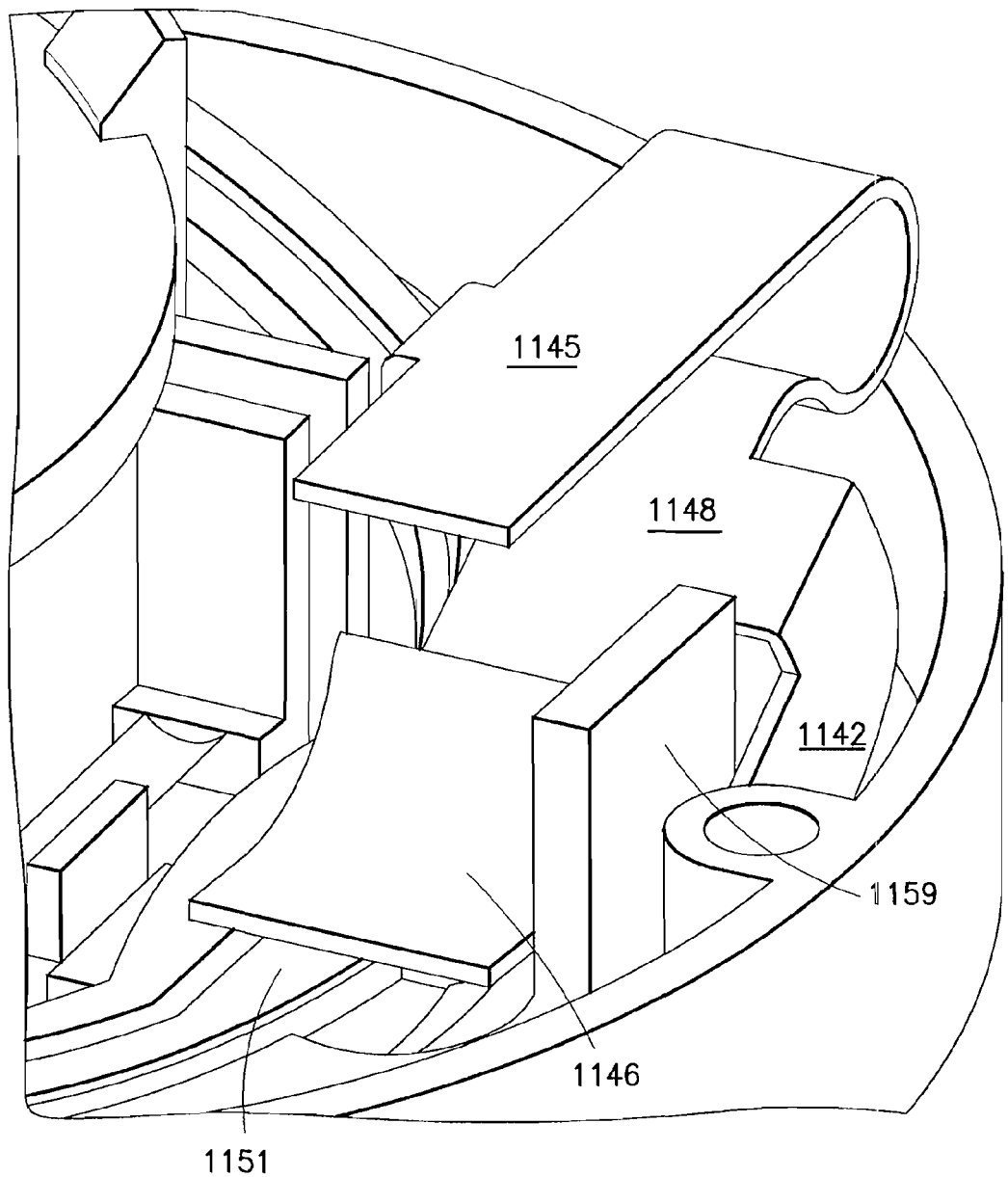

In FIGS. 150 through 156, several improved manifold spring embodiments are shown. In FIGS. 150, 151 and 152, perspective views of a first embodiment of an improved manifold spring are shown. FIGS. 150 and 151 show the spring in a loaded, or flexed position, and FIG. 152 shows the spring in a released or relaxed position. A spring 1140 includes a first and second adjacent member 1148 and 1145 coupled to produce a substantially acute angle when relaxed as shown in FIG. 152. When in a loaded position, the first member 1148 is secured within an arc 1144 provided by the second member 1145. A large, perpendicular member 1142 is provided on the first member 1148 to engage a push button within the device to release the first member 1148 from the arc 1144 and apply pressure via a substantially curved element 1146.

In operation, the loaded spring 1140 is positioned above a needle manifold 1151 within a device. The spring 1140 is positioned above the needle manifold 1151, such as the manifold 520 in FIG. 34. Wherein FIG. 34 illustrates the spring 581 provided to apply a force to the manifold 520, in yet other embodiments of the present invention, the spring 1140 can be positioned above the manifold 520 and provide a force to the manifold. In FIGS. 150 and 151 the spring 1140 is held in a loaded state by the engagement between the first and second members 1148 and 1145. When the push button (not shown) is activated, the perpendicular member 1142 is engaged by contact with a button member 1159, moving the second member 1148 away from the stationary first member arc 1144, until the second member 1148 is released. Once released, the substantially circular contact area 1146 of the second member 1148 drives the manifold 1151. The circular contact area 1146 ensures spring to manifold contact is provided at a center point of the manifold 1151 throughout the expansion of the spring 1140. Such contact further ensures proper manifold travel. Still other embodiments of the improved manifold spring are shown in FIGS. 153 through 156 and perform substantially as described above.

Figure 153:
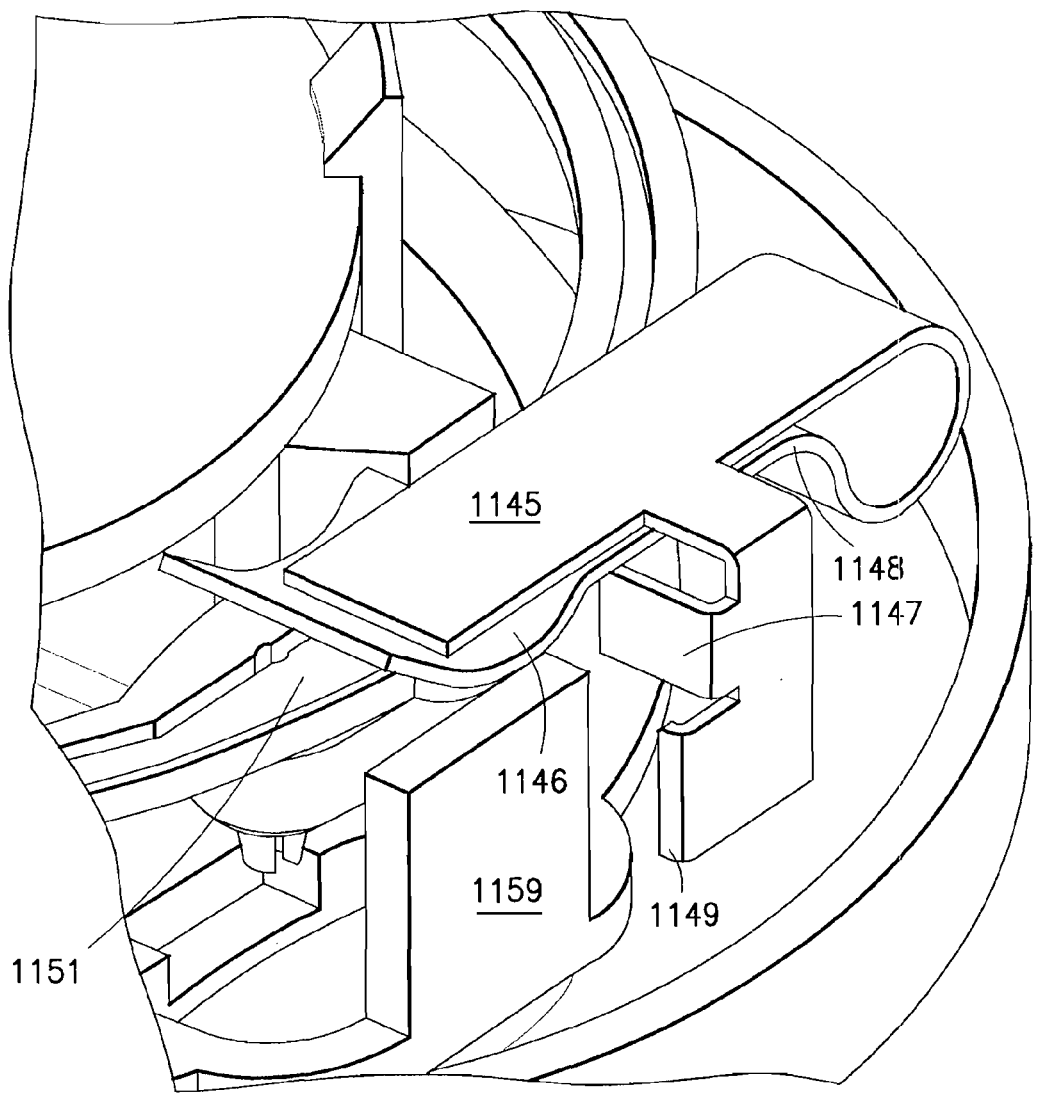
Figure 154:
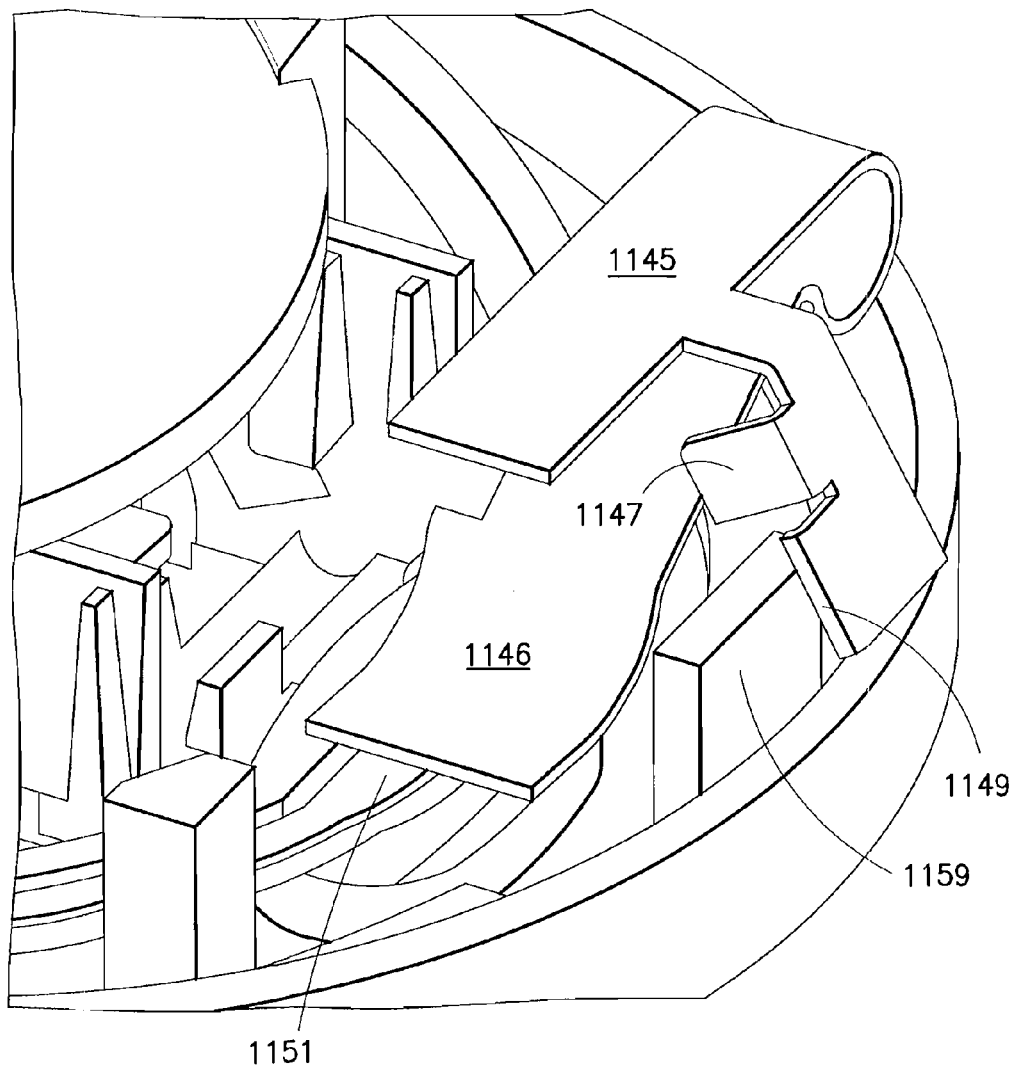
Figure 155:
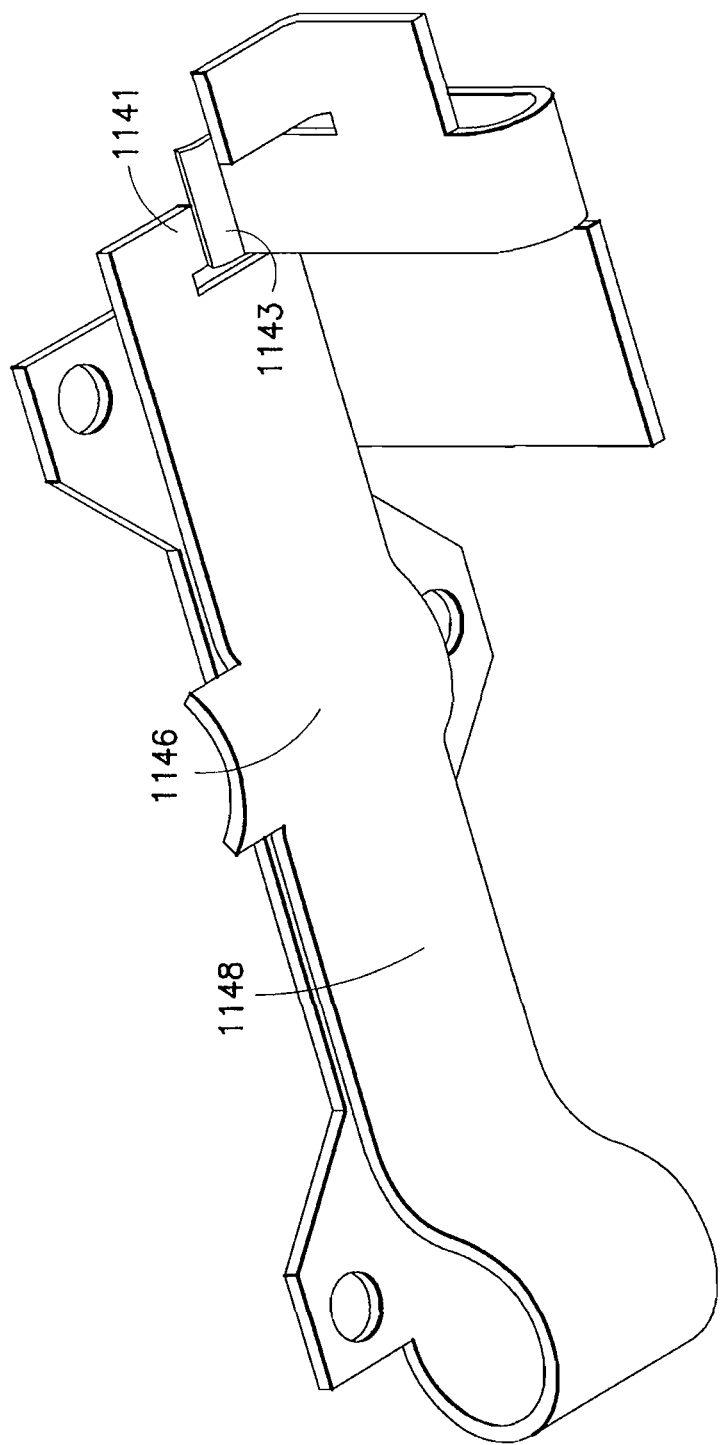
Figure 156:
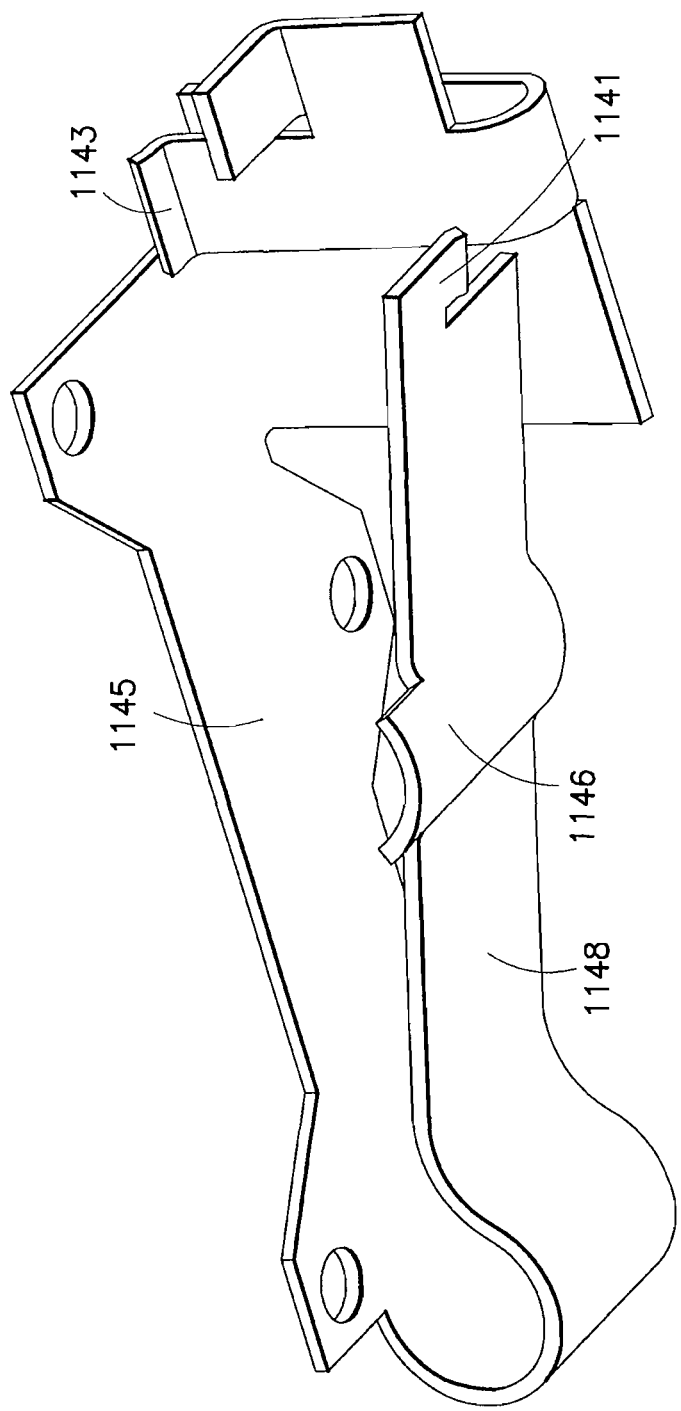

In FIG. 153, the securing arc 1144 of FIG. 150 is replaced with a substantially larger member 1147 extending from a button engagement member 1149. As the button engages the member 1149, the member 1147 releases the spring and presses the manifold 1151 forward, substantially as described above. Likewise in FIG. 155, the securing arc 1144 of FIG. 150 is replaced with an engagement between members 1141 and 1143 and when released, performs substantially as described above. Each includes a small detent means to prevent accidental releases.

In FIGS. 157 through 163, an improved "through the button" fill mechanism and method is shown, which can be used with any of the infusion device embodiments and improvements presented above.

Figure 157:
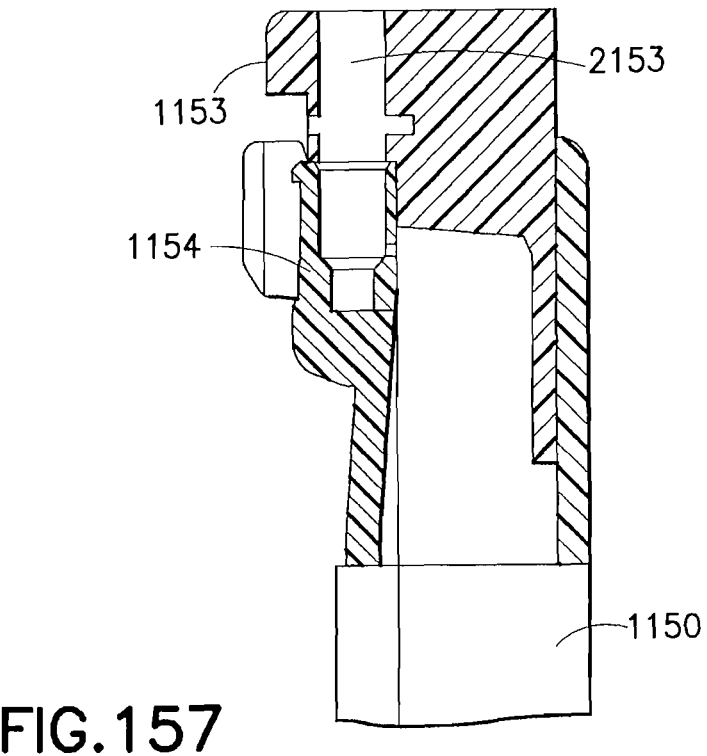
Figure 158:
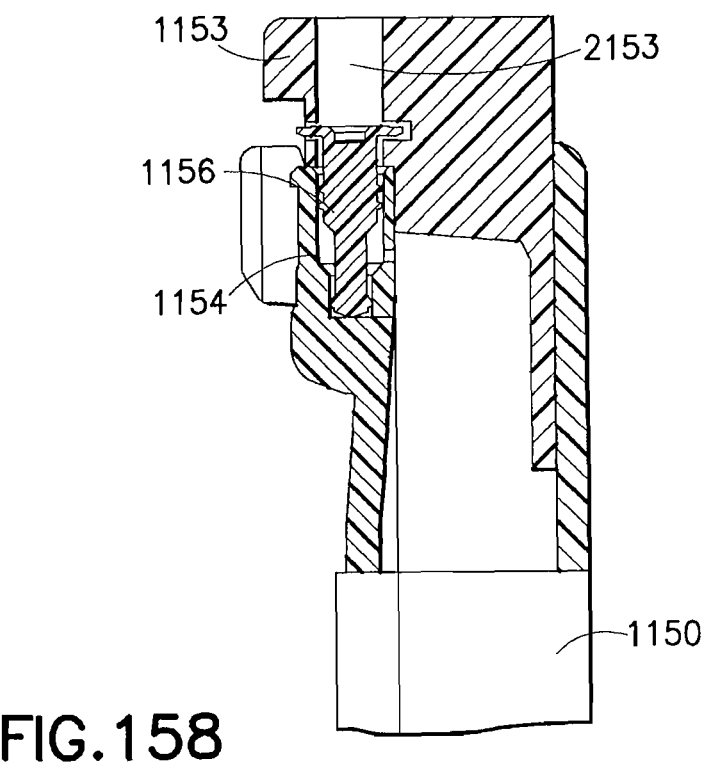
Figure 159:
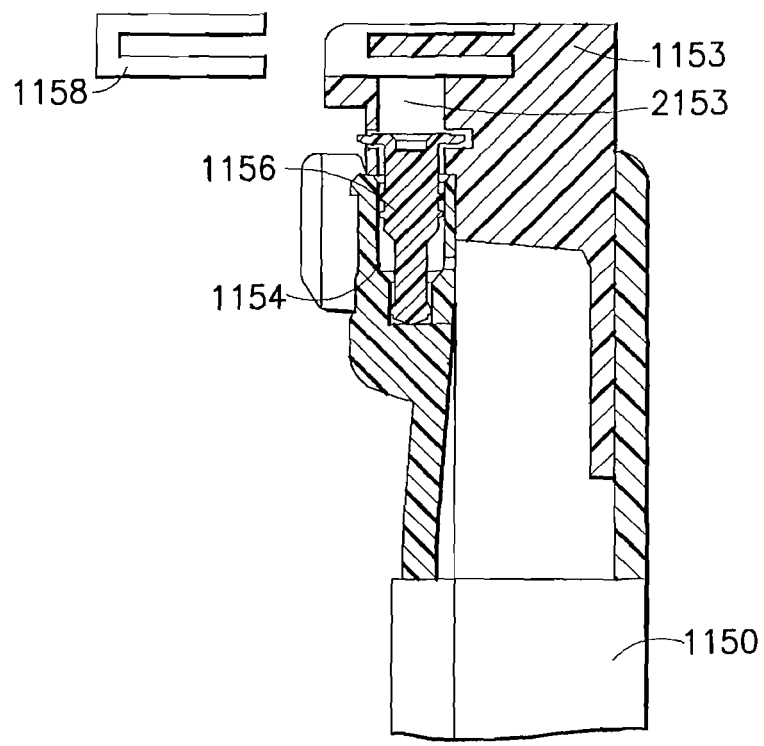
Figure 160:
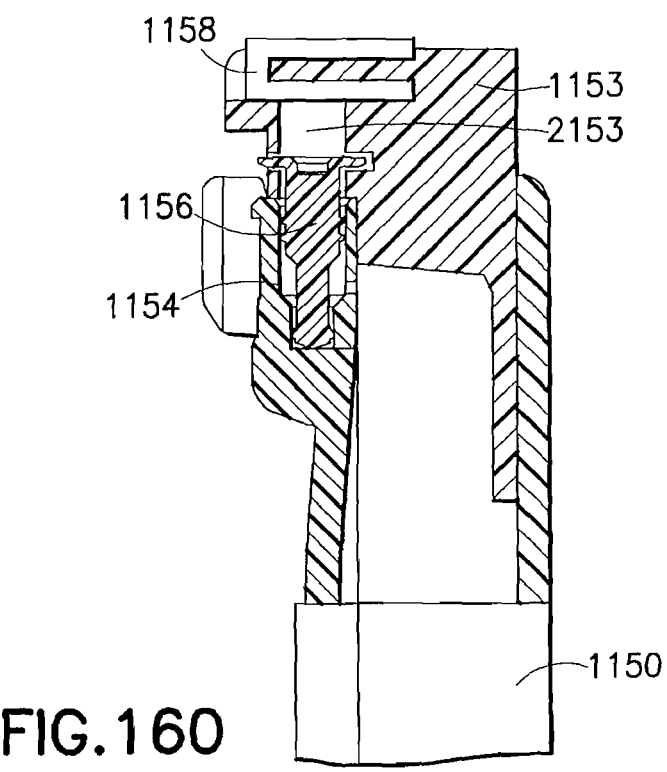
Figure 161:
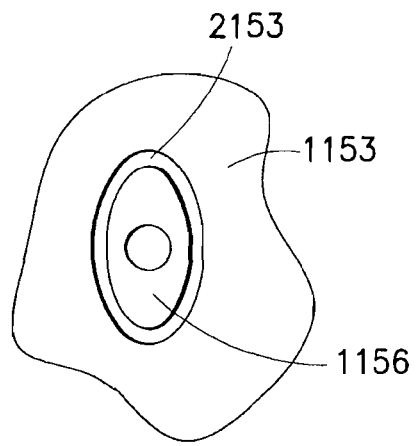
Figure 162:
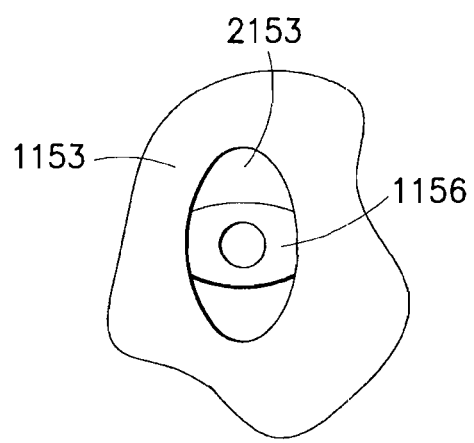
Figure 163:
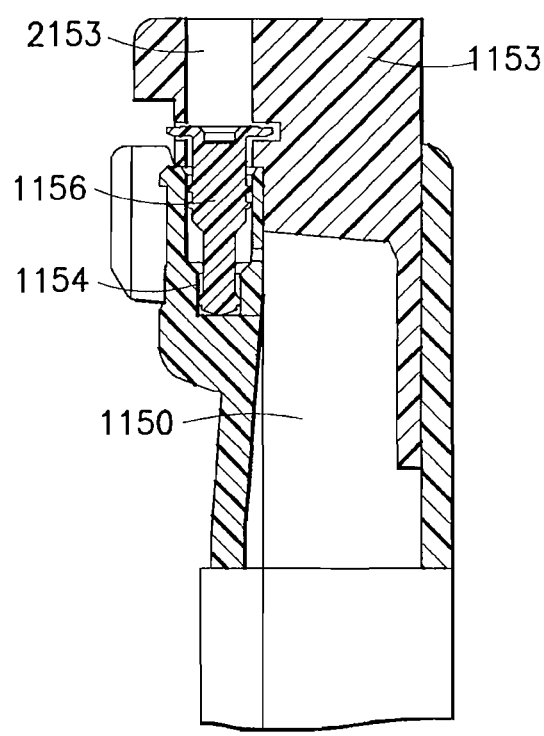

Step 1, shown in FIG. 157, illustrates a filling process. A partial cross-sectional view of a device 1150 shows a push button 1153 positioned adjacent to a reservoir opening 1154. A hole 2153 is included in the push button 1153, which allows filling the device 1150 through the reservoir opening 1154 even after assembly. In step 2 shown in FIG. 158, a valve assembly 1156 is assembled within the reservoir opening 1154 after filling through the button hole 2153. The valve assembly 1156 can be assembled through the hole 2153, therefore, to use the button 1153 to actuate the valve 1156, the hole 2153 needs to be restricted in some manner. In step 3, a member 1158 is provided to close the button hole 2153 access, or window, to allow the activation of the valve 1156 as shown in FIG. 159. Once closed, as shown in FIG. 160, the push button 1153 is ready to be pressed, thereby activating the valve assembly 1156.

In an alternative embodiment of the present invention, the valve 1156 can be inserted through the opening 2153, then rotated to complete step 3. As shown in top views of the button 1153 in FIGS. 161 and 162, the valve 1156 is constructed having a substantially oval profile, which can be slidably inserted in a similarly shaped hole 2153 provided by the button 1153. The oval profiles are designed to be non-symmetrical by rotation as shown in the cross-sectional view of FIG. 163, such that once in position in the reservoir opening, the rotation of the valve 1156 allows the valve flange to be perpendicular to the opening. This allows the push button 1153, even with the opening 2153, to push the valve 1156 when the button 1153 is moved forward. This option eliminates the need for the member 1158 provided to close the button window 2153 to allow the activation of the valve in FIGS. 157 through 160.

Still other improvement embodiments are related to device filling and content indication. As shown in FIGS. 164 through 167, an end-of-dose indicator can be provided with the infusion devices described above allowing a user to see if the drug has been administered, and to a lesser degree, what extent may have been administered.

In some infusion devices, it is not possible to have a transparent reservoir where the user can see completely through the reservoir. Generally, when transparent materials cannot be used with liquids due to chemical interaction, or water/gas transmission rates are too high, a solution can include the use of a combination of transparent and non-transparent materials. The non-transparent materials can be any number of materials, such as a laminated material with aluminum for flexible requirements, or coated materials for rigid requirements. The embodiment of the present invention described below includes a reservoir 1160 that is composed of a flexible, non-transparent material for a membrane 1162, and a rigid transparent material 1164. A visible indicator 1166 to distinguish between the beginning and the end of the drug administration is also provided. This visible indicator can be either the appearance or disappearance of a sign occurring at the end of the infusion.

As shown in FIGS. 164 and 165, a raised relief 1168 constructed of a soft material on the indicator 1166 is in contact with the flexible membrane 1162, and is some distance from the rigid transparent material 1164 due to the contents of the reservoir. However, the raised relief 1168 creates a visible distortion or outline 1169 in the flexible membrane 1162 which is visible through the transparent material 1164. An example of such an outline 1169 is shown in FIG. 164. Once the reservoir 1160 is emptied as shown in FIGS. 166 and 167, the raised relief 1168 is flattened by contact with the rigid transparent material 1164 due to the lack of contents in the reservoir 1160. The distortion 1169 in the flexible membrane 1162 is thereby eliminated, as shown in FIG. 166. The embodiment therefore can be used to provide a direct visualization of the fluid dispensed, however, still other embodiments can provide end of dose indication in any number of ways including timers and pressure controls/sensors.

To provide the embodiment of the present invention described above, a flexible material is provided as the membrane 1162. At the beginning of the injection, the "flexible sign" of the raised relief 1168 is applied on the flexible membrane 1162 and as such, the force applied to the raised relief 1168 is the force applied to the film 1162 and the reservoir contents, which yield to a great degree therefore little deformation of the raised relief 1168 appears. At or near the end of the infusion or injection, the membrane or film 1162 is in contact with the hard transparent part 1164 of the reservoir 1160, and the raised relief 1168 is compressed against the reservoir and the sign of the raised relief 1168 disappears.

In yet another improved visual indication embodiment of the present invention, another feature can be incorporated into the micro infusor device to visually indicate when the medication delivery is complete. As noted above, several designs of infusion devices include a needle manifold in combination with similar components, and which move in the general direction of a patient's skin for insertion. The needle manifold then moves away from the patient's skin for retraction. This feature, in association with the upper and lower case of the outer shell of the device, can be used for providing such an improved visual indicator.

During the infusion process, the lower case is attached to the patient's skin while the upper case is the shell component furthest away from the skin. It is this upper shell which is generally visible to the patient, or person using the infusion device. Located within the infusion device, is a component commonly referred to as a needle manifold substantially as described above. Permanently fixed into this needle manifold are one or more micro-needles, or very small cannula. This needle manifold is also attached to the fluid reservoir in various manners to form a continuous, leak-proof, fluid pathway. The pathway is provided to allow the fluid to travel from the fluid reservoir, through one or more fluid control devices, through the needle manifold and distal end of the micro-needles, and into a patient.

At or near the beginning of the infusion process for drug delivery, the cannula punctures and enters the patient's skin to deliver the fluid, liquid, gas or vapor medication provided by the reservoir. The medication can be selected to be delivered into targeted regions below the epidermis of the patient. To puncture the skin so that drug delivery can occur, the needle manifold is urged by manifold springs in a direction substantially perpendicular to, and towards the patient's skin surface, and in a direction generally parallel with the long axis of the cannula. As noted above, the needle manifold motion may also be designed as a rotating mechanism, however, the protruding indicator elements of this improved visual indicator embodiment can still be incorporated. At or near the termination of the infusion process, the cannula are withdrawn from the patient by moving the needle manifold in a direction generally away from the skin and/or by moving the needle manifold in the direction opposite to its previous motion.

The total distance of needle manifold travel in an example embodiment can be approximately three to six millimeters (3 mm to 6 mm). A preferred design feature however, is to minimize the height or "tallness" of the infusion device in which this travel occurs. For other functional requirements, the needle manifold is typically one of the tallest components in the infusion device. In this sense, a "tall" direction is perpendicular to the skin surface in the area of infusion device placement. For these reasons and to accommodate the necessary motion, the top surfaces of the needle manifold will be close to, or in contact with the inside surface of the upper case while in storage, prior to use, and before the needle manifold motion causes cannula insertion into the skin. When the infusion process is started, the needle manifold moves away from the inside surface of the upper case during cannula insertion, causing a gap or clearance between the upper case and the needle manifold. When fluid infusion is complete, the needle manifold and cannula are retracted, thus returning to their starting position. The embodiment of the present invention includes a feature disposed at the top of the needle manifold that can be visible to the patient or user through a feature in the upper case.

In a first embodiment, the needle manifold can have a cylindrical prismatic or similar prismatic feature that can protrude from and/or above the top surface of the needle manifold. This protruding feature can be integrally molded with the needle manifold body, or it may be a separate part attached to the needle manifold body. The protruding feature is a highly reflective and/or bright contrasting color to optimize visibility.

Corresponding with the needle manifold's protruding feature described above, both in general location and approximate size, an opening can be provided through the top case, or provided as a transparent window or molded lens-shaped device fitted into or through the top case. The protruding feature on the needle manifold would slidably fit into or through the top case opening, or slidably fit into a concavely pocketed area on the inside region of the transparent window. To accommodate a pivoting or textural type indicator, a larger, rectangular, or oval shaped window can be provided in the top case.

As noted above, the protruding feature on the needle manifold is a highly reflective and/or bright contrasting color to optimize visibility. In yet other embodiments, a simple colored indicator can include text, such as the word "Ready", "OK", or "Start", which is visible in the case opening or window.

Additionally, another embodiment having a two-position indicator is possible by adding at least one additional part. This two-position, or pivoting, indicator can include the above text in quotations (i.e., indicia) prior to infusion, and when the needle manifold has traveled down and is in the return stroke, a spring integral or attached to the pivoting indicator, can flip the indicator to make visible additional text such as the word "End", "Done", or "Remove". The moving feature with the indicia may also slide relative to the needle manifold instead of pivoting.

In use, the embodiment of the present invention described above allows ambient light to pass through the transparent lens or window in the top case, which reflects from the protruding indicator surfaces located close to or within the concave pocket of the window. The reflected light is then transmitted back out through the window and is then received by the user's eyes. Essentially, when the needle manifold is in the up, or retracted position, the indicator window of the infusion device appears as a bright object surrounded by a clear lens. The indicator is visible as a color that distinctly contrasts with the surrounding surfaces of the top case.

When the needle manifold is down, or in the "cannula inserted" position, the protruding indicator feature is some distance away from the window. Light passing through the window while in this operating mode has nothing to reflect from and scatters inside the infusion device, therefore the window appears dark. In doing so, this embodiment of the present invention actually indicates the position of the needle manifold and cannula, rather than indicating whether the fluid has been partially, or fully discharged from the infusion device and into the patient. However, other methods of use can be used by the user to interpret the visible changes in the indicator window.

The embodiments described above are commonly packaged for convenience and protection. Therefore, in yet another improvement embodiment of the present invention, a packaging system is provided which allows prefillable devices such as those described above to be sterilized, transported, decontaminated, and filled with contents, such as medicine, as either liquid, gas, powder, and the like. The devices themselves are not decontaminated, but the packaging surface is.

The packaging system shown in FIGS. 168 through 175 comprises an array type package, or nest 1170, which maintains a number of prefillable devices 1175 in a defined position (i.e., vertical), and provides external packaging which can be flexible, like a pliable bag 1185 and 1190, or rigid, like a box 1180.

After production of any infusion device, including improved embodiments described above, the devices can be assembled into openings 1171 of the empty nest 1170 of FIG. 168 until full as shown in FIG. 169, or partially full as shown in FIG. 170. Each opening further includes a number of ribs 1196, described in greater detail below. Then an external packaging, such as bag 1185 and bag 1190 (as shown in FIG. 174 illustrating a complete packaging example), or box 1180 and bag 1190 (as shown in FIG. 175 illustrating a complete packaging example), is provided to guarantee integrity against bacterial contamination. The bag 1185 can be provided with an internal vacuum, and bag 1190 can be provided with or without an internal vacuum. The rigid box 1180 can be provided having a Tyvek, paper, film or rigid cover, and the bag 1190 can be provided with or without an internal vacuum. Typically, the external packaging can include still another package that is added to prevent dust (i.e., a dust cover) from coming into contact with the box or bag. The complete packaging (i.e., the nest 1170 and external packaging) can be sterilized by gamma radiation, ethylene oxide, E-beam, or other appropriate sterilization method.

When the devices 1175 need to be filled, the complete packaging is externally decontaminated to prevent bacteria from entering the filling room which is an aseptic environment. Then the external bag 1190 (i.e., the dust cover) is removed and the box or bag (i.e. 1180 or 1185) of the external packaging is opened to remove the nest 1170 and the nest with devices 1175 is placed on a filling machine (not shown) to then fill the devices 1175.

To ease the filling process, the filling machine can raise the devices 1175 as shown in FIG. 171 using the ribs 1195 and 1196, and large openings 1198 provided in the bottom of each opening 1171 of the nest 1170 as shown in a top view of the nest in FIG. 173. The ribs 1195 and 1196, and openings 1198 are provided to improve the laminar air flow around the devices 1175 and provide a support for the device 1175 if a force is required on the top of the device. The ribs 1195 further can be used to hold the devices 1175 and ribs 1196 can be used to center the devices. For specific filling processes, the devices 1175 need to be maintained in an accurate position to have a filling head of a filling machine (not shown) align with the devices 1175 as indicated by the arrows in FIG. 171. Moving the devices upward as shown in FIG. 171 allows the filling machine to have additional fixtures to align the devices 1175 carefully.

Currently, packaging exists for use with syringes, where the syringes are placed in a nest composed of a plastic plate and chimney, and an external packaging is provided and constructed of a rigid box. The embodiment of the present invention does not include a plate or chimney, but simply an arrangement of ribs 1195 and 1196. The use of ribs 1195 and 1196 ensures a low front surface, and allows the laminar air flow present in the room to flow around the devices 1175 and improve the quality of filling in addition to providing the lifting ability described above.

Other benefits associated with the embodiment described above include the ability to have the flexible bag 1185 instead of the rigid box 1180 as part of the external packaging, then allowing a vacuum in the bag 1185 to provide a visual indicator of the package integrity. In this version, a lost vacuum indicates no integrity. Additionally, the flexible bag 1185 is less expensive to provide than the box 1180. In a preferred embodiment, a configuration is provided with the nest 1170 and the external bag 1185 having no vacuum, and an added second bag 1190 also without vacuum to prevent dust from coming into contact with the first bag.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

What is claimed is:

1. A device for delivering a medicament into a body of a patient by injection into or through a skin surface of said patient, comprising:
    a housing having a bottom surface adapted to contact a skin surface of a patient;
    a needle adapted for penetration of said skin surface and for movement through an aperture;
    a reservoir, disposed within said housing, for containing said medicament;
    a needle holder for holding said needle;
    an activation button slidably disposed with said device;
    a safety member; and
    at least one shield configured to be held in place by said safety member, said shield comprising a ramp configured to directly contact and raise said needle holder to retract said needle into said device;
    wherein said shield is urged to move relative to said bottom surface from a position exposing said needle into a position to at least partially cover said needle or said aperture.

2. The device as claimed in claim 1, wherein said safety member further comprises a detent releasably held by said activation button, wherein said activation of said device is configured to release said detent of said safety member.

3. The device as claimed in claim 2, wherein said safety member further comprises a skin adhesion surface to move said safety member upon release by said activation button and removal from a skin surface, wherein said movement of said safety member releases said shield to be urged into a position to at least partially cover said needle or said aperture.

4. The device as claimed in claim 1, further comprising a spring disposed between said ramp and said activation button, wherein said movement of said activation button is configured to load said spring prior to release of said safety member by said activation button.

5. The device as claimed in claim 1, wherein said ramp is configured to slidably cover said needle or said aperture.

6. The device according to claim 1, wherein movement of said activation button releases said safety member to move, and movement of said safety member releases said shield.

7. The device according to claim 1, wherein said shield is urged to move substantially parallel to said bottom surface.

8. A device for delivering a medicament into a body of a patient by injection into or through a skin surface of said patient, comprising:
    a housing having a bottom surface adapted to contact a skin surface of a patient;
    a needle adapted for penetration of said skin surface and for movement through an aperture;
    a needle holder for holding said needle;
    an activation button slidably disposed with said device;
    a safety member; and
    at least one shield configured to be held in place by said safety member, said shield comprising a ramp configured to directly contact and raise said needle holder to retract said needle into said device;
    wherein said shield is configured to be released from said safety member by movement of said device activation button and removal of said device from a skin surface, and said shield is urged to move relative to said bottom surface into a position to at least partially cover said needle or said aperture.

9. The device according to claim 8, wherein movement of said activation button releases said safety member to move, and movement of said safety member releases said shield.

10. The device according to claim 8, wherein said shield is urged to move substantially parallel to said bottom surface.

11. A device for delivering a medicament into a body of a patient by injection into or through a skin surface of said patient, comprising:
- a housing having a bottom surface adapted to contact a skin surface of a patient;
- an activation button slidably disposed with said device;
- a needle adapted for penetration of said skin surface and for movement through an aperture;
- a needle holder for holding said needle; and
- at least one shield configured to be held in place prior to activation of said device, said shield being urged to move substantially parallel to said bottom surface into a position to at least partially cover said needle or said aperture;
- wherein said shield comprises a ramp to raise said needle holder to retract said needle into said device.

12. The device as claimed in claim 11, further comprising a safety member, wherein said shield is configured to be held in place by said safety member prior to activation of said device.

13. A device with a housing having a bottom surface adapted to contact a skin surface of a patient, and a needle adapted for penetration of said skin surface and for movement through an aperture, comprising:
- an activation button to activate said device thereby inserting said needle into said skin surface;
- a needle holder for holding said needle;
- a safety member; and
- at least one shield configured to be held in place by said safety member, said shield comprising a ramp configured to contact and raise said needle holder to retract said injection needle into said device;
- wherein said shield is configured to be released from said safety member by movement of said device activation button and removal of said device from a skin surface, and said shield is urged to move substantially parallel to said bottom surface from a position exposing said needle into a position to at least partially cover said needle or said aperture.

14. The device as claimed in claim 13, wherein said safety member further comprises a detent releasably held by said activation button, wherein said activation of said device is configured to release said detent of said safety member.

15. The device as claimed in claim 14, wherein said safety member further comprises a skin adhesion surface to move said safety member upon release by said activation button and removal from a skin surface, wherein said movement of said safety member releases said shield to be urged into a position to at least partially cover said needle or said aperture.

16. The device as claimed in claim 13, further comprising a spring disposed between said ramp and said activation button, wherein said movement of said activation button is configured to load said spring prior to release of said safety member by said activation button.

17. The device as claimed in claim 13, wherein said ramp is configured to slidably cover said needle or said aperture.

18. The device according to claim 13, wherein movement of said activation button releases said safety member to move, and movement of said safety member releases said shield.

19. A device for delivering a medicament into a body of a patient by injection into or through a skin surface of said patient, comprising:
- a housing having a bottom surface adapted to contact a skin surface of a patient;
- an activation button slidably disposed with said device;
- a needle adapted for penetration of said skin surface and for movement through an aperture;
- a needle holder for holding said needle; and
- at least one shield configured to be held in place prior to activation of said device, said shield being urged to move substantially parallel to said bottom surface into a position to at least partially cover said needle or said aperture;
- wherein said shield comprises a ramp configured to contact and raise said needle, holder to retract said needle into said device.

* * * * *